United States Patent
Levy et al.

(10) Patent No.: US 10,519,250 B2
(45) Date of Patent: Dec. 31, 2019

(54) PARATHYROID HORMONE RECEPTOR 1 (PTH1R) ANTIBODIES AND USES THEREOF

(71) Applicant: XOMA (US) LLC, Berkeley, CA (US)

(72) Inventors: Raphael D. Levy, Berkeley, CA (US); Hassan Issafras, Berkeley, CA (US); Agnes Choppin Holmes, Berkeley, CA (US); Kirk W. Johnson, Berkeley, CA (US); Amer M. Mirza, Berkeley, CA (US); Daniel H. Bedinger, Berkeley, CA (US); Rachel A. Hunt, Berkeley, CA (US); Toshihiko Takeuchi, Berkeley, CA (US); Kiranjit Kaur Ahluwalia, Berkeley, CA (US); Robyn Cotter, Berkeley, CA (US)

(73) Assignee: XOMA (US) LLC, Emeryville, CA (US)

( * ) Notice: Subject to any disclaimer, the term of this patent is extended or adjusted under 35 U.S.C. 154(b) by 0 days.

(21) Appl. No.: 15/665,788

(22) Filed: Aug. 1, 2017

(65) Prior Publication Data

US 2018/0030154 A1 Feb. 1, 2018

Related U.S. Application Data

(60) Provisional application No. 62/479,637, filed on Mar. 31, 2017, provisional application No. 62/432,338, filed on Dec. 9, 2016, provisional application No. 62/369,745, filed on Aug. 1, 2016.

(51) Int. Cl.
| | |
|---|---|
| *A61K 39/395* | (2006.01) |
| *C12N 5/00* | (2006.01) |
| *C12N 15/00* | (2006.01) |
| *C12P 21/06* | (2006.01) |
| *C12P 19/34* | (2006.01) |
| *C07K 16/00* | (2006.01) |
| *C12P 21/08* | (2006.01) |
| *C07K 16/44* | (2006.01) |
| *A61K 38/02* | (2006.01) |
| *C07K 16/26* | (2006.01) |
| *A61K 39/00* | (2006.01) |
| *C07K 16/28* | (2006.01) |

(52) U.S. Cl.
CPC .............. *C07K 16/44* (2013.01); *A61K 38/02* (2013.01); *A61K 39/00* (2013.01); *A61K 39/395* (2013.01); *A61K 39/39541* (2013.01); *C07K 16/26* (2013.01); *C07K 16/2869* (2013.01); *C07K 2317/76* (2013.01); *G01N 2333/635* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,816,567 A | 3/1989 | Cabilly et al. |
| 4,975,278 A | 12/1990 | Senter et al. |
| 5,057,313 A | 10/1991 | Shih et al. |
| 5,223,409 A | 6/1993 | Ladner et al. |
| 5,229,275 A | 7/1993 | Goroff |
| 5,348,867 A | 9/1994 | Georgiou et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,589,369 A | 12/1996 | Seidman et al. |
| 5,591,669 A | 1/1997 | Krimpenfort et al. |
| 5,624,821 A | 4/1997 | Winter et al. |
| 5,643,768 A | 7/1997 | Kawasaki |
| 5,658,754 A | 8/1997 | Kawasaki |
| 5,723,287 A | 3/1998 | Russell et al. |
| 5,766,886 A | 6/1998 | Studnicka et al. |
| 5,770,429 A | 6/1998 | Lonberg et al. |
| 5,877,293 A | 3/1999 | Adair et al. |
| 5,939,598 A | 8/1999 | Kucherlapati et al. |
| 5,969,108 A | 10/1999 | McCafferty et al. |
| 6,054,287 A | 4/2000 | Gao et al. |
| 6,091,001 A | 7/2000 | Jakobovits et al. |
| 6,114,598 A | 9/2000 | Kucherlapati et al. |
| 6,194,551 B1 | 2/2001 | Idusogie et al. |
| 6,306,393 B1 | 10/2001 | Goldenberg |
| 6,657,103 B1 | 12/2003 | Kucherlapati et al. |
| 6,664,114 B1 | 12/2003 | Lackie et al. |
| 6,699,658 B1 | 3/2004 | Wittrup et al. |

(Continued)

FOREIGN PATENT DOCUMENTS

| | | |
|---|---|---|
| EP | 0404097 A2 | 12/1990 |
| EP | 1391213 A1 | 2/2004 |

(Continued)

OTHER PUBLICATIONS

Paul, Fundamental Immunology, 3r~ Edition,1993, pp. 292-295, under the heading "Fv Structure and Diversity in Three Dimensions" (Year: 1993).*

(Continued)

*Primary Examiner* — Shulamith H Shafer

(74) *Attorney, Agent, or Firm* — Marshall, Gerstein & Borun LLP

(57) ABSTRACT

The present disclosure relates, in general, human antibodies against human parathyroid hormone receptor 1 (PTH1R) and methods of use of such antibodies in the treatment of cancer, Humoral Hypercalcemia of Malignancy (HHM), or Primary Hyperparathyroidism (PHPT) and Secondary Hyperparathyroidism (SHPT) and cachexia.

34 Claims, 41 Drawing Sheets

Specification includes a Sequence Listing.

(56) References Cited

U.S. PATENT DOCUMENTS

| | | | |
|---|---|---|---|
| 6,737,056 | B1 | 5/2004 | Presta |
| 6,833,268 | B1 | 12/2004 | Green et al. |
| 7,150,974 | B1 | 12/2006 | Segre et al. |
| 7,910,544 | B2 | 3/2011 | Gardella et al. |
| 7,985,835 | B2 | 7/2011 | Gardella et al. |
| 8,569,462 | B2 | 10/2013 | Bedinger et al. |
| 8,926,976 | B2 | 1/2015 | Corbin et al. |
| 2002/0004215 | A1 | 1/2002 | Osbourn et al. |
| 2002/0199213 | A1 | 12/2002 | Tomizuka et al. |
| 2003/0028071 | A1 | 2/2003 | Handy et al. |
| 2003/0031667 | A1 | 2/2003 | Deo et al. |
| 2003/0032995 | A1 | 2/2003 | Handy et al. |
| 2003/0092125 | A1 | 5/2003 | Davis et al. |
| 2003/0162256 | A1* | 8/2003 | Juppner ............... C07K 14/461 435/69.1 |
| 2003/0190317 | A1 | 10/2003 | Baca et al. |
| 2003/0194404 | A1 | 10/2003 | Greenfeder et al. |
| 2004/0132101 | A1 | 7/2004 | Lazar et al. |
| 2005/0037421 | A1 | 2/2005 | Honda et al. |
| 2005/0136049 | A1 | 6/2005 | Ledbetter et al. |

FOREIGN PATENT DOCUMENTS

| | | | |
|---|---|---|---|
| WO | WO-81/01145 | A1 | 4/1981 |
| WO | WO-87/005330 | A1 | 9/1987 |
| WO | WO-88/07378 | A1 | 10/1988 |
| WO | WO-91/00906 | A1 | 1/1991 |
| WO | WO-91/017271 | A1 | 11/1991 |
| WO | WO-92/001047 | A1 | 1/1992 |
| WO | WO-92/009690 | A2 | 6/1992 |
| WO | WO-92/015679 | A1 | 9/1992 |
| WO | WO-92/018619 | A1 | 10/1992 |
| WO | WO-92/020791 | A1 | 11/1992 |
| WO | WO-93/001288 | A1 | 1/1993 |
| WO | WO-93/11161 | A1 | 6/1993 |
| WO | WO-94/002602 | A1 | 2/1994 |
| WO | WO-96/11953 | A1 | 4/1996 |
| WO | WO-96/030498 | A1 | 10/1996 |
| WO | WO-96/033735 | A1 | 10/1996 |
| WO | WO-96/034096 | A1 | 10/1996 |
| WO | WO-98/024893 | A2 | 6/1998 |
| WO | WO-99/010494 | A2 | 3/1999 |
| WO | WO-2004/073587 | A2 | 9/2004 |

OTHER PUBLICATIONS

Rudikoff et al. Proc. Natl. Acad. Sci.USA,79(6):1979-1983, Mar. 1982 (Year: 1982).*
Colman P. M. Research in Immunology, 145:33-36,1994 (Year: 1994).*
Lloyd et al. 2009. Protein Engineering, Design & Selection 22:159-168 (Year: 2009).*
Piatesi et al ChemBio Chem 5: 460-466, 2004 (Year: 2004).*
Stancovski et al. Proceedings of the National Academy of Science USA 88:8691-8695, 1991 (Year: 1991).*
Riemer et al. Mol. Immunol. 42: 1121-1124, 2005 (Year: 2005).*
Amstutz et al., In vitro display technologies: novel developments and applications, Curr. Opin. Biotechnol., 12(4):400-5 (2001).
Angal et al., A single amino acid substitution abolishes the heterogeneity of chimeric mouse/human (IgG4) antibody, Mol. Immunol., 30(1):105-8 (1993).
Aplin et al., Preparation, properties, and applications of carbohydrate conjugates of proteins and lipids, CRC Crit. Rev. Biochem., 10(4):259-306 (1981).
Barbas et al., Assembly of combinatorial antibody libraries on phage surfaces: the gene III site, Proc. Natl. Acad. Sci. USA, 88(18):7978-82 (1991).
Batra et al., Recombinant anti-erbB2 immunotoxins containing Pseudomonas exotoxin, Proc. Natl. Acad. Sci. USA, 89(13):5867-71 (1992).
Bayer et al., The avidin-biotin complex in affinity cytochemistry, Methods Enzymol., 62:308-15 (1979).
Better et al., *Escherichia coli* secretion of an active chimeric antibody fragment. *Science*. 240: 1041-3 (1988).
Better et al., Potent anti-CD5 ricin A chain immunoconjugates from bacterially produced Fab' and F(ab')2. *Proc. Natl. Acad. Sci. USA*. 90: 457-61 (1993).
Biocca et al., Expression and targeting of intracellular antibodies in mammalian cells, EMBO J., 9(1):101-8 (1990).
Bird et al., Single-chain antigen-binding proteins, Science, 242(4877):423-6 (1988).
Boulianne et al., Production of functional chimaeric mouse/human antibody, Nature, 312(5995):643-6 (1984).
Brinkmann et al., B3(Fv)-PE38KDEL, a single-chain immunotoxin that causes complete regression of a human carcinoma in mice, Proc. Natl. Acad. Sci. USA, 88(19):8616-20 (1991).
Bruggermann et al., Designer mice: the production of human antibody repertoires in transgenic animals, Year Immunol., 7:33-40 (1993).
Burton et al., Human antibodies from combinatorial libraries, Adv. Immunol., 57:191-280 (1994).
Caron et al., Engineered humanized dimeric forms of IgG are more effective antibodies, J. Exp. Med., 176(4):1191-5 (1992).
Carter et al., Discovery of a small molecule antagonist of the parathyroid hormone receptor by using an N-terminal parathyroid hormone peptide probe, Proc. Natl. Acad. Sci. USA, 104(16):6846-51 (2007).
Carter et al., High level *Escherichia coli* expression and production of a bivalent humanized antibody fragment. *Bio/Technology* 10: 163-7 (1992).
Carter et al., Actions of the small molecule ligands SW106 and AH-3960 on the type-1 parathyroid hormone receptor, Mol. Endocrinol., 29(2):307-21 (2015).
Chaudhary et al., A recombinant immunotoxin consisting of two antibody variable domains fused to Pseudomonas exotoxin, Nature, 339(6223):394-7 (1989).
Cheloha et al., PTH receptor-1 signalling-mechanistic insights and therapeutic prospects, Nat. Rev. Endocrinol., 11(12):712-24 (2015).
Chothia et al., Canonical structures for the hypervariable regions of immunoglobulins, J. Mol. Biol., 196(4):901-17 (1987).
Chothia et al., Conformations of immunoglobulin hypervariable regions, Nature, 342(6252):877-83 (1989).
Clackson et al., Making antibody fragments using phage display libraries, Nature, 352(6336):624-8 (1991).
Co et al., A humanized antibody specific for the platelet integrin gpIIb/IIIa, J. Immunol., 152)6):2968-76 (1994).
Colby et al., Potent inhibition of huntingtin aggregation and cytotoxicity by a disulfide bond-free single-domain intracellular antibody, Proc. Natl. Acad. Sci. USA, 101(51):17616-21 (2004).
Conrath et al., Beta-lactamase inhibitors derived from single-domain antibody fragments elicited in the camelidae, Antimicrob. Agents Chemother., 45(10):2807-12 (2001).
Cortez-Ramozo et al., Efficient cancer therapy with a nanobody-based conjugate, Cancer Res., 64(8):2853-7 (2004).
Darling et al., Kinetic exclusion assay technology: characterization of molecular interactions, Assay Drug Dev. Technol., 2(6):647-57 (2004).
Deonarain et al., Construction, refolding and cytotoxicity of a single chain Fv-seminal ribonuclease fusion protein expressed in *Escherichia coli*, Tumor Targeting, 1:177 (1995).
Desmyter et al., Antigen specificity and high affinity binding provided by one single loop of a camel single-domain antibody, J. Biol. Chem., 276(28):26285-90 (2001).
Dohlsten et al., Monoclonal antibody-superantigen fusion proteins: tumor-specific agents for T-cell-based tumor therapy, Proc. Natl. Acad. Sci. USA, 91(19):8945-9).
Doronina et al., Development of potent monoclonal antibody auristatin conjugates for cancer therapy, Nat. Biotechnol., 21(7):778-84 (2003).
Dresner-Pollak et al., Evaluation in vivo of a potent parathyroid hormone antagonist: [Nle8,18,D-Trp12,Tyr34]bPTH(7-34)NH2, J. Bone Miner. Res., 11(8):1061-5 (1996).
Edge et al., Deglycosylation of glycoproteins by trifluoromethanesulfonic acid, Anal. Biochem., 118(1):131-7 (1981).

(56) References Cited

OTHER PUBLICATIONS

Engvall et al., Enzyme-linked immunosorbent assay, Elisa. 3. Quantitation of specific antibodies by enzyme-labeled anti-immunoglobulin in antigen-coated tubes, J. Immunol., 109(1):129-35 (1972).
Ewert et al., Biophysical properties of camelid V(HH) domains compared to those of human V(H)3 domains, Biochemistry, 41(11):3628-36 (2002).
Eyer et al., Single-domain antibody fragments derived from heavy-chain antibodies: a review, Veterinarni Medicina, 57(9):439-513 (2012).
Ferrara et al., Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II, Biotechnol. Bioeng., 93(5):851-61 (2006).
Findlay et al., Properties of a calcitonin receptor and adenylate cyclase in BEN cells, a human cancer cell line, Cancer Res., 40(4):1311-8 (1980).
Fishwild et al., High-avidity human IgG kappa monoclonal antibodies from a novel strain of minilocus transgenic mice, Nat. Biotechnol., 14(7):845-51 (1996).
Fix, Strategies for delivery of peptides utilizing absorption-enhancing agents, J. Pharm. Sci., 85(12):1282-5 (1996).
Fominaya et al., Target cell-specific DNA transfer mediated by a chimeric multidomain protein. Novel non-viral gene delivery system, J. Biol. Chem., 271(18):10560-8 (1996).
Fredriksson et al., The G-protein-coupled receptors in the human genome form five main families. Phylogenetic analysis, paralogon groups, and fingerprints, Mol. Pharmacol., 63(6):1256-72 (2003).
Friedman et al., Antitumor activity of the single-chain immunotoxin BR96 sFv-PE40 against established breast and lung tumor xenografts, J. Immunol., 150(7):3054-61 (1991).
Fuchs et al., Targeting recombinant antibodies to the surface of *Escherichia coli*: fusion to a peptidoglycan associated lipoprotein, Bio/Technology, 9:1369-73 (Dec. 1991).
Fuentes et al., A PTH/PTHrP receptor antagonist blocks the hypercalcemic response to estradiol-17beta, Am. J. Physiol. Regul. Integr. Comp. Physiol., 293(2):R956-60 (2007).
Gardella et al., International Union of Basic and Clinical Pharmacology. XCIII. The parathyroid hormone receptors—family B G protein-coupled receptors, Pharmacol. Rev., 67(2):310-37 (2015).
Garrard et al., Fab assembly and enrichment in a monovalent phage display system, Bio/Technology, 9(12):1373-7 (1991).
Goding, Conjugation of antibodies with fluorochromes: modifications to the standard methods, J. Immunol. Methods, 13(3-4):215-26 (1976).
Goldenberg, New developments in monoclonal antibodies for cancer detection and therapy, CA Cancer J. Clin., 44(1):43-64 (1994).
Graham et al., Characteristics of a human cell line transformed by DNA from human adenovirus type 5. *J. Gen. Virol.* 36: 59-74 (1977).
Gram et al., In vitro selection and affinity maturation of antibodies from a naive combinatorial immunoglobulin library, Proc. Natl. Acad. Sci. USA, 89(8):3576-80 (1992).
Green, Transgenic mouse strains as platforms for the successful discovery and development of human therapeutic monoclonal antibodies, Curr. Drug Discov. Technol., 11(1):74-84 (2014).
Greenberg et al., A new antigen receptor gene family that undergoes rearrangement and extensive somatic diversification in sharks, Nature, 374(6518):168-73 (1995).
Griffiths et al., Human anti-self antibodies with high specificity from phage display libraries, EMBO J., 12(2):725-34 (1993).
Guss et al., Structure of the IgG-binding regions of streptococcal protein G. *EMBO* 5: 1567-75 (1986).
Hakimuddin et al., A chemical method for the deglycosylation of proteins, Arch. Biochem. Biophys., 259:52-7 (1987).
Hamers-Casterman et al., Naturally occurring antibodies devoid of light chains, Nature, 363(6428):446-8 (1993).
Hanes et al., In vitro selection and evolution of functional proteins by using ribosome display, Proc. Natl. Acad. Sci. USA, 94(10):4937-42 (1997).
Haramoto et al., Upregulation of PTH receptor mRNA expression by dexamethasone in UMR-106 osteoblast-like cells, Oral Dis., 13(1):23-31 (2007).
Hawkins et al., Selection of phage antibodies by binding affinity. Mimicking affinity maturation, J. Mol. Biol., 226(3):889-96 (1992).
Hay et al., Bacteriophage cloning and *Escherichia coli* expression of a human IgM Fab, Hum. Antibodies Hybridomas, 3(2):81-5 (1992).
Heng et al., Making cell-permeable antibodies (Transbody) through fusion of protein transduction domains (PTD) with single chain variable fragment (scFv) antibodies: potential advantages over antibodies expressed within the intracellular environment (Intrabody), Med. Hypotheses, 64(6):1105-8 (2005).
Hinman et al., Preparation and characterization of monoclonal antibody conjugates of the calicheamicins: a novel and potent family of antitumor antibiotics, Cancer Res., 53(14):3336-42 (1993).
Hoare et al., Specificity and stability of a new PTH1 receptor antagonist, mouse TIP(7-39), Peptides, 23(5):989-98 (2002).
Hoey et al., The parathyroid hormone-related protein receptor is expressed in breast cancer bone metastases and promotes autocrine proliferation in breast carcinoma cells, Br. J. Cancer, 88(4):567-73 (2003).
Holliger et al., "Diabodies": small bivalent and bispecific antibody fragments, Proc. Natl. Acad. Sci. USA, 90(14):6444-8 (1993).
Holliger et al., Engineered antibody fragments and the rise of single domains, Nat. Biotechnol., 23(9):1126-36 (2005).
Hoogenboom et al., By-passing immunisation. Human antibodies from synthetic repertoires of germline VH gene segments rearranged in vitro, J. Mol. Biol., 227(2):381-8 (1992).
Hoogenboom et al., Multi-subunit proteins on the surface of filamentous phage: methodologies for displaying antibody (Fab) heavy and light chains, Nucleic Acids Res., 19(15):413-7 (1991).
Huse et al., Generation of a large combinatorial library of the immunoglobulin repertoire in phage lambda, Science, 246-1275-81 (1989).
Huston et al., Protein engineering of antibody binding sites: recovery of specific activity in an anti-digoxin single-chain Fv analogue produced in *Escherichia coli*, Proc. Natl. Acad. Sci. USA, 85(16):5879-83 (1988).
Hutchings et al., Therapeutic antibodies directed at G protein-coupled receptors, MAbs, 2(6):594-606 (2010).
Ishida et al., Production of human monoclonal and polyclonal antibodies in TransChromo animals, Cloning Stem Cells, 4(1):91-102 (2002).
Ito et al., Gastric cancer associated with overexpression of parathyroid hormone-related peptide (PTHrP) and PTH/PTHrP receptor in relation to tumor progression, J. Gastroenterol., 32(3):396-400 (1997).
Jakobovits et al., Analysis of homozygous mutant chimeric mice: deletion of the immunoglobulin heavy-chain joining region blocks B-cell development and antibody production, Proc. Natl. Acad. Sci. USA, 90(6):2551-5 (1993).
Jakobovits et al., Germ-line transmission and expression of a human-derived yeast artificial chromosome, Nature, 362(6417):255-8 (1993).
Jespers et al., Guiding the selection of human antibodies from phage display repertoires to a single epitope of an antigen, Bio/Technology, 12(9):899-903 (1994).
Jo et al., Engineering therapeutic antibodies targeting G-protein-coupled receptors, Exp. Mol. Med., 48:e207 (2016).
Kettleborough et al., Humanization of a mouse monoclonal antibody by CDR-grafting: the importance of framework residues on loop conformation, Protein Eng., 4(7):773-83 (1991).
Klinguer-Hamour et al., World Antibody-Drug Conjugate Summit, Oct. 15-16, 2013, San Francisco, CA, MAbs, 6(1):18-29 (2014).
Kohler et al., Continuous cultures of fused cells secreting antibody of predefined specificity, Nature, 256(5517):495-7 (1975).

(56) References Cited

OTHER PUBLICATIONS

Kreitman et al., Cytotoxic activities of recombinant immunotoxins composed of Pseudomonas toxin or diphtheria toxin toward lymphocytes from patients with adult T-cell leukemia, Leukemia, 7(4):553-62 (1993).
Kremer et al., Hypercalcemia due to PTHrP, Chapter 38 IN: Bilezikian et al. (eds.), The Parathyroids, Basic and Clinical Concepts, Third Edition, Elsevier, pp. 557-576 (2015).
Kuan et al., Recombinant immunotoxin containing a disulfide-stabilized Fv directed at erbB2 that does not require proteolytic activation, Biochemistry, 35(9):2872-7 (1996).
Lee et al., Complete humanization of the mouse immunoglobulin loci enables efficient therapeutic antibody discovery, Nat. Biotechnol., 32(4):356-63 (2014).
Lee et al., Microbial cell-surface display, Trends Biotechnol., 21(1):45-52 (2003).
Lee et al., The application of transgenic mice for therapeutic antibody discovery, Methods Mol. Biol., 901:137-48 (2012).
Lefranc et al., IMGT, the international ImMunoGeneTics information system, Nucleic Acids Res., 33:D593-7 (2005).
Lefranc, The IMGT unique numbering for immunoglobulins, T-cell receptors, and Ig-like domains, The Immunologist, 7/4:132-6 (1999).
Levy et al., Enhancement of antibody fragment secretion into the *Escherichia coli* periplasm by co-expression with the peptidyl prolyl isomerase, FkpA, in the cytoplasm, J. Immunol. Methods, 394(1-2):10-21 (2013).
Lindmark et al., Binding of immunoglobulins to protein A and immunoglobulin levels in mammalian sera. *J. Immunol. Meth.* 62: 1-13 (1983).
Liu et al., Eradication of large colon tumor xenografts by targeted delivery of maytansinoids, Proc. Natl. Acad. Sci. USA, 93(16):8618-23 (1996).
Lode et al., Targeted therapy with a novel enediyene antibiotic calicheamicin $\Theta^1{}_1$ effectively suppresses growth and dissemination of liver metastases in a syngeneic model of murine neuroblastoma, Cancer Res., 58:2925-8 (1998).
Makhoul et al., The best of both worlds—managing the cancer, saving the bone, Nat. Rev. Endocrinol., 1291):29-42 (2016).
Mandler et al., Immunoconjugates of geldanamycin and anti-HER2 monoclonal antibodies: antiproliferative activity on human breast carcinoma cell lines, J. Natl. Cancer Inst., 92(19):1573-81 (2000).
Mandler et al., Modifications in synthesis strategy improve the yield and efficacy of geldanamycin-herceptin immunoconjugates, Bioconjug. Chem., 13(4):786-91 (2002).
Mandler et al., Synthesis and evaluation of antiproliferative activity of a geldanamycin-Herceptin immunoconjugate, Bioorg. Med. Chem. Lett., 10(10):1025-8 (2000).
Marcocci et al., Clinical practice. Primary hyperparathyroidism, N. Engl. J. Med., 365(25):2389-97 (2011).
Marks et al., By-passing immunization. Human antibodies from V-gene libraries displayed on phage, J. Mol. Biol., 222(3):581-97 (1991).
Marks et al., By-passing immunization: building high affinity human antibodies by chain shuffling, Biotechnology (N.Y.), 10(7):779-83 (1992).
Massey, Catalytic antibodies catching on. *Nature*, 328: 457-8 (1987).
Mather et al., Culture of testicular cells in hormone-supplemented serum-free medium. *Annals N.Y. Acad. Sci.* 383: 44-68 (1982).
Mather, Establishment and characterization of two distinct mouse testicular epithelial cell lines. *Biol. Reprod.* 23: 243-251 (1980).
McCafferty et al., Phage antibodies: filamentous phage displaying antibody variable domains, Nature, 348(6301):552-4 (1990).
Mhashilkar et al., Inhibition of HIV-1 Tat-mediated LTR transactivation and HIV-1 infection by anti-Tat single chain intrabodies, EMBO J., 14(7):1542-51 (1995).
Mirrakhimov, Hypercalcemia of Malignancy: An Update on Pathogenesis and Management, N. Am. J. Med. Sci., 7(11):483-93 (2015).
Morrison et al., Chimeric human antibody molecules: mouse antigen-binding domains with human constant region domains, Proc. Natl. Acad. Sci. USA, 81(21):6851-5 (1984).
Morrison et al., Genetically engineered antibody molecules, Adv. Immunol., 44:65-92 (1989).
Neuberger et al., Recombinant antibodies possessing novel effector functions. *Nature*, 312: 604-8 (1984).
Nguyen et al., The specific variable domain of camel heavy-chain antibodies is encoded in the germline, J. Mol. Biol., 274(3):413-8 (1998).
Nicholls et al., Characterization of single-chain antibody (sFv)-toxin fusion proteins produced in vitro in rabbit reticulocyte lysate, J. Biol. Chem., 268(7):5302-8 (1993).
Nuttall et al., Isolation of the new antigen receptor from wobbegong sharks, and use as a scaffold for the display of protein loop libraries, Mol. Immunol., 38(4):313-26 (2001).
Olafsen et al., Characterization of engineered anti-p185HER-2 (scFv-CH3)2 antibody fragments (minibodies) for tumor targeting, Protein Eng. Des. Sel., 17(4):315-23 (2004).
Oliyai et al., Prodrugs of peptides and proteins for improved formulation and delivery, Annu. Rev. Pharmacol. Toxicol., 33:521-44 (1993).
Onuma et al., Generation of a Humanized Monoclonal Antibody Against Human Parathyroid Hormone-related Protein and its Efficacy Against Humoral Hypercalcemia of Malignancy, Anticancer Res., 24(5A):2665-74 (2004).
Padlan, A possible procedure for reducing the immunogenicity of antibody variable domains while preserving their ligand-binding properties, Mol. Immunol., 28(4-5):489-98 (1991).
Padlan, Anatomy of the antibody molecule, Mol. Immunol., 31(3):169-217 (1994).
Pastan et al., Immunotoxins. *Cell*, 47: 641-8 (1986).
Peacock, Calcium metabolism in health and disease, Clin. J. Am. Soc. Nephrol., 5 Suppl 1:S23-30 (2010).
Poljak, Production and structure of diabodies, Structure, 2(12):1121-3 (1994).
Presta et al., Engineering therapeutic antibodies for improved function, Biochem. Soc. Trans., 30(4):487-90 (2002).
Raju, Terminal sugars of Fc glycans influence antibody effector functions of IgGs, Curr. Opin. Immunol., 20(4):471-8 (2008).
Reddy et al., Elimination of Fc receptor-dependent effector functions of a modified IgG4 monoclonal antibody to human CD4, J. Immunol., 164(4):1925-33 (2000).
Revets et al., Nanobodies as novel agents for cancer therapy, Expert Opin. Biol. Ther., 5(1):111-24 (2005).
Riechmann et al., Reshaping human antibodies for therapy, Nature, 332(6162):323-7 (1988).
Riechmann et al., Single domain antibodies: comparison of camel VH and camelised human VH domains, J. Immunol. Methods, 231(1-2):25-38 (1999).
Rosen et al., The effect of PTH antagonist BIM-44002 on serum calcium and PTH levels in hypercalcemic hyperparathyroid patients, Calcif. Tissue Int., 61(6):455-9 (1997).
Rothman et al., Antibody-dependent cytotoxicity mediated by natural killer cells is enhanced by castanospermine-induced alterations of IgG glycosylation, Mol. Immunol., 26(12):1113-23 (1989).
Safdari et al., Antibody humanization methods—a review and update, Biotechnol. Genet. Eng. Rev., 29:175-86 (2013).
Sanger et al., DNA sequencing with chain-terminating inhibitors, Proc. Natl. Acad. Sci. USA, 74(12):5463-7 (1977).
Sarmay et al., Mapping and comparison of the interaction sites on the Fc region of IgG responsible for triggering antibody dependent cellular cytotoxicity (ADCC) through different types of human Fc gamma receptor, Mol. Immunol., 29(5):633-9 (1992).
Schmidt et al., A bivalent single-chain antibody-toxin specific for ErbB-2 and the EGF receptor, Int. J. Cancer, 65(4):538-46 (1996).
Schoonjans et al., Fab chains as an efficient heterodimerization scaffold for the production of recombinant bispecific and trispecific antibody derivatives, J. Immunol., 165(12):7050-7 (2000).
Sergeeva et al., Display technologies: application for the discovery of drug and gene delivery agents, Adv. Drug Deliv. Rev., 58(15):1622-54 (2006).
Shields et al., Lack of fucose on human IgG1 N-linked oligosaccharide improves binding to human Fcgamma RIII and antibody-dependent cellular toxicity, J. Biol. Chem., 277(30):26733-40 (2002).

(56) References Cited

OTHER PUBLICATIONS

Shih et al., A fluorouridine-anti-CEA immunoconjugate is therapeutically effective in a human colonic cancer xenograft model, Int. J. Cancer, 46(6):1101-6 (1990).
Shih et al., Site-specific linkage of methotrexate to monoclonal antibodies using an intermediate carrier, Int. J. Cancer, 41(6):832-9 (1988).
Shimizu et al., Novel parathyroid hormone (PTH) antagonists that bind to the juxtamembrane portion of the PTH/PTH-related protein receptor, J. Biol. Chem., 280(3):1797-807 (2005).
Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-73 (2003).
Shopes et al., A genetically engineered human IgG mutant with enhanced cytolytic activity, J. Immunol., 148(9):2918-22 (1992).
Siegel, Selecting antibodies to cell-surface antigens using magnetic sorting techniques, Methods Mol. Biol., 178:219-26 (2002).
Stech et al., Cell-Free Synthesis Meets Antibody Production: A Review, Antibodies, 4(1):12-33 (2015).
Sternberger et al., The unlabeled antibody enzyme method of immunohistochemistry: preparation and properties of soluble antigen-antibody complex (horseradish peroxidase-antihorseradish peroxidase) and its use in identification of spirochetes, J. Histochem. Cytochem., 18(5):315-33 (1970).
Stevenson et al., A chimeric antibody with dual Fc regions (bisFabFc) prepared by manipulations at the IgG hinge, Anticancer Drug Des., 3(4):219-30 (1989).
Strader et al.,Structure and function of G protein-coupled receptors, Annu. Rev. Biochem., 63:101-32 (1994).
Studnicka et al., Human-engineered monoclonal antibodies retain full specific binding activity by preserving non-CDR complementarity-modulating residues, Protein Eng., 7(6):805-14 (1994).
Thomas et al., PTH and PTH antagonist induce different conformational changes in the PTHR1 receptor, J. Bone Miner. Res., 24(5):925-34 (2009).
Thompson et al., An anti-CD3 single-chain immunotoxin with a truncated diphtheria toxin avoids inhibition by pre-existing antibodies in human blood, J. Biol. Chem., 270(47):28037-41 (1995).
Thotakura et al., Enzymatic deglycosylation of glycoproteins, Methods Enzymol., 138:350-9 (1987).
Umana et al., Engineered glycoforms of an antineuroblastoma IgG1 with optimized antibody-dependent cellular cytotoxic activity, Nat. Biotechnol., 17(2):176-80 (1999).
Urlaub et al., Isolation of Chinese hamster cell mutants deficient in dihydrofolate reductase activity. Proc. Natl. Acad. Sci. USA . 77: 4216-20 (1980).
Vallera et al., Anti-graft-versus-host disease effect of DT390-anti-CD3sFv, a single-chain Fv fusion immunotoxin specifically targeting the CD3 epsilon moiety of the T-cell receptor, Blood, 88(6):2342-53 (1996).
Verhoeyen et al., Reshaping human antibodies: grafting an antilysozyme activity, Science, 239(4847):1534-6 (1988).
Ward et al., Binding activities of a repertoire of single immunoglobulin variable domains secreted from *Escherichia coli*, Nature, 341(6242):544-6 (1989).
Wels et al., EGF receptor and p185erbB-2-specific single-chain antibody toxins differ in their cell-killing activity on tumor cells expressing both receptor proteins, Int. J. Cancer, 60(1):137-44 (1995).
Wheeler et al., Intrabody-based strategies for inhibition of vascular endothelial growth factor receptor-2: effects on apoptosis, cell growth, and angiogenesis, FASEB J., 17(12):1733-5 (2003).
Willems et al., Optimizing expression and purification from cell culture medium of trispecific recombinant antibody derivatives, J. Chromatogr. B Analyt. Technol. Biomed. Life Sci., 786(1-2):161-76 (2003).
Winter et al., Making antibodies by phage display technology, Annu. Rev. Immunol., 12:433-55 (1994).
Wittrup, Protein engineering by cell-surface display, Curr. Opin. Biotechnol., 12(4):395-9 (2001).
Wolff et al., Monoclonal antibody homodimers: enhanced antitumor activity in nude mice, Cancer Res., 53(11):2560-5 (1993).
Wu et al., Fab-based bispecific antibody formats with robust biophysical properties and biological activity, MAbs, 7(3):470-82 (2015).
Yamane-Ohnuki et al., Establishment of FUT8 knockout Chinese hamster ovary cells: an ideal host cell line for producing completely defucosylated antibodies with enhanced antibody-dependent cellular cytotoxicity, Biotechnol. Bioeng., 87(5):614-22 (2004).
Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells, Int. J. Cancer, 56(2):244-8 (1994).
Yang et al., Over-expression of parathyroid hormone Type 1 receptor confers an aggressive phenotype in osteosarcoma, Int. J. Cancer, 121(5):943-54 (Sep. 2007).
Madiraju et al., Mechanism of parathyroid hormone-mediated suppression of calcification markers in human intervertebral disc cells, Eur. Cell Mater., 25:268-83 (May 2013).
McKinstry et al., Structural basis for antibody discrimination between two hormones that recognize the parathyroid hormone receptor, J. Biol. Chem., 284(23):15557-63 (Jun. 2009).
Richard et al., Humoral hypercalcemia of malignancy: severe combined immunodeficient/beige mouse model of adult T-cell lymphoma independent of human T-cell lymphotropic virus type-1 tax expression, Am. J. Pathol., 158(6):2219-28 (Jun. 2001).
International Application No. PCT/US2017/044789, International Search Report and Written Opinion, dated Nov. 13, 2017.
International Application No. PCT/US2017/044789, International Preliminary Report on Patentability, dated Feb. 5, 2019.

\* cited by examiner

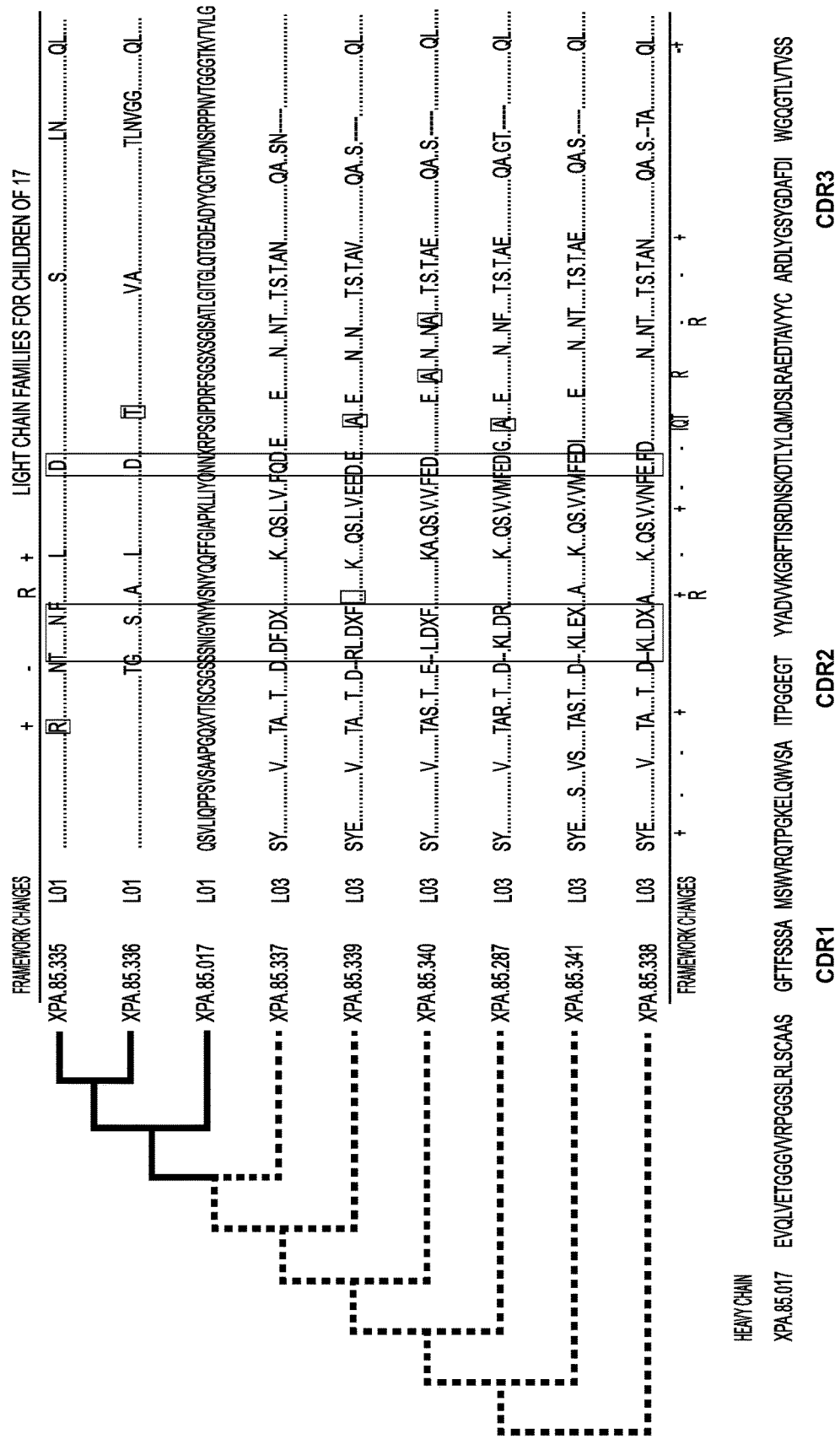

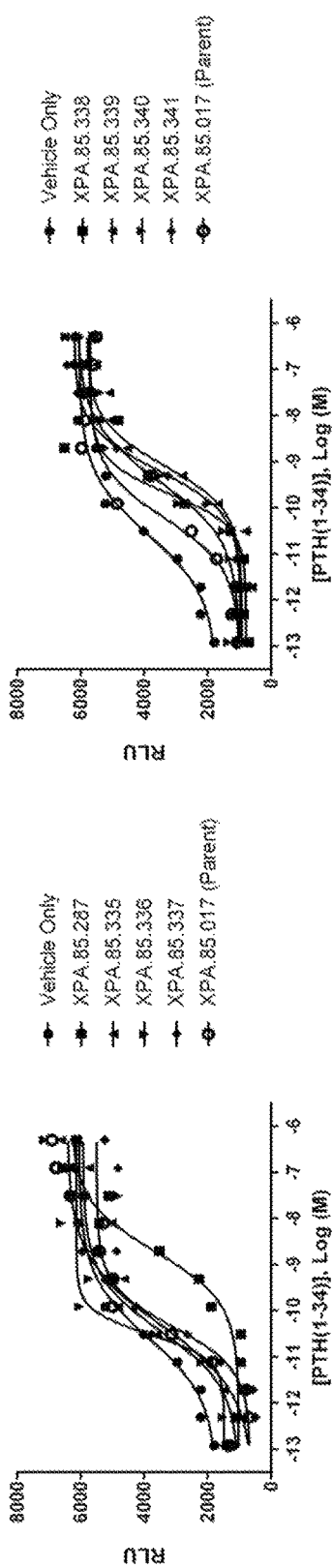
FIG. 10A
FIG. 10B
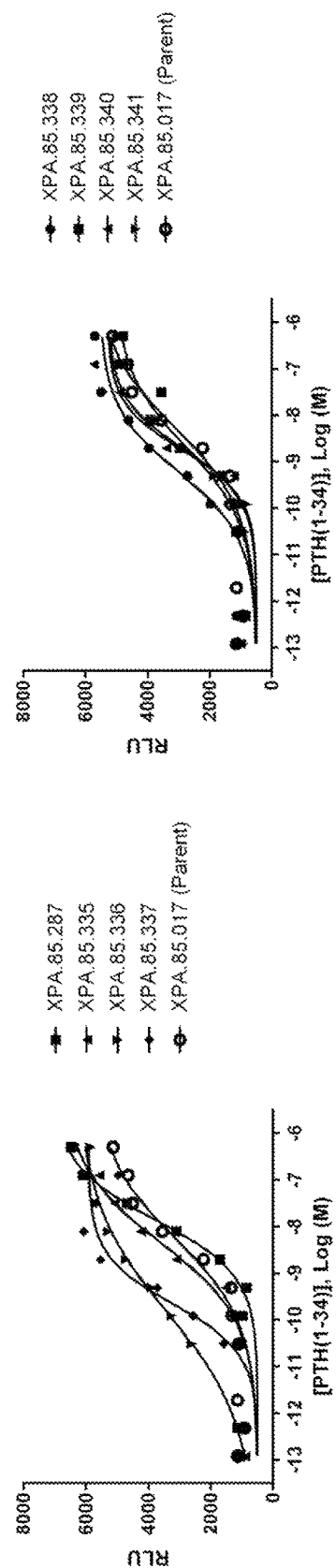
FIG. 10C
FIG. 10D

FIG. 21

| SEQ ID NO: | Name | Sequence |
|---|---|---|
| 1 | XPA.85.332 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 2 | XPA.85.012 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 3 | XPA.85.345 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 4 | XPA.85.329 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 5 | XPA.85.326 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 6 | XPA.85.328 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 7 | XPA.85.288 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 8 | XPA.85.342 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 9 | XPA.85.333 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 10 | XPA.85.343 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 11 | XPA.85.327 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 12 | XPA.85.330 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 13 | XPA.85.334 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 14 | XPA.85.344 | QMQLVQSGAEVKKPGSSVKVSCKASGGTFSSYAISWVRQAPGQGLEWMGGIIPIFGTANYAQKF |

FIG. 21 (cont'd)

| SEQ ID NO: | Name | Sequence |
|---|---|---|
| 15 | HC Variable Region | QGRVTITADESTSTAYMELSSLRSEDTAVYYCARGYVVARLWGQGTLVTVSSASTKGPS |
| 16 | XPA.85.346 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 17 | XPA.85.331 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 18 | XPA.85.347 HC Variable Region | QMQLVQSGAEVKKPGSSVKVSCKASGGTFSSYAISWVRQAPGQGLEWMGGIIPIFGTANYAQKF QGRVTITADESTSTAYMELSSLRSEDTAVYYCARGYVVARLWGQGTLVTVSSASTKGPS |
| 19 | XPA.85.017 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 20 | XPA.85.341 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 21 | XPA.85.335 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 22 | XPA.85.340 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 23 | XPA.85.339 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 24 | XPA.85.287 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 25 | XPA.85.336 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 26 | XPA.85.337 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 27 | XPA.85.338 HC Variable Region | EVQLVETGGGVVRPGGSLRLSCAASGFTFSSSAMSWVRQTPGKELQWVSAITPGGEGTYYADVV KGRFTISRDNSKDTLYLQMDSLRAEDTAVYYCARDLYGSYGDAFDIWGQGTLVTVSSASTKGPS |
| 28 | XPA.85.332HCDR1 | GGTFSSYA |
| 29 | XPA.85.332HCDR2 | IIPIFGTA |
| 30 | XPA.85.332HCDR3 | ARGYVVARL |
| 31 | XPA.85.012HCDR1 | GGTFSSYA |
| 32 | XPA.85.012HCDR2 | IIPIFGTA |

FIG. 21 (cont'd)

| SEQ ID NO: | Name | Sequence |
|---|---|---|
| 32 | XPA.85.012HCDR3 | ARGYVVARL |
| 33 | XPA.85.345HCDR1 | GGTFSSYA |
| 34 | XPA.85.345HCDR2 | IIPIFGTA |
| 35 | XPA.85.345HCDR3 | ARGYVVARL |
| 36 | XPA.85.329HCDR1 | GGTFSSYA |
| 37 | XPA.85.329HCDR2 | IIPIFGTA |
| 38 | XPA.85.329HCDR3 | ARGYVVARL |
| 39 | XPA.85.326HCDR1 | GGTFSSYA |
| 40 | XPA.85.326HCDR2 | IIPIFGTA |
| 41 | XPA.85.326HCDR3 | ARGYVVARL |
| 42 | XPA.85.328HCDR1 | GGTFSSYA |
| 43 | XPA.85.328HCDR2 | IIPIFGTA |
| 44 | XPA.85.328HCDR3 | ARGYVVARL |
| 45 | XPA.85.288HCDR1 | GGTFSSYA |
| 46 | XPA.85.288HCDR2 | IIPIFGTA |
| 47 | XPA.85.288HCDR3 | ARGYVVARL |
| 48 | XPA.85.342HCDR1 | GGTFSSYA |
| 49 | XPA.85.342HCDR2 | IIPIFGTA |
| 50 | XPA.85.342HCDR3 | ARGYVVARL |
| 51 | XPA.85.333HCDR1 | GGTFSSYA |
| 52 | XPA.85.333HCDR2 | IIPIFGTA |
| 53 | XPA.85.333HCDR3 | ARGYVVARL |
| 54 | XPA.85.343HCDR1 | GGTFSSYA |
| 55 | XPA.85.343HCDR2 | IIPIFGTA |
| 56 | XPA.85.343HCDR3 | ARGYVVARL |
| 57 | XPA.85.327HCDR1 | GGTFSSYA |
| 58 | XPA.85.327HCDR2 | IIPIFGTA |
| 59 | XPA.85.327HCDR3 | ARGYVVARL |
| 60 | XPA.85.330HCDR1 | GGTFSSYA |
| 61 | XPA.85.330HCDR2 | IIPIFGTA |

FIG. 21 (cont'd)

| SEQ ID NO: | Name | Sequence |
|---|---|---|
| 62 | XPA.85.330HCDR3 | ARGYVVARL |
| 63 | XPA.85.334HCDR1 | GGTFSSYA |
| 64 | XPA.85.334HCDR2 | IIPIFGTA |
| 65 | XPA.85.334HCDR3 | ARGYVVARL |
| 66 | XPA.85.344HCDR1 | GGTFSSYA |
| 67 | XPA.85.344HCDR2 | IIPIFGTA |
| 68 | XPA.85.344HCDR3 | ARGYVVARL |
| 69 | XPA.85.346HCDR1 | GGTFSSYA |
| 70 | XPA.85.346HCDR2 | IIPIFGTA |
| 71 | XPA.85.346HCDR3 | ARGYVVARL |
| 72 | XPA.85.331HCDR1 | GGTFSSYA |
| 73 | XPA.85.331HCDR2 | IIPIFGTA |
| 74 | XPA.85.331HCDR3 | ARGYVVARL |
| 75 | XPA.85.347HCDR1 | GGTFSSYA |
| 76 | XPA.85.347HCDR2 | IIPIFGTA |
| 77 | XPA.85.347HCDR3 | ARGYVVARL |
| 78 | XPA.85.017HCDR1 | GFTFSSSA |
| 79 | XPA.85.017HCDR2 | ITPGGEGT |
| 80 | XPA.85.017HCDR3 | ARDLYGSYGDAFDI |
| 81 | XPA.85.341HCDR1 | GFTFSSSA |
| 82 | XPA.85.341HCDR2 | ITPGGEGT |
| 83 | XPA.85.341HCDR3 | ARDLYGSYGDAFDI |
| 84 | XPA.85.335HCDR1 | GFTFSSSA |
| 85 | XPA.85.335HCDR2 | ITPGGEGT |
| 86 | XPA.85.335HCDR3 | ARDLYGSYGDAFDI |
| 87 | XPA.85.340HCDR1 | GFTFSSSA |
| 88 | XPA.85.340HCDR2 | ITPGGEGT |
| 89 | XPA.85.340HCDR3 | ARDLYGSYGDAFDI |
| 90 | XPA.85.339HCDR1 | GFTFSSSA |
| 91 | XPA.85.339HCDR2 | ITPGGEGT |

FIG. 21 (cont'd)

| SEQ ID NO: | Name | Sequence |
|---|---|---|
| 92 | XPA.85.339HCDR3 | ARDLYGSYGDAFDI |
| 93 | XPA.85.287HCDR1 | GFTFSSSA |
| 94 | XPA.85.287HCDR2 | ITPGGEGT |
| 95 | XPA.85.287HCDR3 | ARDLYGSYGDAFDI |
| 96 | XPA.85.336HCDR1 | GFTFSSSA |
| 97 | XPA.85.336HCDR2 | ITPGGEGT |
| 98 | XPA.85.336HCDR3 | ARDLYGSYGDAFDI |
| 99 | XPA.85.337HCDR1 | GFTFSSSA |
| 100 | XPA.85.337HCDR2 | ITPGGEGT |
| 101 | XPA.85.337HCDR3 | ARDLYGSYGDAFDI |
| 102 | XPA.85.338HCDR1 | GFTFSSSA |
| 103 | XPA.85.338HCDR2 | ITPGGEGT |
| 104 | XPA.85.338HCDR3 | ARDLYGSYGDAFDI |
| 105 | XPA.85.332 | ETTLTQSPAFMSASVGDRVTITCQASQDINNFLNWYQQKPGKAPKFLIYDASNLEKGVPSKFSG RGSGTEFTLTISSLQPEDIATYYCQQYRDFPLITFGQGTRLEIKRTVAAPS |
| 106 | XPA.85.012 LC Variable Region | DVVMTQSPLSLPVTPGEPASISCRSSQSLVYGDGHNYLAWYLQKPGQSPQLLIYLGSNRASGVP DRFSGSGSGTDFTLKISRVEAEDVGVYYCMQGLQTPLTFGGGTKLEIKRTVAAPS |
| 107 | XPA.85.345 | ETTLTQSPAFMSASVGDRVTITCQASQDINNFLNWYQQKPGKAPKFLIYDASNLEKGVPSRFSG RGSGTEFTLTISSLQPEDIATYYCQQYRDFPLITFGQGTRLEIKRTVAAPS |
| 108 | XPA.85.329 LC Variable Region | DIVMTQTPLSLSVTPGQPASISCKSSQSLLHIDGLTYLYWYLQKPGQPPQLLIYEVSHRFSGVS DKFSGSGSGTDFTLTISRVEAEDVGVYYCMQSLHLPITFGQGTRLEIKRTVAAPS |
| 109 | XPA.85.326 LC Variable Region | DIVMTQTPLSLSVTPGQPASISCKSSQSLLHIDGLTYLYWYLQKPGQPPQLLIYEVSHRFSGVS DKFSGSGSGTDFTLTISRVEAEDVGVYYCMQSLHLPITFGQGTRLEIKRTVAAPS |
| 110 | XPA.85.328 LC Variable Region | DVVMTQTPLSLSVTPGQPASISCKSSQSLLHIDGKTYLYWYLQKSGQSPQLLIYEVSNRFSGVP DTFSGSGSGTDFTLKISRVEAEDVGVYYCMQSLHFPITFGQGTRLEIKRTVAAPS |
| 111 | XPA.85.288 | DVVMTQTPLSLSVTPGQPASISCKSSQSLLHIDGKTYLYWYLQKSGQSPQLLIYEVSNRFSGVP DTFSGSGSGTDFTLKISRVEAEDVGVYYCMQSLHFPITFGQGTRLEIKRTVAAPS |
| 112 | XPA.85.342 LC Variable Region | ETTLTQSPTFMSASVGDRVTITCQASQDINNFLNWYQQKPGKAPKFLIYDASNLEKGVPSRFSG RGSGTEFTLTISSLQPEDIATYYCQQYRDFPLITFGQGTRLEIKRTVAAPS |
| 113 | XPA.85.333 | DVVMTQTPLSLSVTPGQPASISCKSSQSLLHIDGKAYLYWYLQKPGQSPHLLIREVSTRFSGVS |

FIG. 21 (cont'd)

| SEQ ID NO: | Name | Sequence |
|---|---|---|
| 114 | LC Variable Region | DRFTGSGSGTDFTLEISRVEAEDVGVYYCMQGLHLPPTFGQGTKVEIKRTVAAPS |
| 115 | XPA.85.343 LC Variable Region | DVVMTQTPLSLSVTPGQPASISCKSSQSLLHIDGRTYLYWYLQKAGQPPQLLIYEVSNRFSGVP DRFSGSGSGTDFTLKISRVEAEDVGVYYCMQSIHFPLTFGGGTKLEIKRTVAAPS |
| 116 | XPA.85.327 LC Variable Region | DIVMTQTPLSLSVTPGQPASITCKSSQSLLHIDGNTYLYWYLQRPGQPPQLLIYEISNRFSGVP DRFSGSGSGTDFTLKISRVEAEDVGVYYCMQSLHFPITFGQGTRLEIKRTVAAPS |
| 117 | XPA.85.330 LC Variable Region | DIVMTQTPLSLSVTPGQPASISCKSSQSLLHIDGNTYLYWYLQRPGQPPQLLIYEISNRFSGVP DRFSGSGSGTDFTLKISRVEAEDVGVYYCMQSLHFPITFGQGTRLEIKRTVAAPS |
| 118 | XPA.85.334 LC Variable Region | DIVMTQTPLSLSVTPGQPASITCKSSQSLLHIDGKTYLYWFLQKPGQPPQLLIYEVSNRFSGVP DRFSGTGSGTDFTLKISRVEAEDVGVYYCMQSLHFPITFGPGTRLEIKRTVAAPS |
| 119 | XPA.85.344 LC Variable Region | DVVMTQTPLSLSVTPGQPASFSCKSTQSLLWRDGNTYLYWYLQKPGQSPQLLIYEVSGRFSGVP ERFSGSGSGTDFTLEISRVEAEDVGVYYCMQSIHFPLTFGGGTKLEIKRTVAAPS |
| 120 | XPA.85.346 LC Variable Region | DIVMTQTPLSLSVTPGQPASITCKSSQSLLHIDGKTYLYWFLQKPGQPPQLLIYEVSNRFSGVP DRFSGSGSGTDFTLKISRVEAEDVGLYYCMQSLHLPITFGQGTRLEIKRTVAAPS |
| 121 | XPA.85.331 LC Variable Region | DVVMTQSPLSLPVTPGEPASISCRSSQSLLHIDGFNYLQWYLQKPGQSPQLLVHLGSFRASGVP DRFSGSGSGTDFTLEISRVEAEDVGLYYCMQGLQTPPTFGPGTKVEIKRTVAAPS |
| 122 | XPA.85.347 LC Variable Region | DIVMTQTPLSLSVTPGQPASISCKSSQSLFHDHGRTHLSWYLQKPGQPPQLLIFEASNRFSGVP GSKSGTSATLGITGLQTGDEADYYCGTWDNSRSPPWVFGGGTKVTVLGQPKA |
| 123 | XPA.85.017 LC Variable Region | SYELTQPPSVSVSPGQTASITCSGDEADYYCQAWDSSWVFGGGTQLTVLGQPKA NSGNTATLTISGTQAEDEADYYCQAWDSSWVFGGGTQLTVLGQPKA |
| 124 | XPA.85.341 LC Variable Region | QSVLTQPPSVSVSAAPGQKVTISCSGNTSNIGNNFVSWYQQLPGTAPKLLIYDNNKRPSGIPDRFS GSKSGTSATLGISGLQTGDEADYYCGTWDNSLNPPWVFGGGTQLTVLGQPKA |
| 125 | XPA.85.335 LC Variable Region | SYVLTQPPSVSVAPGQTASITCSGDNLGEKFVSWYQQKAGQSPVLVIFEDNKRPSGIPERFAGS NSGNRATLTIRGTQAEDEADYYCQAWDSSWVFGGGTQLTVLGQPKA |
| 126 | XPA.85.340 LC Variable Region | SYELTQPPSVSVAFGQTATITCSGDRLGDKFISWYQQKPGQSPLLVIFEDNERPSRIPERFSGS NSGNSATLTISGTQAVDEADYYCQAWDSSWVFGGGTQLTVLGQPKA |
| 127 | XPA.85.339 LC Variable Region | SYVLTQPPSVSVAPGQTARITCSGDKLGDRYVSWYQQKPGQSPVLVMFEDTGRPAGIPERFSGS NSGNTATLTISGTQAEDEADYYCQAWGTSWVFGGGTQLTVLGQPKA |
| 128 | XPA.85.287 LC Variable Region | QSVLTQPPSVSVSAAPGQKVTISCSGTGSNYVAWYQQLPGTAPKLLIYDDNKRPSGTPDRFS |

FIG. 21 (cont'd)

| SEQ ID NO: | Name | Sequence |
|---|---|---|
| 129 | LC Variable Region XPA.85.337 | GSKSGTSATLVIAGLQTGDEADYYCGTWDNTLNVGGVFGGGTQLTVLGQPKA |
| 130 | LC Variable Region XPA.85.338 | SYVLTQPPSVSVSVAPGQTATITCSGDDFGDKYVSWYQQKPGQSPLLVIFQDNERPSGIPERFSGS NSGNTATLTISGTQAMDEADYYCQAWDSNWVFGGGTKVTVLGQPKA SYELTQPPSVSVAPGQTATITCSGDKLGDKYASWYQQKPGQSPVLVMFENRDRPSGIPDRFSGS NSGNTATLTISGTQAMDEADYYCQAWDSSTAWVFGGGTQLTVLGQPKA |
| 131 | XPA.85.332LCDR1 | QDINNF |
| 132 | XPA.85.332LCDR2 | DAS |
| 133 | XPA.85.332LCDR3 | QQYRDFPLT |
| 134 | XPA.85.012LCDR1 | QSLVYGDGHNY |
| 135 | XPA.85.012LCDR2 | LGS |
| 136 | XPA.85.012LCDR3 | MQGLQTPLT |
| 137 | XPA.85.345LCDR1 | QDINNF |
| 138 | XPA.85.345LCDR2 | DAS |
| 139 | XPA.85.345LCDR3 | QQYRDFPLT |
| 140 | XPA.85.329LCDR1 | QSLLHIDGLTY |
| 141 | XPA.85.329LCDR2 | EVS |
| 142 | XPA.85.329LCDR3 | MQSLHLPIT |
| 143 | XPA.85.326LCDR1 | QSLLHIDGLTY |
| 144 | XPA.85.326LCDR2 | EVS |
| 145 | XPA.85.326LCDR3 | MQSLHLPIT |
| 146 | XPA.85.328LCDR1 | QSLLHIDGKTY |
| 147 | XPA.85.328LCDR2 | EVS |
| 148 | XPA.85.328LCDR3 | MQSLHFPIT |
| 149 | XPA.85.288LCDR1 | QSLLHIDGKTY |
| 150 | XPA.85.288LCDR2 | EVS |
| 151 | XPA.85.288LCDR3 | MQSLHFPIT |
| 152 | XPA.85.342LCDR1 | QDINNF |
| 153 | XPA.85.342LCDR2 | DAS |
| 154 | XPA.85.342LCDR3 | QQYRDFPLT |
| 155 | XPA.85.333LCDR1 | QSLLHIDGKAY |

FIG. 21 (cont'd)

| SEQ ID NO: | Name | Sequence |
|---|---|---|
| 156 | XPA.85.333LCDR2 | EVS |
| 157 | XPA.85.333LCDR3 | MQGLHLPPT |
| 158 | XPA.85.343LCDR1 | QSLLHIDGRTY |
| 159 | XPA.85.343LCDR2 | EVS |
| 160 | XPA.85.343LCDR3 | MQSIHFPLT |
| 161 | XPA.85.327LCDR1 | QSLLHIDGNTY |
| 162 | XPA.85.327LCDR2 | EIS |
| 163 | XPA.85.327LCDR3 | MQSLHFPIT |
| 164 | XPA.85.330LCDR1 | QSLLHIDGNTY |
| 165 | XPA.85.330LCDR2 | EIS |
| 166 | XPA.85.330LCDR3 | MQSLHFPIT |
| 167 | XPA.85.334LCDR1 | QSLLHIDGKTY |
| 168 | XPA.85.334LCDR2 | EVS |
| 169 | XPA.85.334LCDR3 | MQSLHFPIT |
| 170 | XPA.85.344LCDR1 | QSLLWRDGNTY |
| 171 | XPA.85.344LCDR2 | EVS |
| 172 | XPA.85.344LCDR3 | MQSIHFPLT |
| 173 | XPA.85.346LCDR1 | QSLLHIDGKTY |
| 174 | XPA.85.346LCDR2 | EVS |
| 175 | XPA.85.346LCDR3 | MQSLHLPIT |
| 176 | XPA.85.331LCDR1 | QSLLHIDGFNY |
| 177 | XPA.85.331LCDR2 | LGS |
| 178 | XPA.85.331LCDR3 | MQGLQTPPT |
| 179 | XPA.85.347LCDR1 | QSLFHDHGRTH |
| 180 | XPA.85.347LCDR2 | EAS |
| 181 | XPA.85.347LCDR3 | MQGIHLPPA |
| 182 | XPA.85.017LCDR1 | SSNIGYNY |
| 183 | XPA.85.017LCDR2 | DNN |
| 184 | XPA.85.017LCDR3 | GTWDNSRSPPWV |
| 185 | XPA.85.341LCDR1 | KLGEKYEDFQAWDSSWV |

FIG. 21 (cont'd)

| SEQ ID NO: | Name | Sequence |
|---|---|---|
| 186 | XPA.85.341LCDR2 | EDT |
| 187 | XPA.85.341LCDR3 | QAWDSSWV |
| 188 | XPA.85.335LCDR1 | TSNIGNNF |
| 189 | XPA.85.335LCDR2 | DDN |
| 190 | XPA.85.335LCDR3 | GTWDNSLNPPWV |
| 191 | XPA.85.340LCDR1 | NLGEKF |
| 192 | XPA.85.340LCDR2 | EDN |
| 193 | XPA.85.340LCDR3 | QAWDSSWV |
| 194 | XPA.85.339LCDR1 | RLGDKF |
| 195 | XPA.85.339LCDR2 | EDN |
| 196 | XPA.85.339LCDR3 | QAWDSSWV |
| 197 | XPA.85.287LCDR1 | KLGDRY |
| 198 | XPA.85.287LCDR2 | EDT |
| 199 | XPA.85.287LCDR3 | QAWGTSWV |
| 200 | XPA.85.336LCDR1 | GSNIGSNY |
| 201 | XPA.85.336LCDR2 | DDN |
| 202 | XPA.85.336LCDR3 | GTWDNTLNVGGV |
| 203 | XPA.85.337LCDR1 | DFGDKY |
| 204 | XPA.85.337LCDR2 | QDN |
| 205 | XPA.85.337LCDR3 | QAWDSNWV |
| 206 | XPA.85.338LCDR1 | KLGDKY |
| 207 | XPA.85.338LCDR2 | ENR |
| 208 | XPA.85.338LCDR3 | QAWDSSTAWV |
| 209 | XPA.85.332 HC n.t. | CAGATGCAGCTGGTGCAGTCTGGGGCTGAGGTGAAGAAGCCTGGGGCCTCAGTGAAGGTCTCCTGCAAGGCTTCTGG AGGCACCTTCAGCAGCTATGCTATCAGCTGGGTGCGACAGGCCCCTGGACAAGGGCTTGAGTGGATGGGAGGGATCA TCCCTATCTTTGGTACAGCAAACTACGCACAGAAGTTCCAGGGCAGAGTCACGATTACCGCGGACGAATCCACGAGC ACAGCCTACATGGAGCTGAGCAGCCTGAGATCTGAGGACACGGCCGTGTATTACTGTGCGAGAGGGTATGTAGTAGC CAGACTCTGGGGCCAAGGGAACCCTGGTCACCGTCAGCTCA |
| 210 | XPA.85.012 HC n.t. | CAGATGCAGCTGGTGCAGTCTGGGGCTGAGGTGAAGAAGCCTGGGGCCTCCTGCAAGGCTTCTGG AGGCACCTTCAGCAGCTATGCTATCAGCTGGGTGCGACAGGCCCCTGGACAAGGGCTTGAGTGGATGGGAGGGATCA TCCCTATCTTTGGTACAGCAAACTACGCACAGAAGTTCCAGGGCAGAGTCACCATTACCGCGGACGAATTCCACGAGC ACAGCCTACATGGAGCTGAGCAGCCTGAGATCTGAGGACACGGCCGTGTATTACTGTGCGAGAGGGTATGTAGTAGC |

FIG. 21 (cont'd)

| SEQ ID NO: | Name | Sequence |
|---|---|---|
| 211 | XPA.85.345 HC n.t. | CAGATGCAGCTGGTGCAGTCTGGGGCTGAGGTGAAGAAGCCTGGGGCCTCAGTGAAGGTCTCCTGCAAGGCTTCTGG<br>AGGCACCTTCAGCAGCTATGCTATCAGCTGGGTGCGACAGGCCCCTGGACAAGGGCTTGAGTGGATGGGAGGGATCA<br>TCCCTATCTTTGGTACAGCAAACTACGGCCCAGAAGTTCCAGGGCAGAGTCACGATTACCGCGGACGAATCCACGAGC<br>ACAGCCTACATGGAGCTGAGCAGCCTGAGATCTGAGGACACGGCCGTGTATTACTGTGCGAGAGGGTATGTAGTAGC<br>CAGACTCTGGGGCCAGGGAACCCTGGTCACCGTCAGCTCA |
| 212 | XPA.85.329 HC n.t. | CAGATGCAGCTGGTGCAGTCTGGGGCTGAGGTGAAGAAACCGGCTCCTCCGTGAAGGTGTCCTGCAAGGCCTCCGG<br>CGGCACCTTCTCCAGCTACCGCGCCATCTCCTGGGTCGCACAGGCCCCAGGGCCTGGAATGGATGGGCGGCATCA<br>TCCCCATCTTCGGCACCGCCAACTACGCCCAGAAATTCCAGGGCAGAGTGACCATCACCGCCGACGAGTCCACCTCC<br>ACCGCCTACATGGAACTGTCCTCCCTGCGGAGCGAGGACACCGCCGTGTACTACTGCGCCAGAGGCTACGTGGTGGC<br>CAGACTCTGGGGCCAGGGCACCCTGGTGACCGTCAGCTCA |
| 213 | XPA.85.326 HC n.t. | CAGATGCAGCTGGTGCAGTCTGGGGCTGAGGTGAAGAAGCCTGGATCCTCGTGAAGGTCTCCTGCAAGGCTTCTGG<br>AGGCACCTTCAGCAGCTATGCTATCAGCTGGGTGCGACAGGCCCCTGGACAAGGGCTTGAGTGGATGGGAGGGATCA<br>TCCCTATCTTTGGTACAGCAAACTACGGCCCAGAAGTTCCAGGGCAGAGTCACGATTACCGCGGACGAATCCACGAGC<br>ACAGCCTACATGGAGCTGAGCAGCCTGAGATCTGAGGACACGGCCGTGTATTACTGTGCGAGAGGGTATGTAGTAGC<br>CAGACTCTGGGGCCAGGGAACCCTGGTCACCGTCAGCTCA |
| 214 | XPA.85.328 HC n.t. | CAGATGCAGCTGGTGCAGTCTGGGGCTGAGGTGAAGAAACCGGCTCCTCCGTGAAGGTGTCCTGCAAGGCCTCCGG<br>CGGCACCTTCTCCAGCTACCGCGCCATCTCCTGGGTCGCACAGGCCCCAGGGCCTGGAATGGATGGGCCGCATCA<br>TCCCCATCTTCGGCACCGCCAACTACGCCCAGAAATTCCAGGGCAGAGTGACCATCACCGCCGACGAGTCCACCTCC<br>ACCGCCTACATGGAACTGTCCTCCCTGCGGAGCGAGGACACCGCCGTGTACTACTGCGCCAGAGGCTACGTGGTGGC<br>CAGACTCTGGGGCCAGGGCACCCTGGTGACCGTGAGCTCA |
| 215 | XPA.85.288 HC n.t. | CAGATGCAGCTGGTGCAGTCTGGCAGTCTGGGGCTGAGGTGAAGAAGCCTGGGTGAAGGTCTCCTGCAAGGCTTCTGG<br>AGGCACCTTCAGCAGCTATGCTATCAGCTGGGTGCGACAGGCCCCTGGACAAGGCTTGAGTGGATGGGAGGGATCA<br>TCCCTATCTTTGGTACAGCAAACTACGGCCCAGAAGTTCCAGGGCAGAGTCACGATTACCGCGGACGAATCCACGAGC<br>ACAGCCTACATGGAGCTGAGCAGCCTGAGATCTGAGGACACGGCCGTGTATTACTGTGCGAGAGGGTATGTAGTAGC<br>CAGACTCTGGGGCCAGGGAACCCTGGTCACCGTCAGCTCA |
| 216 | XPA.85.342 HC n.t. | CAGATGCAGCTGGTGCAGTCTGGGGCTGAGGTGAAGAAGCCTGGGTCCTCCGTGAAGGTCTCCTGCAAGGCTTCTGG<br>AGGCACCTTCAGCAGCTATGCTATCAGCTGGGTGCGACAGGCCCCTGGACAAGGGCTTGAGTGGATGGGAGGGATCA<br>TCCCTATCTTTGGTACAGCAAACTACGGCCAGAAGTTCCAGGGCAGAGTCACGATTACCGCGGACGAATCCACGAGC<br>ACAGCCTACATGGAGCTGAGCAGCCTGAGATCTGAGGACACGGCCGTGTATTACTGTGCGAGAGGGTATGTAGTAGC<br>CAGACTCTGGGGCCAGGGAACCCTGGTCACCGTCAGCTCA |
| 217 | XPA.85.333 HC n.t. | CAGATGCAGCTGGTGCAGTCTGGGGCTGAGGTGAAGAAGCCTGGATCCTCGTGAAGGTCTCCTGCAAGGCTTCTGG<br>AGGCACCTTCAGCAGCTATGCTATCAGCTGGGTGCGACAGGCCCCTGGACAAGGGCTTGAGTGGATGGGAGGGATCA<br>TCCCTATCTTTGGTACAGCAAACTACGGCCAGAAGTTCCAGGGCAGAGTCACGATTACCGCGGACGAATCCACGAGC<br>ACAGCCTACATGGAGCTGAGCAGCCTGAGATCTGAGGACACGGCCGTGTATTACTGTGCGAGAGGGTATGTAGTAGC<br>CAGACTCTGGGGCCAGGGAACCCTGGTCACCGTCAGCTCA |
| 218 | XPA.85.343 | CAGATGCAGCTGGTGCAGTCTGGGGCTGAGGTGAAGAAGCCTGGATCCTCGTGAAGGTCTCCTGCAAGGCTTCTGG |

FIG. 21 (cont'd)

| SEQ ID NO: | Name | Sequence |
|---|---|---|
| 219 | HC n.t. | AGGCACCTTCAGCAGCTATGCAGCTGGGTGCGACAGGCCCCTGGACAAGGGCTTGAGTGGATGGGAGGGATCA TCCCTATCTTGGTACAGAGTCCACAGACAGAATCCAGGAGAGTCACGCGGGACGAATTCACGAGC ACAGCCTACATGGAGCTGAGCCTGAGATCTGAGGACACGGCCGTGTATTACTGTGCGAGAGGGTATGTAGTAGC CAGACTCTGGGGCCAGGGAACCCTGGTCACCGTCAGCTCA |
| 220 | XPA.85.327 HC n.t. | CAGATGCAGCTGGTGCAGTCTGGGGCTGAGGTGAAGAAGCCTGGATCCTCGGTGAAGGTCTCCTGCAAGGCTTCTGG AGGCACCTTCAGCAGCTATGCTATCAGCTGGGTGCGACAGGCCCCTGGACAAGGGCTTGAGTGGATGGGAGGGATCA TCCCTATCTTTGGTACAGCAAACTACGCAGCAGCTGAGCAAGGGCAGAGTCACGATTACCGCGGACGAATCCACGAGC ACAGCCTACATGGAGCTGAGCCTGAGATCTGAGGACACGGCCGTGTATTACTGTGCGAGAGGGTATGTAGTAGC CAGACTCTGGGGCCAGGGAACCCTGGTCACCGTCAGCTCA |
| 221 | XPA.85.330 HC n.t. | CAGATGCAGCTGGTGCAGTCTGGGGCTGAGGTGTCTCCGTGAAGTGTCTCCTGCAAGGTGTCCTGCAAGGCCTCCGG CGGCACCTTCTCCAGCTACGCCATCTCCTGGGTGCGACAGGCCCAGGCCTGGAATGGATGGCGCATGATCA CGGCCAATCTTCGGCACCGCACTACGCCCAACTACGCCCAGAAATTCCAGGCAGAGTGACCATCACCGCCGACGAGTCCACCTCC ACCGCCTACATGGAACTGTCCTCCCTGCGAGCGAGGACACGGCCGTGTACTACTGCGCCAGAGGCTACGTGGTGGC CAGACTGTGGGGCCAGGGCACCCTGGTCACCGTCAGCTCA |
| 222 | XPA.85.334 HC n.t. | CAGATGCAGCTGGTGCAGTCTGGGGCTGAGGTGAAGAAGCCTGGATCCTCGGTGAAGGTCTCCTGCAAGGCTTCTGG AGGCACCTTCAGCAGCTATGCTATCAGCTGGGTGCGACAGGCCCCTGGACAAGGGCTTGAGTGGATGGGAGGGATCA TCCCTATCTTTGGTACAGCAAACTACGCAGCAGCTGAGCAAGGGCAGAGTTCCAGGCAGAGTCACGATTACCGCGGACGAGATTCCACA ACAGCCTACATGGAGCTGAGCCTGAGATCTGAGGACACGGCCGTGTATTACTGTGTAATACTGTGCGAGAGGGTATGTAGTAGC CAGACTCTGGGGCCAGGGAACCCTGGTCACCGTCAGCTCA |
| 223 | XPA.85.344 HC n.t. | GATGTTGTGATGACTCAGAGTCCACCTCACCCTGTCCGTCCCTGGACAGCGGCCTCCTTCTCCTGCAAGCTCAC TCAGAGCCTCCTGTGCGTGCGTACAGTTCCGGCCGATTCTCTGGAGTGCCAGAGAGATTCAGTGGCAGCGGGTCAGGGACAGATTCAACA TCATCTATGAACTCAGCCGGGTGAGGCTGAGGATGTGGGGGTTTATTACTGCATGCAAAGTATACACTTTCCTCACTTT CTGGAAATCAGCCGGGTGAGGCTGAGGATGTGGGGGTTTATTACTGCATGCAAAGTATACACTTTCCTCACTTT CGGCGGAGGGACCAAGCTGGAGATCAAACGT |
| 224 | XPA.85.346 HC n.t. | CAGATGCAGCTGGTGCAGTCTGGGGCTGAGGTGAAGAAGCCTGGATCCTCGGTGAAGGTCTCCTGCAAGGCTTCTGG AGGCACCTTCAGCAGCTATGCTATCAGCTGGGTGCGACAGGCCCCTGGACAAGGGCTTGAGTGGATGGGAGGGATCA TCCCTATCTTGGTACAGAGTCCACAGACAGAATCCAGGAGAGTCACGCGGGACGAATCCACGAGC ACAGCCTACATGGAGCTGAGCCTGAGATCTGAGGACACGGCCGTGTATTACTGTGCGAGAGGGTATGTAGTAGC CAGACTCTGGGGCCAGGGAACCCTGGTCACCGTCAGCTCA |
| 225 | XPA.85.331 HC n.t. | CAGATGCAGCTGGTGCAGTCTGGGGCTGAGGTGAAGAAGCCTGGATCCTCGGTGAAGGTCTCCTGCAAGGCTTCTGG AGGCACCTTCAGCAGCTATGCTATCAGCTGGGTGCGACAGGCCCCTGGACAAGGGCTTGAGTGGATGGGAGGGATCA TCCCTATCTTTGGTACAGCAAACTACGCAGCAGCTGAGCAAGGGCAGAGTTCACGATTACCGCGGACGAATCCACGAGC ACAGCCTACATGGAGCTGAGCCTGAGATCTGAGGACACGGCCGTGTATTACTGTGCGAGAGGGTATGTAGTAGC CAGACTCTGGGGCCAGGGAACCCTGGTCACCGTCAGCTCA |
| 226 | XPA.85.347 HC n.t. | CAGATGCAGCTGGTGCAGTCTGGGGCTGAGGTGAAGAAGCCTGGATCCTCGGTGAAGGTCTCCTGCAAGGCTTCTGG AGGCACCTTCAGCAGCTATGCAGCTGGGTGCGACAGGCCCCTGGACAAGGGCTTGAGTGGATGGGAGGGATCA TCCCTATCTTTGGTACAGCAAACTACGCAGCAGCTGAGCAAGGGCAGAGTTCACGATTACCGCGGACGAATCCACGAGC |

FIG. 21 (cont'd)

| SEQ ID NO: | Name | Sequence |
|---|---|---|
| 226 | XPA.85.017 HC n.t. | ACAGCCTACATGAGCTGAGAGCTGAGGACCTGAGATCTGAGGACAGGCCGTGTATTACTGTGCGAGAGGGTATGTAGTAGC CAGACTCTGGGGCCAGGGAACCCTGGTCACCGTCAGCTCA |
| 227 | XPA.85.341 HC n.t. | GAGGTGCAGCTGGTGGAGTCTGGGGGAGGCGTGGTCCAGCCTGGGAGGTCCCTGAGACTCTCCTGTGCAGCCTCTGG ATTCACCTTTAGCAGCTCTGCCATGAGCTGGGTCCGCCAGGCTCCAGGGAAGGGGCTGGAGTGGGTCTCAGCTATTA CTCCTGGTGGTGAGGGGACATACTACGCAGAGACTCCGTGAAGGGCCGGTTCACCATCTCCAGAGACAATTCCAAGGAC ACGCTGTATCTGCAAATGAACAGCCTGAGAGACCGAGGACACGGCTGTGTATTACTGTGCCAGAGATTTGTACGGGAG CTACGGTGATGCTTTTGATATCTGGGGCCAAGGGACACTGGTCACCGTCAGCTCA |
| 228 | XPA.85.335 HC n.t. | GAGGTGCAGCTGGTGGAGTCTGGGGGAGGCGTGGTCCAGCCTGGGAGGTCCCTGAGACTCTCCTGTGCAGCCTCTGG ATTCACCTTTAGCAGCTCTGCCATGAGCTGGGTCCGCCAGGCTCCAGGGAAGGGGCTGGAGTGGGTCTCAGCTATTA CTCCTGGTGGTGAGGGGACATACTACGCAGAGACTCCGTGAAGGGCCGGTTCACCATCTCCAGAGACAATTCCAAGGAC ACGCTGTATCTGCAAATGGACAGCCTGAGAGACCGAGGACACGGCTGTGTATTACTGTGCCAGAGATTTGTACGGGAG CTACGGTGATGCTTTTGATATCTGGGGCCAAGGGACACTGGTCACCGTCAGCTCA |
| 229 | XPA.85.340 HC n.t. | GAGGTGCAGCTGGTGGAGTCTGGGGGAGGCGTGGTCCAGCCTGGGAGGTCCCTGAGACTCTCCTGTGCAGCCTCTGG ATTCACCTTTAGCAGCTCTGCCATGAGCTGGGTCCGCCAGGCTCCAGGGAAGGGGCTGGAGTGGGTCTCAGCTATTA CTCCTGGTGGTGAGGGGACATACTACGCAGAGACTCCGTGAAGGGCCGGTTCACCATCTCCAGAGACAATTCCAAGGAC ACGCTGTATCTGCAAATGGACAGCCTGAGAGACCGAGGACACGGCTGTGTATTACTGTGCCAGAGATTTGTACGGGAG CTACGGTGATGCTTTTGATATCTGGGGCCAAGGGACACTGGTCACCGTCAGCTCA |
| 230 | XPA.85.339 HC n.t. | GAGGTGCAGCTGGTGTGAGACTCTGCCATGAGCTCTGCCATGAGCTGGGTCCGCCAGACTCGGCCTGGGAGGTCCCTGAGACTCTCCTGTGCAGCCTCTGG ATTCACCTTTAGCAGCTCTGTGAGGGGACATACTACGCAGAGACTCCGTGAAGGGCCGGTTCACCATCTCCAGAGACAATTCCAAGGAC ACGCTGTATCTGCAAATGGACAGCCTGAGAGACCGAGGACACGGCTGTGTATTACTGTGCCAGAGATTTGTACGGGAG CTACGGTGATGCTTTTGATATCTGGGGCCAAGGGACACTGGTCACCGTCAGCTCA |
| 231 | XPA.85.287 HC n.t. | GAGGTGCAGCTGGTGGAGTCTGGGGGAGGCGTGGTCCAGCCTGGGAGGTCCCTGAGACTCTCCTGTGCAGCCTCTGG ATTCACCTTTAGCAGCTCTGTGGGGACATACTACGCAGAGACTCCGTGAAGGGCCGGTTCACCATCTCCAGAGACAATTCCAAGGAC ACGCTGTATCTGCAAATGGACAGCCTGAGAGACCGAGGACACGGCTGTGTTTATTACTGTGCCAGAGATTTGTACGGGAG CTACGGTGATGCTTTTGATATCTGGGGCCAAGGGACACTGGTCACCGTCAGCTCA |
| 232 | XPA.85.336 HC n.t. | GAGGTGCAGCTGGTGGAGTCTGGGGGAGGCGTGGTCCAGCCTGGGAGGTCCCTGAGACTCTCCTGTGCAGCCTCTGG ATTCACCTTTAGCAGCTCTGCCATGAGCTGGGTCCGCCAGACTCGTGAAGGGCCGGTTCACCATCTGCAGAGACAATTCCAAGGAC ACGCTGTATCTGCAAATGGACAGCCTGAGAGACCGAGGACACGGCTGTGTTTATTACTGTGCGAGAGATTTGTACGGGAG CTACGGTGATGCTTTTGATATCTGGGGCCAAGGGACACTGGTCACCGTCAGCTCA |

FIG. 21 (cont'd)

| SEQ ID NO: | Name | Sequence |
|---|---|---|
| 233 | XPA.85.337 HC n.t. | GAGGTGCAGCTGGTGGAGTCTGGGGGAGGTGTGGTACGGCCTGGGGGGTCCCTGAGACTCTCCTGTGCAGCCTCTGG ATTCACCTTTAGCAGCTCTGCCATGAGCTGGGTCCGCCAGACTCCAGGGAAGGGGCTGGAGTGGGTCTCAGCTATTA CTCCTGGTGGTGAGGGACATACTACGCAGAGACTCCGTGAAGGGCCGGTTCACCATCTCCAGAGACAATTCCAAGAAC ACGCTGTATCTGCAAATGAACAGCCTGAGAGCCGAGGACACTGGTCACCGTCAGCTCA CTACGGTGATGCTTTTGATATCTGGGGCCAAGGGACACTGGTCACCGTCTCCTCA |
| 234 | XPA.85.338 HC n.t. | GAGGTGCAGCTGGTGGAGTCTGGGGGAGGTGTGGTACGGCCTGGGGGGTCCCTGAGACTCTCCTGTGCAGCCTCTGG ATTCACCTTTAGCAGCTCTGCCATGAGCTGGGTCCGCCAGACTCCAGGGAAGGAACTGCAGTGGGTCTCAGCTATTA CTCCTGGTGGTGAGGGACATACTACGCAGAGACTCCGTGAAGGGCCGGTTCACCATCTCCAGAGACAATTCCAAGAAC ACGCTGTATCTGCAAATGAACAGCCTGAGAGCCGAGGACACTGGTGTTATTACTGTGCGAGAGATTGTACGGGAG CTACGGTGATGCTTTTGATATCTGGGGCCAAGGGACACTGGTCACCGTCTCCTCA |
| 235 | XPA.85.332 LC n.t. | GAAACGACACTCACGCAGTCTCCAGCATTCATGCAGACATCTGTGGGAGACAGAGTCACCATCACTTGCCAGGTCTAG TCAGGACATTAACAACTTTTTAAATTGGTATCAGCAGAAACCAGGGAAAGCCCCCTAAGTTCCTGATCTACGATGCTT CCAATTTGGAAAAAGGGGTCCCATCAAAGTTCAGTGGGCGTGGATCTGGGACAGAATTCACTCTCACCATCAGCAGC CTGCAGCCTGAAGATATTGCAACATATTACTGTCAACAATATGTGATTTCCGCTCACCTTGGCCAAGGGACACG ACTGGAGATTAAACGT |
| 236 | XPA.85.012 LC n.t. | GATGTTGTGATGACTCAGTCTCCATGTCCCTGTCCCCGTCACCCTGGAGAGCCGGCCTCCATCTCCTGCAGGTCTAG TCAGAGCCTCGTCTATGGTAGTGATGGAAACACCTATTTGGCTTGGACCTGCAGAAGCCAGGGCAGTCTCCACAGCTCC TGATCTATTTGGTTCTAATCGGGCCTCTGAGGATGTTGGGGTTTATTACTGCATGCAAGGTCTACAAGTCCGCTCACTTT CTGAAAATCAGCAGAGTGGAGGCTGAGGATGTTGGGATTTATTACTGCATGCAAGGTCTACAAACTCCGCTCACTTT CGGCGGAGGGACCAAGCTGGAGATCAAACGT |
| 237 | XPA.85.345 LC n.t. | GAAACGACACTCACGCAGTCTCCAGCATTCATGCAGACATCTGTGGGAGACAGAGTCACCATCACTTGCCAGGTCTAG TCAGGACATTAACAACTTTTTAAATTGGTATCAGCAGAAACCAGGGAAAGCCCCCTAAGTTCCTGATCTACGATGCTT CCAATTTGGAAAAAGTGTCCCATCAAAGTTCAGTGGGCGTGGATCTGGGACAGAATTACTCTCACCATCAGCAGC CTACAGCCTGAAGATATTGCTACATATTACTGTCAACAATATGTGATTTCCGCTCACCTTCGGCCAAGGGACACG ACTGGAGATTAAACGT |
| 238 | XPA.85.329 LC n.t. | GACATCGTGATGACCCAGAGCCCACTCTCCCTGTCCGTGACCCTGGGACAGCCGGCCTCCATCTCCTGCAAGTCCTC CCAGTCCCTGCTCTACGAGTGTGCCACATCGACAATATGGGGTATCTCGACAAGTTCTCCGCTCTGCAGAAGCCCAGCTGC TGATCTACGAGGTCCGGGTGGAAGCCGAGGACGGGGTCGTGTACTACTGCGCGTGTACTACTCGAGAGCCCTGCCATCACCTT CGGCCAGGGCACCGCACCCGGCTGGAAATCAAGCGT |
| 239 | XPA.85.326 LC n.t. | GATATTGTGATGACCCAGACTCCACTCTCTCCTGTCCCGTCACCCCTGGAGACGCCGGCCTCCATCTCCTGCAAGTCTAG TCAGAGCCTCCTGCATATTGATGGAACTATTTGTATTGGTACCTGCAGAAGCCAGGCCAGGCTCCACAGCTCC TGATCTATGAAGTTCCCACCGGGTTCTCTGGAGTCCTGGACTCAGATAAGTTCAGTGGCAGTGGATCAGGCAGAGTTCACA CTGACAATCAGCACCGGTGAGGCTGAGGATGTGGAGTTTATTACTGCATGCAGAGTTTACACCTTCGATCACCTT CGGCCAAGGGACACGACTGGAGATTAAACGT |
| 240 | XPA.85.328 LC n.t. | GATGTGGTGATGACCCAGAGCCCACTCTCCCTGTCCGTGACCCTGGGACAGCCAGGCCTCCATCTCCTGCAAGTCCTC CCAGTCCCTGCTCTACGAGTGTGCCACATCGACAGGCAAGACCTACCTGTACTGGTATCTGCAGAAGTCCGAGTTCACC |

FIG. 21 (cont'd)

| SEQ ID NO: | Name | Sequence |
|---|---|---|
| 241 | XPA.85.288 LC n.t. | TGATCTACGAGGTCTCCAACCGGTTCTCCGGCGTCGCCGGGACACCTTCTCCGGCTCTGGCACCGACTTCACC CTGAAGATCTCCCGGGTTGAAGCCGGAGGACGTGTACTACTGCATGCAGAGCCTGCACTTCCCCATCACCTT CGGCCAGGGCACCGGCTGGAAATCAAGCGT |
| 242 | XPA.85.342 LC n.t. | GATGTTGTGATGACTCAGAGACTCCAGAGATTGATGGAAAGCCAGTTATTGTATTGGTACCTGCAGAAGTCC TCAGAGCCTCCTGCATATTGATGGAAAGACCACTATTTGTATTGATGCCAGAAGCCCTATCTCCTGAAGTCC TGATCTATGAGGTTTCCAACCGGTTCTCTGGAGTGGGAGCTGAGATGTGGAGTTTACTACTGCATGCAGAGATTCACA CTGAAAATCAGCCGGGGACACGACTGGAGATTAAACGT |
| 243 | XPA.85.333 LC n.t. | GAAACGACACTCACGCAGTCTCCAACATTCATGCCAGCATCTGTGGAGACAGAGTCACCATCACTTGCCAGGCGAG TCAGGACATTAACAACTTTTTAAATTGGTATCAGCAGAAACCAGGGAAAGCCCCTAAGTTCCTGATCTACGATGCTT CCAATTGGGAAAAAAGGTCTCCCATCAAGGTTCAGTGGCGTGGATCTGGGACAGAATTTACTCTCACCATCAGCAGC CTACAGCCTGAAGATATTGCTACATATTACTGTCAACAATATCGTAACAATATCGTGATTTCCCGCTCACCTTCGGCCAAGGGACACG ACTCGAGATTAAACGT |
| 244 | XPA.85.343 LC n.t. | GATGTTGTGATGACTCAGAGACTCCACTCTCCTGCCCTGCCGTCACCCTGGACGCCGCCTCGGCTCCAGTCCAG TCAGAGCCTCCTACATATTGATGGAAAGACCACTATTTGTATTGGTACCTGCAGAAGCCAGGCCAGTCCCACACCTCC TAATCCGTGAAGTCTCTCACCCGGTTCTCTGGAGTCAGGCGTCAGGACAGCTCAGGGACAGATTCACA TTGGAAAATCAGCCGGGTGAGGCTGAGGATGTTGGGGTTTATTACTGCATGCAAGGTTTACACCTTCCTCCGACGTT CGGCCAAGGGACACAAGTGAAATCAAACGT |
| 245 | XPA.85.327 LC n.t. | GATGTTGTGATGACTCAGAGACTCCACTCTCCTGTCCGTCACCCTGGACAGCCGGCTCCGGCCAGTCTAG TCAGAGCCTCCTGCATATTGATGGAAGACCACCTATCTGTATTGGTACCTGCAGAGGCCAGGCCAGCTCC TGATCTATGAAATTCCAACCGGTTCTCTGGAGTGCCAGATAGGTTCAGTGGCAGTGGATCAAAGATACACATTTCCTCTCCACTT CTGAAGATTCAGCGGGGACACGACTGGAGATTAAACGT CGGCCAAGGGACCAAGCTGGAGATCAAACGT |
| 246 | XPA.85.330 LC n.t. | GACATCGTGATGACTCAGAGCCAGAGACTCCACTCTCCTGTCCGTCACCCTGGACACCCCTGGCCAGCATCTCCAGCATCCTCCAGCATCCTCCAGCATCTGC CCAGTCCCTGCTGCACATCGACAGATCCAACCAGCAACACCTACCTGTACTGGTATCTGCAGGCCTACTGC TGATCTACGAGATCTCCAACCGGTTCTCCAGAGTGGAAACCGGAGGACGTGGGGTTCCGTTCCAAAGGTTACACGATTCACA CTGAAGATCTCCCGGGTTGAAGCCGGAGGACGTGTACTACTGCATGCAAGCAGAGATTTCACCT CGGCCAGGGCACCAAGCTGGAAATCAAGCGT |
| 247 | XPA.85.334 LC n.t. | GATATTGTGATGACTCAGAGACTCCACTCTCCTGTCCGTCACCCTGGACACCCCTGGCCAGCATCTCCAGCATCTAG TCAGTCCCTCCTACATATTGATGGAAAGACCTATTTGTATTGGTTCTGCAGAAGCCAGGCCAGGCCAGTTCACAACTTT TGATCTATGAAGTTCCAACCGGTGAGGCTGAGGCTGAGTTGCCGTTTATTATTACTGCATGCAAGTTTACACAGTTTCACA CTGAAGATCAGCCGGGTGAGGCTGAGGACTGTGGCCGTTTATTATTACTGCATGCAAGTTTACACAGTTTCACA CTGAAAAATCAGCCGGGTGAGGCTGAGGACTGGTGCCGTTTATTATTACTGCATGCAAGTTTACAGTTTCGATCACCTT |

FIG. 21 (cont'd)

| SEQ ID NO: | Name | Sequence |
|---|---|---|
| 248 | XPA.85.344 LC n.t. | CGGCCCAGGACACGACTGGAGATTAAACGT CAGATGCAGCTGGTGCAGTCTGGGGCTGAGGTGAAGAAGCCTGGATCCTGGTGAAGGTCTCCTGCAAGGCTTCTGG AGGCACCTTCAGCACCTTTGGTACAGCAGCTATGCAGCTATCAGCTGGGTGCGACAGGCCCCTGGACAAGGGCTTGAGTGATGGAGGGATCA TCCCTATCTTTGGTACAGCAAACTACGCACAGAATCCAGGGACAGAGTTCACGATTACCGCGGACGAATCCACGAGC ACAGCCTACATGGAGCTGAGCAGCCTGAGGACACGGCCGTGTATTACTGTGCGAGAGGGTATGTAGTAGC CAGACTCTGGGGCCAAGGGAACCCTGGTCACCGTCAGCTCA |
| 249 | XPA.85.346 LC n.t. | GATATTGTGATGACCCAGACTCCACTCTCCTCTGTCCGTCACCCCTGGAGACAGCCGGCCTCCATTACCTGCAAGTCTAG TCAGAGCCTCCTCACATATTGATGGAAAGACCTATTTGTATTTGGTTCTTGCAGAAGCCAGGCCAGCCTCCACAGCTCC TGATCTATGAAGTTTCAAACCGGTTCTCTGGAGTGCCGATAGGTTCAGTGGCACAGGGACAGATTTCACA CTGAAAATCAGCCGGTGAGCTGGAGGATGTTGGGCTTTATTACTGCATGCAGAGTTTACACCTTCCGATCACCTT CGGCCAAGGGACACGACTGGAGATTAAACGT |
| 250 | XPA.85.331 LC n.t. | GATGTTGTGATGACTCAGTCTCCACTCTCCCCTGCCGTCACCCTGGAGAGCCGGCCTCCATCTCCTGCAGGTCTAG TCAGAGCCTCCTACATATTGATGGATTTAATTATTTGCAATGTGACCTGCAGAAGCCAGGCCAGTCTCCACAGCTCC TGGTCCATTTGGGTTCTTTCTTTCGGGCCTCCACCTGTTCCCTGACAGTTCAGTGGCAGTTGGATCAGGCACAGATTTTACA CTGGAAATCAGCAGAGTTGAGGCTGAGGATCTGTGGAGGCTTCTGCATGCAAGGTCTACAAACTCCTCCCACTTT CGGCCCTGGGACCAAAGTGGAGATCAAACGT |
| 251 | XPA.85.347 LC n.t. | GATATTGTGATGACCCAGACTCCACTCTCCTCTGTCCGTCACCCCTGGACAGCCGGCCTCCATCTCCTGCAAGTCTAG TCAGAGCCTGTTTCATGATCATGGAAGGACCACTGTTGTCTTGGTACCTGCAGAAGCCAGGCCAGCCTCCACAGCTCC TGATCTTTGAAGTTTCCAACCGGTTCTCTGGAGTGCCAGATAGGTTCAGTGGCAGCGGGGGTCAGGGACAGATTTCACA CTGAAGATCAGCCGGTGGAGCTGGAGGATGTTGGGGTTTATTACTGCATGCAAGGTATACACCTTCCTCCGGCTTT CGGCGGAGGGACCAAGCTGGAGATCAAACGT |
| 252 | XPA.85.017 LC n.t. | CAGTCTGTGTTGACGCAGCCGCCCTCAGTGTCTGCGGGCCCAGGACAGAAGGTCACCATCTCCTGCTCTGGAAGCAG CTCCAACATTGGCTATAATTACGTATCCTGGTACCAGCAGTTCCCAGGAACAGCCCCAAACTCCTCATTTATGACA GGACTCCAGACTGGGGGACGAGGTTCTCTGGCTCCAAGTCTGGCACGTCAGCCACCTGGGCATCACC CAGGGGACCAAGGTGACCGTCCTAGGT |
| 253 | XPA.85.341 LC n.t. | TCCTATGAGCTGACACAGCCATCCTCAGTGTCAGTGTCAGCCCAGGCACAGACAGCCAGCATCACCTGCTCTGGAGATAA ATTGGGCCCTGAAAAATATGCTTCCTGGTATCAACAGAAGCCAGGCCAGTCCCCTGTCCTGGTCATGTTTGAAGATACGA AGCGGCCCTCAAGGATCCCTGAGCGATTCTCTGGCTCCAGTTGTCAGACTCGAGCACATCAGCCGGGACC CAGGCTGAAGATGAGGCTGACTATTACTGTCAGGCGTGGGATTGCGGCGGAGGCACCCAGCTGAC CGTCCTAGGT |
| 254 | XPA.85.335 LC n.t. | CAGTCTGTGCTGACGCAGCCGCCCTCAGTGTCTGCGGCCCAGGACAGAAGGTCACCATCTCCTGCTCTGGAAACAC CTCCAACATTGGAAATAATTTTGTATCCTGGTACCAGCAGCTCCCAGGAACAGCTCCCAAAGTCCTGGCACGCTCCTCC ATAATAAGCGACCCTCAGGATCTCCTGGGAGTCCGATTATTACTGCGCACACTGGGATATAACAGCCTGAATCCTCCTTGGGTGTTCGG GGAGGCACCCAAGCTGACCGTCCTAGGT |
| 255 | XPA.85.340 | TCCTATGTGCTGACTCAGCCACCCTCAGTGTCCGTGGCCCCAGGACAGACAGCCAGCATCACCTGCTCTGGAGATAA |

FIG. 21 (cont'd)

| SEQ ID NO: | Name | Sequence |
|---|---|---|
| 256 | LC n.t. | TTTGGGGGAAAAATTGTTTCCTGAGCTATCAACAGAAGGCAGGCCAGTCCCCTGTCTTGGTCATCTTTGAAGATAATA AGCGGCCCTCAGGATCCCCTGAGCGATTCGCTGGCTCCAACTCTGGGAACAGAGCCACTCTGACCATCAGGGGACC CAGGCTGAAGATGAGGCTGACTATTACTGTCAGGCGTGGGACAGCAGCTGGTGTTCGGCGGAGGCACCCAGCTGAC CGTCCTAGGT |
| 257 | XPA.85.339 LC n.t. | TCCTATGAGCTGACACAGCCACCCTCAGTGTCCGTGGCCCCAGGACAGACAGCCACCATCACCTGCTCTGGAGATAG ATTGGGCGATAAATTTATCTCTTGGTATCAGCAGAAGCCAGGCCAGTCCCCTACTGGTCATCTTTGAAGATAACG AACGGCCCTCGAGGATCCCCTGAGCGATTCTCTGGCTCCAACTCTGCCACTCTGACCATCAGCGGGACC CAGGCTGTAGATGAGGCTGACTATTACTGTCAGGCGTGGGACAGCAGTTGGTGTTCGGCGGAGGCACCCAGCTGAC CGTCCTAGGT |
| 258 | XPA.85.287 LC n.t. | TCCTATGTGCTGACTCAGCCACCCTCAGTGTCCGTGGCCCCAGGACAGACAGCCCGTATCACCTGCTCTGGAGATAA ATTGGGGGATAGATATGTTTCCTGGTATCAGCAGAAGCCAGGCCAGTCCCCTGTGTTGGTCATGTTTGAAGATACCG GCGGGCCCGCAGGGATCCCCTGAGCGATTCTCTGGCTCCAACTCTGGGAACACAGCCACTCTGACCATCAGCGGGACC CAGGCAGAAGATGAGGCTGACTATTACTGTCAGGCGTGGGACCACCTGGGTTTTCGGCGGAGGCACCCAGCTGAC CGTCCTAGGT |
| 259 | XPA.85.336 LC n.t. | CAGTCTGTGCTGACGCAGCCAGCCCTCAGTGTCTGCGGCCCAGGACAGAAGGTCACCATCTCCTGCTCTGGAACCGG CTCCAACATTGGCAGTAATTATGTCGCCTGGTATCAGCAGCTCCCAGGAACAGCCCCCAAACTCCTCATTTATGACG ATAATAAGCGACCCTCAGGGATTCCTGACCGATTCTCTGGCTCCAAGTCTGGCACGTCGGCCACCCTGGTCATCGCC GGACTCCAGACTGGGGACGAGGCCGATTATTATTGTGAACATGGGATAACACCCTGAATGTTGGGGGGTCTTCGG CGGAGGCACCCAGCTGACCGTCCTAGGT |
| 260 | XPA.85.337 LC n.t. | TCCTATGTGCTGACTCAGCCACCCTCAGTGTCCGTGGCCCCAGGACAGACAGCCACCATCACCTGCTCTCAGGAGATGA TTTCGGCGATAAGTATGTGTCTTGGTATCAACAGAAGCCAGGCCAGTCCCCTACTGGTCATCTTTCAGGATAACG AGCGGCCCCTCTAGGGATCCCCTGAGCGATTCTCTGGCTCCAACTCTGGGAACACTGACCATCAGCGGACC CAGGCTATGGATGAGGCTGACTATTACTGTCAGGCGTGGGACAGCAATTGGGTGTTCGGCGGAGGACCAAGGTCAC CGTCCTAGGT |
| 260 | XPA.85.338 LC n.t. | TCCTATGAGCTGACACAGCCACCCTCAGTGTCCGTGGCCCCAGGACAGACAGCCACCATCACCTGCTCTGTTTGAGATAA ATTGGGGGATAAATAATGCTTCCTGGTATCAGCAGAAGCCAGGCCAGTCCCCTGTCTTGGTCATGTTTGAGAATCGTG ACCGGCCCTATGGGATCCCCTGACCGATTCTCTGGCTCCAATTCTGGAACACAGCCACTCTGACCATCAGCGGGACC CAGGCTATGGATGAGGCTGACTATTACTGTCAGGCACTGCATGGGTATTCGGCGGAGGCACCCA GCTGACCGTCCTAGGT |

PARATHYROID HORMONE RECEPTOR 1 (PTH1R) ANTIBODIES AND USES THEREOF

This application claims the priority benefit of U.S. Provisional Patent Application No. 62/369,745, filed Aug. 1, 2016, U.S. Provisional Patent Application No. 62/432,338, filed Dec. 9, 2016 and U.S. Provisional Patent Application No. 62/479,637, filed Mar. 31, 2017, herein incorporated by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: Filename: 50986_SeqListing.txt; Size: 108,540 bytes, created on Jul. 28, 2017.

FIELD OF THE INVENTION

The present disclosure relates, in general, to parathyroid hormone receptor 1 (PTH1R) antibodies and therapy for treating conditions associated with increased parathyroid hormone expression, increased parathyroid hormone related protein expression or PTH1R expression comprising administering to a subject in need thereof a therapeutically effective amount of an PTH1R antibody.

BACKGROUND

G protein-coupled receptors (GPCRs) are a group of plasma membrane receptors that transduce signals from extracellular ligands to signals in intracellular relay proteins, the heterotrimeric GTP binding proteins (G proteins). GPCRs represent one of largest and most diverse protein families in mammalian genomes. (Hutchings et al., 2010 *mAbs* 2:6, 594-606; Strader et al., 1994 *Annual Review of Biochemistry* 63:101-132). GPCRs are characterized by having an extracellular N-terminus, 7-transmembrane spanning (TM) domains and an intracellular C-terminus (Hutchings et al., 2010 mAbs 2:6, 594-606). In vertebrates, these receptors can be classified into families based on their sequence similarity within the 7 TM domains, Class 1 (rhodopsin-like family), Class 2 (secretin and adhesion family), Class 3 (the glutamate family), and Class F (frizzled family) (Hutchings et al., 2010 *mAbs* 2:6, 594-606; Fredriksson et al., 2003 *Mol Pharmacol.* 63(6):1256-72).

The parathyroid hormone receptor (PTHR) is a class 2 GPCR that activates the adenylyl cyclase/cAMP signaling pathway. Similar to all class 2 GPCRs that bind peptide hormones, the PTHR has a relatively large (~160 amino acid)N-terminal extracellular domain, herein termed the N domain, that plays a major role in hormone binding (Shimizu et al., 2004 *J Biol Chem.* 280(3):1797-807). Two types of PTHR, type 1 (PTH1R) and type 2 (PTH2R) have been identified. PTH1R mediates the actions of two polypeptide ligands; parathyroid hormone (PTH), an endocrine hormone that regulates the levels of calcium and inorganic phosphate in the blood by acting on bone and kidney, and PTH-related protein (PTHrP), a paracrine-factor that regulates cell differentiation and proliferation programs in developing bone and other tissues (Gardella et al., 2015 *Pharmacol Rev.* 67(2): 310-337). PTH a principal regulator of bone remodeling and calcium ion homeostasis, exerts its effects by binding and activating the PTHR (Shimizu et al., 2004 *J Biol Chem.* 280(3):1797-807).

SUMMARY OF THE INVENTION

The invention provides materials, methods, and uses relating to antibodies against parathyroid hormone receptor 1 (PTH1R). The disclosure provides antibodies that bind PTH1R. In particular, the present disclosure provides methods of use of such antibodies in the treatment of cancer, Humoral Hypercalcemia of Malignancy (HHM), Primary Hyperparathyroidism (PHPT), Secondary Hyperparathyroidism (SHPT) and cachexia.

In various embodiments, the disclosure provides an antibody specific for PTH1R with an affinity $K_d$ of $10^{-6}$ M or less. In various embodiments, the disclosure provides an antibody specific for PTH1R with an affinity $K_d$ of $2\times10^{-6}$ M or less. In exemplary embodiments, an anti-PTH1R antibody described herein binds at least with an affinity of $10^{-6}$ M, $10^{-7}$ M, $10^{-8}$ M, $10^{-9}$ M or less. In other embodiments, an antibody described herein binds to PTH1R with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% higher affinity (e.g., preferentially binds to PTH1R) compared to binding to PTH2R. In certain embodiments, the affinity is measured by surface plasmon resonance or KinExA assay.

In a related aspect, the antibody binds the N-terminal portion of PTH1R. In a further aspect, the disclosure contemplates an antibody that does not bind parathyroid hormone receptor 2 (PTH2R). In various aspects the antibody binds PTH1R on the surface of a cell. In certain aspects the antibody binds allosterically to PTH1R.

In a preferred embodiment, the antibody is a negative modulator antibody, optionally wherein the antibody is capable of weakening the binding affinity between PTH or PTHrP and with PTH1R by at least about 2-fold, optionally up to 1000-fold. In other embodiments, an antibody described herein is capable of weakening the binding affinity between PTH or PTHrP with at least 2-1000 fold, 10-100 fold, 2-fold, 5-fold, 10-fold, 25-fold, 50-fold, 100-fold, 200-fold, 300-fold, 400-fold, 500-fold, 600-fold, 700-fold, 800-fold, 900-fold or 1000-fold.

In a various embodiments, the antibody inhibits calcium flux in a cell in response to stimulation of the receptor with parathyroid hormone (PTH) or parathyroid hormone related protein (PTHrP). In related embodiments, the antibody inhibits PTH- or PTHrP-mediated cyclic adenosine monophosphate (cAMP) accumulation.

In one embodiment, the PTH1R antibody is a monoclonal antibody.

In one aspect, the disclosure provides an antibody that binds parathyroid hormone receptor 1 (PTH1R) comprising (a) a heavy chain complementary determining repeat (CDR)1 amino acid sequence set forth in FIG. 21 or SEQ ID NOs: 27, 30, 33, 36, 39, 42, 45, 48, 51, 54, 57, 60, 63, 66, 69, 72, 75, 78, 81, 84, 87, 90, 93, 96, 99, 102, or a variant thereof in which one or two amino acids have been changed; (b) a heavy chain CDR2 amino acid sequence set forth in FIG. 21 or SEQ ID NOs: 28, 31, 34, 37, 40, 43, 46, 49, 52, 55, 58, 61, 64, 67, 70, 73, 76, 79, 82, 85, 88, 91, 94, 97, 100, 103 that is from the same heavy chain variable region as (a), or a variant thereof in which one or two amino acids have been changed; and (c) a heavy chain CDR3 amino acid sequence set forth in FIG. 21 or SEQ ID NOs: 29, 32, 35, 38, 41, 44, 47, 50, 53, 56, 59, 62, 65, 68, 71, 74, 77, 80, 83, 86, 89, 92, 95, 98, 101, 104 that is from the same heavy chain variable region as (a), or a variant thereof in which one or two amino acids have been changed.

In a related aspect, the disclosure provides an antibody that binds parathyroid hormone receptor 1 (PTH1R) comprising: (a) a heavy chain CDR1 amino acid sequence set forth in FIG. 21 or SEQ ID NOs: 27, 30, 33, 36, 39, 42, 45, 48, 51, 54, 57, 60, 63, 66, 69, 72, 75, 78, 81, 84, 87, 90, 93, 96, 99, 102, or a variant thereof having at least 70% identity thereto; (b) a heavy chain CDR2 amino acid sequence set forth in SEQ ID NOs: 28, 31, 34, 37, 40, 43, 46, 49, 52, 55, 58, 61, 64, 67, 70, 73, 76, 79, 82, 85, 88, 91, 94, 97, 100, 103 that is from the same heavy chain variable region as (a), or a variant thereof having at least 70% identity thereto; and (c) a heavy chain CDR3 amino acid sequence set forth in SEQ ID NOs: 29, 32, 35, 38, 41, 44, 47, 50, 53, 56, 59, 62, 65, 68, 71, 74, 77, 80, 83, 86, 89, 92, 95, 98, 101, 104 that is from the same heavy chain variable region as (a), or a variant thereof having at least 70% identity thereto.

In a further aspect, the disclosure contemplates an antibody that binds an antibody that binds parathyroid hormone receptor 1 (PTH1R) comprising: (a) a heavy chain CDR1 amino acid sequence set forth in SEQ ID NOs: 27, 30, 33, 36, 39, 42, 45, 48, 51, 54, 57, 60, 63, 66, 69, 72, 75, 78, 81, 84, 87, 90, 93, 96, 99, 102, or a variant thereof having at least 70% identity thereto; (b) an independently selected heavy chain CDR2 amino acid sequence set forth in in FIG. 21 or SEQ ID NOs: 28, 31, 34, 37, 40, 43, 46, 49, 52, 55, 58, 61, 64, 67, 70, 73, 76, 79, 82, 85, 88, 91, 94, 97, 100, 103, or a variant thereof having at least 70% identity thereto; and (c) an independently selected heavy chain CDR3 amino acid sequence set forth in in FIG. 21 or SEQ ID NOs: 29, 32, 35, 38, 41, 44, 47, 50, 53, 56, 59, 62, 65, 68, 71, 74, 77, 80, 83, 86, 89, 92, 95, 98, 101, 104, or a variant thereof having at least 70% identity thereto.

In certain embodiments, at least two of the heavy chain CDR1, CDR2 or CDR3 amino acid sequences are set forth in FIG. 21 or SEQ ID NOs: 27-104. In a related embodiment, three of the heavy chain CDR1, CDR2 and CDR3 amino acid sequences are set forth in FIG. 21 or SEQ ID NOs: 27-104.

In some embodiments, an antibody contemplated herein comprises an amino acid sequence at least 85% identical to a heavy chain variable region amino acid sequence set forth in FIG. 21 or SEQ ID NOs: 1-26. In some embodiments, provided herein is an antibody that comprises an amino acid sequence at least 95% identical to a heavy chain variable region amino acid sequence set forth in FIG. 21 or SEQ ID NOs: 1-26.

It is further contemplated that an antibody described herein comprises a polypeptide sequence having an amino acid sequence at least 70% identical over all three HCDRs in a heavy chain variable region, the amino acid sequences of HCDR1, HCDR2 and HCDR3 set forth in FIG. 21 or SEQ ID NOs: 27-104.

In certain embodiments, an antibody contemplated herein comprises one or more heavy chain framework amino acids have been replaced with corresponding amino acid(s) from another human antibody amino acid sequence.

In one embodiment, an antibody contemplated herein further comprises any one of the light chain CDR amino acid sequences set forth in FIG. 21 or SEQ ID NOs: 131-208. In some embodiments, an antibody comprises at least two of the light chain CDR amino acid sequences set forth in FIG. 21 or SEQ ID NOs: 131-208. In other embodiments, an antibody comprises at least three of the light chain CDR amino acid sequences set forth in FIG. 21 or SEQ ID NOs: 131-208.

In another aspect, an antibody described herein comprises (a) a light chain CDR1 amino acid sequence set forth in FIG. 21 or SEQ ID NOs: 131, 134, 137, 140, 143, 146, 149, 152, 155, 158, 161, 164, 167, 170, 173, 176, 179, 182, 185, 188, 191, 194, 197, 200, 203, 206, or a variant thereof in which one or two amino acids have been changed, or a consensus sequence thereof set out in FIG. 21; (b) a light chain CDR2 amino acid sequence set forth in FIG. 21 or SEQ ID NOs: 132, 135, 138, 141, 144, 147, 150, 153, 156, 159, 162, 165, 168, 171, 174, 177, 180, 183, 186, 189, 192, 195, 198, 201, 204, 207 that is from the same light chain variable region as (a), or a variant thereof in which one or two amino acids have been changed, or a consensus sequence thereof set out in FIG. 21; and (c) a light chain CDR3 amino acid sequence set forth in FIG. 21 or SEQ ID NOs: 133, 136, 139, 142, 145, 148, 151, 154, 157, 160, 163, 166, 169, 172, 175, 178, 181, 184, 187, 190, 193, 196, 199, 202, 205, 208 that is from the same light chain variable region as (a), or a variant thereof in which one or two amino acids have been changed, or a consensus sequence thereof set out in FIG. 21.

In alternative embodiments, an antibody contemplated herein comprises: (a) a light chain CDR1 amino acid sequence set forth in FIG. 21 or SEQ ID NOs: 131, 134, 137, 140, 143, 146, 149, 152, 155, 158, 161, 164, 167, 170, 173, 176, 179, 182, 185, 188, 191, 194, 197, 200, 203, 206, or a variant thereof in which one or two amino acids have been changed; (b) an independently selected light chain CDR2 amino acid sequence set forth in FIG. 21 or SEQ ID NOs: 132, 135, 138, 141, 144, 147, 150, 153, 156, 159, 162, 165, 168, 171, 174, 177, 180, 183, 186, 189, 192, 195, 198, 201, 204, 207, or a variant thereof in which one or two amino acids have been changed; and (c) an independently selected light chain CDR3 amino acid sequence set forth in FIG. 21 or SEQ ID NOs: 133, 136, 139, 142, 145, 148, 151, 154, 157, 160, 163, 166, 169, 172, 175, 178, 181, 184, 187, 190, 193, 196, 199, 202, 205, 208, or a variant thereof in which one or two amino acids have been changed.

In certain embodiments, at least two of the light chain CDR1, CDR2 or CDR3 amino acid sequences are set forth in FIG. 21 or SEQ ID NOs: 131-208.

It is further contemplated that an antibody described herein comprises an amino acid sequence at least 70% identical to a light chain variable region amino acid sequence set forth in FIG. 21 or SEQ ID NOs: 105-130. In a related embodiment, the antibody comprises an amino acid sequence at least 85% identical to a light chain variable region amino acid sequence set forth in FIG. 21 or SEQ ID NOs: 105-130. In a further embodiment, the antibody comprises an amino acid sequence at least 95% identical to a light chain variable region amino acid sequence set forth in FIG. 21 or SEQ ID NOs: 105-130. In still another embodiment, the antibody comprises a light chain variable region amino acid sequence set forth in FIG. 21 or SEQ ID NOs: 105-130.

In a further embodiment, an antibody described herein comprises a polypeptide sequence having an amino acid sequence at least 70% identical over all three LCDRs of a light chain variable region, the amino acid sequences of LCDR1, LCDR2 and LCDR3 set forth in FIG. 21 or SEQ ID NOs: 131-208.

In certain embodiments, an antibody described herein comprises (i) an amino acid sequence at least 70% identical over all three LCDRs, of a light chain variable region, the amino acid sequences of LCDR1, LCDR2 and LCDR3 set forth in FIG. 21 or SEQ ID NOs: 131-208 and (ii) an amino acid sequence at least 70% identical over all three HCDRs of a heavy chain variable region, the amino acid sequences of HCDR1, HCDR2 and HCDR3 set forth in FIG. 21 or SEQ ID NOs: 27-104.

In another aspect, the disclosure provides an antibody that binds parathyroid hormone receptor 1 (PTH1R) comprising a light chain variable region and/or a heavy chain variable region, wherein (a) the light chain variable region comprises at least a CDR1 selected from SEQ ID NOs: 131, 134, 137, 140, 143, 146, 149, 152, 155, 158, 161, 164, 167, 170, 173, 176, 179, 182, 185, 188, 191, 194, 197, 200, 203, 206 or sequences at least 80% identical thereto, a CDR2 selected from SEQ ID NOs: 132, 135, 138, 141, 144, 147, 150, 153, 156, 159, 162, 165, 168, 171, 174, 177, 180, 183, 186, 189, 192, 195, 198, 201, 204, 207 or sequences at least 80% identical thereto, and/or a CDR3 selected from SEQ ID NOs: 133, 136, 139, 142, 145, 148, 151, 154, 157, 160, 163, 166, 169, 172, 175, 178, 181, 184, 187, 190, 193, 196, 199, 202, 205, 208 or sequences at least 80% identical thereto; and/or wherein (b) the heavy chain variable region comprises at least a CDR1 selected from SEQ ID NOs: 27, 30, 33, 36, 39, 42, 45, 48, 51, 54, 57, 60, 63, 66, 69, 72, 75, 78, 81, 84, 87, 90, 93, 96, 99, 102 or sequences at least 80% identical thereto, a CDR2 selected from SEQ ID NOs: 28, 31, 34, 37, 40, 43, 46, 49, 52, 55, 58, 61, 64, 67, 70, 73, 76, 79, 82, 85, 88, 91, 94, 97, 100, 103 or sequences at least 80% identical thereto, and/or a CDR3 selected from SEQ ID NOs: 29, 32, 35, 38, 41, 44, 47, 50, 53, 56, 59, 62, 65, 68, 71, 74, 77, 80, 83, 86, 89, 92, 95, 98, 101, 104 or sequences at least 80% identical thereto.

In a related embodiment, an antibody described herein comprises (a) a light chain variable region comprising at least a CDR1 selected from SEQ ID NO: 131, 134, 137, 140, 143, 146, 149, 152, 155, 158, 161, 164, 167, 170, 173, 176, 179, 182, 185, 188, 191, 194, 197, 200, 203, 206 or sequences at least 90% identical thereto, a CDR2 selected from SEQ ID NO: 132, 135, 138, 141, 144, 147, 150, 153, 156, 159, 162, 165, 168, 171, 174, 177, 180, 183, 186, 189, 192, 195, 198, 201, 204, 207 or sequences at least 90% identical thereto, and a CDR3 selected from SEQ ID NO: 133, 136, 139, 142, 145, 148, 151, 154, 157, 160, 163, 166, 169, 172, 175, 178, 181, 184, 187, 190, 193, 196, 199, 202, 205, 208 or sequences at least 90% identical thereto; and/or wherein (b) the heavy chain variable region comprises at least a CDR1 selected from SEQ ID NO: 27, 30, 33, 36, 39, 42, 45, 48, 51, 54, 57, 60, 63, 66, 69, 72, 75, 78, 81, 84, 87, 90, 93, 96, 99, 102 or sequences at least 90% identical thereto, a CDR2 selected from SEQ ID NO: 28, 31, 34, 37, 40, 43, 46, 49, 52, 55, 58, 61, 64, 67, 70, 73, 76, 79, 82, 85, 88, 91, 94, 97, 100, 103 or sequences at least 90% identical thereto, and a CDR3 selected from SEQ ID NO: 29, 32, 35, 38, 41, 44, 47, 50, 53, 56, 59, 62, 65, 68, 71, 74, 77, 80, 83, 86, 89, 92, 95, 98, 101, 104 or sequences at least 90% identical thereto.

In some embodiments, an antibody of the disclosure further comprises a heavy chain constant region, wherein the heavy chain constant region is a modified or unmodified IgG, IgM, IgA, IgD, IgE, a fragment thereof, or combinations thereof.

In certain embodiments, an antibody is provided in which one or more light chain framework amino acids have been replaced with corresponding amino acid(s) from another human antibody amino acid sequence, optionally wherein the framework comprises one or more of the changes set out in FIGS. 1A and 1B.

In one aspect, the antibody of the disclosure is selected from the group consisting of XPA.85.012, XPA.85.017, XPA.85.288, XPA.85.328, XPA.85.329, XPA.85.330 and XPA.85.349.

In one embodiment, an antibody described herein further comprises a human light chain constant region attached to said light chain variable region. In some embodiments, the light chain constant region is a modified or unmodified lambda light chain constant region, a kappa light chain constant region, a fragment thereof, or combinations thereof.

In another aspect, the disclosure provides an isolated nucleic acid molecule comprising a nucleotide sequence that encodes the heavy chain or light chain as described herein. In various embodiments the nucleotide sequences encoding the antibody variable regions are set out in SEQ ID NOs: 209-234 (heavy chain) and 235-260 (light chain).

In various embodiments, the nucleic acid molecule comprises a nucleotide sequence that encodes the light chain variable region amino acid sequence of any one of SEQ ID NOs: 105-130 or a fragment thereof. In one embodiment, the nucleic acid molecule comprises the light chain variable region nucleotide sequence of any one of SEQ ID NOs: 235-260, or a fragment thereof. In further embodiments, the nucleic acid molecule comprises a nucleotide sequence that encodes the heavy chain variable region amino acid sequence of any one of SEQ ID NOs: 1-26 or a fragment thereof. In one embodiment, the nucleic acid molecule comprises the heavy chain variable region nucleotide sequence of any one of SEQ ID NOs: 209-234, or a fragment thereof. Nucleic acid molecules of the disclosure further include all nucleic acid sequences, including the sequences in SEQ ID NOs: 209-260, and nucleic acid sequences comprising degenerate codons based on the diversity of the genetic code, encoding an amino acid sequence of the heavy and light chain variable regions of an antibody described herein or any HCDRs or LCDRs described herein, and encoding the CDR amino acid sequences as set out in SEQ ID NOs: 27-104 and 131-208, as well as nucleic acids that hybridize under highly stringent conditions, such as those described herein, to a nucleic acid sequence encoding an amino acid sequence of the heavy and light chain variable regions of an antibody described herein set out in SEQ ID NOs: 1-26 or 105-130 or any HCDRs or LCDRs described herein as set out in SEQ ID NOs: 27-104 or 131-208.

In some embodiments, the nucleic acid molecule encodes a VL amino acid sequence that is at least 60, 65, 70, 75, 80, 85, 90, 91, 92, 93, 94, 95, 96 97, 98 or 99% identical to a VL amino acid sequence set out in SEQ ID NOs: 105-130. In a related aspect, the VL amino acid sequence is a consensus sequence. Nucleic acid molecules of the disclosure include nucleic acids that hybridize under highly stringent conditions, such as those described herein, to a nucleic acid sequence encoding the light chain variable region amino acid sequence of SEQ ID NOs: 105-130, or that has the light chain variable region nucleic acid sequence of SEQ ID NOs: 235-260. In some embodiments, the nucleic acid encodes the amino acid sequence of the heavy chain CDRs of said antibody set out in SEQ ID NO: 131-208.

It is further contemplated that a nucleic acid molecule of the disclosure comprises a nucleotide sequence that encodes the VH amino acid sequence of any one of antibodies described herein, or a fragment thereof. In some embodiments, the nucleic acid encodes the amino acid sequence of the heavy chain and/or light chain CDRs of said antibody. In some embodiments, said fragment is a contiguous fragment comprising heavy chain and/or light chain CDR1-CDR3. In one embodiment, said fragment comprises at least one, two or three of a heavy chain and/or light chain CDR1, CDR2, or CDR3 region, optionally with a different human or human consensus framework, and optionally with 1, or up to 2, or up to 3 mutations in the CDRs. CDR amino acid sequences are set out in SEQ ID NOs: 27-104 and 131-208.

In a related aspect, the nucleic acid molecule comprises a nucleotide sequence that encodes the heavy chain variable region amino acid sequence of one of heavy chain of SEQ ID NOs: 1-26, or a fragment thereof. In one embodiment, the nucleic acid molecule comprises the heavy chain variable region having a nucleotide sequence set out in SEQ ID NOs: 209-234, or a fragment thereof.

In some embodiments, the nucleic acid molecule encodes a VH amino acid sequence that is at least 70%, 75%, 80%, 85%, 90%, 95%, 96%, 97%, 98% or 99% identical to a VH amino acid sequence set out in SEQ ID NOs: 1-26. In a related aspect, the VH amino acid sequence is a consensus sequence. Nucleic acid molecules of the disclosure further include nucleic acids that hybridize under highly stringent conditions, such as those described herein, to a nucleic acid sequence encoding the heavy chain variable region amino acid sequence of SEQ ID NOs: 1-26, or that has the heavy chain variable region nucleic acid sequence of any one of SEQ ID NOs: 209-234.

It is further contemplated that the nucleic acids of the disclosure may encode a full-length light chain or heavy chain of an antibody selected from the antibodies set out in FIG. 21 wherein a full-length light chain or full-length heavy chain comprises a light chain constant region or a heavy chain constant region, respectively, light chain constant regions optionally include unmodified or modified kappa or lambda regions, and heavy constant regions include unmodified or modified constant regions of any of the classes, such as IgG1, IgG2, IgG3, IgG4, IgM, IgA, IgD, or IgE. Modified IgG4 constant regions include constant regions containing one or more of the mutations Ser228Pro and Leu235Glu (Angal et al., (1993) *Mol. Immunol.* 30: 105-108; Reddy et al., (2000) *J. Immunol.* 164: 1925-1933).

In one aspect, the full length variable light chain antibody comprises the amino acid sequences set out in SEQ ID NOs: 105-130. It is further contemplated that the nucleotide sequence encoding the full-length light chain encodes the amino acid sequences set out in SEQ ID NOs: 105-130 and comprises the nucleotide sequences set forth in SEQ ID NOs: 235-260.

In one aspect, the full length variable heavy chain antibody comprises the sequences in any one of SEQ ID NOs: 1-26. Further provided are nucleotide sequences that encode the full-length heavy chain variable region amino acid sequences set out in SEQ ID NOs: 1-26, and comprise the nucleotide sequences set forth in any one of SEQ ID NOs: 209-234.

In a further aspect, the disclosure provides an expression vector comprising a nucleic acid molecule contemplated herein operably linked to an expression control sequence. Also contemplated is a host cell comprising an expression vector or a nucleic acid molecule of the disclosure. In certain embodiments, the disclosure provides a host cell comprising a nucleic acid molecule encoding a heavy chain and a light chain variable region, wherein the heavy chain and light chain nucleic acids are expressed by different nucleic acids or on the same nucleic acid.

In a related aspect, the disclosure provides a method of using the host cell as described herein to produce an antibody, the method comprising culturing the host cell under suitable conditions and recovering said antibody. Also provided is an antibody produced by the method disclosed herein.

The disclosure further contemplates a sterile pharmaceutical composition comprising the antibody as disclosed herein and a pharmaceutically acceptable carrier.

In another aspect, the disclosure provides a method for treating hypercalcemia associated with increased parathyroid hormone or parathyroid hormone related protein expression comprising the step of administering to a subject in need thereof a therapeutically effective amount of an antibody or a pharmaceutical composition contemplated herein.

In another aspect, the disclosure provides a method for treating a disease, condition or disorder associated with increased parathyroid hormone expression, increased parathyroid hormone related protein expression or increased PTH1R expression comprising the step of administering to a subject in need thereof a therapeutically effective amount of an antibody or a pharmaceutical composition contemplated herein.

In another aspect, the disclosure provides a method for treating a disease, condition or disorder is selected from the group consisting of cancer, PTH- or PTHrP-induced hypercalcemia, Humoral Hypercalcemia of Malignancy (HHM), familial hypocalciuric hypercalcemia, tuberculosis, sarcoidosis, Primary Hyperparathyroidism (PHPT), Secondary Hyperparathyroidism (SHPT) and cachexia.

In various embodiments, the disease is PHPT and the subject is a non-surgical patient or a patient who has failed surgery. In various embodiments, the disease is SHPT and the subject has chronic kidney disease.

In various embodiments, the disclosure provides a method for treating cancer wherein the administration reduces the incidence of cancer metastasis in the subject compared to a subject not receiving the antibody.

In a related aspect, the disclosure provides a method for treating cancer comprising administering to a subject in need thereof a therapeutically effective amount of an antibody or a pharmaceutical composition contemplated herein. In certain embodiments, the cancer is selected from the group consisting of bone cancer, lung cancer, hepatocellular cancer, pancreatic cancer, kidney cancer, fibrotic cancer, breast cancer, myeloma squamous cell carcinoma, colorectal cancer and prostate cancer. In related aspects the cancer is metastatic. In a related aspect, the metastasis includes metastasis to the bone or skeletal tissues, liver, lung, kidney or pancreas.

In various embodiments, administering to a subject in need thereof a therapeutically effective amount of an antibody or a pharmaceutical composition contemplated herein ameliorates one or more symptoms of hypercalcemia.

In various embodiments, administering to a subject in need thereof a therapeutically effective amount of an antibody or a pharmaceutical composition contemplated herein ameliorates one or more symptoms of wasting syndrome or cachexia in PTHrP induced HHM.

In various embodiments, administering to a subject in need thereof a therapeutically effective amount of an antibody or a pharmaceutical composition contemplated herein extends HHM survival due to reduced hypercalcemia and/or wasting syndrome.

In various embodiments, the antibody disclosed herein is administered intravenously, intraarterially, intraperitoneally, intramuscularly, intradermally or subcutaneously. In related embodiments, the antibody disclosed herein is administered in combination with a second agent. In related embodiments, the antibody disclosed herein is administered once per week, once every 2 weeks, twice per month, once monthly, once every two months, or once every three months.

In various embodiments, the antibody compositions can be administered intravenously, subcutaneously or intramuscularly, in a dose range of 0.3-30 mg/kg twice weekly or every 1, 2 or 4 weeks. In various embodiments, the dose can be 0.3, 1, 2, 3, 4, 5, 6, 7, 8, 9, 10 or 30 mg/kg. In various embodiments, the antibody compositions can be administered intravenously in a dose range of 0.3-3 mg/kg, 1 to 6 mg/kg, or 2 to 6 mg/kg twice weekly or every 1, 2 or 4 weeks. Alternatively, the antibody compositions can be administered intravenously, subcutaneously or intramuscularly in a dose range of 0.5-5 mg/kg twice weekly or every 1, 2 or 4 weeks.

In various embodiments, the disclosure provides a method for administering a composition comprising an antibody or a pharmaceutical composition disclosed herein in the treatment a condition or disorder associated with increased parathyroid hormone expression or increased parathyroid hormone related protein expression.

In various embodiments, the disclosure provides a method for administering a composition comprising an antibody or a pharmaceutical composition disclosed herein in the treatment a condition or disorder associated with hypercalcemia.

In one aspect, the PTH1R antibody is a monoclonal antibody (or active fragments thereof) that can cross react, detect, bind to and neutralize PTH1R from multiple species (e.g. the human PTH1R antibody disclosed herein can cross react, detect, bind to and neutralize mouse PTH1R. Mouse PTH1R antibody disclosed herein can cross react, detect, bind to and neutralize human PTH1R).

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "certain embodiments", "further embodiment", "specific exemplary embodiments", and/ or "another embodiment", each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

The headings herein are for the convenience of the reader and not intended to be limiting. Additional aspects, embodiments, and variations of the invention will be apparent from the Detailed Description and/or Drawing and/or claims.

BRIEF DESCRIPTION OF THE DRAWINGS

FIGS. 1A-1B: A multiple sequence alignment of the light chains of selected clones against the parent sequence. Multiple sequence alignments (MSA) of the light chain amino acids of clones relating to XPA.85.012 (FIG. 1A) or from clones relating to XPA.85.017 (FIG. 1B), were performed against the parent sequence using the ClustalW algorithm. This alignment was used to generate a phylogenetic tree using CLCBio Sequence viewer software. The tree was exported in Newick format. The MSA was exported in FASTA format and run through the EMBOSS program Showalign to convert the alignment to dot-identity format. A script was written using the R language to combine the tree with the corresponding dot-identify alignment sequence, color-coded by light chain family. The branch line formats also correspond to light chain family to make it easy to read in B/W format. In the displayed alignment, the parent sequence is shown completely. Where other sequences are identical, the residue is shown as a dot. The differences are displayed. CDR regions identified using the IMGT numbering system are called out by boxes on the alignment. Framework differences from the parent are identified. This was done by running the parental light chain through a software program (PHEnom; XOMA (US) LLC)) and looking at the position frequency matrix that was displayed in the results. If a framework change in a sequence was toward a canonical amino acid, it is shown as (+), if away from canonical sequence (in terms of frequency) it is shown as (−). If the residue is not seen in the frequency matrix, it is an amino acid rarely used in that position and it is indicated by an (R) and the amino acid is indicated with square brackets. When the sequences belong to a different family that the parental, the family member closest to the parental is used as the "seed" in this PHEnom analysis.

(FIG. 8). Cells were washed twice with FACS Buffer and antibody binding was detected with anti-human IgG APC. None of the antibodies tested showed specific binding to CHO cells overexpressing human PTH2R. Anti-KLH.G2 was used a negative control for binding. All the tested antibodies were specific to PTH1R.

FIGS. 10A-10D: Following affinity engineering of XPA.85.017 (open circles) by light chain shuffling, CHOK1 cells stably overexpressing either human (FIGS. 10A and 10B). or mouse PTH1R (FIGS. 10C and 10D) were preincubated for 30 min at 37° C. with 267 nM (40 µg/ml) of variant IgGs, followed by induction with increasing concentrations of PTH(1-34) for 45 min at 37° C. Variant IgGs exhibited a range of inhibition of ligand-mediated cAMP accumulation (Gs/PKA pathway) via human and mouse PTH1R.

FIG. 18A, hPTH(1-34) was continuously infused subcutaneously (Alzet mini pump, model 2ML1; 10 µl/hr, 10 mg/kg/day) in normal Sprague Dawley rats (Harlan) for 7 days to mimic PTH hypersecretion in patients with hyperparathyroidism. Calcium was measured as a biomarker to assess in vivo neutralization by a single intravenous administration of Ab288 (2 or 10 mg/kg; n=5/group), BM2 (10 mg/kg; n=5), or isotype control (10 mg/kg, n=2) 24 hr after pump implantation. Serum calcium was measured before pump implantation (Predose), 24, 27 (3 hr post dose), 48, 72, 96, 120, 144 and 168 hr post pump implantation. FIG. 18B, antibodies, Ab328, Ab329 and Ab330 (2 mg/kg IV) along with Ab288 were tested in a similar study where serum calcium was measured before pump implantation (Predose), 24, 27 (3 hr post dose), 48, 72, 96 and 120 hr post pump implantation. All antibodies significantly lowered levels of calcium 24 hr post dose and throughout the infusion, with Ab288 and Ab328 producing the most dramatic reduction.

FIG. 19A, calcium was measured as a biomarker to assess in vivo neutralization by a single intravenous administration of Ab288 (2 or 10 mg/kg; n=4/group), anti-PTHrP antibody MCB1.1 (10 mg/kg; n=5), or isotype control (10 mg/kg, n=3) 24 hr after pump implantation. Serum calcium was measured before pump implantation (Predose), 24, 26 (2 hr post dose), 48, 72, 96, 120 and 144 hr post pump implantation. FIG. 19B, body weights were measured before pump implantation (Predose), 26 (2 hr post dose), 48, 96 and 144 hr post pump implantation.

FIG. 21: Sequence table for Heavy Chain (HC), Light Chain (LC) Complementarity-determining regions (CDRs) and variable regions. HC and LC CDRs and variable regions for XPA.85.332, XPA.85.012, XPA.85.345, XPA.85.329, XPA.85.326, XPA.85.328, XPA.85.288, XPA.85.342, XPA.85.333, XPA.85.343, XPA.85.327, XPA.85.330, XPA.85.334, XPA.85.344, XPA.85.346, XPA.85.331, XPA.85.347, XPA.85.017, XPA.85.341, XPA.85.335, XPA.85.340, XPA.85.339, XPA.85.287, XPA.85.336, XPA.85.337 and XPA.85.338 antibodies and their respective Sequence Identifier (SEQ ID) numbers are provided.

DETAILED DESCRIPTION

Figure 1A:
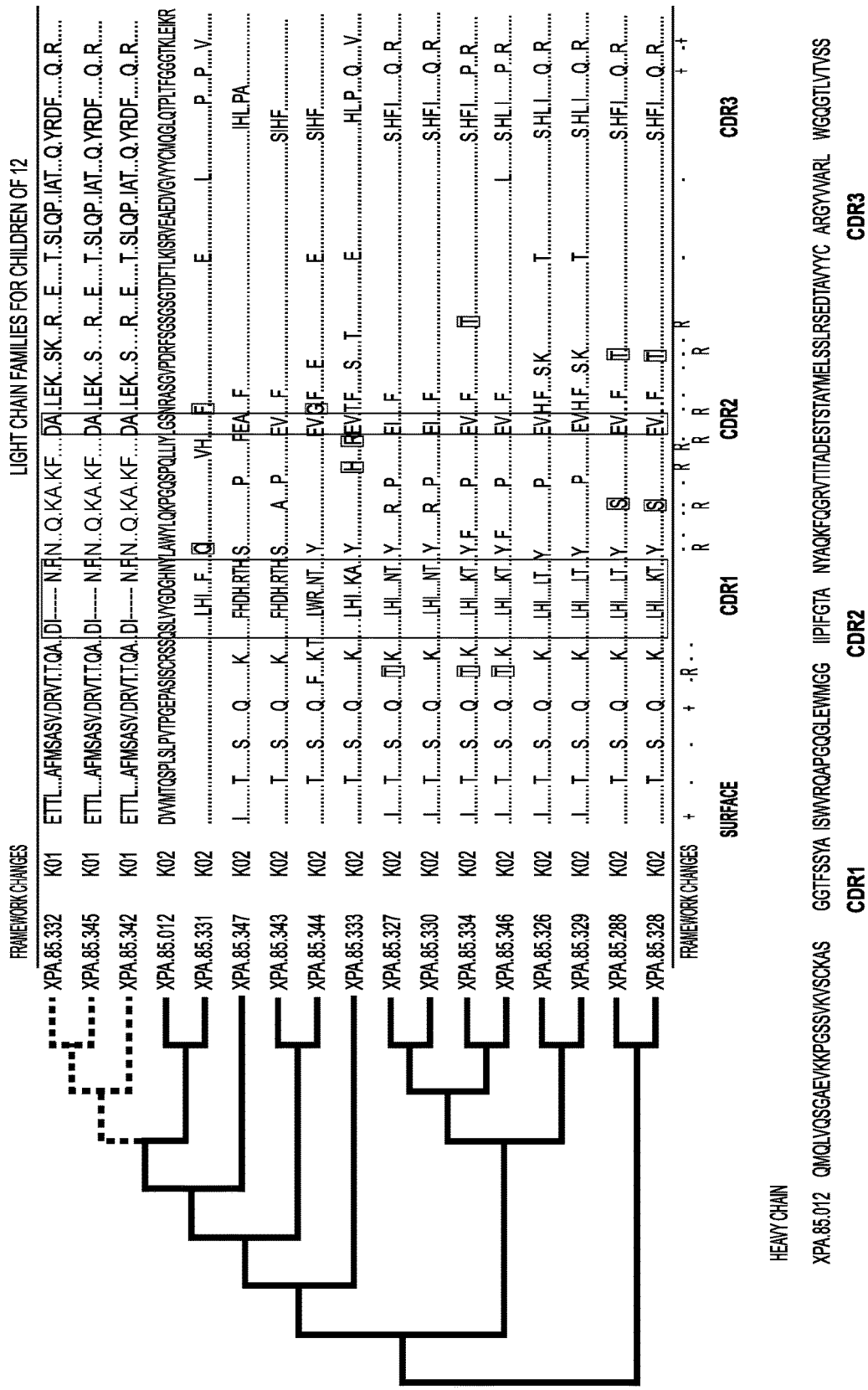

The invention provides materials, methods, and uses relating to human antibodies against PTH1R. In particular, the present disclosure provides methods of use of such antibodies in the treatment of hypercalcemia, cancer, Humoral Hypercalcemia of Malignancy (HHM), Primary Hyperparathyroidism (PHPT) and Secondary Hyperparathyroidism (SHPT) and cachexia.

The present disclosure provides molecules or agents that interact with parathyroid hormone receptor 1 (PTH1R) and inhibit or block one or more functional effects, such as for example signaling through binding partners, PTH and PTHrP. The present disclosure provides therapeutics for treating hypercalcemia, cancer, Humoral Hypercalcemia of Malignancy (HHM), or Primary Hyperparathyroidism (PHPT), Secondary Hyperparathyroidism (SHPT) and cachexia.

Definitions

The terminology used herein is for the purpose of describing particular embodiments only and is not intended to be limiting.

"cAMP" as used herein, refers to cyclic adenosine monophosphate.

"CHO" as used herein, refers to Chinese hamster ovary cells.

"CHOK1" as used herein, refers to a subclone of the parental CHO cell line, which was derived from the ovary of an adult Chinese hamster.

"ERK1/2" as used herein, refers to extracellular signal-regulated kinase.

"FLAG" as used herein, is a polypeptide protein tag that can be added to a recombinant PTH1R protein.

"HHM" as used herein, refers to humoral hypercalcemia of malignancy.

"MAPK" as used herein, refers to mitogen-activated protein kinase.

"PTH" as used herein, refers to parathyroid hormone.

"PTH1R" as used herein, refers to parathyroid hormone receptor 1. Also known as PTHR1.

"PHPT" as used herein, refers to primary hyperparathyroidism.

"PTHrP" as used herein, refers to parathyroid hormone-related protein, and is also known as parathyroid hormone-like protein (PTHLP) or parathyroid hormone-like hormone (PTHLH).

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.* 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, *J. Mol. Biol.* 196:901-917, 1987; Chothia et al., *Nature* 342:878-883, 1989.

The hypervariable region of an antibody refers to the CDR amino acid residues of an antibody which are responsible for antigen-binding. The hypervariable region comprises amino acid residues from a CDR [e.g., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (e.g., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., *J. Mol. Biol.* 196: 901-917 (1987)]. CDRs have also been identified and numbered according to ImMunoGenTics (IMGT) numbering (Lefranc, M.-P., *The Immunologist*, 7, 132-136 (1999); Lefranc, M.-P. et al., *Dev. Comp. Immunol.*, 27, 55-77 (2003), which describes the CDR locations in the light and heavy chain variable domains as follows: CDR1, approximately residues 27 to 38; CDR2, approximately residues 56 to 65; and, CDR3, approximately residues 105 to 116 (germline) or residues 105 to 117 (rearranged). In one embodiment, it is contemplated that the CDRs are located at approximately residues 26-31 (L1), 49-51 (L2) and 88-98 (L3) in the light chain variable domain and approximately residues 26-33 (H1), 50-58 (H2) and 97-111 (H3) in the heavy chain variable domain of an antibody heavy or light chain of approximately similar length to those disclosed herein. However, one of skill in the art understands that the actual location of the CDR residues may vary from the projected residues described above when the sequence of the particular antibody is identified.

Framework or FR residues are those variable domain residues other than the hypervariable region residues.

"Heavy chain variable region" as used herein refers to the region of the antibody molecule comprising at least one complementarity determining region (CDR) of said antibody heavy chain variable domain. The heavy chain variable region may contain one, two, or three CDR of said antibody heavy chain.

"Light chain variable region" as used herein refers to the region of an antibody molecule, comprising at least one complementarity determining region (CDR) of said antibody light chain variable domain. The light chain variable region may contain one, two, or three CDRs of said antibody light chain, which may be either a kappa or lambda light chain depending on the antibody.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies, Fcabs), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), an antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the reference antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of a target antigen to which it binds. Accordingly, a "neutralizing" anti-target antibody is capable of eliminating or significantly reducing a biological function, such as enzyme activity, ligand binding, or intracellular signaling.

An "allosteric antibody" or "an antibody that binds allosterically" an antibody that binds to a portion of PTH1R that is distinct from the active ligand-binding site, i.e., is noncompetitive with the natural ligands for the receptor. It is contemplated that an allosteric antibody does not appreciably change the binding affinity of PTH or PTHrP and PTH1R by more than 2-fold. In various embodiments, the antibody is a negative modulator that binds allosterically to PTH1R, optionally, wherein the antibody is capable of weakening the binding affinity between PTH or PTHrP and with PTH1R by at least about 2-fold, optionally up to 1000-fold.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an antibody that "specifically binds" is "target specific", is "specific for" target or is "immunoreactive" with the target antigen refers to an antibody or antibody substance that binds the target antigen with greater affinity than with similar antigens. In one aspect of the disclosure, the target-binding polypeptides, or fragments, variants, or derivatives thereof, will bind with a greater affinity to human target as compared to its binding affinity to target of other, i.e., non-human, species, but binding polypeptides that recognize and bind orthologs of the target are within the scope provided.

For example, a polypeptide that is an antibody or fragment thereof "specific for" its cognate antigen indicates that the variable regions of the antibodies recognize and bind the polypeptide of interest with a detectable preference (i.e., able to distinguish the polypeptide of interest from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody for use in the methods of the present disclosure are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies for use in the methods can be produced using any method known in the art.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous. Moreover, epitopes may be mimetic (mimotopes) in that they comprise a three dimensional structure that is identical to the epitope used to generate the antibody, yet comprise none or only some of the amino acid residues found in the target that were used to stimulate the antibody immune response. As used herein, a mimotope is not considered a different antigen from the epitope bound by the selective binding agent; the selective binding agent recognizes the same three-dimensional structure of the epitope and mimotope.

The term "derivative" when used in connection with antibody substances and polypeptides of the present disclosure refers to polypeptides chemically modified by such techniques as ubiquitination, conjugation to therapeutic or diagnostic agents, labeling (e.g., with radionuclides or various enzymes), covalent polymer attachment such as PEGylation (derivatization with polyethylene glycol) and insertion or substitution by chemical synthesis of amino acids such as ornithine, which do not normally occur in human proteins. Derivatives retain the binding properties of underivatized molecules of the disclosure.

The term "therapeutically effective amount" is used herein to indicate the amount of target-specific composition of the disclosure that is effective to ameliorate or lessen symptoms or signs of disease to be treated.

The terms "treat", "treated", "treating" and "treatment", as used with respect to methods herein refer to eliminating, reducing, suppressing or ameliorating, either temporarily or permanently, either partially or completely, a clinical symptom, manifestation or progression of an event, disease or condition. Such treating need not be absolute to be useful.

The present methods provides for use of target-specific antibodies, which may comprise those exemplary sequences set out herein, fragments, variants and derivatives thereof, pharmaceutical formulations including target-specific antibodies recited herein. Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody disclosed herein, if it comprises a constant domain, may be of any of these subclasses or isotypes.

The antibodies used in the present methods may exhibit binding affinity to one or more PTH1R antigens of a $K_d$ of less than or equal to about $2 \times 10^{-6}$ M, less than or equal to about $10^{-6}$ M, or less than or equal to about $10^{-7}$ M, or less than or equal to about $10^{-8}$ M, or less than or equal to about $10^{-9}$ M, $10^{-10}$ M, $10^{-11}$ M, or $10^{-12}$ M or less. In one embodiment the antibodies have a $K_d$ of at least $2 \times 10^6$ M. Such affinities may be readily determined using conventional techniques, such as by equilibrium dialysis; by using surface plasmon resonance (SPR) technology (e.g., the BIAcore 2000 instrument, using general procedures outlined by the manufacturer); by radioimmunoassay using $^{125}$I labeled target antigen; or by another method set forth in the examples below or known to the skilled artisan. The affinity data may be analyzed, for example, by the method of Scatchard et al., (Ann N.Y. Acad. Sci., 51:660, 1949).

A KinExA kinetic exclusion assay is also useful to measure the affinity of an antibody for its antigen. KinExA technology measures binding events in the solution phase, rather than binding events between a solution phase and a solid phase. In addition, while many methods for measuring binding events require at least one reactant be modified through immobilization or labeling, the KinExA method does not require modification of molecules under study. The KinExA method is believed to allow a wider range of binding constants to be measured than other methods currently available. Additional description about KinExA devices and operation for antibody characterization is available from the manufacturer (Sapidyne Instruments, Inc., Boise, Id.) and can be found in the published literature, for example U.S. Pat. No. 6,664,114 and Darling et al., "Kinetic Exclusion Assay Technology: Characterization of Molecular Interactions." Assay and Drug Development Technologies, 2004, 2:647-657.

Parathyroid Hormone Receptor 1

Parathyroid hormone receptor 1 (PTH1R) is composed of an N-terminal extracellular domain (N-ECD), seven TM helices, three ECs, three intracellular loops (ICs), and a C-terminal intracellular domain (C-ICD) (Thomas et al., 2008 *J Bone Miner Res.* 24(5): 925-934). This protein is a receptor for parathyroid hormone (PTH) and for parathyroid hormone related peptide (PTHrP). The activity of PTH1R is mediated by G proteins which activate adenylyl cyclase and also a phosphatidylinositol-calcium second messenger system. PTH1R is highly expressed in bone, kidney and growth plates, and in other tissues is expressed at lower levels at various times throughout development (e.g. skeleton, heart, and mammary glands) (Cheloha et al., 2015 *Nature Reviews Endocrinology* 11, 712-724; Shimizu et al., 2004 *JBC* 280 (3):1797-807). Both elevated PTH and PTHrP cause hypercalcemia resulting in symptoms of stones (kidney stones), bone loss (bone resorption), and psychotic overtones (depression, anxiety, cognitive dysfunction, insomnia, coma). In cancer patients, elevated PTHrP levels lead to increased osteoclastic bone resorption and hypercalcemia, a condition known as humoral hypercalcemia of malignancy (Cheloha et al., 2015 *Nature Reviews Endocrinology* 11, 712-724).

Humoral Hypercalcemia of Malignancy

Humoral Hypercalcemia of Malignancy (HHM) results from excessive production of PTHrP by certain tumors (Hoare et al., 2002 Peptides 23: 989-998). HHM is a very common complication of particular cancers such as breast cancer and multiple myeloma, and lung carcinoma (Findlay et al., 1980 *Cancer Research* 40, 1311-1317). In 2012, 2.7% of cancer patients had HHM in the US (solid tumors and hematological malignancies).

Primary Hyperparathyroidism

Disorders of the parathyroid glands include hyperparathyroidism and hypoparathyroidism. Primary Hyperparathyroidism (PHPT) occurs when the primary defect is in the parathyroid gland itself, resulting in release of excess PTH (Shimizu et al., 2005 *JBC* 280(3):1797-807). PHPT can result in dysbolism of calcium, thereby causing disorders such as hypercalcemia, hypophosphatemia, osteitis fibrosa, nephrolithiasis, and hypertension. PHPT is also the most common cause of hypercalcemia (Marcocci et al., 2011 *NEJM* 365:2389-2397). Excessive circulating levels of PTH, as occurs in cases of hyperparathyroidism, or PTHrP, as frequently occurs in cancer because of secretion by malignant tumors, produces a hypercalcemic state, which can be severely debilitating and potentially fatal (Shimizu et al., 2005 *JBC* 280(3):1797-807).

Therapy for hyperparathyroidism is usually directed at surgical removal of the offending parathyroid tissue. Patients with HHM usually cannot be cured surgically, and must be managed medically usually directed at preventing bone resorption (bisphosphonates or calcitonin) or promoting calcium excretion by the kidneys (saline diuresis) with variable effectiveness (Rosen et al. *Calcif. Tissue Int.* 61, 455-459).

PTH1R Inhibitors

PTH1R antagonists have been shown to be of benefit in cases of HHM and hyperparathyroidism (Dresner-Pollak et al. 1996 *J. Bone Miner. Res.* 11, 1061-1065; Cheloha et al., 2015 *Nature Reviews Endocrinology* 11, 712-724). The development of small-molecule ligands that mimic the actions of the agonist peptides has been a challenging goal for the PTH1R. Several inhibitors of PTH1R for use in treating HHM and PHPT are known in the art (U.S. Pat. Nos. 7,150,974; 7,985,835; 7,910,544).

PTH1R Antibodies

In various embodiments, the disclosure provides an antibody specific for PTH1R with an affinity $K_d$ of $10^{-6}$ M or less. In various embodiments, the disclosure provides an antibody specific for PTH1R with an affinity $K_d$ of $2\times10^{-6}$M or less. In exemplary embodiments, an anti-PTH1R antibody described herein binds at least with an affinity of $10^{-6}$ M, $10^{-7}$ M, $10^{-8}$ M, $10^{-9}$ M or less. In other embodiments, an antibody described herein binds to PTH1R with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% higher affinity (e.g., preferentially binds to PTH1R) compared to binding to PTH2R. In certain embodiments, the affinity is measured by surface plasmon resonance or KinExA assay.

In a related aspect, the antibody binds the N-terminal portion of PTH1R. In a further aspect, the disclosure contemplates an antibody that does not bind parathyroid hormone receptor 2 (PTH2R). In various aspects the antibody binds PTH1R on the surface of a cell. In certain aspects the antibody binds allosterically to PTH1R.

In a preferred embodiment, the antibody is a negative modulator antibody, optionally wherein the antibody is capable of weakening the binding affinity between PTH or PTHrP and with PTH1R by at least about 2-fold, optionally up to 1000-fold. In other embodiments, an antibody described herein is capable of weakening the binding affinity between PTH or PTHrP with at least 2-1000 fold, 10-100 fold, 2-fold, 5-fold, 10-fold, 25-fold, 50-fold, 100-fold, 200-fold, 300-fold, 400-fold, 500-fold, 600-fold, 700-fold, 800-fold, 900-fold or 1000-fold.

In a various embodiments, the antibody inhibits calcium flux in a cell in response to stimulation of the receptor with parathyroid hormone (PTH) or parathyroid hormone related protein (PTHrP). In related embodiments, the antibody inhibits PTH- or PTHrP-mediated cyclic adenosine monophosphate (cAMP) accumulation.

In one embodiment, the PTH1R antibody is a monoclonal antibody.

In one aspect, the disclosure provides an antibody that binds parathyroid hormone receptor 1 (PTH1R) comprising (a) a heavy chain complementary determining repeat (CDR)1 amino acid sequence set forth in FIG. 21 or SEQ ID NOs: 27, 30, 33, 36, 39, 42, 45, 48, 51, 54, 57, 60, 63, 66, 69, 72, 75, 78, 81, 84, 87, 90, 93, 96, 99, 102, or a variant thereof in which one or two amino acids have been changed; (b) a heavy chain CDR2 amino acid sequence set forth in FIG. 21 or SEQ ID NOs: 28, 31, 34, 37, 40, 43, 46, 49, 52, 55, 58, 61, 64, 67, 70, 73, 76, 79, 82, 85, 88, 91, 94, 97, 100, 103 that is from the same heavy chain variable region as (a), or a variant thereof in which one or two amino acids have been changed; and (c) a heavy chain CDR3 amino acid sequence set forth in FIG. 21 or SEQ ID NOs: 29, 32, 35, 38, 41, 44, 47, 50, 53, 56, 59, 62, 65, 68, 71, 74, 77, 80, 83, 86, 89, 92, 95, 98, 101, 104 that is from the same heavy chain variable region as (a), or a variant thereof in which one or two amino acids have been changed.

In a related aspect, the disclosure provides an antibody that binds parathyroid hormone receptor 1 (PTH1R) comprising: (a) a heavy chain CDR1 amino acid sequence set forth in FIG. 21 or SEQ ID NOs: 27, 30, 33, 36, 39, 42, 45, 48, 51, 54, 57, 60, 63, 66, 69, 72, 75, 78, 81, 84, 87, 90, 93, 96, 99, 102, or a variant thereof having at least 70% identity thereto; (b) a heavy chain CDR2 amino acid sequence set forth in SEQ ID NOs: 28, 31, 34, 37, 40, 43, 46, 49, 52, 55, 58, 61, 64, 67, 70, 73, 76, 79, 82, 85, 88, 91, 94, 97, 100, 103 that is from the same heavy chain variable region as (a), or a variant thereof having at least 70% identity thereto; and (c) a heavy chain CDR3 amino acid sequence set forth in SEQ ID NOs: 29, 32, 35, 38, 41, 44, 47, 50, 53, 56, 59, 62, 65, 68, 71, 74, 77, 80, 83, 86, 89, 92, 95, 98, 101, 104 that is from the same heavy chain variable region as (a), or a variant thereof having at least 70% identity thereto.

In a further aspect, the disclosure contemplates an antibody that binds an antibody that binds parathyroid hormone receptor 1 (PTH1R) comprising: (a) a heavy chain CDR1 amino acid sequence set forth in SEQ ID NOs: 27, 30, 33, 36, 39, 42, 45, 48, 51, 54, 57, 60, 63, 66, 69, 72, 75, 78, 81, 84, 87, 90, 93, 96, 99, 102, or a variant thereof having at least 70% identity thereto; (b) an independently selected heavy chain CDR2 amino acid sequence set forth in in FIG. 21 or SEQ ID NOs: 28, 31, 34, 37, 40, 43, 46, 49, 52, 55, 58, 61, 64, 67, 70, 73, 76, 79, 82, 85, 88, 91, 94, 97, 100, 103, or a variant thereof having at least 70% identity thereto; and (c) an independently selected heavy chain CDR3 amino acid sequence set forth in in FIG. 21 or SEQ ID NOs: 29, 32, 35, 38, 41, 44, 47, 50, 53, 56, 59, 62, 65, 68, 71, 74, 77, 80, 83, 86, 89, 92, 95, 98, 101, 104, or a variant thereof having at least 70% identity thereto.

In certain embodiments, at least two of the heavy chain CDR1, CDR2 or CDR3 amino acid sequences are set forth in FIG. 21 or SEQ ID NOs: 27-104. In a related embodiment, three of the heavy chain CDR1, CDR2 and CDR3 amino acid sequences are set forth in FIG. 21 or SEQ ID NOs: 27-104.

In some embodiments, an antibody contemplated herein comprises an amino acid sequence at least 85% identical to a heavy chain variable region amino acid sequence set forth in FIG. 21 or SEQ ID NOs: 1-26. In some embodiments, provided herein is an antibody that comprises an amino acid sequence at least 95% identical to a heavy chain variable region amino acid sequence set forth in FIG. 21 or SEQ ID NOs: 1-26.

It is further contemplated that an antibody described herein comprises a polypeptide sequence having an amino acid sequence at least 70% identical over all three HCDRs in a heavy chain variable region, the amino acid sequences of HCDR1, HCDR2 and HCDR3 set forth in FIG. 21 or SEQ ID NOs: 27-104.

In another embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to all three HCDRs in the heavy chain variable region of an antibody sequence in FIG. 21 or the CDRs set out in SEQ ID NOs: 27-104.

In a related embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to all three LCDRs in the light chain variable region of an antibody sequence in FIG. 21 or the CDRs set out in SEQ ID NOs: 131-208.

In a further embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to all six CDRs in the heavy chain and light chain variable regions of an antibody sequence in FIG. 21 or the CDRs set out in SEQ ID NOs: 27-104 and 131-208.

In certain embodiments, an antibody contemplated herein is one in which one or more heavy chain framework amino acids have been replaced with corresponding amino acid(s) from another human antibody amino acid sequence.

In one embodiment, an antibody contemplated herein further comprises any one of the light chain CDR amino acid sequences set forth in FIG. 21 or SEQ ID NOs: 131-208. In some embodiments, an antibody comprises at least two of the light chain CDR amino acid sequences set forth in FIG. 21 or SEQ ID NOs: 131-208. In other embodiments, an antibody comprises at least three of the light chain CDR amino acid sequences set forth in FIG. 21 or SEQ ID NOs: 131-208.

In another aspect, an antibody described herein comprises (a) a light chain CDR1 amino acid sequence set forth in FIG. 21 or SEQ ID NOs: 131, 134, 137, 140, 143, 146, 149, 152, 155, 158, 161, 164, 167, 170, 173, 176, 179, 182, 185, 188, 191, 194, 197, 200, 203, 206, or a variant thereof in which one or two amino acids have been changed, or a consensus sequence thereof set out in FIG. 21; (b) a light chain CDR2 amino acid sequence set forth in FIG. 21 or SEQ ID NOs: 132, 135, 138, 141, 144, 147, 150, 153, 156, 159, 162, 165, 168, 171, 174, 177, 180, 183, 186, 189, 192, 195, 198, 201, 204, 207 that is from the same light chain variable region as (a), or a variant thereof in which one or two amino acids have been changed, or a consensus sequence thereof set out in FIG. 21; and (c) a light chain CDR3 amino acid sequence set forth in FIG. 21 or SEQ ID NOs: 133, 136, 139, 142, 145, 148, 151, 154, 157, 160, 163, 166, 169, 172, 175, 178, 181, 184, 187, 190, 193, 196, 199, 202, 205, 208 that is from the same light chain variable region as (a), or a variant thereof in which one or two amino acids have been changed, or a consensus sequence thereof set out in FIG. 21.

In alternative embodiments, an antibody contemplated herein comprises: (a) a light chain CDR1 amino acid sequence set forth in FIG. 21 or SEQ ID NOs: 131, 134, 137, 140, 143, 146, 149, 152, 155, 158, 161, 164, 167, 170, 173, 176, 179, 182, 185, 188, 191, 194, 197, 200, 203, 206, or a variant thereof in which one or two amino acids have been changed; (b) an independently selected light chain CDR2 amino acid sequence set forth in FIG. 21 or SEQ ID NOs: 132, 135, 138, 141, 144, 147, 150, 153, 156, 159, 162, 165, 168, 171, 174, 177, 180, 183, 186, 189, 192, 195, 198, 201, 204, 207, or a variant thereof in which one or two amino acids have been changed; and (c) an independently selected light chain CDR3 amino acid sequence set forth in FIG. 21 or SEQ ID NOs: 133, 136, 139, 142, 145, 148, 151, 154, 157, 160, 163, 166, 169, 172, 175, 178, 181, 184, 187, 190, 193, 196, 199, 202, 205, 208, or a variant thereof in which one or two amino acids have been changed.

In certain embodiments, at least two of the light chain CDR1, CDR2 or CDR3 amino acid sequences are set forth in FIG. 21 or SEQ ID NOs: 131-208.

It is further contemplated that an antibody described herein comprises an amino acid sequence at least 70% identical to a light chain variable region amino acid sequence set forth in FIG. 21 or SEQ ID NOs: 105-130. In a related embodiment, the antibody comprises an amino acid sequence at least 85% identical to a light chain variable region amino acid sequence set forth in FIG. 21 or SEQ ID NOs: 105-130. In a further embodiment, the antibody comprises an amino acid sequence at least 95% identical to a light chain variable region amino acid sequence set forth in FIG. 21 or SEQ ID NOs: 105-130. In still another embodiment, the antibody comprises a light chain variable region amino acid sequence set forth in FIG. 21 or SEQ ID NOs: 105-130.

In a further embodiment, an antibody described herein comprises a polypeptide sequence having an amino acid sequence at least 70% identical over all three LCDRs of a light chain variable region, the amino acid sequences of LCDR1, LCDR2 and LCDR3 set forth in FIG. 21 or SEQ ID NOs: 131-208.

In certain embodiments, an antibody described herein comprises (i) an amino acid sequence at least 70% identical over all three LCDRs, of a light chain variable region, the amino acid sequences of LCDR1, LCDR2 and LCDR3 set forth in FIG. 21 or SEQ ID NOs: 131-208 and (ii) an amino acid sequence at least 70% identical over all three HCDRs of a heavy chain variable region, the amino acid sequences of HCDR1, HCDR2 and HCDR3 set forth in FIG. 21 or SEQ ID NOs: 27-104.

In another aspect, the disclosure provides an antibody that binds parathyroid hormone receptor 1 (PTH1R) comprising a light chain variable region and/or a heavy chain variable region, wherein (a) the light chain variable region comprises at least a CDR1 selected from SEQ ID NOs: 131, 134, 137, 140, 143, 146, 149, 152, 155, 158, 161, 164, 167, 170, 173, 176, 179, 182, 185, 188, 191, 194, 197, 200, 203, 206 or sequences at least 80% identical thereto, a CDR2 selected from SEQ ID NOs: 132, 135, 138, 141, 144, 147, 150, 153, 156, 159, 162, 165, 168, 171, 174, 177, 180, 183, 186, 189, 192, 195, 198, 201, 204, 207 or sequences at least 80% identical thereto, and/or a CDR3 selected from SEQ ID NOs: 133, 136, 139, 142, 145, 148, 151, 154, 157, 160, 163, 166, 169, 172, 175, 178, 181, 184, 187, 190, 193, 196, 199, 202, 205, 208 or sequences at least 80% identical thereto; and/or wherein (b) the heavy chain variable region comprises at least a CDR1 selected from SEQ ID NOs: 27, 30, 33, 36, 39, 42, 45, 48, 51, 54, 57, 60, 63, 66, 69, 72, 75, 78, 81, 84, 87, 90, 93, 96, 99, 102 or sequences at least 80% identical thereto, a CDR2 selected from SEQ ID NOs: 28, 31, 34, 37, 40, 43, 46, 49, 52, 55, 58, 61, 64, 67, 70, 73, 76, 79, 82, 85, 88, 91, 94, 97, 100, 103 or sequences at least 80% identical thereto, and/or a CDR3 selected from SEQ ID NOs: 29, 32, 35, 38, 41, 44, 47, 50, 53, 56, 59, 62, 65, 68, 71, 74, 77, 80, 83, 86, 89, 92, 95, 98, 101, 104 or sequences at least 80% identical thereto.

In a related embodiment, an antibody described herein comprises (a) a light chain variable region comprising at least a CDR1 selected from SEQ ID NO: 131, 134, 137, 140, 143, 146, 149, 152, 155, 158, 161, 164, 167, 170, 173, 176, 179, 182, 185, 188, 191, 194, 197, 200, 203, 206 or sequences at least 90% identical thereto, a CDR2 selected from SEQ ID NO: 132, 135, 138, 141, 144, 147, 150, 153, 156, 159, 162, 165, 168, 171, 174, 177, 180, 183, 186, 189, 192, 195, 198, 201, 204, 207 or sequences at least 90% identical thereto, and a CDR3 selected from SEQ ID NO: 133, 136, 139, 142, 145, 148, 151, 154, 157, 160, 163, 166, 169, 172, 175, 178, 181, 184, 187, 190, 193, 196, 199, 202, 205, 208 or sequences at least 90% identical thereto; and/or wherein (b) the heavy chain variable region comprises at least a CDR1 selected from SEQ ID NO: 27, 30, 33, 36, 39, 42, 45, 48, 51, 54, 57, 60, 63, 66, 69, 72, 75, 78, 81, 84, 87, 90, 93, 96, 99, 102 or sequences at least 90% identical thereto, a CDR2 selected from SEQ ID NO: 28, 31, 34, 37, 40, 43, 46, 49, 52, 55, 58, 61, 64, 67, 70, 73, 76, 79, 82, 85, 88, 91, 94, 97, 100, 103 or sequences at least 90% identical thereto, and a CDR3 selected from SEQ ID NO: 29, 32, 35, 38, 41, 44, 47, 50, 53, 56, 59, 62, 65, 68, 71, 74, 77, 80, 83, 86, 89, 92, 95, 98, 101, 104 or sequences at least 90% identical thereto.

In some embodiments, an antibody of the disclosure further comprises a heavy chain constant region, wherein the heavy chain constant region is a modified or unmodified IgG, IgM, IgA, IgD, IgE, a fragment thereof, or combinations thereof.

In certain embodiments, an antibody is provided in which one or more light chain framework amino acids have been replaced with corresponding amino acid(s) from another human antibody amino acid sequence, optionally wherein the framework comprises one or more of the changes set out in FIGS. 1A and 1B.

In one aspect, the antibody of the disclosure is selected from the group consisting of XPA.85.012, XPA.85.017, XPA.85.288, XPA.85.328, XPA.85.329, XPA.85.330 and XPA.85.349.

In one embodiment, an antibody described herein further comprises a human light chain constant region attached to said light chain variable region. In some embodiments, the light chain constant region is a modified or unmodified lambda light chain constant region, a kappa light chain constant region, a fragment thereof, or combinations thereof.

In another aspect, the disclosure provides an isolated nucleic acid molecule comprising a nucleotide sequence that encodes the heavy chain or light chain as described herein. In various embodiments the nucleotide sequences encoding the antibody variable regions are set out in SEQ ID NOs: 209-234 (heavy chain) and 235-260 (light chain).

In various embodiments, the nucleic acid molecule comprises a nucleotide sequence that encodes the light chain variable region amino acid sequence of any one of SEQ ID NOs: 105-130 or a fragment thereof. In one embodiment, the nucleic acid molecule comprises the light chain variable region nucleotide sequence of any one of SEQ ID NOs: 235-260, or a fragment thereof. In further embodiments, the nucleic acid molecule comprises a nucleotide sequence that encodes the heavy chain variable region amino acid sequence of any one of SEQ ID NOs: 1-26 or a fragment thereof. In one embodiment, the nucleic acid molecule comprises the heavy chain variable region nucleotide sequence of any one of SEQ ID NOs: 209-234, or a fragment thereof. Nucleic acid molecules of the disclosure further include all nucleic acid sequences, including the sequences in SEQ ID NOs: 209-260, and nucleic acid sequences comprises degenerate codons based on the diversity of the genetic code, encoding an amino acid sequence of the heavy and light chain variable regions of an antibody described herein or any HCDRs or LCDRs described herein, and encoding the CDR amino acid sequences as set out in SEQ ID NOs: 27-104 and 131-208, as well as nucleic acids that hybridize under highly stringent conditions, such as those described herein, to a nucleic acid sequence encoding an amino acid sequence of the heavy and light chain variable regions of an antibody described herein set out in SEQ ID NO: 1-26 or 105-130 or any HCDRs or LCDRs described herein as set out in SEQ ID NOs: 27-104 or 131-208.

In some embodiments, the nucleic acid molecule encodes a VL amino acid sequence that is at least 60, 65, 70, 75, 80, 85, 90, 91, 92, 93, 94, 95, 96 97, 98 or 99% identical to a VL amino acid sequence set out in SEQ ID NOs: 105-130. In a related aspect, the VL amino acid sequence is a consensus sequence. Nucleic acid molecules of the disclosure include nucleic acids that hybridize under highly stringent conditions, such as those described herein, to a nucleic acid sequence encoding the light chain variable region amino acid sequence of SEQ ID NOs: 105-130, or that has the light chain variable region nucleic acid sequence of SEQ ID NOs: 235-260. In some embodiments, the nucleic acid encodes the amino acid sequence of the heavy chain CDRs of said antibody set out in SEQ ID NO: 131-208.

It is further contemplated that a nucleic acid molecule of the disclosure comprises a nucleotide sequence that encodes the VH amino acid sequence of any one of antibodies described herein, or a fragment thereof. In some embodiments, the nucleic acid encodes the amino acid sequence of the heavy chain and/or light chain CDRs of said antibody. In some embodiments, said fragment is a contiguous fragment comprising heavy chain and/or light chain CDR1-CDR3. In one embodiment, said fragment comprises at least one, two or three of a heavy chain and/or light chain CDR1, CDR2, or CDR3 region, optionally with a different human or human consensus framework, and optionally with 1, or up to 2, or up to 3 mutations in the CDRs. CDR amino acid sequences are set out in SEQ ID NOs: 27-104 and 131-208.

In a related aspect, the nucleic acid molecule comprises a nucleotide sequence that encodes the heavy chain variable region amino acid sequence of one of heavy chain of SEQ ID NOs: 1-26, or a fragment thereof. In one embodiment, the nucleic acid molecule comprises the heavy chain variable region having a nucleotide sequence set out in SEQ ID NOs: 209-234, or a fragment thereof.

In some embodiments, the nucleic acid molecule encodes a VH amino acid sequence that is at least 70%, 75%, 80%, 85%, 90%, 95%, 96%, 97%, 98% or 99% identical to a VH amino acid sequence set out in SEQ ID NOs: 1-26. In a related aspect, the VH amino acid sequence is a consensus sequence. Nucleic acid molecules of the disclosure further include nucleic acids that hybridize under highly stringent conditions, such as those described herein, to a nucleic acid sequence encoding the heavy chain variable region amino acid sequence of SEQ ID NOs: 1-26, or that has the heavy chain variable region nucleic acid sequence of any one of SEQ ID NOs: 209-234.

It is further contemplated that the nucleic acids of the disclosure may encode a full-length light chain or heavy chain of an antibody selected from the antibodies set out in FIG. 21 wherein a full-length light chain or full-length heavy chain comprises a light chain constant region or a heavy chain constant region, respectively, light chain constant regions optionally include unmodified or modified kappa or lambda regions, and heavy constant regions include unmodified or modified constant regions of any of the classes, such as IgG1, IgG2, IgG3, IgG4, IgM, IgA, IgD, or IgE.

In one aspect, the full length variable light chain antibody comprises the amino acid sequences set out in SEQ ID NOs: 105-130. It is further contemplated that the nucleotide sequence encoding the full-length light chain encodes the amino acid sequences set out in SEQ ID NOs: 105-130 and comprises the nucleotide sequences set forth in SEQ ID NOs: 235-260.

In one aspect, the full length variable heavy chain antibody comprises the sequences in any one of SEQ ID NOs: 1-26. Further provided are nucleotide sequences that encode the full-length heavy chain variable region amino acid sequences set out in SEQ ID NOs: 1-26, and comprise the nucleotide sequences set forth in any one of SEQ ID NOs: 209-234.

It is further contemplated that antibodies of the present disclosure may be used as smaller antigen binding fragments of the antibody that are well-known in the art and described herein, as well as derivatives and modified antibodies as described herein.

Monoclonal Antibodies

Monoclonal antibody refers to an antibody obtained from a population of substantially homogeneous antibodies. Monoclonal antibodies are generally highly specific, and may be directed against a single antigenic site, in contrast to polyclonal antibody preparations that typically include different antibodies directed against the same or different determinants (epitopes). In addition to their specificity, monoclonal antibodies are advantageous in that they are synthesized by the homogeneous culture, uncontaminated by other immunoglobulins with different specificities and characteristics.

As described below, antibodies, including monoclonal, humanized, and other antibodies described herein, contemplated herein are typically generated recombinantly or through other methods of manipulating the genetic code in vitro or in vivo, and are therefore not necessarily reflective of a particular antibody that is found in nature.

Monoclonal antibodies may be made by the hybridoma method first described by Kohler et al. (*Nature*, 256:495-7, 1975) (Harlow & Lane; Antibodies: A Laboratory Manual, Cold Spring Harbor Laboratory Press: Cold Spring Harbor, N.Y. (1988); Goding, Monoclonal Antibodies: Principles and Practice, pp. 59-103 (Academic Press, 1986), or may be made by recombinant DNA methods (see, e.g., U.S. Pat. No. 4,816,567). The monoclonal antibodies may also be isolated from phage antibody libraries using the techniques described in, for example, Clackson et al., (*Nature* 352:624-628, 1991) and Marks et al., (*J. Mol. Biol.* 222:581-597, 1991). Additional methods for producing monoclonal antibodies are well-known to a person of ordinary skill in the art.

Monoclonal antibodies, such as those produced by the above methods, are suitably separated from culture medium, ascites fluid, or serum by conventional immunoglobulin purification procedures such as, for example, protein A-Sepharose, hydrophobic interaction chromatography (HIC), ion exchange chromatography, hydroxyapatite chromatography, gel electrophoresis, dialysis, and/or affinity chromatography.

It is further contemplated that antibodies of the present disclosure may be used as smaller antigen binding fragments of the antibody that are well-known in the art and described herein.

Antibody Fragments

Antibody fragments comprise a portion of an intact full length antibody, preferably an antigen binding or variable region of the intact antibody. Examples of antibody fragments include Fab, Fab', F(ab')2, Fcab, and Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; VHH containing antibodies; and other polypeptides formed from antibody fragments. See for example Holliger & Hudson, 2005 *Nat. Biotech.* 23:1126-36; Eyer & Hruska, *Veterinarni Medicina* 57: 439-513, 2012.

Papain digestion of antibodies produces two identical antigen-binding fragments, called "Fab" fragments, monovalent fragments consisting of the VL, VH, CL and CH domains each with a single antigen-binding site, and a residual "Fc" fragment, whose name reflects its ability to crystallize readily. Pepsin treatment yields a F(ab')2 fragment, a bivalent fragment comprising two Fab fragments linked by a disulfide bridge at the hinge region, that has two "Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding, resulting in a single-chain antibody (scFv), in which a VL and VH region are paired to form a monovalent molecule via a synthetic linker that enables them to be made as a single protein chain (Bird et al., *Science* 242:423-426, 1988, and Huston et al., *Proc. Natl. Acad. Sci.* USA 85:5879-5883, 1988). For a review of scFv see Pluckthun, in The Pharmacology of Monoclonal Antibodies, vol. 1 13, Rosenburg and Moore eds., Springer-Verlag, New York, pp. 269-315 (1994). An Fd fragment consists of the VH and CH1 domains.

Additional antibody fragments include a domain antibody (dAb) fragment (Ward et al., *Nature* 341:544-546, 1989) which consists of a VH domain. Diabodies are bivalent antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., *Proc. Natl. Acad. Sci. USA* 90:6444-6448, 1993, and Poljak et al., *Structure* 2:1121-1123, 1994). Diabodies can be bispecific or monospecific.

Functional heavy-chain antibodies devoid of light chains are naturally occurring in nurse sharks (Greenberg et al., *Nature* 374:168-73, 1995), wobbegong sharks (Nuttall et al., *Mol Immunol.* 38:313-26, 2001) and Camelidae (Hamers-Casterman et al., *Nature* 363: 446-8, 1993; Nguyen et al., *J. Mol. Biol.* 275: 413, 1998), such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure H2L2 (referred to as "heavy-chain antibodies" or "HCAbs"). Camelid VHH reportedly recombines with IgG2 and IgG3 constant regions that contain hinge, CH2, and CH3 domains and lack a CH1 domain (Hamers-Casterman et al., supra). For example, llama IgG1 is a conventional (H2L2) antibody isotype in which VH recombines with a constant region that contains hinge, CH1, CH2 and CH3 domains, whereas the llama IgG2 and IgG3 are heavy chain-only isotypes that lack CH1 domains and that contain no light chains. Camelid VHH domains have been found to bind to antigen with high affinity (Desmyter et al., *J. Biol. Chem.* 276:26285-90, 2001) and possess high stability in solution (Ewert et al., *Biochemistry* 41:3628-36, 2002). Classical VH-only fragments are difficult to produce in soluble form, but improvements in solubility and specific binding can be obtained when framework residues are altered to be more VHH-like. (See, e.g., Reichman, et al., *J Immunol Methods* 1999, 231:25-38). Methods for generating antibodies having camelid heavy chains are described in, for example, in U.S. Patent Publication Nos. 20050136049 and 20050037421.

The variable domain of an antibody heavy-chain, a fully functional antigen-binding fragment with a molecular mass of only 15 kDa, is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods as described in Revets et al, *Expert Opin. Biol. Ther.* 5(1):111-24 (2005).

Production of bispecific Fab-scFv ("bibody") and trispecific Fab-(scFv)(2) ("tribody") are described in Schoonjans et al. (J Immunol. 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH1 (Fd) chains, e.g., to produce a tribody two scFvs are fused to C-term of Fab while in a bibody one scFv is fused to C-term of Fab. Additional Fab-based bispecific formats are described in Wu et al., *mAbs* 7: 470-482, 2015.

A "minibody" consisting of scFv fused to CH3 via a peptide linker (hingeless) or via an IgG hinge has been described in Olafsen, et al., Protein Eng Des Sel. 17(4):315-23, 2004.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al (EMBO J 14:1542-51, 1995) and Wheeler et al. (*FASEB J.* 17:1733-5. 2003). Transbodies are cell-permeable antibodies in which a protein transduction domain (PTD) is fused with single chain variable fragment (scFv) antibodies Heng et al., (*Med Hypotheses.* 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

Thus, a variety of compositions comprising one, two, and/or three CDRs (e.g., a single CDR alone or in tandem, 2, 3, or other multiple repeats of the CDRs, or combinations of 2 or 3 CDRs alone or in tandem repeats; optionally, with a spacer amino acid sequence between the CDRs or repeats) of a heavy chain variable region or a light chain variable region of an antibody may be generated by techniques known in the art.

Chimeric and Humanized Antibodies

Because chimeric or humanized antibodies are less immunogenic in humans than the parental non-human (e.g., mouse) monoclonal antibodies, they can be used for the treatment of humans with far less risk of anaphylaxis.

Chimeric monoclonal antibodies, in which the variable Ig domains of a non-human (e.g., mouse) monoclonal antibody are fused to human constant Ig domains, can be generated using standard procedures known in the art (See Morrison et al., *Proc. Natl. Acad. Sci.* USA 81, 6841-6855 (1984); and, Boulianne et al, *Nature* 312, 643-646, (1984)).

Humanized antibodies may be achieved by a variety of methods including, for example: (1) grafting the non-human complementarity determining regions (CDRs) onto a human framework and constant region (a process referred to in the art as humanizing through "CDR grafting"), (2) transplanting the entire non-human variable domains, but "cloaking" them with a human-like surface by replacement of surface residues (a process referred to in the art as "veneering"), or, alternatively, (3) substituting human amino acids at positions determined to be unlikely to adversely affect either antigen binding or protein folding, but likely to reduce immunogenicity in a human environment (e.g., HUMAN ENGINEERING™). In the present disclosure, humanized antibodies will include both "humanized," "veneered" and "HUMAN ENGINEERED™" antibodies. These methods are disclosed in, e.g., Jones et al., *Nature* 321:522 525 (1986); Morrison et al., *Proc. Natl. Acad. Sci.*, U.S.A., 81:6851-6855 (1984); Morrison and Oi, *Adv. Immunol.*, 44:65-92 (1988); Verhoeyer et al., *Science* 239:1534-1536 (1988); Padlan, Molec. Immun. 28:489-498 (1991); Padlan, *Molec. Immunol.* 31:169-217 (1994); Studnicka et al. U.S. Pat. No. 5,766,886; Studnicka et al., (*Protein Engineering* 7: 805-814, 1994; Co et al., *J. Immunol.* 152, 2968-2976 (1994); Riechmann, et al., *Nature* 332:323-27 (1988); and Kettleborough et al., *Protein Eng.* 4:773-783 (1991) each of which is incorporated herein by reference. CDR grafting techniques are known in the field, see for example, Riechmann, et al. 1988 *Nature* 332:323-27). Additional antibody humanization methods are reviewed by Safdan et al., *Biotech. Gen. Eng. Rev.* 29: 175-86, 2013.

Human Antibodies from Transgenic Animals

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268; Green L L, *Curr Drug Discovery Technol.*, 11(1), 74-84, 2014; Lee E C et al., *Nature Biotechnology,* 32:356-363, 2014; Lee E C and Owen M, *Methods Mol Biol.,* 901:137-48, 2012).

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851 (1996)), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (Cloning Stem Cells. 4:91-102 (2002)) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TCMOUSE™ with various human antigens produces antibody responses comprising human antibodies.

See also Jakobovits et al., Proc. Natl. Acad. Sci. USA, 90:2551 (1993); Jakobovits et al., *Nature,* 362:255-258 (1993); Bruggermann et al., Year in Immunol., 7:33 (1993); and U.S. Pat. Nos. 5,591,669, 5,589,369, 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. Antibodies produced by phage technology are produced as antigen binding fragments—usually Fv or Fab fragments—in bacteria and thus lack effector functions. Effector functions can be introduced by one of two strategies: The fragments can be engineered, for example, into complete antibodies for expression in mammalian cells, or into bispecific antibody fragments with a second binding site capable of triggering an effector function.

By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the disclosure may be obtained in this way.

In another example, antibody producing cells can be extracted from non-immunized animals, RNA isolated from the extracted cells and reverse transcribed to produce cDNA, which is amplified using a primer, and inserted into a phage display vector such that antibodies are expressed on the phage. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the disclosure can be isolated by screening of a recombinant combinatorial antibody library, for example a scFv or Fab phage display library, prepared using human VL and VH cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum. Antibod. Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J. Mol. Biol.* 226:889-896; Clackson et al. (1991) *Nature* 352:624-628; Gram et al. (1992) *Proc. Natl. Acad. Sci.* USA 89:3576-3580; Garrad et al. (1991) *Bio/Technology* 9:1373-1377; Hoogenboom et al. (1991) *Nuc Acid Res* 19:4133-4137; and Barbas et al. (1991) *Proc. Natl. Acad. Sci.* USA 88:7978-7982, and Omidfar & Daneshpour, *Exp. Op. Drug Disc.* 10: 651-669, 2015.

In one embodiment, to isolate human antibodies specific for the target antigen with the desired characteristics, a human VH and VL library are screened to select for antibody fragments having the desired specificity. The antibody libraries used in this method may be scFv libraries prepared and screened as described herein and in the art (McCafferty et al., PCT Publication No. WO 92/01047, McCafferty et al., (*Nature* 348:552-554 (1990)); and Griffiths et al., (EMBO J 12:725-734 (1993)). The antibody libraries preferably are screened using target protein as the antigen.

Alternatively, the Fd fragment (VH-CH1) and light chain (VL-CL) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol,* 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); Winter, G., et al., Annu. Rev. Immunol. 12, 433-455 (1994); U.S. patent publication no. 20020004215 and WO 92/01047; U.S. patent publication no. 20030190317; and U.S. Pat. Nos. 6,054,287 and 5,877,293.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, Ike, ZJ/Z, Ff and one of the class II phages Xf, Pf1 and Pf3. The phage may be M13, or fd or a derivative thereof.

Once initial human VL and VH segments are selected, "mix and match" experiments, in which different pairings of selected VL and VH segments are screened for target binding, to select preferred VL/VH pair combinations (See, for example, Kang et al., *Proc. Natl. Acad. Sci.* 88: 11120-11123, 1991). Additionally, to further improve the quality of the antibody, the VL and VH segments of the preferred VL/VH pair(s) can be randomly mutated, preferably within the any of the CDR1, CDR2 or CDR3 region of VH and/or VL, in a process analogous to the in vivo somatic mutation process responsible for affinity maturation of antibodies during a natural immune response. This in vitro affinity maturation can be accomplished by amplifying VL and VH regions using PCR primers complementary to the VH CDR1, CDR2, and CDR3, or VL CDR1, CDR2, and CDR3, respectively, which primers have been "spiked" with a random mixture of the four nucleotide bases at certain positions such that the resultant PCR products encode VL and VH segments into which random mutations have been introduced into the VH and/or VL CDR3 regions. These randomly mutated VL and VH segments can be rescreened for binding to target antigen.

Following screening and isolation of a target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the disclosure, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (Bio/Technology, 10:779-783 (1992)).

Methods for display of peptides on the surface of yeast, microbial and mammalian cells have also been used to identify antigen specific antibodies. See, for example, U.S. Pat. Nos. 5,348,867; 5,723,287; 6,699,658; Wittrup, *Curr Op. Biotech.* 12:395-99 (2001); Lee et al., *Trends in Biotech.* 21(1) 45-52 (2003); Surgeeva et al, *Adv. Drug Deliv. Rev.* 58: 1622-54 (2006). Antibody libraries may be attached to yeast proteins, such as agglutinin, effectively mimicking the cell surface display of antibodies by B cells in the immune system.

In addition to phage display methods, antibodies may be isolated using in vitro display methods and microbial cell display, including ribosome display and mRNA display (Amstutz et al, Curr. Op. Biotech. 12: 400-05 (2001)). Selection of polypeptides using ribosome display is described in Hanes et al., (Proc. Natl Acad Sci USA, 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Amino Acid Sequence Variants

Modified polypeptide compositions comprising one, two, three, four, five, and/or six CDRs of an antibody may be generated, wherein a CDR is altered to provide increased specificity or affinity to the target molecule. Sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see e.g. Sambrook et al., Molecular Cloning: A Laboratory Manual, 2nd Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

Modifications may be made by conservative or non-conservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the disclosure are described in the art. See e.g., U.S. Pat. No. 8,569,462

As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Non-conservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Altered Glycosylation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Fc glycans influence the binding of IgG to Fc receptors and C1q, and are therefore important for IgG effector functions. Antibody variants with modified Fc glycans and altered effector function may be produced. For example, antibodies with modified terminal sugars such as sialic acids, core fucose, bisecting N-acetylglucosamine, and mannose residues may have altered binding to the FcγRIIIa receptor and altered ADCC activity. In a further example, antibodies with modified terminal galactose residues may have altered binding to C1q and altered CDC activity (Raju, Curr. Opin. Immunol. 20:471-78, 2008).

Also contemplated for use in the methods are antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. 87:614-22 (2004)). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol Immunol. 26:1113-23 (1989)). Some host cell strains, e.g. Lec13 or rat hybridoma YB2/0 cell line naturally produce antibodies with lower fucosylation levels. (Shields et al., *J Biol Chem.* 277:26733-40 (2002); Shinkawa et al., *J Biol Chem.* 278:3466-73 (2003)). An increase in the level of bisected carbohydrate, e.g. through recombinantly producing antibody in cells that overexpress GnTIII enzyme, has also been determined to increase ADCC activity (Umana et al., *Nat Biotechnol.* 17:176-80 (1999)). It has been predicted that the absence of only one of the two fucose residues may be sufficient to increase ADCC activity (Ferrara et al., Biotechnol Bioeng. 93:851-61 (2006)). Glycosylation of antibodies and methods are reviewed in Niewa and Satoh, *J. Pharmaceutical Sciences* 104:930-41, 2015.

Variants with Altered Effector Function

Other modifications of the antibodies for use in the methods are contemplated. In one aspect, it may be desirable to modify an antibody used herein with respect to effector function, for example, to enhance the effectiveness of the antibody in treating cancer. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., (J. Exp Med. 176: 1191-1195 (1992)) and Shopes, B. (J. Immunol. 148: 2918-2922 (1992)). Homodimeric antibodies with enhanced anti-tumor activity may also be prepared using heterobifunctional cross-linkers as described in Wolff et al., (Cancer Research 53: 2560-2565 (1993)). Alternatively, an antibody can be engineered which has dual Fc regions and may thereby have enhanced complement lysis and ADCC capabilities. See Stevenson et al., (Anti-Cancer Drug Design 3: 219-230 (1989)). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response.

In certain embodiments of the present disclosure, it may be desirable to use an antibody fragment, rather than an intact antibody, to increase therapeutic efficacy, for example. In this case, it may be desirable to modify the antibody fragment in order to increase its serum half-life, for example, adding molecules such as PEG or other water soluble polymers, including polysaccharide polymers, to antibody fragments to increase the half-life.

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the CL region or VL region, or both, of the antibody fragment.

Thus, antibodies of the present disclosure may comprise a human Fc portion, a human consensus Fc portion, or a variant thereof that retains the ability to interact with the Fc salvage receptor, including variants in which cysteines involved in disulfide bonding are modified or removed, and/or in which the a methionine is added at the N-terminus and/or one or more of the N-terminal 20 amino acids are removed, and/or regions that interact with complement, such as the C1q binding site, are removed, and/or the ADCC site is removed [see, e.g., Sarmay et al., *Molec. Immunol.* 29:633-9 (1992)].

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA See also Presta et al., (Biochem. Soc. Trans. 30:487-490, 2001), incorporated herein by reference in its entirety, which described several positions in the Fc region of IgG1 were found which improved binding only to specific Fc gamma receptors (R) or simultaneously improved binding to one type of Fc gamma R and reduced binding to another type. Selected IgG1 variants with improved binding to Fc gamma RIIIa were then tested in an in vitro antibody-dependent cellular cytotoxicity (ADCC) assay and showed an enhancement in ADCC when either peripheral blood mononuclear cells or natural killer cells were used.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes variants with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII U.S. Pat. No. 5,624,821, incorporated by reference herein in its entirety, reports that C1q binding activity of an murine antibody can be altered by mutating amino acid residue 318, 320 or 322 of the heavy chain and that replacing residue 297 (Asn) results in removal of lytic activity.

U.S. Patent Publication No. 20040132101, incorporated by reference herein in its entirety, describes variants with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Covalent Modifications

Antibodies comprising covalent modifications are also contemplated for use in the methods. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Other modifications include histidlyl, lysinyl arginyl, tyrosyl, glutaminyl and asparaginyl hydroxylation of proline and lysine. Methods for making such modifications are disclosed in U.S. Pat. No. 8,926,976, incorporated herein by reference, and in the art.

Carboxyl side groups (aspartyl or glutamyl) are selectively modified by reaction with carbodiimides (R-N.dbd..C.dbd.N-R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 and in Aplin and Wriston, (CRC Crit. Rev. Biochem., pp. 259-306 (1981)).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al., (*Arch. Biochem. Biophys.* 259: 52 (1987)) and by Edge et al., (Anal. Biochem. 118: 131 (1981)). Enzymatic cleavage of carbohydrate moieties on antibodies can be achieved by the use of a variety of endo- and exo-glycosidases as described by Thotakura et al., (*Meth. Enzymol.* 138: 350 (1987)).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art.
Derivatives As stated above, derivative, when used in connection with antibody substances and polypeptides, refers to polypeptides chemically modified by such techniques as ubiquitination, conjugation to therapeutic or diagnostic agents, labeling (e.g., with radionuclides or various enzymes), covalent polymer attachment such as PEGylation (derivatization with polyethylene glycol) and insertion or substitution by chemical synthesis of amino acids such as ornithine. Derivatives of the antibodies disclosed herein are also useful as therapeutic agents and may be used in the methods herein.

The conjugated moiety can be incorporated in or attached to an antibody substance either covalently, or through ionic, van der Waals or hydrogen bonds, e.g., incorporation of radioactive nucleotides, or biotinylated nucleotides that are recognized by streptavadin.

Polyethylene glycol (PEG) may be attached to the antibody substances to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the antibody substances of the disclosure via acylation or reductive alkylation through a natural or engineered reactive group on the PEG moiety (e.g., an aldehyde, amino, thiol, or ester group) to a reactive group on the antibody substance (e.g., an aldehyde, amino, or ester group). Addition of PEG moieties to antibody substances can be carried out using techniques well-known in the art. See, e.g., International Publication No. WO 96/11953 and U.S. Pat. No. 4,179,337.

Ligation of the antibody substance with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

An antibody may be administered in its "naked" or unconjugated form, or may be conjugated directly to other therapeutic or diagnostic agents, or may be conjugated indirectly to carrier polymers comprising such other therapeutic or diagnostic agents. In some embodiments the antibody is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Suitable chemotherapeutic agents include: daunomycin, doxorubicin, methotrexate, and vindesine (Rowland et al., (1986) supra). Suitable toxins include: bacterial toxins such as diphtheria toxin; plant toxins such as ricin; small molecule toxins such as geldanamycin (Mandler et al., *J. Natl. Cancer Inst.* 92(19): 1573-81 (2000); Mandler et al., *Bioorg. Med. Chem. Letters* 10:1025-1028 (2000); Mandler et al., *Bioconjugate Chem.* 13.786-91 (2002)), maytansinoids (EP 1391213; Liu et al., *Proc. Natl. Acad. Sci.* USA 93:8618-23 (1996)), auristatins (Doronina et al., *Nat. Biotech.* 21: 778-84 (2003) and calicheamicin (Lode et al., *Cancer Res.* 58:2928 (1998); Hinman et al., *Cancer Res.* 53:3336-3342 (1993)). Antibody-Drug Conjugates and methods are reviewed in Ducry L, *mAbs.* 6(1), 2014 and Shen W C, AAPS., 17: 3-7 (2015).

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)).

Conjugation of antibody moieties is described in U.S. Pat. No. 6,306,393. General techniques are also described in Shih et al., Int. J. Cancer 41:832-839 (1988); Shih et al., *Int. J. Cancer* 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate. Examples of agents to which the antibody can be conjugated include any of the cytotoxic or chemotherapeutic agents described herein.

Alternatively, conjugated antibodies can be prepared by directly conjugating an antibody component with a therapeutic agent. The general procedure is analogous to the indirect method of conjugation except that a therapeutic agent is directly attached to an oxidized antibody component. For example, a carbohydrate moiety of an antibody can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., *Int. J. Cancer* 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Antibody Fusion Proteins

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., *Nature* 339:394 (1989), Brinkmann et al., *Proc. Nat'l Acad. Sci. USA* 88:8616 (1991), Batra et al., *Proc. Nat'l Acad. Sci. USA* 89:5867 (1992), Friedman et al., *J. Immunol.* 150:3054 (1993), Wels et al., *Int. J. Can.* 60:137 (1995), Fominaya et al., *J. Biol. Chem.* 271:10560 (1996), Kuan et al., *Biochemistry* 35:2872 (1996), and Schmidt et al., *Int. J. Can.* 65:538 (1996). Antibody-toxin fusion proteins containing a diphtheria toxin moiety have been described by Kreitman et al., *Leukemia* 7:553 (1993), Nicholls et al., *J. Biol. Chem.* 268:5302 (1993), Thompson et al., *J. Biol. Chem.* 270:28037 (1995), and Vallera et al., *Blood* 88:2342 (1996). Deonarain et al., *Tumor Targeting* 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., *Proc. Nat'l Acad. Sci. USA* 91:8945 (1994), reported an antibody-toxin fusion protein comprising Staphylococcal enterotoxin-A.

Illustrative of toxins which are suitably employed in the preparation of such fusion proteins are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, C A—A Cancer Journal for Clinicians 44:43 (1994). Other suitable toxins are known to those of skill in the art.

Antibodies of the present disclosure may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful in the present disclosure include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as α-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the disclosure into free active drugs (See, e.g., Massey, *Nature* 328: 457-458 (1987). Antibody-abzyme conjugates can be prepared as described herein for delivery of the abzyme to a tumor cell population.

The enzymes above can be covalently bound to the antibodies by techniques well known in the art such as the use of the heterobifunctional crosslinking reagents discussed above. Alternatively, fusion proteins comprising at least the antigen binding region of an antibody of the disclosure linked to at least a functionally active portion of an enzyme of the disclosure can be constructed using recombinant DNA techniques well known in the art (See, e.g., Neuberger et al., *Nature* 312:604-608 (1984)).

Recombinant Production of Antibodies

DNA encoding an antibody described herein may be isolated and sequenced using conventional procedures (e.g., by using oligonucleotide probes that are capable of binding specifically to genes encoding the heavy and light chains of the antibodies). Usually this requires cloning the DNA or, preferably, mRNA (i.e., cDNA) encoding the antibodies. Cloning and sequencing is carried out using standard techniques, such as for example polymerase chain reaction (PCR), (see, e.g., Sambrook et al. (1989) Molecular Cloning: A Laboratory Guide, Vols 1-3, Cold Spring Harbor Press; Ausubel, et al. (Eds.), Protocols in Molecular Biology, John Wiley & Sons (1994)), which are incorporated herein by reference).

Sequencing is carried out using standard techniques (see, e.g., Sambrook et al. (1989) Molecular Cloning: A Laboratory Guide, Vols 1-3, Cold Spring Harbor Press, and Sanger, F. et al. (1977) *Proc. Natl. Acad. Sci.* USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

In an alternative embodiment, the amino acid sequence of an immunoglobulin of interest may be determined by direct protein sequencing. Suitable encoding nucleotide sequences can be designed according to a universal codon table.

For recombinant production of the antibodies, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence, which are known and described in the art.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, petunia, tomato, tobacco, lemna, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/−DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, (Graham et al., *J. Gen Virol.* 36: 59, 1977); baby hamster kidney cells (BHK, ATCC CCL 10); mouse sertoli cells (TM4, Mather, (*Biol. Reprod.* 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y Acad. Sci.* 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind target.

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (*Science* 240:1041-43, 1988; *ICSU Short Reports* 10:105 (1990); and *Proc. Natl. Acad. Sci. USA* 90:457-461 (1993) describe a procedure for isolating antibodies which are secreted to the periplasmic space of *E. coli*. See also, (Carter et al., *Bio/Technology* 10:163-167 (1992).

Alternatively, the antibody can be synthesized in a cell-free system using prokaryotic or eukaryotic in vitro translation (see Stech and Kubick, Antibodies 4:12-33, 2015).

The antibody composition can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13, 1983). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE® chromatography on an anion or cation exchange resin (such as a polyaspartic acid column), chromatofocusing, SDS-PAGE, and ammonium sulfate precipitation are also available depending on the antibody to be recovered.

Screening Methods

Effective therapeutics depend on identifying efficacious agents devoid of significant toxicity. Antibodies may be screened for binding affinity by methods known in the art. For example, gel-shift assays, Western blots, radiolabeled competition assay, co-fractionation by chromatography, coprecipitation, cross linking, ELISA, surface plasmon resonance, KinExA and the like may be used, which are described in, for example, Current Protocols in Molecular Biology (1999) John Wiley & Sons, NY, which is incorporated herein by reference in its entirety.

Methods for assessing neutralizing biological activity of anti-PTH1R compounds are known in the art. See, e.g., International Patent application WO 2004073587; Haramoto et al., 2007 *Oral Dis.* 13(1):23-31.

Additional methods for assessing the biological activity and neutralization of PTH1R (e.g., by PTH1R antibodies) are known in the art. For example, neutralization can be measured by neutralization assays and expressed as an IC50 value. The IC50 value can be calculated for a given molecule by determining the concentration of molecule needed to elicit half inhibition of the maximum biological response of a second molecule or cell activity. The lower the IC50, the greater the potency of the molecule to inhibit the desired protein activity.

Combination Therapy

A PTH1R antibody of the present disclosure may be administered with a second agent and the combination may be useful to treat a disease or disorder as described herein. In the case of the use of antibodies to PTH1R, if more than one PTH1R antibody is effective at binding to respective target antigen, it is contemplated that two or more antibodies to different epitopes of the target antigen may be mixed such that the combination of antibodies provides still further improved efficacy against a condition or disorder to be treated with inhibitors of PTH1R. Compositions comprising one or more antibody of the invention may be administered to persons or mammals suffering from, or predisposed to suffer from, a condition or disorder associated with the target polypeptide PTH1R or that will be improved by blocking the activity of PTH or PTHrP through PTH1R.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Alternatively, the second agent may be other therapeutic agents, such as cytokines, growth factors, inhibitors and antibodies to other target antigens.

It is contemplated the therapeutic agents of the present disclosure may be given simultaneously, in the same formulation. It is further contemplated that the agents are administered in a separate formulation and administered concurrently, with concurrently referring to agents given within 30 minutes of each other. It is further contemplated that a second agent may be given simultaneously.

In another aspect, an antibody to PTH1R is administered prior to administration of the other composition. Prior administration refers to administration of an antibody within the range of one week prior to treatment with the other agent, up to 30 minutes before administration of the other agent. It is further contemplated that an agent is administered subsequent to administration of another composition or agent. Subsequent administration is meant to describe administration from 30 minutes after antibody treatment up to one week after antibody administration. It is further contemplated that a second agent maybe administered in this manner prior, or subsequent to, administration of the PTH1R antibody.

It is further contemplated that other adjunct therapies may be administered, where appropriate. For example, the patient may also be administered surgical therapy, chemotherapy, a cytotoxic agent, photodynamic therapy or radiation therapy where appropriate.

It is further contemplated that when the therapeutic agents herein are administered in combination with a second agent, such as for example, wherein the second agent is a cytokine or growth factor, or a chemotherapeutic agent, the administration also includes use of a radiotherapeutic agent or radiation therapy. The radiation therapy administered in combination with an antibody composition is administered as determined by the treating physician, and at doses typically given to patients being treated for cancer.

A cytotoxic agent refers to a substance that inhibits or prevents the function of cells and/or causes destruction of cells. The term is intended to include radioactive isotopes (e.g., I131, I125, Y90 and Re186), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the disclosure.

In one embodiment the second agent is denosumab (Xgeva®, Prolia®). In other embodiments the second agent is a bisphosphonate (e.g. zoledronic acid). In other embodiments the second agent is a calcitonin.

Chemotherapeutic and other agents contemplated for use with the antibodies of the present disclosure include, but are not limited to those listed in Table 1:

TABLE 1

Chemotherapeutic and other agents contemplated for use with the antibodies of the present disclosure

| | |
|---|---|
| Alkylating agents | Natural products |
| Nitrogen mustards | Antimitotic drugs |
| mechlorethamine | Taxanes |
| cyclophosphamide | paclitaxel |
| ifosfamide | Vinca alkaloids |
| melphalan | vinblastine (VLB) |
| chlorambucil | vincristine |
| Nitrosoureas | vinorelbine |
| carmustine (BCNU) | Taxotere ® (docetaxel) |
| lomustine (CCNU) | estramustine |
| semustine (methyl-CCNU) | estramustine phosphate |
| Ethylenimine/Methyl-melamine | Epipodophylotoxins |
| thriethylenemelamine (TEM) | etoposide |
| triethylene thiophosphoramide | teniposide |
| (thiotepa) | Antibiotics |
| hexamethylmelamine | actimomycin D |
| (HMM, altretamine) | daunomycin (rubido-mycin) |
| Alkyl sulfonates | doxorubicin (adria-mycin) |
| busulfan | mitoxantroneidarubicin |
| Triazines | bleomycin |
| dacarbazine (DTIC) | splicamycin (mithramycin) |
| Antimetabolites | mitomycinC |
| Folic Acid analogs | dactinomycin |
| methotrexate | aphidicolin |
| Trimetrexate | Enzymes |
| Pemetrexed | L-asparaginase |
| (Multi-targeted antifolate) | L-arginase |
| Pyrimidine analogs | Radiosensitizers |
| 5-fluorouracil | metronidazole |
| fluorodeoxyuridine | misonidazole |
| gemcitabine | desmethylmisonidazole |
| cytosine arabinoside | pimonidazole |
| (AraC, cytarabine) | etanidazole |

TABLE 1-continued

Chemotherapeutic and other agents contemplated for use with the antibodies of the present disclosure

| | |
|---|---|
| 5-azacytidine | nimorazole |
| 2,2'-difluorodeoxy-cytidine | RSU 1069 |
| Purine analogs | EO9 |
| 6-mercaptopurine | RB 6145 |
| 6-thioguanine | SR4233 |
| azathioprine | nicotinamide |
| 2'-deoxycoformycin | 5-bromodeozyuridine |
| (pentostatin) | 5-iododeoxyuridine |
| erythrohydroxynonyl-adenine | bromodeoxycytidine |
| (EHNA) | Miscellaneous agents |
| fludarabine phosphate | bisphosphonates |
| 2-chlorodeoxyadenosine | RANKL inhibitor |
| (cladribine, 2-CdA) | denosumab |
| Type I Topoisomerase Inhibitors | Platinum coordination |
| camptothecin | complexes |
| topotecan | cisplatin |
| irinotecan | carboplatin |
| Biological response modifiers | oxaliplatin |
| G-CSF | nthracenedione |
| GM-CSF | mitoxantrone |
| Differentiation Agents | Substituted urea |
| retinoic acid derivatives | hydroxyurea |
| Hormones and antagonists | Methylhydrazine derivatives |
| Adrenocorticosteroids/antagonists | N-methylhydrazine (MIH) |
| calcitonin | procarbazine |
| prednisone and equiv-alents | Adrenocortical suppressant |
| dexamethasone | mitotane (o,p'- DDD) |
| ainoglutethimide | ainoglutethimide |
| Progestins | Cytokines |
| hydroxyprogesterone caproate | interferon (α, β, γ) |
| medroxyprogesterone acetate | interleukin-2 |
| megestrol acetate | Photosensitizers |
| Estrogens | hematoporphyrin derivatives |
| diethylstilbestrol | Photofrin ® |
| ethynyl estradiol/equivalents | benzoporphyrin derivatives |
| Antiestrogen | Npe6 |
| tamoxifen | tin etioporphyrin (SnET2) |
| Androgens | pheoboride-a |
| testosterone propionate | bacteriochlorophyll-a |
| fluoxymesterone/equivalents | naphthalocyanines |
| Antiandrogens | phthalocyanines |
| flutamide | zinc phthalocyanines |
| gonadotropin-releasing | Radiation |
| hormone analogs | X-ray |
| leuprolide | ultraviolet light |
| Nonsteroidal antiandrogens | gamma radiation |
| flutamide | visible light |
| | infrared radiation |
| | microwave radiation |

Treatment of Disorders

In another embodiment, any of the types of antibodies described herein may be used in the methods. In exemplary embodiments, the target specific antibody is a human, chimeric or humanized antibody. In another exemplary embodiment, the target is human and the patient is a human patient. Alternatively, the patient may be a mammal that expresses a target protein that target specific antibody cross-reacts with. The antibody may be administered to a non-human mammal expressing a target protein with which the antibody cross-reacts (e.g. a primate) for veterinary purposes or as an animal model of human disease.

In one embodiment, the disclosure provides a method for treating hypercalcemia associated with increased PTH or PTHrP protein expression comprising the step of administering to a subject in need thereof a therapeutically effective amount of a PTH1R antibody or a pharmaceutical composition contemplated herein.

In another embodiment, the disclosure provides a method for treating a disease, condition or disorder associated with increased parathyroid hormone expression, increased parathyroid hormone related protein expression or increased PTH1R expression comprising the step of administering to a subject in need thereof a therapeutically effective amount of an antibody or a pharmaceutical composition contemplated herein.

In another embodiment, the disclosure provides a method for treating a disease, condition or disorder selected from the group consisting of cancer, PTH- or PTHrP-induced hypercalcemia, Humoral Hypercalcemia of Malignancy (HHM), familial hypocalciuric hypercalcemia, tuberculosis, sarcoidosis, Primary Hyperparathyroidism (PHPT), Secondary Hyperparathyroidism (SHPT) and cachexia.

In various embodiments, administering to a subject in need thereof a therapeutically effective amount of an antibody or a pharmaceutical composition contemplated herein ameliorates one or more symptoms of hypercalcemia.

In various embodiments, administering to a subject in need thereof a therapeutically effective amount of an antibody or a pharmaceutical composition contemplated herein ameliorates one or more symptoms include wasting syndrome in PTHrP induced HHM, extension of HHM survival due to reduced hypercalcemia and/or wasting syndrome. PTHrP and PTH1R have been implicated in breast cancer and gastric cancer progression (Hoey et al., 2003 Br J Cancer. 88(4): 567-573; Ito et al., 1997 J Gastroenterol. 32(3):396-400). Furthermore overexpression of PTHrP and PTH1R in breast tumor cells has been shown to promote the growth of such cells in skeletal metastases by stimulating their proliferation in an autocrine fashion (Hoey et al., 2003 Br J Cancer. 88(4): 567-573).

In one embodiment, the disclosure provides a method for treating cancer or preventing the recurrence of cancer comprising administering to a subject in need thereof a therapeutically effective amount of a PTH1R antibody or a pharmaceutical composition as contemplated herein.

Exemplary conditions or disorders that can be treated with antibodies of the present disclosure include cancers, such as a cancer selected from the group consisting of bone cancer, lung cancer, hepatocellular cancer, pancreatic cancer, kidney cancer, fibrotic cancer, breast cancer, myeloma, squamous cell carcinoma, colorectal cancer and prostate cancer. In related aspects the cancer is metastatic. In a related aspect, the metastasis includes metastasis to the bone or skeletal tissues, liver, lung, kidney or pancreas. It is contemplated that the methods herein reduce tumor size or tumor burden in the subject, and/or reduce metastasis in the subject. In various embodiments, the methods reduce the tumor size by 10%, 20%, 30% or more. In various embodiments, the methods reduce tumor size by 10%, 15%, 20%, 25%, 30%, 35%, 40%, 45%, 50%, 55%, 60%, 65%, 70%, 75%, 80%, 85%, 90%, 95% or 100%.

In one embodiment, treatment of cancer in an animal in need of said treatment, comprises administering to the animal an effective amount of an antibody of PTH1R or a composition comprising an antibody described herein.

The conditions treatable by methods of the present disclosure preferably occur in mammals. Mammals include, for example, humans and other primates, as well as pet or companion animals such as dogs and cats, laboratory animals such as rats, mice and rabbits, and farm animals such as horses, pigs, sheep, and cattle.

Formulation of Pharmaceutical Compositions

To administer antibodies of the present disclosure to human or test animals, it is preferable to formulate the antibodies in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds may form solvates with water or common organic solvents. Such solvates are contemplated as well.

The antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the antibodies may be suitably administered by pulse infusion, particularly with declining doses of the antibody. Preferably the dosing is given by injections, most preferably intravenous, intra muscular or subcutaneous injections, depending in part on whether the administration is brief or chronic. Other administration methods are contemplated, including topical, particularly transdermal, transmucosal, rectal, oral or local administration e.g. through a catheter placed close to the desired site.

Pharmaceutical compositions of the present disclosure containing the antibodies described herein as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present disclosure.

Formulation of the pharmaceutical composition will vary according to the route of administration selected (e.g., solution, emulsion). An appropriate composition comprising the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the antibodies are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

The antibodies described herein can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

The PTH1R antibodies described herein can be prepared and administered as a co-formulation with one or more additional antibodies. In one aspect, at least two of the antibodies recognize and bind different antigens. In another aspect, at least two of the plurality of antibodies can specifically recognize and bind different epitopes of the same antigen.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of antibody is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (J. Pharm. Sci., 85:1282-1285 (1996)) and Oliyai and Stella (Ann. Rev. Pharmacol. Toxicol., 32:521-544 (1993)).

Antibody compositions contemplated for use to inhibit target activity, including binding of the target to its cognate receptor or ligand, target-mediated signaling, and the like. In particular, the compositions exhibit inhibitory properties at concentrations that are substantially free of side effects, and are therefore useful for extended treatment protocols. For example, co-administration of an antibody composition with another, more toxic, cytotoxic agent can achieve beneficial inhibition of a condition or disorder being treated, while effectively reducing the toxic side effects in the patient.

In addition, the properties of hydrophilicity and hydrophobicity of the compositions contemplated for use in the present disclosure are well balanced, thereby enhancing their utility for both in vitro and especially in vivo uses, while other compositions lacking such balance are of substantially less utility. Specifically, compositions contemplated for use in the disclosure have an appropriate degree of solubility in aqueous media which permits absorption and bioavailability in the body, while also having a degree of solubility in lipids which permits the compounds to traverse the cell membrane to a putative site of action. Thus, antibody compositions contemplated are maximally effective when they can be delivered to the site of target antigen activity.

Administration and Dosing

In one aspect, methods of the present disclosure include a step of administering a pharmaceutical composition. In certain embodiments, the pharmaceutical composition is a sterile composition.

Methods of the present disclosure are performed using any medically-accepted means for introducing therapeutics directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near or at site of the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, once per week, once every 2 weeks, twice per month, once monthly, once every two months, or once every three months, or at a longer interval.

The amounts of antibody composition in a given dosage may vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveals optimal dosages for particular disease states and patient populations.

Also contemplated in the present disclosure, the amounts of PTH1R antibody in a given dosage may vary according to the size of the individual to whom the therapy is being administered as well as the characteristics of the disorder being treated. The antibody compositions can be administered in a dose range of 0.1 to 15 mg, twice weekly as an intravenous infusion over 30-60 minutes every 1, 2 or 4 weeks until disease progression or unacceptable toxicity. In various embodiments, the antibody compositions can be administered intravenously, subcutaneously or intramuscularly, in a dose range of 0.3-30 mg/kg twice weekly or every 1, 2 or 4 weeks. In various embodiments, the dose can be 1, 2, 3, 4, 5, 6, 7, 8, 9, 10 or 30 mg/kg. In various embodiments, the antibody compositions can be administered intravenously in a dose range of 0.3-3 mg/kg, 1 to 6 mg/kg or 2 to 6 mg/kg twice weekly or every 1, 2 or 4 weeks. Alternatively, the antibody compositions can be administered intravenously, subcutaneously or intramuscularly in a dose range of 0.5-5 mg/kg twice weekly or every 1, 2 or 4 weeks.

It will also be apparent that dosing may be modified if additional therapeutics are administered in combination with therapeutics of the disclosure.

Kits

As an additional aspect, the disclosure includes kits which comprise one or more compounds or compositions packaged in a manner which facilitates their use to practice methods of the disclosure. In one embodiment, such a kit includes a compound or composition described herein, packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the antibody composition.

Additional aspects and details of the disclosure will be apparent from the following examples, which are intended to be illustrative rather than limiting.

EXAMPLES

Example 1: Discovery of Antibodies that Bind to PTH1R

A. Phage Panning and Rescue

In order to identify antibodies that bind the PTH1R, three rounds of cell panning using naïve scFv or Fab antibody phage libraries (Schwimmer et al. 2013 *J. Immun. Meth.* 391(1-2):60-71) were performed. Kappa and lambda chain libraries were panned together. For the first round of phage panning, about 50× library equivalents were blocked at RT for 1 hr in 5% FCS/PBS in the presence of the FLAG peptide (Sigma Aldrich). Non-specific binders to CHO-K1 (parental cells) were then deselected against $5 \times 10^7$ CHO-K1 cells that did not express the PTH1R receptor. Subsequently, deselected cells were allowed to bind to $1.5 \times 10^8$ CHO-PTH1R cells expressing the full-length human receptor in the presence of the FLAG peptide for 2 hr at 37° C. The receptor-bound phage were then washed with 5% FCS-PBS and then with PBS. The duration of washes was increased in each successive round of panning in order to elevate the stringency of selection. Bound phage was then eluted via the addition of 100 mM Trimethylamine (TEA) elution buffer (Merck-TX1200-5) and neutralized with an equal volume of 1 M Tris-HCl, pH 7.4. Eluted and neutralized phage was then used to infect TG1 bacterial cells expressing the cyt-FkpA chaperone variant (Levy et al. 2013 *J. Immun. Meth.* 394(1-2):10-21) at OD600 ~0.5. Infection was performed at 37° C. for 1 hr with shaking at 100 rpm. Cells were then plated on 2YT agarose plates that were supplemented with 100 µg/mL carbenicillin, 34 µg/ml chloramphenicol and 2% glucose and incubated overnight at 30° C.

In order to rescue phage for the next round of panning, 50×-100× output was superinfected with the helper phage M13K07 (New England Biolabs, MA). Cells were harvested and allowed to grow at 37° C., starting from OD600-0.05. When the OD600 nm ~0.5, cells were infected with M13K07 at multiplicity of infection (MOI) ~20, at 37° C. for 1 hour with rotation at 100 rpm. Following infection, cells were pelleted and transferred to new 2YT media supplemented with 50 µg/mL kanamycin, 100 µg/mL carbenicillin and 0.2% arabinose in order to allow the expression of the chaperone cytFkpA. Following overnight growth of bacterial cultures at 25° C., phage was harvested following centrifugation at 4° C. and then PEG-precipitated to be used as input for the next round of panning. Selection enrichment was monitored by the amount of phage input used for each panning round versus the resulting phage output titer.

Alternatively, rescued phage resulting from the second round of panning, were allowed to bind to CHO cells engineered to express human PTH1R. Phage bound to CHO-PTH1R cells were then isolated using cell sorting methods based on those described by Siegel et al., 2002 *Methods Mol. Biol.* 178: 219-226.

B. Screening

Library panning outputs were screened by FACS. Plates containing periplasmic bacterial extracts of selected clones were prepared using standard protocols. They were then screened by FACS for binding to CHO cells expressing human PTH1R with a FLAG tag on the N-terminus, versus binding to parental CHO-K1 cells. An anti-FLAG tag monoclonal antibody was used as a positive control to detect PTH1R-expressing cells.

Antibody fragments binding PTH1R were then reformatted into human IgG1, IgG2 or IgG4 antibodies. The variable heavy (VH) and light (VL) chains of the selected scFv or Fab fragments were amplified by PCR, cloned into plasmid vectors containing the antibody constant region sequences, and transiently transfected into 293E cells using standard methods to generate IgG2 antibodies for further characterization. Reformatted antibodies were tested for PTH1R binding and in functional assays, as described below.

Example 2: Affinity Maturation

Based on initial binding and functional characterization studies, two antibodies, XPA.85.012 and XPA.85.017 were selected for affinity maturation using light chain shuffling.

A. Selection of the XPA.85.012 Affinity-Matured Variants
Light Chain Library Construction The VH region of XPA.85.012 was cloned into plasmid DNA containing two different kappa chain Fab libraries. The resulting library sizes for the resulting libraries, XPA85.012.010 and XPA85.012.050, were $7.6 \times 10^8$ cfu and $2.1 \times 10^9$ cfu respectively. Each library was rescued (50× library equivalents) using TG1+cytFkpA cells (Levy et al. 2013 *J. Immun. Meth.* 394(1-2):10-21).

Phage Panning and Rescue

Recombinant N-terminal extracellular domain of the human PTH1R receptor (N-ECD PTH1R, R&D Systems, MN) was biotinylated with EZ-Link NHS-PEG4-Biotin (Thermo Scientific, Rockford, Ill.) using the manufacturer's protocol and 20-fold molar excess of biotin reagent. Non-reactive NHS-PEG4-Biotin was removed by spinning twice with Zeba™ Spin Desalting columns (7 K MWCO) (Thermo Scientific, Rockford, Ill.). The biotinylation of N-ECD PTH1R was confirmed by surface plasmon resonance (SPR).

For the first round of phage panning, 100× library equivalents of XPA85.012.010 and XPA85.012.050 ($7.6 \times 10^{10}$ cfu and $2.1 \times 10^{11}$ cfu, respectively) were blocked on ice for 1 hr in 1 mL of 3% BSA/PBS. Binders to streptavidin were deselected from blocked phage by adding blocked phage to streptavidin-coated magnetic beads (Dynabeads™ M-280 Streptavidin, Thermo Fisher Scientific, Carlsbad, Calif.) and incubated with rotation for 45 minutes at room temperature. The deselection step was repeated once more. A magnet was used to separate beads from phage. Concurrent to the deselection steps, 40 pmoles of biotinylated N-ECD PTH1R was allowed to bind to streptavidin-coated magnetic beads by incubating at room temperature with rotation for 45 minutes. Selection was performed by adding deselected phage to biotinylated N-ECD PTH1R bound to magnetic streptavidin beads and incubated with rotation for 1.5 hours. After selection, unbound phage was removed by three 5 minute washes with 3% BSA/PBS+0.1% Tween-20, followed by three 5 minute washes with 3% BSA/PBS and one quick wash with PBS. Bound phage was eluted from beads after the final wash step by the addition of 100 mM TEA with rotation at room temperature for 20 minutes. Eluted phage was neutralized with the addition of equal volume 1 M Tris-HCl, pH 7.4 and beads were neutralized with the addition of 1 mL 1 M Tris-HCl, pH 7.4. Eluted and bead-bound neutralized phage were used separately to infect log growing TG1+cytFkpA bacterial cells (OD600 ~0.5). Infection was at 37° C. for 30 min without shaking, followed by 30 min additional incubation at 37° C. with shaking at 100 rpm. Cells were plated on 2YT media supplemented with 100 µg/mL carbenicillin, 34 µg/mL chloroamphenicol and 2% glucose (2YTCCG) agar bioassay plates and incubated overnight at 30° C. to allow for overnight lawn growth. All plates were scraped and cells were combined to make bacterial glycerol stocks.

In preparation for use as input for the next round, 100× of previous round output was rescued by superinfection using M13K07 helper phage (New England Biolabs, Carlsbad, Calif.). This was done by inoculating 2YTCCG media with cells scraped from previous panning round output. OD600 nm was measured for starting culture and adjusted to reflect a starting OD600 nm of ~0.05. Cells were grown at 37° C. with shaking until cells reached log-growing phase of OD600 nm ~0.5. Cells were infected with M13K07 helper phage at a multiplicity of infection (MOI)=~20, at 37° C. for 30 min without shaking, followed by an additional 30 min incubation at 37° C. with shaking at 100 rpm. After infection at 37° C., cells were pelleted and transferred to new 2YT media supplemented with 25 µg/mL kanamycin, 100 µg/mL carbenicillin and 0.2% L-arabinose. Cultures were grown overnight at 25° C. Phage was separated from cells and debris by centrifugation and resulting supernatant was recovered and PEG-6000/NaCl precipitated. Selection enrichment was monitored by the amount of input used for each panning round and the resulting phage output titer.

For the second and third panning rounds, the same solution phase protocols followed in round one were used with the following exceptions. Phage input amount used in panning round two were ~$1.0 \times 10^{10}$ cfu and for round three ~$4.0 \times 10^8$ to $5 \times 10^{10}$ cfu. For round two, 10 pmoles of biotinylated antigen was used in selection, and for round three, 1.0 and 0.4 pmoles of biotinylated antigen was used. In round two, the wash conditions were five 5 minute washes with 3% BSA/PBS+0.1% Tween-20, followed by five 5 minute washes with 3% BSA/PBS and one quick wash with PBS. In round three, two wash conditions were implemented using the Kingfisher instrument (Thermo Fisher Scientific) to wash unbound phage from beads after selections. In the first wash condition, the Kingfisher was programmed to wash beads 8 times with 3% BSA/PBS-0.1% Tween-20 for 4 minutes followed 8 times with 3% BSA/PBS for 4 minutes ending with a 1 ml PBS wash. Bound phage were collected using the magnet and eluted as previously mentioned with eluted and bead bound phage kept separate for TG1+cytFpKA infections, bacterial glycerol stocks and the picking of single clones. In the second wash condition, the Kingfisher was programmed to wash beads 5 times with 3% BSA/PBS-0.1% Tween-20 for 4 minutes followed 5 times with 3% BSA/PBS for 4 minutes ending with a 1 ml 1% BSA/PBS wash at 4° C. with rotation overnight followed by one quick PBS wash. Bound phage were collected using the magnet and eluted as previously mentioned with eluted and bead bound phage kept separate for TG1+cytFkpA infections, bacterial glycerol stocks and the picking of single clones.

B. Selection of the XPA.85.017 Affinity-Matured Variants
Light Chain Library Construction The VH region of XPA.85.017 was cloned into plasmid DNA containing two different lambda chain Fab libraries. The resulting library sizes for the resulting libraries, XPA.85.017.010 and XPA.85.017.031, were $8.21 \times 10^8$ cfu and $7.51 \times 10^8$ cfu respectively. Each library was rescued (50× library equivalents) using TG1+cytFkpA (Levy et al., 2013 *J. Immun. Meth.* 394(1-2):10-21)

Phage Panning and Rescue

Panning was performed on recombinant N-terminal extracellular domain of human PTH1R as described above except that for the first round of phage panning, concurrent to the deselection steps, 10 pmoles rather than 40 pmoles of biotinylated N-ECD PTH1R was allowed to bind to streptavidin-coated magnetic beads.

For the second and third panning rounds, the same solution phase protocols followed in round one above were used with the following exceptions. Phage input amount used in panning rounds two and three was ~$1.0 \times 10^{10}$ cfu. For round two, 1 pmoles of biotinylated antigen was used in selection; for round three, 0.5 and 0.1 pmoles of biotinylated antigen was used. An additional panning condition was introduced in round 3 using a 30 min selection (rather than 1.5 hr) and 0.5 pmoles. Following the second and third rounds of selection, the Kingfisher instrument was used to wash unbound phage from beads. In round two, the Kingfisher was programmed to wash beads 5 times with PBS-0.1% TWEEN+3% BSA for 5 minutes followed by 5 times with 3% BSA/PBS for 5 minutes. In round three panning, beads were washed 7 times with PBS-0.1% TWEEN+3% BSA for 5 minutes, followed by 7 times with 1×PBS+3% BSA 5 minute washes and a final quick wash with PBS. An overnight wash with 500× fold excess cold N-ECD PTH1R antigen was added to the 0.5 and 0.1 pmoles arms with varying duration of selection.

C. Screening

Bacterial periplasmic extracts containing secreted antibody fragments for use in screening for PTH1R binders were prepared by standard methods. In order to assess the improved binding kinetics of the light chain shuffled mutants, off-rate screening of crude antibody fragments was performed using surface plasmon resonance (SPR). The primary antibody panning and antibody discovery had utilized CHO-K1 cells over-expressing the full length human PTH1R. Further testing demonstrated that both the XPA.85.012 and XPA.85.017 clones bound to a soluble recombinant N-Terminal extracellular domain (ECD) which could be utilized in SPR based high throughput screening and affinity characterization.

The SPR screening assays were performed on a BIACORE 4000 (GE Healthcare) using a direct binding assay format. In these assays, a CM5 BIACORE chip was prepared via standard amine coupling chemistry using the BIACORE Amine Coupling kit (GE Healthcare, Piscataway, N.J.). The human PTH1R N-terminal ECD (R&D Systems) was diluted to 4 µg/mL in acetate pH 4.5 and injected for 5 minutes. This immobilizes approximately 1500 RU of ECD. Periplasmic extracts were diluted 1:1 with HBS-EP+ (10 mM HEPES, 150 mM NaCl, 3 mM EDTA and 0.05% v/v Surfactant P20) (Teknova, Hollister Calif.) with 5 mg/mL BSA and filtered through a 0.2 µM Millex GV filter plate (Millipore) and then injected at 30 uL/minute for 240 seconds with a 300 second dissociation. Regeneration after each PPE injection was 20 seconds of 10 mM Glycine pH 3.0. The running buffer used was HBS-EP+ with 2.5 mg/mL BSA (Sigma Aldrich, St. Louis Mo.). The stability early report point in the BIACORE 4000 software was used to evaluate PPE binding levels and dissociation (kd) was determined.

Selected clones with improved off-rates were reformatted as IgG1, IgG2 or IgG4 antibodies as described in Example 1. FIGS. 1A and 1B show multiple sequence alignments (MSA) of the light chain amino acids of families for children of 12 (FIG. 1A) or families for children of 17 (FIG. 1B), were performed against the parent sequence using the ClustalW algorithm.

Example 3: IgG Affinity Measurement by SPR

In order to measure the on-rate ($k_a$) and off-rate ($k_d$) constants for the various reformatted antibodies an SPR approach was pursued.

An anti-human IgG-Fc CM5 sensor chip (GE Healthcare) was prepared using standard amine coupling as described by the manufacturer's protocol for the capture Ab on a BIACORE 4000 system (GE Healthcare). Briefly, the chip surface was activated with a 10 minute injection at 10 µL/minute of a freshly mixed 1:1 solution of 0.1 M N-Hydroxysuccinimide (NHS) and 0.4 M 1-Ethyl-3-(3-dimethylaminopropyl) carbodiimide hydrochloride (EDC). Following the activation injection, 15 ug/mL anti-human IgG-Fc antibody in acetate pH 4.5 was injected at 10 µL/minute for 10 minutes to achieve a high density capture surface. 7 minutes of 1M Ethanolamine hydrochloride-NaOH pH 8.5 was injected to block the surface. The NHS, EDC, and Ethanolamine used were from the BIACORE Amine Coupling Kit.

Kinetic Analysis was performed using HBS-EP+ (Teknova) with 2.5 mg/mL BSA (Sigma Aldrich, St. Louis Mo.). Antibodies were diluted to 0.5 µg/mL and captured to achieve a surface density of 100 to 200 RU. PTH1R N-terminal ECD samples were injected at four concentrations of 200, 50, 12.5, and 3.125 nM as well as blank injections. Injections were performed at 30 µL/minute for 240 seconds with a 360 second dissociation time. Regeneration was then performed with one 60 second injection 3M MgCl.

Figure 2:
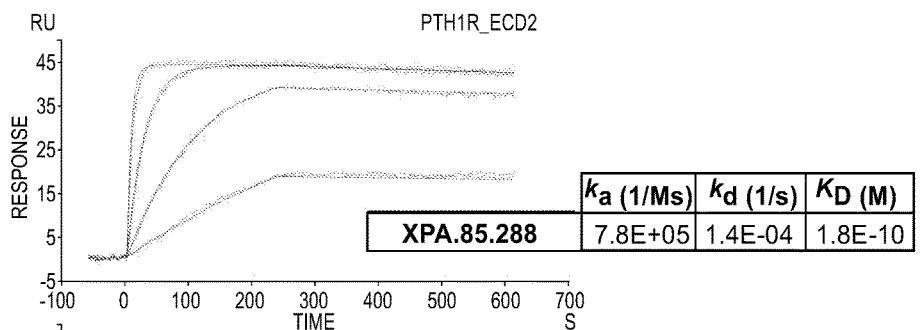
FIGS. 2A-2D: Representative SPR derived kinetic data comparing the parental clones XPA.85.012 (FIG. 2B) and XPA.85.017 (FIG. 2D) with their respective higher affinity light chain variants XPA.85.288 (FIG. 2A) and XPA.85.287 (FIG. 2C) respectively. The IgGs were captured to the sensor surface via the Fc region and recombinant PTH1R N-terminal ECD was injected at 200, 50, 12.5, and 3.125 nM as described in the example method.
Figure 2:
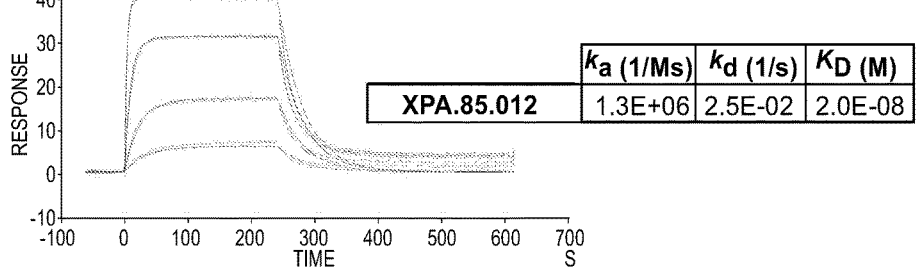
Figure 2:
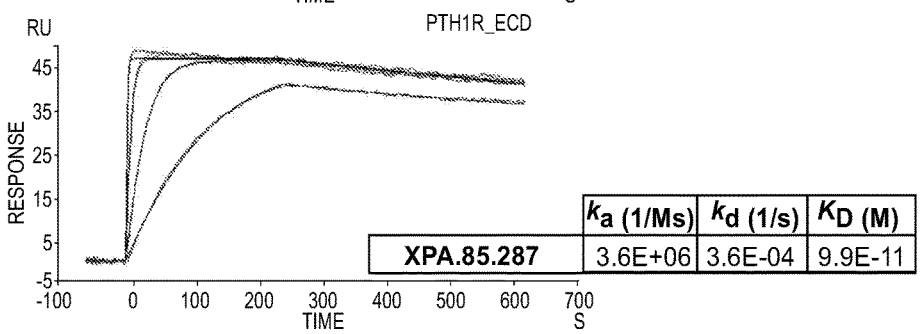
Figure 2:
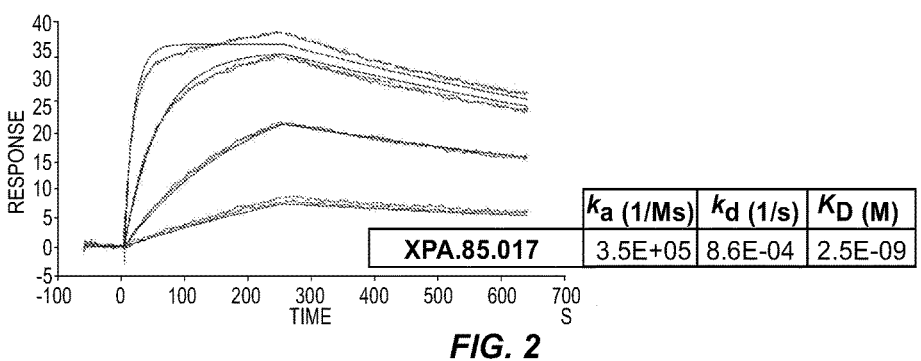

The data were analyzed using BIACORE 4000 Evaluation Software and was double referenced by subtracting both the blank flow cell data and the averaged bracketing blank injections. The data was fit by simultaneously fitting the an off-rate ($k_d$) and on-rate ($k_a$), and calculating the $K_D$ as $K_D = k_d/k_a$. Measured rate constants are shown in Table 2 and representative data is included in FIG. 2.

TABLE 2

SPR Based Affinity Estimates

| Clone | $k_a$ (1/Ms) | $k_d$ (1/s) | $K_D$ (M) |
| --- | --- | --- | --- |
| XPA.85.012 | 1.3E+06 | 2.5E−02 | 2.0E−08 |
| XPA.85.017 | 3.5E+05 | 8.6E−04 | 2.5E−09 |
| XPA.85.287 | 3.6E+06 | 3.6E−04 | 9.9E−11 |
| XPA.85.288 | 7.8E+05 | 1.4E−04 | 1.8E−10 |
| XPA.85.326 | 3.8E+05 | 7.3E−05 | 1.9E−10 |
| XPA.85.327 | 7.4E+05 | 1.1E−04 | 1.5E−10 |
| XPA.85.328 | 5.6E+05 | 1.8E−04 | 3.2E−10 |
| XPA.85.329 | 3.4E+05 | 7.6E−05 | 2.2E−10 |
| XPA.85.330 | 4.7E+05 | 9.0E−05 | 1.9E−10 |
| XPA.85.331 | 1.6E+06 | 3.5E−04 | 2.2E−10 |
| XPA.85.332 | 2.4E+06 | 1.7E−03 | 7.1E−10 |
| XPA.85.333 | 1.8E+06 | 5.4E−04 | 3.0E−10 |
| XPA.85.334 | 8.6E+05 | 2.1E−04 | 2.5E−10 |
| XPA.85.335 | 8.0E+05 | 1.9E−03 | 2.4E−09 |
| XPA.85.336 | 1.1E+06 | 1.9E−02 | 1.7E−08 |
| XPA.85.337 | 6.1E+05 | 4.6E−04 | 7.5E−10 |
| XPA.85.338 | 1.3E+06 | 5.7E−04 | 4.3E−10 |
| XPA.85.339 | 2.9E+06 | 6.5E−04 | 2.2E−10 |
| XPA.85.340 | 1.4E+06 | 1.1E−03 | 7.5E−10 |
| XPA.85.341 | 1.9E+06 | 6.0E−04 | 3.1E−10 |
| XPA.85.342 | 2.3E+06 | 1.2E−03 | 5.2E−10 |
| XPA.85.343 | 1.1E+06 | 4.5E−04 | 4.2E−10 |
| XPA.85.344 | 1.3E+06 | 2.3E−04 | 1.8E−10 |
| XPA.85.345 | 2.3E+06 | 1.3E−03 | 5.6E−10 |
| XPA.85.346 | 4.5E+05 | 1.4E−04 | 3.1E−10 |
| XPA.85.347 | 8.8E+05 | 7.7E−04 | 8.7E−10 |

The affinity data as measured in this assay using captured antibodies demonstrated increased affinity binding (lower $K_D$) of the affinity matured variants of both the XPA.85.012 and the XPA.85.017 clones to the human recombinant ECD.

Example 4: FACS Binding Assays

A. Binding of XPA.85.012 and XPA.85.017 on CHOK1 and CHO Human PTH1R Cells

Figure 3A:
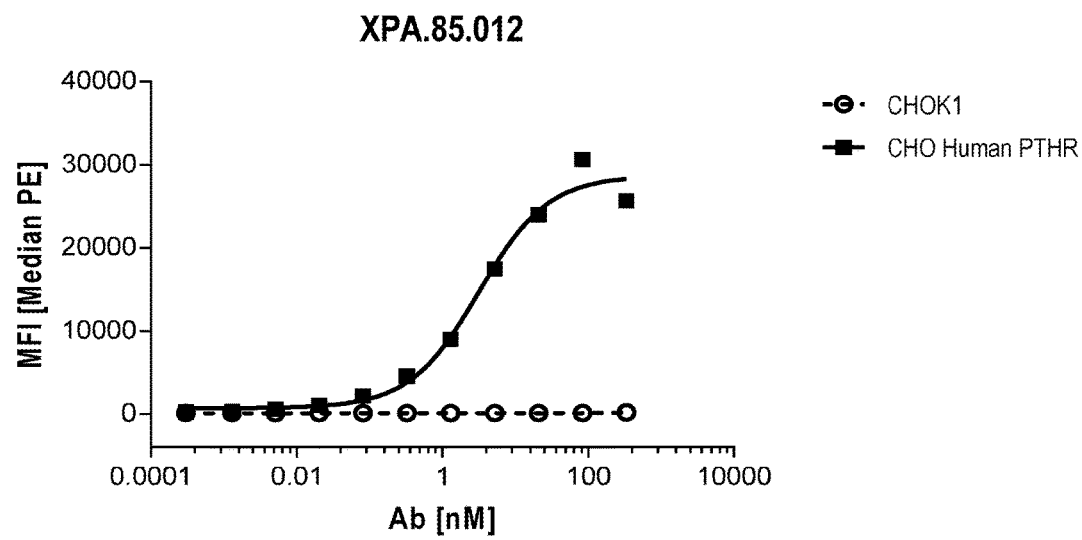
FIGS. 3A-3B: Binding Curves of XPA.85.012 and XPA.85.017 on CHOK1 (open circles) and CHO human PTH1R (solid squares) cells. Binding Curves of XPA.85.012 (FIG. 3A). Binding Curves of XPA.85.017 (FIG. 3B). Both antibodies bind specifically to PTH1R expressed on CHO human PTH1R cells.
Figure 3B:
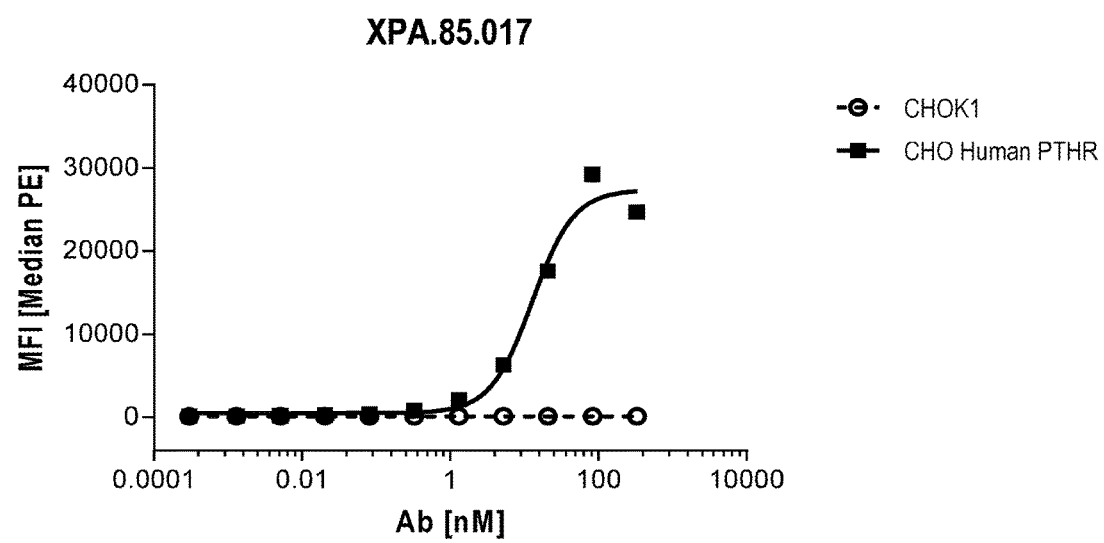

To assess antibody binding specificity of XPA.85.012 and XPA.85.017 to human PTH1R, CHO cells overexpressing human PTH1R were used in a flow based assay. Binding data for XPA.85.012 and XPA.85.017 is shown FIGS. 3A and 3B, respectively. CHOK1 parent cells were also used as a negative cell line. Cells were plated in a 96-well v-bottom plate (Costar: Fisher Scientific, Waltham, Mass.) with increased concentrations of antibodies. Cells and antibodies were incubated for 30 minutes at 4° C. Following two washes with FACS Buffer (0.5% BSA+0.1% NaN3 in DPBS), cells were incubated with R-Phycoerythrin AffiniPure F(ab')$_2$ Fragment Goat Anti-Human IgG (H+L) (Jackson ImmunoResearch, West Grove, Pa.) for 20 minutes at 4° C. Cells were washed twice and resuspended in FACS Buffer. Samples were acquired using BD Cytometer (BD Biosciences, San Jose, Calif.) and data were analyzed using FlowJo (FlowJo, LLC, Ashland, Oreg.) and Prism (GraphPad Software, La Jolla, Calif.).

Figure 4A:
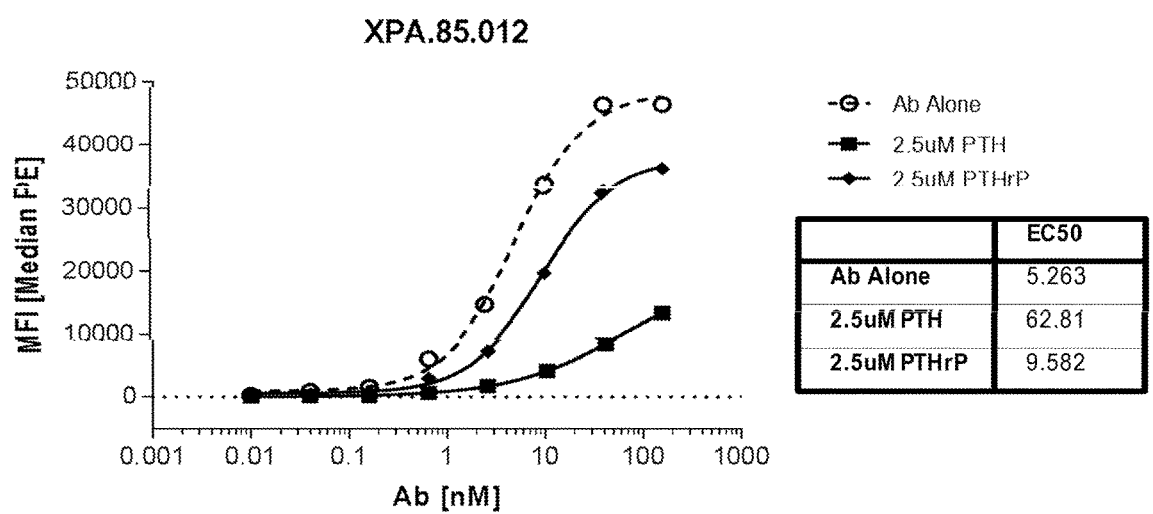
FIGS. 4A-4B: XPA.85.012 and XPA.85.017 Binding in the Presence of PTH or PTHrP. Increasing concentrations of anti-PTH1R antibodies were incubated with CHO human PTH1R cells in the presence or absence of saturating concentrations of PTH or PTHrP. Antibody binding was detected with R-Phycoerythrin anti-human IgG antibody alone (open circles), antibody with 2.5 µM PTH (solid squares), and antibody with 2.5 µM PTHrP (solid diamond). Binding Curves of XPA.85.012 (FIG. 4A). Binding Curves of XPA.85.017 (FIG. 4B). Both antibodies bound to PTH1R in the presence of either PTH or PTHrP, though antibody binding to PTH1R was reduced in the presence of either ligand.
Figure 4B:
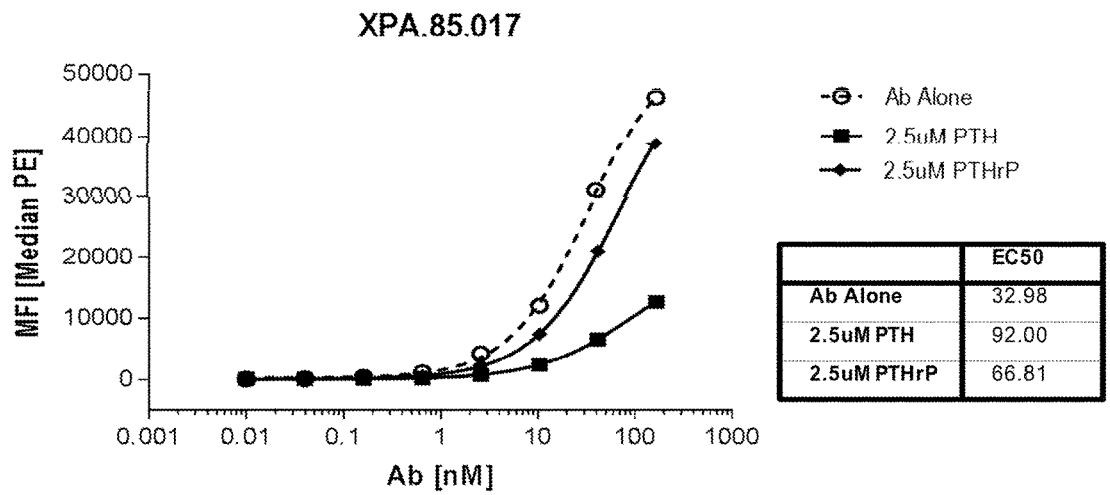

B. XPA.85.012 and XPA.85.017 Binding Affinity in the Presence and Absence of PTH and PTHrP To assess antibody differential binding to the PTH1R ligands, increasing concentrations of anti-PTH1R antibodies were incubated with CHO human PTH1R cells for 60 minutes in the presence or absence of saturating concentration of PTH and PTHrP. Binding data for XPA.85.012 and XPA.85.017 is shown FIGS. 4A and 4B, respectively. Following two washes with FACS Buffer (0.5% BSA+0.1% NaN3 in DPBS), cells were incubated with R-Phycoerythrin AffiniPure F(ab')$_2$ Fragment Goat Anti-Human IgG (H+L) (Jackson ImmunoResearch, West Grove, Pa.) for 20 minutes at 4° C. Cells were then washed twice and resuspended in FACS Buffer. Samples were acquired using BD Cytometer (BD Biosciences, San Jose, Calif.) and data were analyzed using FlowJo (FlowJo, LLC, Ashland, Oreg.) and Prism (GraphPad Software, La Jolla, Calif.).

C. Kinetics (On Rate) of XPA.85.012 and XPA.85.017

Figure 5A:
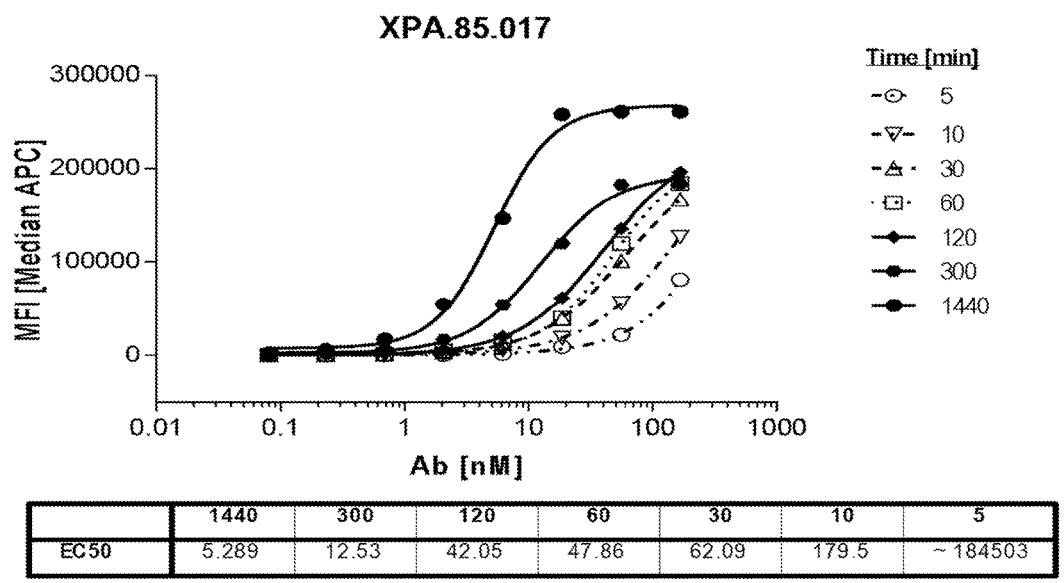
FIGS. 5A-5B: On-Rate of XPA.85.012 and XPA.85.017 by Flow Cytometry. Increasing antibody concentrations were incubated with CHO human PTH1R cells for a certain amount of time. Antibody binding was detected with anti-human IgG APC. A time course was run for XPA.85.017 due to its slow on rate when compared to XPA.85.012 (FIG. 5A). In the graph, as the incubation time increases, the antibody binding curve is shifted to the left. This shows that the antibody has not reached equilibrium and it takes time for the antibody to bind. XPA.85.012 has a faster on-rate (FIG. 5B). Antibody binding at 1 hr (open circles) has a similar EC50 value as the 24 hr incubation time point (solid hexagon). XPA.85.012 can reach binding equilibrium within 1 hr whereas it can take XPA.85.017 24 hr to reach binding equilibrium. Once both antibodies reach equilibrium, they have similar EC50 values.
Figure 5B:
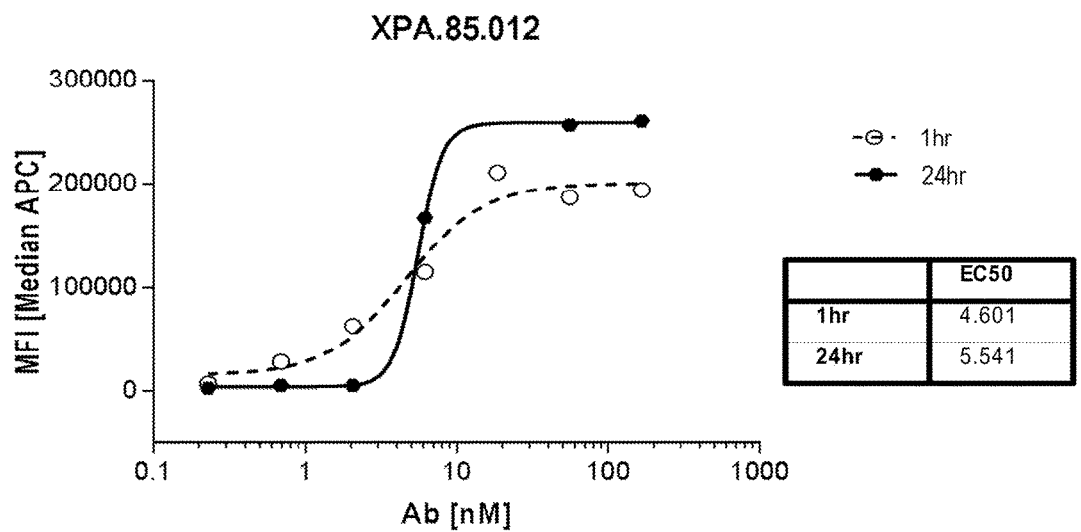

SPR data showed that XPA.85.012 has a faster on rate than XPA.85.017. A flow based assay was developed to confirm the on rate of both antibodies. First, XPA.85.017 on rate was assessed by flow cytometry (FIG. 5A). Increasing concentrations of XPA.85.017 were incubated with CHO human PTH1R cells for a certain amount of time, from 5 minutes to 24 hours. Antibody binding for XPA.85.012 is shown in FIG. 5B. In summary, XPA.85.012 can bind within 1 hr whereas it can take XPA.85.017 24 hr to bind. All time points were stopped at the same time except for the 24 hr samples. Cells were then washed twice with FACS Buffer (0.5% BSA+0.1% NaN3 in DPBS) and incubated with Allophycocyanin (APC) AffiniPure F(ab')$_2$ Fragment Goat Anti-Human IgG (H+L) (Jackson ImmunoResearch, West Grove, Pa.) for 20 minutes at 4° C. Following two washes, cells were resuspended in FACS Buffer. Samples were acquired using BD Cytometer (BD Biosciences, San Jose, Calif.) and data were analyzed using FlowJo (FlowJo, LLC, Ashland, Oreg.) and Prism (GraphPad Software, La Jolla, Calif.).

D. Assessment of Species Cross Reactivity of Anti-PTH1R Antibodies

CHOK1 overexpressing PTH1R orthologs and endogenous cell lines were used to assess species cross-reactivity. CHO human PTH1R and CHO mouse PTH1R cells were generated in house and UMR106 and Saos-2 were purchased from ATCC. UMR106 and Saos-2 are both osteosarcoma cell line expressing the rat and human PTH1R, respectively. All four cell lines were used to assess species cross reactivity.

Figure 6A:
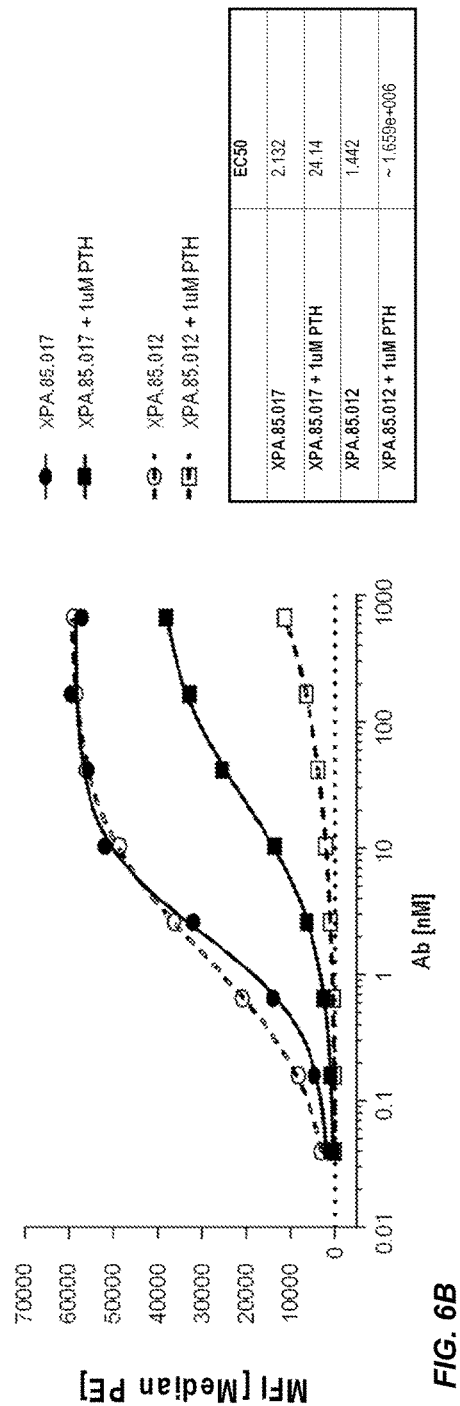
FIGS. 6A-6D: XPA.85.012 and XPA.85.017 species cross-reactivity and differential binding profiles. Increasing concentrations of anti-PTH1R antibodies were incubated for 24 hr with cells expressing PTH1R orthologs in the presence or absence of saturating concentration of PTH or PTHrP. Antibody binding was detected with R-Phycoerythrin anti-human IgG. Both XPA.85.012 and XPA.85.017 were cross-reactive to the different PTH1R orthologs and both antibodies bound better in the absence of the ligands, PTH (square symbol) or PTHrP (diamond symbol). Antibodies binding to CHO cells expressing human PTH1R+/−PTH (FIG. 6A) or +/−PTHrP (FIG. 6B). Antibodies binding to CHO cells expressing mouse PTH1R+/−PTH (FIG. 6C) or +/−PTHrP (FIG. 6D).
Figure 6B:
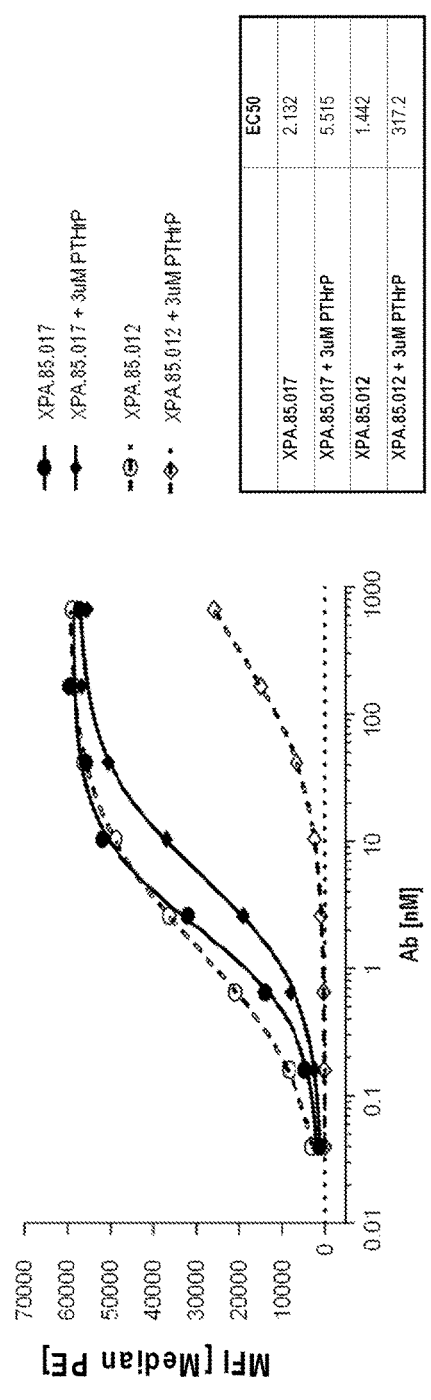
Figure 6C:
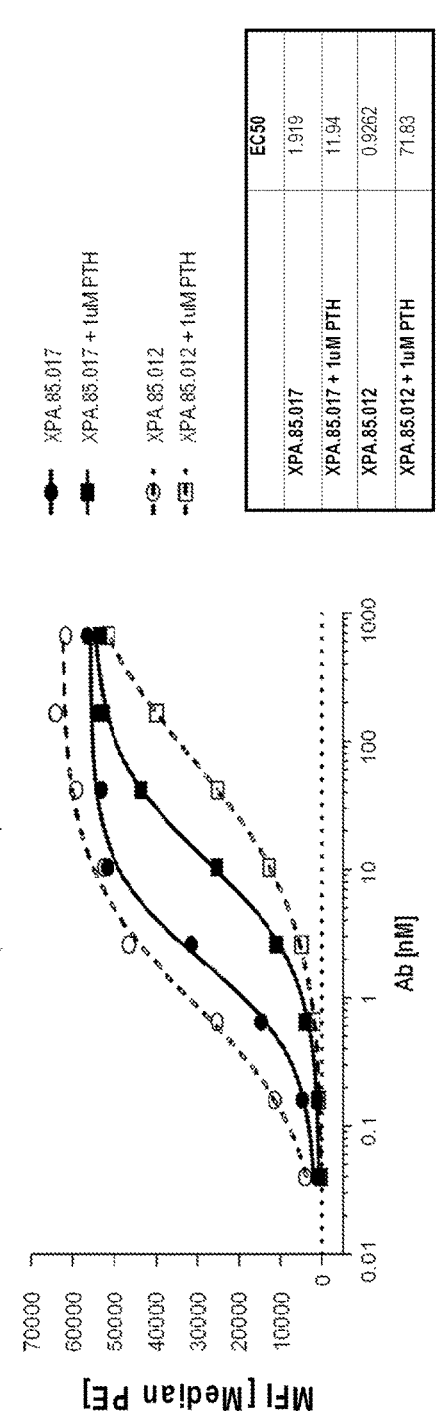
Figure 6D:
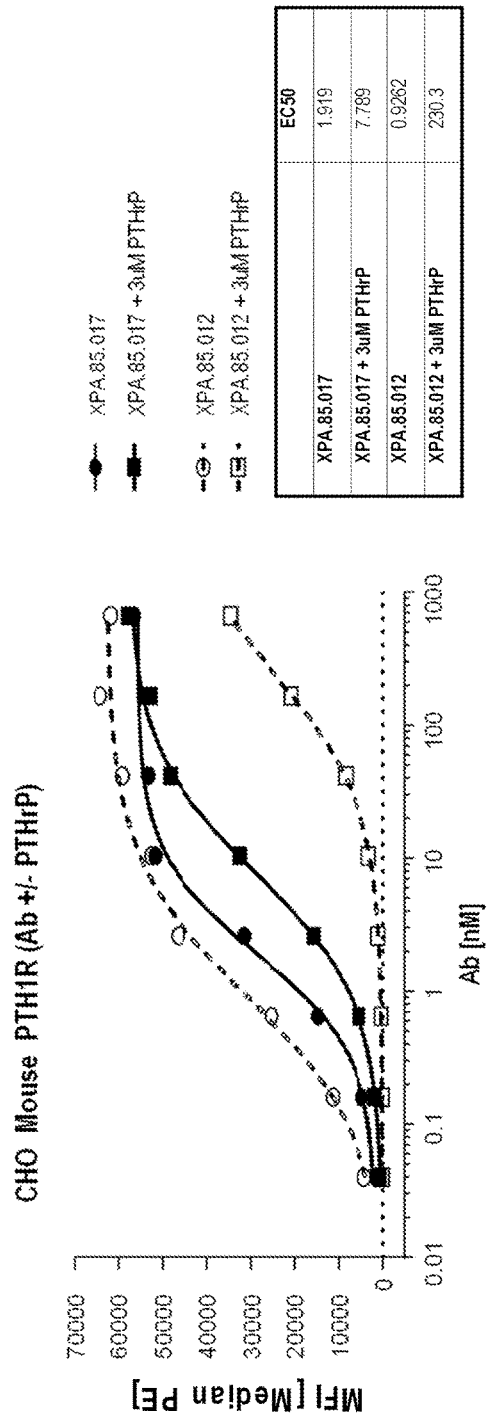
Figure 7A:
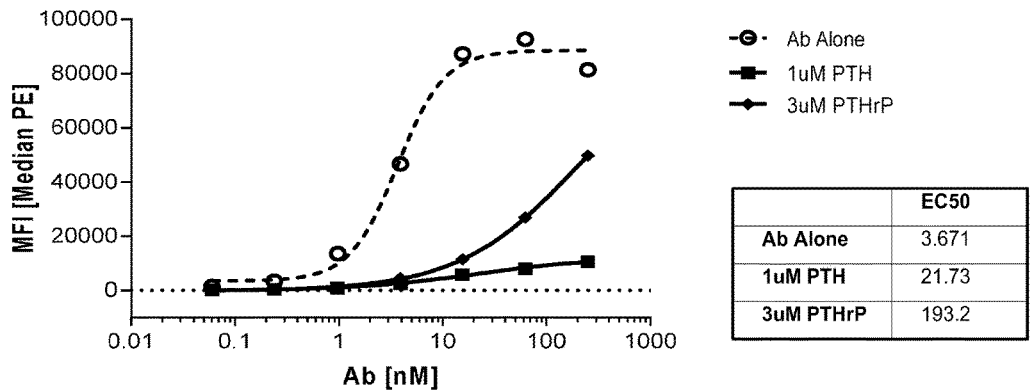
FIGS. 7A-7C: Antibodies binding to Saos-2 overexpressing human PTH1R in the Presence or Absence of PTH and PTHrP. Increasing concentrations of anti-PTH1R antibodies were incubated with Saos-2 human PTH1R cells in the presence or absence of saturating concentrations of PTH or PTHrP. XPA.85.328 (FIG. 7A), XPA.85.329 (FIG. 7B), XPA.85.330 (FIG. 7C). Antibody binding was detected with R-Phycoerythrin anti-human IgG. Antibody alone (open circles) antibody with 1 µM PTH (solid squares), and antibody with 3 µM PTHrP (solid diamond). All three antibodies showed reduced binding to PTH1R in the presence of either PTH or PTHrP.
Figure 7B:
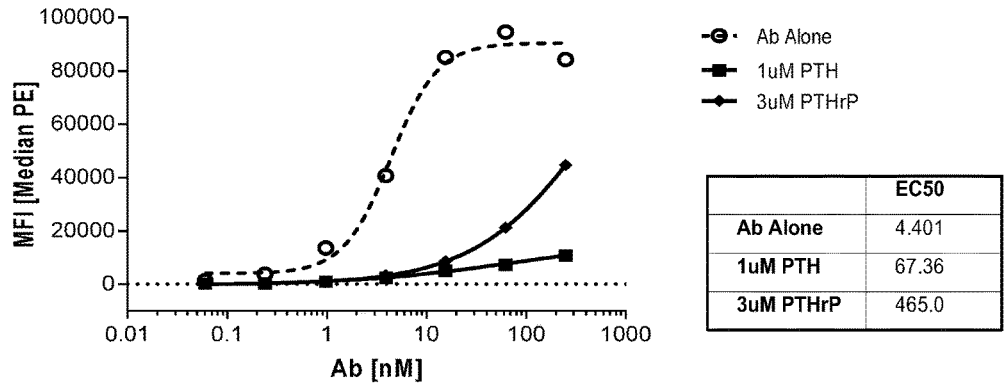
Figure 7C:
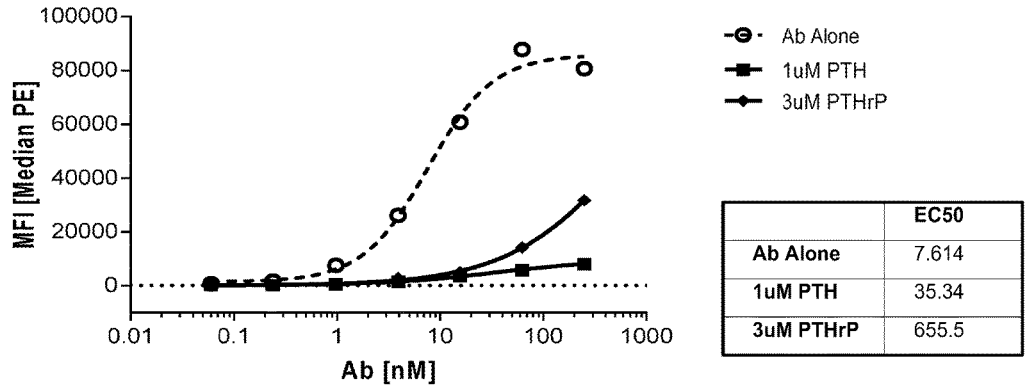

Anti-PTH1R antibodies were screened for both binding to the cell lines expressing PTH1R orthologs and for differential binding in the presence or absence of the ligands (PTH or PTHrP). To assess antibody binding and differential binding, increasing concentrations of anti-PTH1R antibodies were incubated with all four cell lines in the presence or absence of saturating concentration of PTH and PTHrP. Binding data is shown for XPA.85.017 and XPA.85.012 antibodies to CHO cells expressing human PTHR in the presence and absence of PTH (FIG. 6A) or PTHrP (FIG. 6B). Binding data is shown for XPA.85.017 and XPA.85.012 antibodies to CHO cells expressing mouse PTHR in the presence and absence of PTH (FIG. 6C) or PTHrP (FIG. 6D).

Antibodies and cells were incubated for 24 hours to allow the slower on-rate antibody, XPA.85.017, to reach equilibrium. Following two washes with FACS Buffer (0.5% BSA+0.1% NaN3 in DPBS), cells were incubated with Phycoerythrin AffiniPure F(ab')$_2$ Fragment Goat Anti-Human IgG (H+L) (Jackson ImmunoResearch, West Grove, Pa.) for 20 minutes at 4° C. Cells were then washed twice and resuspended in FACS Buffer. Samples were acquired using BD Cytometer (BD Biosciences, San Jose, Calif.) and data were analyzed using FlowJo (FlowJo, LLC, Ashland, Oreg.) and Prism (GraphPad Software, La Jolla, Calif.).

E. Binding of Affinity Matured XPA.85.017 Variants to CHOK1, CHO Human PTH1R, and CHO Mouse PTH1R at Equilibrium Condition in the Presence or Absence of PTH1R Ligands To characterize antibody binding to PTH1R, cells were labeled with either CellTrace™ CFSE or CellTrace™ Violet. Unlabeled CHOK1 parent, CHO human PTH1R labeled with CellTrace™CFSE, and CHO mouse PTH1R labeled with CellTrace™Violet were pooled together and stained with increasing concentrations of antibody. Antibodies were incubated for 24 hr at 4° C. followed by two washes with FACS Buffer (0.5% BSA, 0.1% NaN3 in DPBS). Cells were then incubated with Allophycocyanin (APC) AffiniPure F(ab')$_2$ Fragment Goat Anti-Human IgG (H+L) (Jackson ImmunoResearch, West Grove, Pa.) for 20 minutes at 4° C. Followed by two washes, cells were resuspended in FACS Buffer. Samples were acquired using BD Cytometer (BD Biosciences, San Jose, Calif.) and data were analyzed using FlowJo (FlowJo, LLC, Ashland, Oreg.) and Prism (GraphPad Software, La Jolla, Calif.). EC50 Values of antibodies binding to CHO human PTH1R and CHO mouse PTH1R cells are shown in Table 3. Selected XPA.85.017 antibody variants were assessed for differential binding on CHO human and CHO mouse PTH1R cells and showed a decrease in binding when in the presence of either of the PTH1R ligands. Lower EC50 values were observed in the absence of the ligands (Table 4).

TABLE 3

XPA.85.017 Variants $EC_{50}$ Values on CHO Human PTH1R and CHO Mouse PTH1R cells at equilibrium condition.

| anti-PTHR Ab | $EC_{50}$ [nM] | |
|---|---|---|
| | CHO Human PTHR | CHO Mouse PTHR |
| XPA.85.012 | 0.7926 | 0.8866 |
| XPA.85.017 | 0.7183 | 1.047 |
| XPA.85.287 | 0.04398 | 0.2163 |
| XPA.85.335 | 0.2651 | 0.384 |
| XPA.85.336 | 0.3416 | 14.71 |
| XPA.85.337 | 1.265 | 3.273 |
| XPA.85.338 | 0.1806 | 0.6804 |
| XPA.85.339 | 0.1423 | 0.2338 |
| XPA.85.340 | 0.1674 | 0.322 |
| XPA.85.341 | 0.202 | 0.3425 |

TABLE 4

Differential Binding Profiles for Selected XPA.85.017 Variants.

| | $EC_{50}$ [nM] | | | | | |
|---|---|---|---|---|---|---|
| | CHO Human PTHR | | | CHO Mouse PTHR | | |
| anti-PTHR Ab | Antibody Alone | Ab + 1 uM PTH | Ab + 3 uM PTHrP | Antibody Alone | Ab + 1 uM PTH | Ab + 3 uM PTHrP |
| XPA.85.017 | 0.5984 | 19.47 | 6.595 | 1.137 | 1.962 | 11.77 |
| XPA.85.287 | 0.09091 | 1.865 | 0.3042 | 0.2808 | 0.2061 | 1.515 |
| XPA.85.339 | 0.09841 | 2.984 | 0.4791 | 0.2575 | 0.3273 | 18.68 |
| XPA.85.341 | 0.1956 | 5.387 | 1.109 | 0.3371 | 0.7778 | 14.46 |

F. Binding of Affinity Matured XPA.85.012 Variants to CHOK1, CHO Human PTH1R, CHO Mouse PTH1R, UMR106, and Saos-2 Cells To characterize antibody binding to PTH1R, cells were labeled with either CellTrace™ CFSE or CellTrace™ Violet. Unlabeled human PTH1R, CHOK1 and Saos-2 labeled with CellTrace™CFSE, and CHO mouse PTH1R and UMR106 labeled with CellTrace™Violet were pooled together and stained with increasing concentrations of antibody. Antibodies were incubated for 1 hr at 4° C. followed by two washes with FACS Buffer (0.5% BSA, 0.1% NaN3 in DPBS). Cells were then incubated with Allophycocyanin (APC) AffiniPure F(ab')$_2$ Fragment Goat Anti-Human IgG (H+L) (Jackson ImmunoResearch, West Grove, Pa.) for 20 minutes at 4° C. Followed by two washes, cells were resuspended in FACS Buffer. Samples were acquired using BD Cytometer (BD Biosciences, San Jose, Calif.) and data were analyzed using FlowJo (FlowJo, LLC, Ashland, Oreg.) and Prism (GraphPad Software, La Jolla, Calif.). All antibodies recognized PTH1R expressed on CHO human PTH1R, CHO mouse PTH1R, and UMR106. These antibodies also do not bind nonspecifically to CHOK1 parent and Saos-2 cells (Table 5).

TABLE 5

FACS Binding Profiles of XPA.85.012 Variants.

| Antibody | CHOK1 | CHO Human PTH1R | CHO Mouse PTH1R | UMR106 |
|---|---|---|---|---|
| XPA.85.288 | – | + | + | + |
| XPA.85.326 | – | + | + | + |
| XPA.85.327 | – | + | + | + |
| XPA.85.331 | – | + | + | + |
| XPA.85.332 | – | + | + | + |
| XPA.85.333 | – | + | + | + |
| XPA.85.334 | – | + | + | + |
| XPA.85.342 | – | + | + | + |
| XPA.85.343 | – | + | + | + |
| XPA.85.344 | – | + | + | + |
| XPA.85.345 | – | + | + | + |
| XPA.85.346 | – | + | + | + |
| XPA.85.347 | – | + | + | + |

(+) indicates binding and (–) indicates no binding.

G. Antibody Binding Specificity to Human PTH1R on Saos-2 Overexpressing Human PTH1R Cells To confirm specificity of the anti-PTH1R antibodies, antibodies were screened against Saos-2 overexpressing human PTH1R cells in the presence or absence of both ligands, PTH or PTHrP (FIG. 7A-7D).

Figure 8:
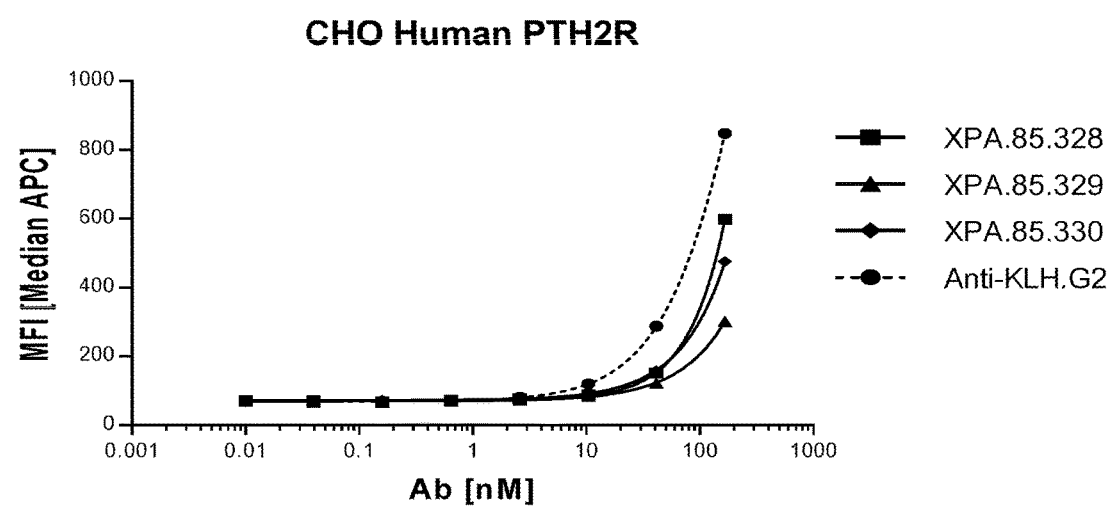
FIG. 8: Anti-PTH1R antibodies bind specifically to PTH1R. Increasing concentrations of anti-PTH1R antibodies were added to CHO cells overexpressing human PTH2R and incubated for 1 hr at 4° C.

H. Assessment of PTH2R Cross-Reactivity Using CHO Overexpressing Human PTH2R Cells Anti-PTH1R antibodies (XPA.85.328, XPA.85.329, and XPA.85.330) were screened against CHO cells overexpressing human PTH2R to determine receptor cross-reactivity (FIG. 8). PTH2R has a 51% homology to PTH1R. To confirm anti-PTH1R antibodies binding specificity to PTH1R only, increasing concentration of antibodies were incubated with CHO human PTH2R for 1 hr at 4° C. Following two washes, cells were incubated with Allophycocyanin (APC) AffiniPure F(ab')$_2$ Fragment Goat Anti-Human IgG (H+L) (Jackson ImmunoResearch, West Grove, Pa.) for 20 minutes at 4° C. Cells were washed twice and resuspended in FACS Buffer. Samples were acquired using BD Cytometer (BD Biosciences, San Jose, Calif.) and data were analyzed using FlowJo (FlowJo, LLC, Ashland, Oreg.) and Prism (GraphPad Software, La Jolla, Calif.). As shown in FIG. 8, all antibodies showed no binding to CHO human PTH2R (i.e. no cross-reactivity to PTH2R) and are specific to PTH1R. Anti-KLH.G2 was used a negative control for binding.

Example 5: Functional Assays

A. cAMP Accumulation Assays

In most (if not all) cell types, activation of PTH1R results in stimulation of adenylyl cyclase and accumulation of intracellular cAMP via coupling to Gs, followed by stimulation of protein kinase A (PKA). The functional activity of purified, reformatted IgGs was routinely tested by measuring their ability to antagonize PTH1R-mediated cAMP accumulation via inhibition of the Gs/PKA pathway Human PTH1R CHOK1 Clone 22 and mouse PTH1R CHOK1 cells were grown in ExCell 302 Serum-Free Media for CHO Cells (Sigma, St. Louis, Mo.) containing 4 mM L-Glutamine and 0.4 mg/ml Geneticin (Life Technologies; ThermoFisher Scientific, Waltham, Mass.). On the day of the experiment, cells were harvested by centrifugation (1500 rpm for 3 min at room temperature). Growth media was gently aspirated, and cells were washed once in Dulbecco's Phosphate Buffered Saline, No Calcium or Magnesium (DPBS; Life Technologies; ThermoFisher Scientific, Waltham, Mass.). Cells were then spun down a second time at 1500 rpm for 3 min at room temperature. Wash solution was gently aspirated and cells were resuspended in assay buffer [DPBS containing 0.1% BSA and 1 mM 3-Isobutyl-1-methylxanthine (IBMX; Sigma-Aldrich, St. Louis, Mo.)]. Cells were counted using a Vi-CELL (Beckman Coulter, Indianapolis, Ind.), and adjusted to a density of 2.5×1E$^6$ viable cells/ml or 50,000 cells/well using assay buffer. 20 µl/well of cells were dispensed to 96-well, white, flat bottom, tissue culture treated assay plates (Corning). Cells were preincubated with 5 µl of 6×IgG for 30 min at 37° C. Following preincubation, cAMP accumulation was induced for 45 min at 37° C. by the addition of 5 µl of 6× ligand [(either PTH(1-34) or PTHrP(1-34)]. cAMP accumulation was measured using a HitHunter cAMP for Biologics kit (DiscoveRx, Fremont, Calif.) per manufacturer's instructions. Human PTH(1-34) was purchased from Bio-Techne (Minneapolis, Minn.) and human PTHrP(1-34) was obtained from Sigma-Aldrich (St. Louis, Mo.). Stock solutions of both peptides were prepared in DPBS containing 0.1% BSA, aliquotted and stored at −80° C. Ligand and IgG dilutions were made using DPBS containing 0.1% BSA and 1 mM IBMX. Chemiluminescent signal was measured using a FlexStation 3 (Molecular Devices, Sunnyvale, Calif.). Data are expressed as relative luminescence units (RLUs). Curve-fitting was carried out using GraphPad Prism 6.0 (GraphPad Software Inc., San Diego, Calif.).

Figure 9A:
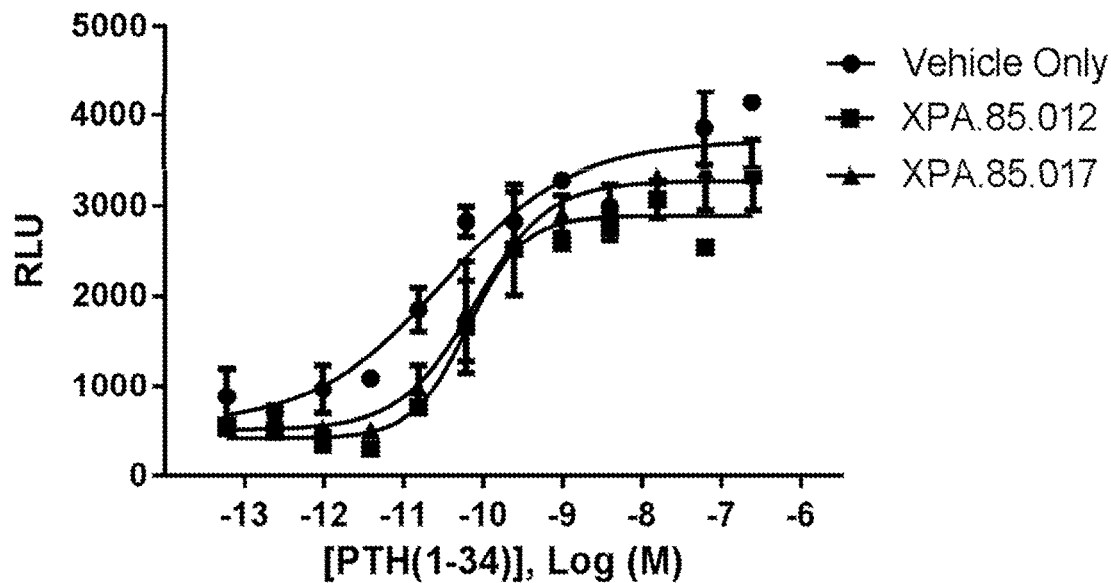
FIGS. 9A-9D: Anti-PTH1R antibodies inhibit ligand-mediated cAMP accumulation and calcium mobilization. Human PTH1R CHOK1 cells were preincubated for 30 min at 37° C. with 267 nM (40 µg/ml) of either XPA.85.012 (solid squares) or XPA.85.017 (solid triangles), followed by induction with increasing concentrations of either PTH(1-34) (FIGS. 9A and 9C) or PTHrP(1-34) (FIGS. 9B and 9D). Both antibodies inhibited ligand-mediated cAMP accumulation (Gs/PKA pathway, FIGS. 9A and 9B) and calcium mobilization (Gq/PKC pathway, FIGS. 9C and 9D).
Figure 9B:
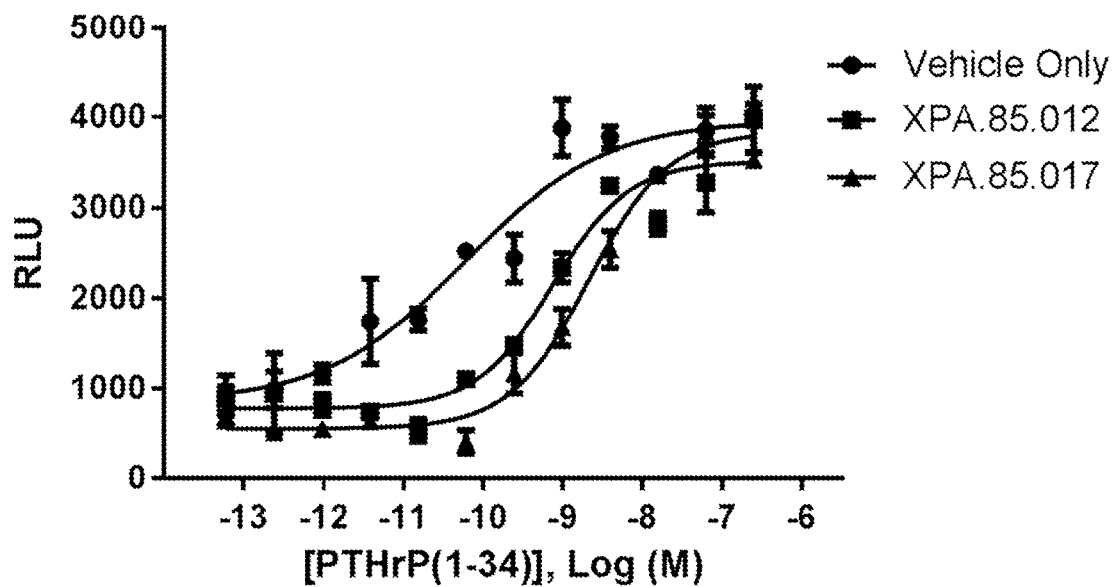

Human PTH1R CHOK1 Clone 22 cells were preincubated for 30 min at 37° C. with 267 nM (40 µg/ml) of either XPA.85.012 (solid squares) or XPA.85.017 (solid triangles), followed by induction with increasing concentrations of either PTH(1-34) (FIG. 9A) or PTHrP(1-34) (FIG. 9B). Both antibodies inhibited ligand-mediated cAMP accumulation (Gs/PKA pathway).

Following affinity engineering of XPA.85.017 (open circles) by light chain shuffling, CHOK1 cells stably over-expressing either human (FIG. 10A and FIG. 10B) or mouse PTH1R (FIG. 10C and FIG. 10D) were preincubated for 30 min at 37° C. with 267 nM (40 µg/ml) of variant IgGs, followed by induction with increasing concentrations of PTH(1-34) for 45 min at 37° C. Variant IgGs exhibited a range of inhibition of ligand-mediated cAMP accumulation (Gs/PKA pathway) at human and mouse PTH1R.

SaOS-2 and UMR106 cells were obtained from ATCC (Manassas, Va.). SaOS-2 cells were grown in McCoy's 5A (Modified) Medium (Life Technologies; ThermoFisher Scientific, Waltham, Mass.) containing 15% heat-inactivated fetal bovine serum (FBS) (Hyclone; ThermoFisher Scientific, Waltham, Mass.). UMR106 cells were grown in Dulbecco's Modified Eagle Medium containing 4.5 g/L D-glucose, supplemented with 10% heat-inactivated FBS, 1 mM sodium pyruvate (Life Technologies; ThermoFisher Scientific, Waltham, Mass.), and 2 mM L-Glutamine. SaOS-2 cells were seeded in 96-well assay plates at a density of 50,000 cells/well for 3 days, then serum starved overnight in medium containing no FBS but supplemented with 1% BSA. UMR106 cells were seeded in 96-well assay plates at a density of 35,000 cells/well for 1 day, then serum starved overnight in medium containing no FBS but supplemented with 1% BSA. Antagonism of cAMP accumulation by IgGs was measured as described previously for CHOK1 cell lines.

Figure 11A:
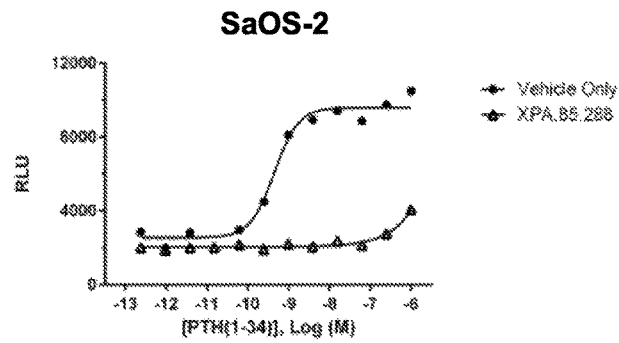
FIGS. 11A-11D Comparison of variant and parental IgGs activities in cAMP assays using SaOS-2 and UMR106 cells, which endogenously express native human and rat PTH1R, respectively. IgGs (267 nM or 40 µg/ml) were preincubated with cells for 30 min at 37° C. prior to induction of cAMP accumulation by PTH(1-34) or PTHrP(1-34) for 45 min at 37° C. Data are presented as mean+SEM, and represent the average of RLUs measured in singlicate (FIGS. 11A and 11D) or duplicate (FIGS. 11B and 11C) wells. Affinity engineering of XPA.85.017 by light chain shuffling resulted in XPA.85.287. This variant showed a significant improvement in activity against human PTH1R (FIG. 11B) (open squares) versus parent (solid squares), with little change in activity against rat PTH1R (FIG. 11C). In contrast, affinity engineering of XPA.85.012 (solid triangles) resulted in a variant, XPA.85.288 (open triangles), showing a significant improvement in activity against both native human PTH1R (FIG. 11A), as well as native rat PTH1R (FIG. 11C). The XPA.85.288 was also found to significantly inhibit PTHrP-induced cAMP in SaOS-2 cells expressing native human PTH1R (FIG. 11D).
Figures 11B, 11C:
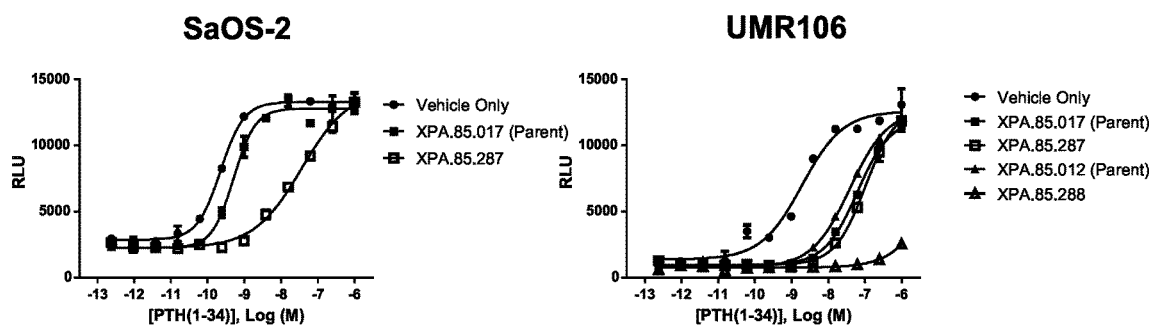
Figure 11D:
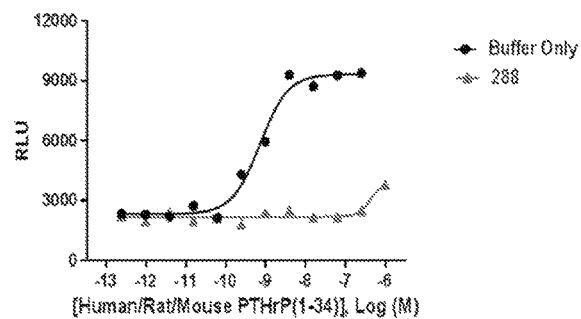

Affinity engineering of XPA.85.017 by light chain shuffling resulted in XPA.85.287. This variant showed a significant improvement in activity against human PTH1R (FIG. 11B, open squares) vs. parent (solid squares), with little change in activity against rat PTH1R (FIG. 11C). In contrast, affinity engineering of XPA.85.012 (solid triangles) resulted in a variant, XPA.85.288 (open triangles), showing a significant improvement in activity against both human PTH1R (data not shown) as well as rat PTH1R. The XPA.85.288 was also found to significantly inhibit PTHrP-induced cAMP in SaOS-2 Cells Expressing Native Human PTH1R (FIG. 11D).

Figure 12A:
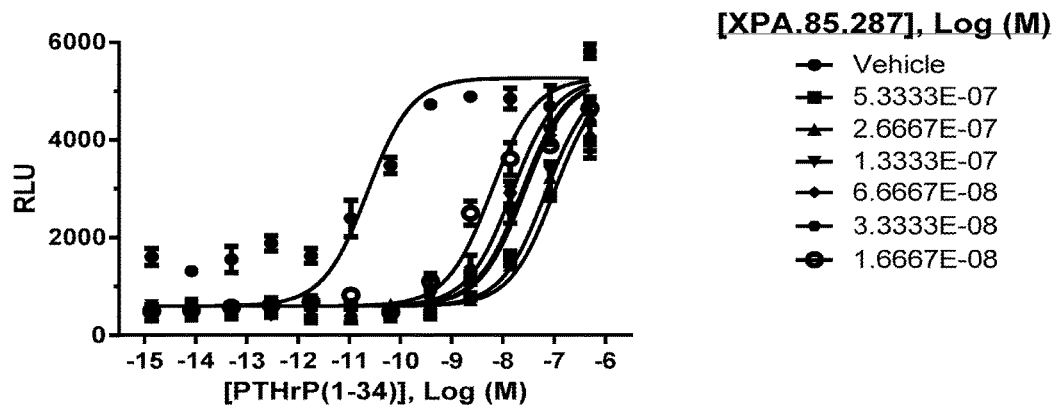
FIGS. 12A-12B: Concentration-response curves for PTHrP(1-34) and increasing concentrations of XPA.85.287 (an affinity engineered variant of XPA.85.017) in cAMP assays using Human PTH1R CHOK1 (FIG. 12A) and Mouse PTH1R CHOK1 (FIG. 12B) cells. Schild regression analyses were performed using GraphPad Prism 6.0 (GraphPad Software Inc., San Diego, Calif.), revealing non-parallel rightward shifts in concentration-response curves. These results are consistent with a non-competitive (allosteric) mechanism of action of the variant IgG.
Figure 12B:
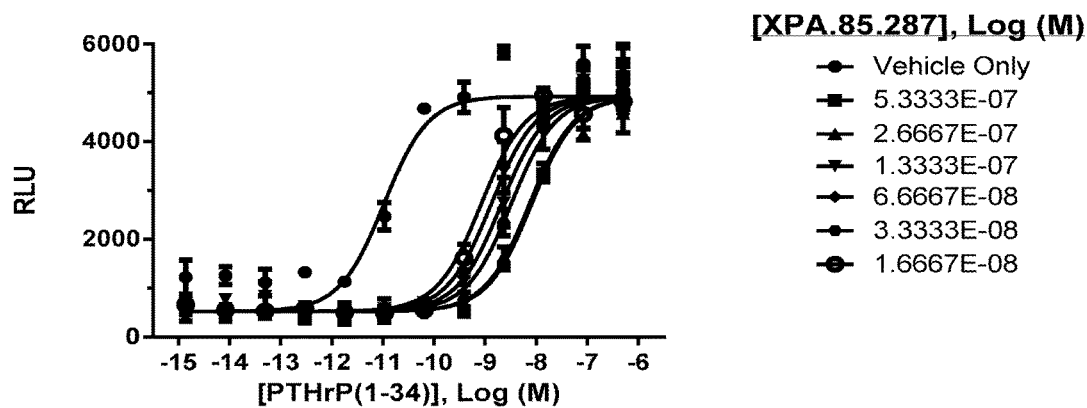

Concentration-response curves were performed for PTHrP(1-34) and increasing concentrations of XPA.85.287 (an affinity engineered variant of XPA.85.017) in cAMP assays using human PTH1R CHOK1 (FIG. 12A) and mouse PTH1R CHOK1 (FIG. 12B) cells. Schild regression analyses were performed using GraphPad Prism 6.0 (GraphPad Software Inc., San Diego, Calif.), revealing non-parallel rightward shifts in concentration-response curves. These results are consistent with a non-competitive (allosteric) mechanism of action of the variant IgG.

Figure 13A:
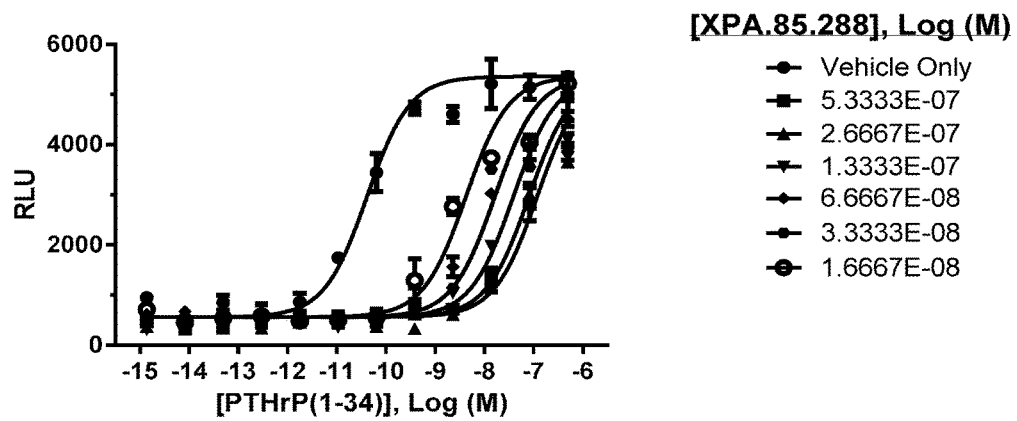
FIGS. 13A-13B: Concentration-response curves for PTHrP(1-34) and increasing concentrations of XPA.85.288 (an affinity engineered variant of XPA.85.012) in cAMP assays using Human PTH1R CHOK1 (FIG. 13A) and Mouse PTH1R CHOK1 (FIG. 13B) cells. Schild regression analyses were performed using GraphPad Prism 6.0 (GraphPad Software Inc., San Diego, Calif.), revealing non-parallel rightward shifts in concentration-response curves. These results are consistent with a non-competitive (allosteric) mechanism of action of the variant IgG.
Figure 13B:
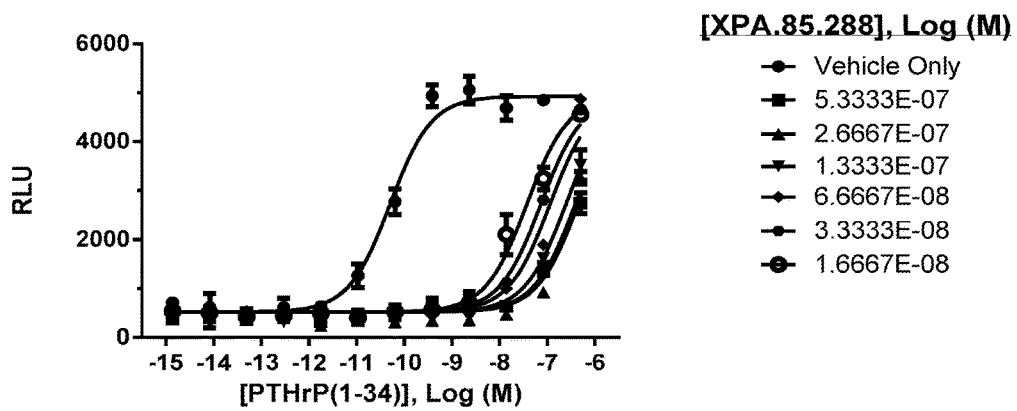

Concentration-response curves were performed for PTHrP(1-34) and increasing concentrations of XPA.85.288 (an affinity engineered variant of XPA.85.012) in cAMP assays using human PTH1R CHOK1 (FIG. 13A) and mouse PTH1R CHOK1 (FIG. 13B) cells. Schild regression analyses were performed using GraphPad Prism 6.0 (GraphPad Software Inc., San Diego, Calif.), revealing non-parallel rightward shifts in concentration-response curves. These results are consistent with a non-competitive (allosteric) mechanism of action of the variant IgG.

B. Calcium Mobilization Assays

Activation of PTH1R in some cell types leads to Gq coupling, activation of phospholipase CP and hydrolysis of membrane-associated phosphatidylinositol to form inositol phosphates, increases in intracellular calcium, and activation of calcium-dependent enzymes, including protein kinase C (PKC). The functional activity of purified, reformatted anti-PTH1R IgGs was tested by measuring their ability to antagonize PTH1R-mediated calcium mobilization via inhibition of the Gq/PKC pathway.

Human PTH1R CHOK1 Clone 22 and mouse PTH1R CHOK1 cells were grown in ExCell 302 Serum-Free Media for CHO Cells (Sigma, St. Louis, Mo.) containing 4 mM L-Glutamine and 0.4 mg/ml Geneticin (Life Technologies, Waltham, Mass.). Cells were seeded at 35,000 cells/well in 100 µl/well of growth media on 96-well, black/clear bottom, tissue culture treated, Poly-D-Lysine coated assay plates (Corning BioCoat; Corning, N.Y.) and incubated overnight at 37° C. [5% $CO_2$, 95% relative humidity]. The next day, 100 µl/well of 2× Calcium 5 loading dye (Molecular Devices, Sunnyvale, Calif.) containing 5 mM probenecid (Sigma-Aldrich, St. Louis, Mo.) was prepared according to manufacturer's instructions and added, and plates were incubated for 30 min at 37° C. Following incubation, 25 µl of loading dye/growth media was manually removed from each well, followed by addition of 25 µl of 10× test IgG (antibody dilutions were prepared in 1×HBSS containing 20 mM HEPES). Plates were then returned to the incubator for an additional 30 min at 37° C. After that, assay plates were centrifuged at 1500 rpm for 3 min at room temperature. Plates were then placed in a FlexStation 3 (Molecular Devices, Sunnyvale, Calif.) prewarmed to 37° C. to equilibrate for 5 min prior to assay. Basal fluorescence was recorded every second for 19 seconds prior to the addition of 50 µl of 5× ligand (either PTH(1-34) or PTHrP(1-34)). Fluorescence was recorded every second for 1 min, then every 6 seconds for an additional 2 min. Data was expressed as "Max-Min", and curve-fitting was carried out using GraphPad Prism 6.0 (GraphPad Software Inc., San Diego, Calif.). Human PTH(1-34) was purchased from Bio-Techne (Minneapolis, Minn.) and human PTHrP(1-34) was obtained from Sigma-Aldrich (St. Louis, Mo.). Stock solutions of both peptides were prepared in DPBS containing 0.1% BSA, aliquotted and stored at −80° C.

Figure 9C:
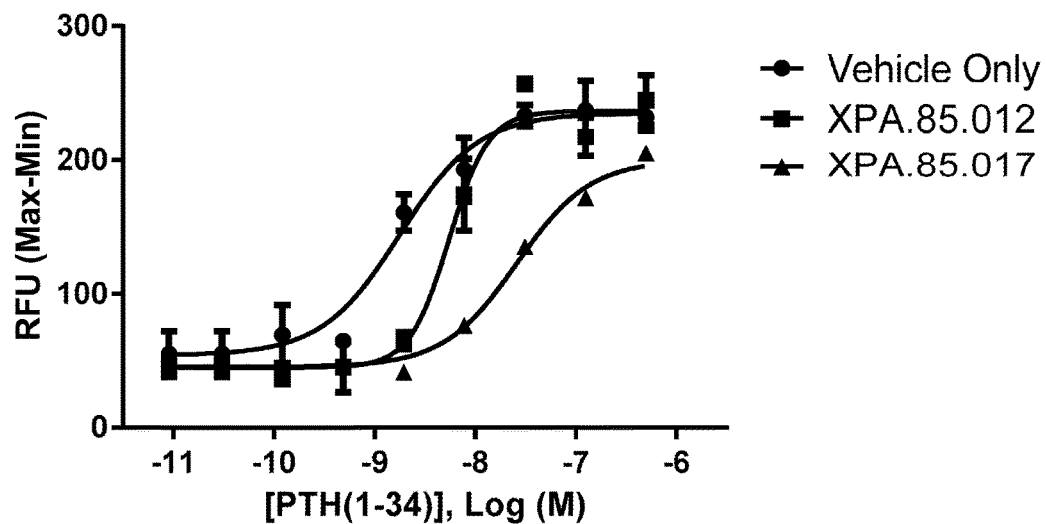
Figure 9D:
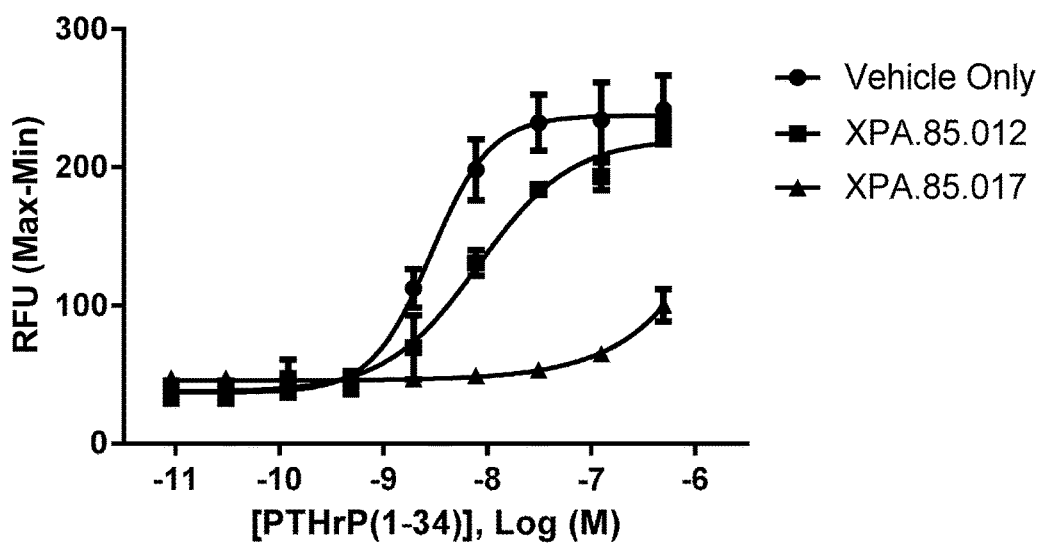

Human PTH1R CHOK1 Clone 22 cells were preincubated for 30 min at 37° C. with 267 nM (40 µg/ml) of either XPA.85.012 (solid squares) or XPA.85.017 (solid triangles), followed by induction with increasing concentrations of either PTH(1-34) (FIG. 9C) or PTHrP(1-34) (FIG. 9D). Both antibodies inhibited ligand-mediated calcium mobilization (Gs/PKA pathway).

TABLE 6

EC50 values in pM for PTH(1-34) and PTHrP(1-34) in the presence of variant IgGs derived from affinity engineering of XPA.85.017 (parent) by light chain shuffling

| Ligand | cAMP Assay Human PTH1R CHOK1 Ligand EC50 (pM) | | cAMP Assay Mouse PTH1R CHOK1 Ligand EC50 (pM) | | cAMP Assay SaOS-2 (Endogenous Human PTH1R) Ligand EC50 (pM) | | cAMP Assay UMR106 (Endogenous Rat PTH1R) Ligand EC50 (pM) | |
|---|---|---|---|---|---|---|---|---|
| | PTH(1-34) | PTHrP(1-34) | PTH(1-34) | PTHrP(1-34) | PTH(1-34) | PTHrP(1-34) | PTH(1-34) | PTHrP(1-34) |
| Vehicle Only | 30.7 ± 7.7 (10) | 61.4 ± 18.1 (3) | 30.6 ± 10.8 (5) | 43.1 ± 17.8 (3) | 524.5 ± 130.5 (6) | 698.7 ± 128.8 (4) | 646.6 ± 210.6 (8) | 333.2 ± 68.3 (6) |
| XPA.85.017 (Parent) | 140.6 ± 49.9 (4) 5-fold shift | 967.6 ± 491.0 (3) 16-fold shift | 2811.0 ± 1097.1 (3) 91-fold shift | 3742.3 ± 1288.1 (3) 87-fold shift | 797.8 ± 202.4 (2) No shift | ND | 23820 ± 5968.1 (4) 37-fold shift | 7776.7 ± 1052.0 (3) 23-fold shift |
| XPA.85.287 | 908.3 ± 341.3 (4) 29-fold shift | 52700 (1) >100-fold shift | 13640 (1) >100-fold shift | 5766 (1) >100-fold shift | 78600 ± 18179 (3) >100-fold shift | 62200 ± 21400 (3) 89-fold shift | 66700 ± 16628 (3) >100-fold shift | 11590 (1) 35-fold shift |
| XPA.85.335 | 42.9 ± 5.3 (2) | ND | 4545 (1) | ND | ND | 6412 (1) | ND | ND |
| XPA.85.336 | 18.1 ± 8.4 (2) | ND | 144.4 (1) | ND | ND | 23580 (1) | ND | ND |
| XPA.85.337 | 107.2 ± 44.9 (2) | ND | 219.4 (1) | ND | ND | 27080 (1) | 2877 (1) | ND |
| XPA.85.338 | 244.5 ± 28.9 (2) | ND | 1802 (1) | ND | 32790 (1) | 32950 (1) | 7861 (1) | ND |
| XPA.85.339 | 612.8 ± 140.6 (2) | ND | 1952 (1) | ND | 24768 ± 10586 (3) | 31450 (1) | 7900 ± 21 (2) | 3481 (1) |
| XPA.85.340 | 403.5 ± 15.9 (2) | ND | 614.2 (1) | ND | 4169 (1) | 11850 (1) | 8100 (1) | ND |
| XPA.85.341 | 403.9 ± 175.5 (2) | ND | 2147 (1) | ND | 38100 (1) | 62990 (1) | 13740 (1) | ND |

Variant IgGs were tested at 267 nM (40 µg/ml), and were preincubated with cells for 30 min at 37° C. prior to induction for 45 min at 37° C. Fold-shift in ligand EC50 was calculated relative to the EC50 of ligand in the "Vehicle Only" control group. Number of experiments is indicated in parentheses.
ND = Not Determined.

TABLE 7

Percent inhibition of cAMP accumulation mediated by 1 µM of either PTH(1-34) or PTHrP(1-34) in the presence of variant IgGs derived from affinity engineering of XPA.85.012 (parent) by light chain shuffling.

| | cAMP Assay SaOS-2 (Endogenous Human PTH1R) % Inhibition at 1 µM of ligand | | cAMP Assay UMR106 (Endogenous Rat PTH1R) % Inhibition at 1 µM of ligand | |
|---|---|---|---|---|
| Ligand | PTH(1-34) | PTHrP(1-34) | PTH(1-34) | PTHrP(1-34) |
| XPA.85.012 (Parent) | ND | 0 (1) | 0 (1) | 0 (1) |
| XPA.85.288 | 79 (2) | 79 (1) | 73 (2) | 45 (1) |
| XPA.85.329 | 79 (1) | 90 (1) | 50 (1) | 41 (1) |
| XPA.85.330 | 85 (1) | 89 (1) | 55 (1) | 56 (1) |
| XPA.85.331 | 67 (1) | 72 (1) | 42 (1) | 37 (1) |
| XPA.85.332 | ND | ND | ND | ND |
| XPA.85.333 | ND | ND | ND | ND |
| XPA.85.334 | ND | ND | ND | ND |
| XPA.85.342 | 0 (2) | 17 (1) | 6 (1) | 0 (1) |
| XPA.85.343 | ND | ND | ND | ND |
| XPA.85.344 | ND | ND | ND | ND |
| XPA.85.345 | ND | ND | ND | ND |
| XPA.85.346 | 72 (1) | 75 (1) | 40 (1) | 31 (1) |
| XPA.85.347 | ND | ND | ND | ND |

Number of experiments is indicated in parentheses
ND = Not Determined

Variant IgGs were tested at 267 nM or 40 µg/ml, and were preincubated with cells for 30 min at 37° C. prior to induction of cAMP accumulation for 45 min at 37° C.
Data represent average RLUs in duplicate wells.

TABLE 8

IC50 values of variant IgGs derived from affinity engineering of XPA.85.012 (parent) by light chain shuffling.

| Antibody Name | cAMP Assay Human PTH1R CHOK1 PTHrP(1-34) IC50 (nM) | cAMP Assay Human PTH1R CHOK1 PTH(1-34) IC50 (nM) | cAMP Assay Mouse PTH1R CHOK1 PTHrP(1-34) IC50 (nM) | cAMP Assay Mouse PTH1R CHOK1 PTH(1-34) IC50 (nM) |
|---|---|---|---|---|
| XPA.85.012 (Parent) | ND | ND | ND | ND |
| XPA.85.328 | 7.06 | 11.82 | 2.23 | ND |
| XPA.85.329 | 6.54 | 16.55 | 2.66 | ND |
| XPA.85.330 | 8.23 | 10.6 | 2.82 | ND |
| XPA.85.331 | 8.86 | 14.21 | 3.2 | ND |
| XPA.85.332 | 5.03 | 12.1 | 2.3 | ND |
| XPA.85.333 | 5.61 | 11.43 | 2.04 | ND |
| XPA.85.334 | 12.39 | 51.19* | 3.32 | ND |
| XPA.85.342 | ND | ND | ND | ND |
| XPA.85.343 | 17.77 | 14.38 | 3.87 | ND |
| XPA.85.344 | 15.28 | 15.53 | 3.89 | ND |
| XPA.85.345 | 12.14 | 14.19 | 2.53 | ND |
| XPA.85.346 | 14.57 | 29.85* | 3.57 | ND |
| XPA.85.347 | Partial | Partial | 2.9 | ND |

*Curve does not reach a plateau
ND = Not Determined
Variant IgGs were tested at a range of concentrations (0-66.67 nM or 10 µg/ml), and were preincubated with cells for 30 min at 37° C. prior to induction of cAMP accumulation by either PTH(1-34) or PTHrP(1-34) for 45 min at 37° C. Data represent average RLUs in duplicate wells. Variants exhibited a range of antagonism of ligand-mediated cAMP accumulation, particularly against the human PTH1R.

C. M-CSF Secretion by Saos-2 Osteoblasts

PTH and PTHrP act on the PTH1R receptor expressed in osteoblasts and osteocytes to stimulate the production of macrophage colony stimulating factor (M-CSF) and the surface expression Receptor activator of nuclear factor kappa-B ligand (RANKL). The increased production of M-CSF and RANKL expression by these bone cells drives the differentiation and activation of bone resorbing osteoclasts, which leads to increased level of calcium efflux from the bone and bone demineralization. Both of these growth factors are required for the PTH/PTHrP mediated differentiation and activation of human osteoclasts (Matsuzaki et al., 1999 Endocrinology 140:925-32; Itoh et al., 2000 Journal of bone and mineral research: the official journal of the American Society for Bone and Mineral Research 15:1766-75).

To assess the ability of these antibodies inhibit the PTH or PTHrP stimulated secretion of osteoclastogenic growth factors, an M-CSF secretion experiment using the osteoblastic cell line Saos-2 was employed.

Saos-2 cells (ATCC, Manassas Va.) were grown at 37° C. with 5% $CO_2$ and saturating humidity in 15% McCoy's 5A medium (Life Technologies) with 15% FBS (Hyclone/GE Life Sciences, Logan, Utah) plated at 50,000 cells/well into a 96 well culture plate in growth media and allowed to form a confluent monolayer for 48 hours. Then the media was replaced with MEM-α (Life Technologies) with 10% FBS and incubated for an additional 72 to 96 hours. The media was aspirated from the wells and replaced with 2× antibody treatments in the same MEM-α based media as above. The antibody treatments were incubated at 37° C. for 20 to 30 minutes prior to the addition of the PTH (1-34) or PTHrP (1-36) peptide dilutions in media. The ligands were diluted to achieve the shown final concentration following addition to the assay well. For ligand titration experiments the final antibody concentration is 40 μm/mL (267 nM). The plate was returned to the incubator and incubated at 37° C. for 48 hours. The supernatant from the treatment wells were then analyzed by a plate based immuno-assay which measures human M-CSF (MesoScale Diagnostics, Rockville Md.) following the manufacturer's instructions and read on a Sector Imager 6000 (MesoScale Diagnostics). For the antibody titration experiment, the same protocol was followed except that a fixed concentration of ligand (12.5 nM PTHrP (1-36)) was used and the concentration of antibody was varied.

Figure 14A:
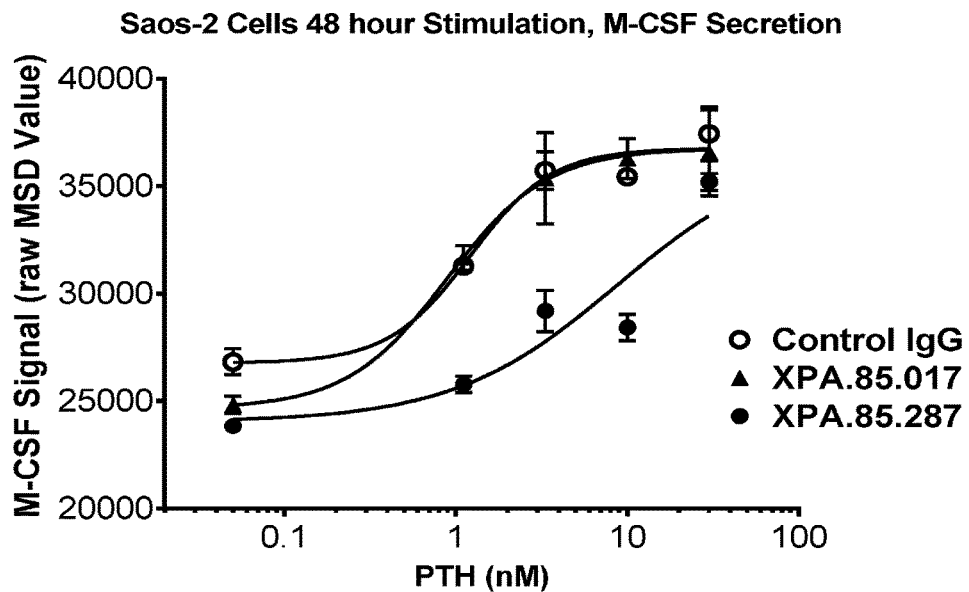
FIGS. 14A-14B: Effects of PTH1R antibodies on PTH stimulated secretion of M-CSF by Saos-2 cells. Post confluent Saos-2 cells were treated for 48 hr with the specified concentrations of PTH (1-34) peptide in the presence of 40 µg/mL antibody. The clone XPA.85.017 (triangles) is shown along with a light chain swapped variant XPA.85.287 (solid circles) and the negative control IgG (open circles) (FIG. 14A). Five of the affinity enhanced light chain swapped variants containing the XPA.85.012 heavy chain were shown to inhibit PTH stimulated M-CSF secretion (FIG. 14B). Control IgG (open circles), XPA.85.288 (solid circles), XPA.85.342 (inverted triangles), XPA.85.346 (open squares), XPA.85.331 (open triangles), and XPA.85.327 (solid squares).
Figure 14B:
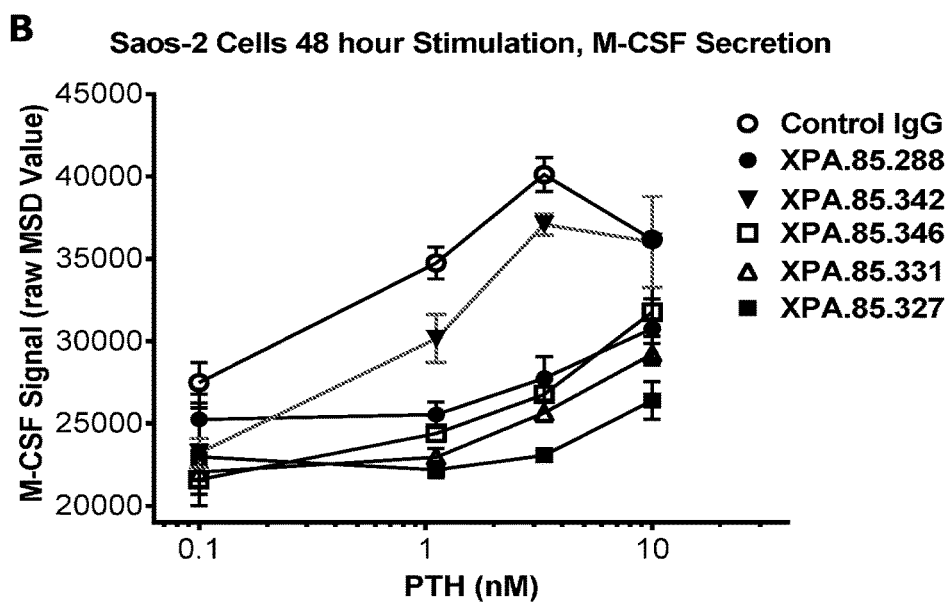

The affinity matured antibodies demonstrated the ability to inhibit the PTH stimulated increases in M-CSF secretion by Saos-2 cells. The antibody XPA.85.287 shifted the PTH (1-34) dose response curve by approximately 7 fold (1.2 nM to 8.7 nM) (FIG. 14A). In a separate experiment, the light chain variants XPA.85.288, XPA.85.346, XPA.85.331, and XPA.327 all shift the PTH (1-34) dose response curve greater than 10 fold (FIG. 14B).

Figure 15A:
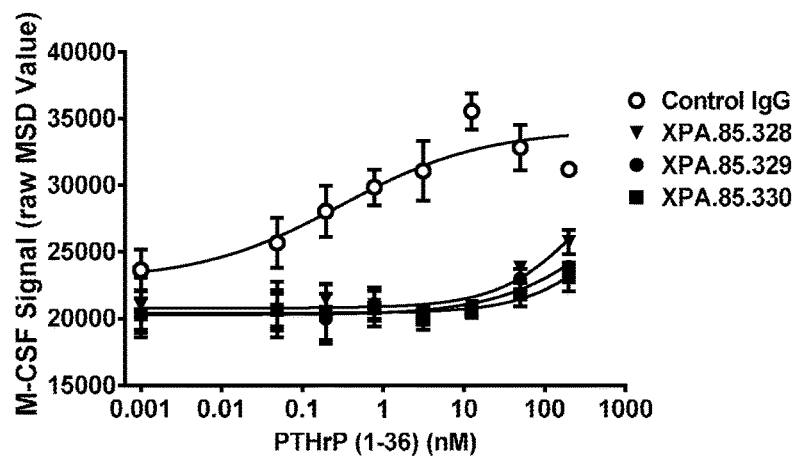
FIGS. 15A-15C: Effects of PTH1R antibodies on PTHrP stimulated secretion of M-CSF by Saos-2 cells. Post confluent Saos-2 cells were treated for 48 hr with the specified concentrations of PTHrP (1-36) peptide in the presence of 40 µg/mL antibody. Negative control IgG (open circles), XPA.85.328 (inverted triangles), XPA.85.329 (solid circles), XPA.85.330 (squares). Three of the affinity enhanced light chain swapped variants with the XPA.85.012 heavy chain were shown to inhibit PTHrP stimulated M-CSF secretion at a fixed antibody concentration of 40 m/mL (FIG. 15A). A fixed PTHrP (1-36) concentration of 12.5 nM was tested against a various concentrations of the antibodies (FIG. 15B). In a separate experiment, the parental clones XPA.85.012 and XPA.85.017 were compared to their affinity matured variants XPA.85.288 and XPA.85.287 respectively at 40 µg/mL (FIG. 15C).
Figure 15B:
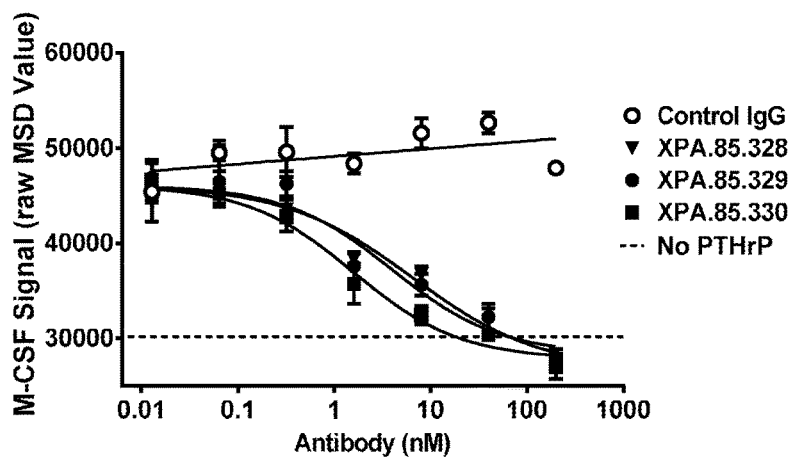
Figure 15C:
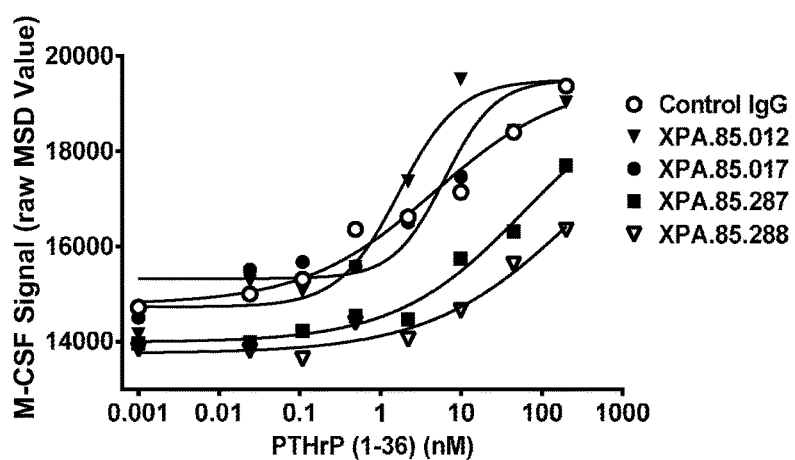

Affinity matured light chain variants also inhibited PTHrP mediated increases in M-CSF secretion by Saos-2 cells. At a fixed antibody concentration of 40m/mL, XPA.85.328, XPA.329, and XPA.85.330 inhibit PTHrP (1-36) stimulated M-CSF secretion dose response by greater than 200 fold (FIG. 15A). In a separate experiment, the parental clones XPA.85.012 and XPA.85.017 were compared to their affinity matured variants XPA.85.288 and XPA.85.287 respectively. The affinity matured clones showed significant inhibition of PTHrP induced M-CSF secretion whereas the parental clones did not (FIG. 15C). The antibody dose response of this effect was also evaluated against a fixed PTHrP (1-36) concentration of 12.5 nM. XPA.85.328, XPA.329, and XPA.85.330 fully neutralized M-CSF production induced by the 12.5 nM PTHrP treatment with EC50s of 6.6 nM, 4.0 nM, and 1.5 nM respectively, (FIG. 15B).

D. ERK Phosphorylation

The MAPK (mitogen-activated protein kinase) ERK1/2 (extracellular signal-regulated kinase) is phosphorylated and activated following ligand stimulation of the PTH1R. This pathway activation is representative of a convergent signaling event requiring inputs from both the G-protein mediated adenylate cyclase pathway and the β-Arrestin mediated pathway and has been shown to be required for renal calcium transport (Gesty-Palmer et al.,2006 JBC 281: 10856-64; Sneddon et al., 2000 Endocrinology 141:4185-93).

In order to determine the ability of the anti-PTH1R antibodies to modulate the MAPK pathway, experiments were carried out which evaluated their ability to inhibit PTH and PTHrP mediated ERK1/2 phosphorylation at Thr202/Tyr204; Thr185/Tyr187.

CHO-PTH1R cells were serum starved at $1 \times 10^6$ cells/mL in RPMI 1640 (Life Technologies) with 0.5% BSA (Sigma), and incubated overnight at on a shaking platform at 37° C. and 5% $CO_2$. The next day, cells were seeded at a density of 100,000 cells per well in assay buffer (PBS+0.5% BSA) into 96-well U-bottom plates. Subsequently, 50 μL per well of antibodies diluted to 400 nM (2×-60 μg/mL) in assay buffer was added to cells. After 10 minutes of incubation at 37° C. 25 μL/well of the diluted Ligands (4× of final concentration) were added to the wells containing the cells and antibodies, and incubated for 5 minutes at 37° C. Then, 100 μl of cold PBS per well was added to stop the reaction. The plate was centrifuged for 3 minutes at 4° C. and the media was removed. Then 80 ul of ice cold MSD lysis buffer was added to cells and resuspended. The plate was incubated on a shaking platform for 1 hour at 4° C. to completely lyse cells. The total and phosphorylated ERK were measured using an MSD whole cell lysate Phospho-ERK1/2 kit (MesoScale Diagnostics cat. K11107D-1) as per the manufacturer's instructions and read on a Sector Imager 6000 (MesoScale Diagnostics). Curves were fit by nonlinear regression using the sigmoidal dose-response equation in GraphPad Prism version 6.05 (GraphPad, San Diego, Calif.).

Figures 16A, 16B:
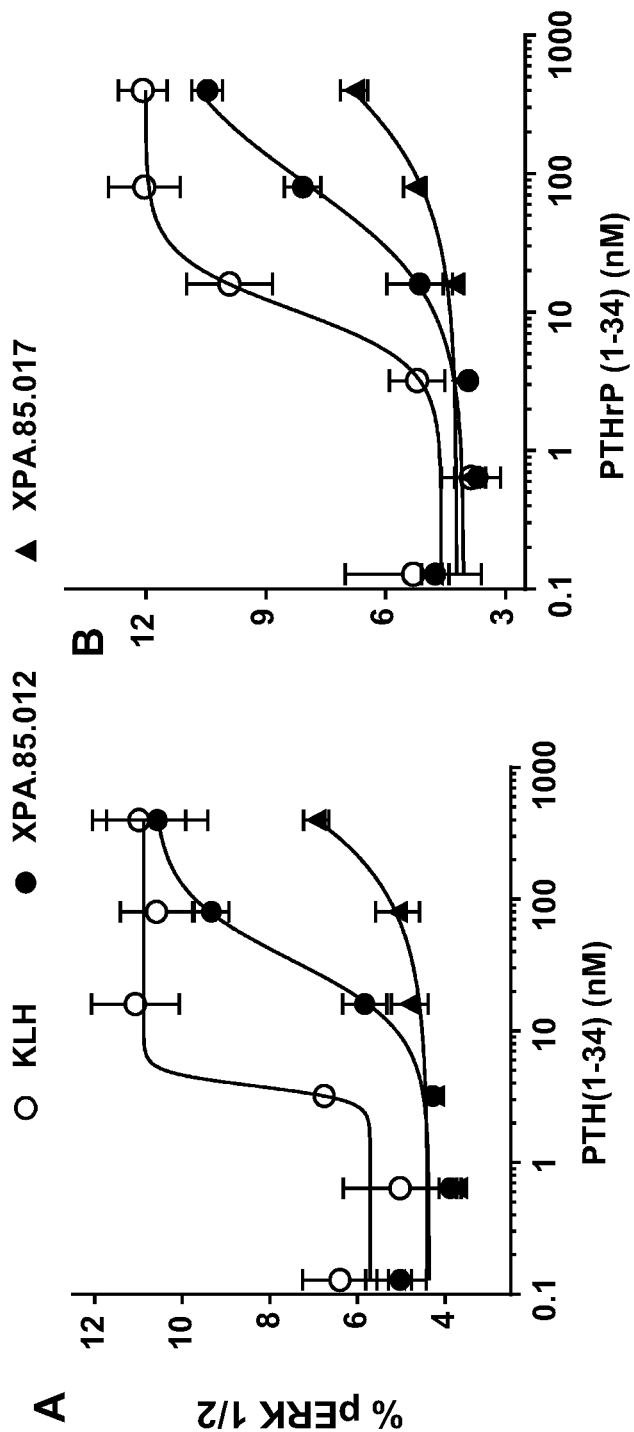
FIGS. 16A-16B: Concentration-response curves for PTH (FIG. 16A) and PTHrP (FIG. 16B) peptide stimulation of hPTH1R mediated phosphorylation of ERK1/2 in the presence of 200 nM of antibody. CHO-hPTH1R cells were incubated for 10 minutes at 37° C. with the antibodies followed by a 5 minute incubation with increasing concentrations of peptide ligand, then the cells were lysed and the level of ERK1/2 phosphorylation was determined by immuno-assay. Data points shown are mean values+/−SEM. Antibodies: Negative Control IgG (open circles), XPA.85.012 (solid circles), and XPA.85.017 (solid triangles).

The antibody XPA.85.012 increased the EC50 of PTH (1-34) induced ERK1/2 phosphorylation by approximately 9 fold (3.8 nM to 34.6 nM) (FIG. 16A) and the EC50 of PTHrP (1-34) induced ERK1/2 phosphorylation increased roughly 6 fold (EC50 of 10.6 nM to 62.5 nM) (FIG. 16B). The antibody XPA.85.017 increased the EC50 of PTH (1-34) induced ERK phosphorylation by greater than 100 fold (3.8 nM to >500 nM) (FIG. 16A) and the EC50 of PTHrP (1-34) increased roughly 80 fold (EC50 of 10.6 nM to 887 nM) (FIG. 16B).

Example 6: Manufacturability Improvements

A. Evaluation of V Region Sequences for Selected Antibody Candidates

The light and heavy chain V region amino acid sequences of selected antibody candidates were evaluated for the presence of "non-human" amino acids using Human Engineering software (HE™, U.S. Pat. No. 5,766,886) and for N-linked glycan, oxidation and deamidation signals using bioinformatics software. Based on these analyses for certain antibodies, amino acid changes were incorporated by site directed mutagenesis or gene synthesis.

B. CHO-K1 Manufacturability Assessment of Selected Antibody Candidates

Transient expression in CHO-K1 cells was used to evaluate manufacturability of multiple antibody.

DNAs encoding the light and heavy chain V regions were cloned into transient expression plasmids containing antibody signal sequences and light chain (LC) or heavy chain (HC) constant regions, respectively and transfected into suspension-adapted CHO-K1 cells in deep well 96 well plates. Expression plasmids were tested at LC:HC plasmid ratios (by weight) of 1:1, 2:1, 4:1 and 1:2 with the DNA quantity in each transfection kept constant by the addition of empty plasmid DNA. Duplicate transfections are performed for each antibody. Two control antibodies, XB10 and XE17, are included as controls for high and low expression, respectively. Following transfection, plates were incubated on a shaker platform in a $CO_2$ incubator for 7 days with a temperature shift from 37° C. to 32° C. 24 hr post-transfection. Supernatants were assayed for antibody titer using an Octet instrument with Protein A sensor tips.

Selected antibody candidates were evaluated for expression using this assay. Based on the results observed for some of the antibodies, the DNA sequences encoding the HC and LC V regions along with the signal sequences were optimized for expression in CHO cells (GeneArt). The optimized antibodies then were re-tested for manufacturability. In cases where expression optimization was carried out, while the DNA sequences were different, the amino acid sequences for the light and heavy chain V regions remained the same unless Human Engineering analysis indicated the need for an amino acid change. The antibodies with optimized DNA sequences are shown in Table 9B.

LC:HC ratio. Highest expression is highlighted in bold. Expression optimization was performed for three of the antibodies.

For the affinity-matured antibodies XPA.85.287, XPA.85.339. XPA.85.340 and XPA.85.341, highest expression was observed at a HC:LC ratio of 1:2 (Table 9A). Although expression was lower at a HC:LC ratio of 1:1 than at 1:2, the level achieved at a 1:1 ratio is acceptable for cell line development. Three other affinity-matured antibodies, XPA.85.288, XPA.85.326 and XPA.85.327 displayed very low expression at a 1:1 HC:LC ratio. A significant improvement in expression was observed for all three of these antibodies especially at HC:LC ratio of 1:1 after expression optimization of the V region DNA sequences. XPA.58.328 (optimized version of XPA.85.288) displayed >10-fold increase vs. XPA.85.288. XPA.85.329 (optimized version of XPA.85.326) displayed a ~3.5-fold increase vs. XPA.85.326 and XPA.85.330 (optimized version of XPA.85.327) displayed ~6.5-fold increase vs. XPA.85.327 (Table 9B).

Four additional affinity-matured antibodies, XPA.85.331, XPA.85.332, XPA.85.333 and XPA.85.324 also were evaluated for CHO manufacturability. All four antibodies displayed low expression at a HC:LC ratio of 1:1 being ≤ than

TABLE 9A

XPA.85.287, XPA.85.339, XPA.85.340 and XPA.85.341

| HC:LC Ratio | Titer relative to XB10 (average result from duplicate transfections) | | | | | |
|---|---|---|---|---|---|---|
| | XB10 | XE17 | XPA.85.287 | XPA.85.339 | XPA.85.340 | XPA.85.341 |
| 1:1 | 100 | 21 | 49 | 50 | 77 | 71 |
| 1:2 | 51 | 15 | 97 | 60 | 83 | 74 |
| 1:4 | 17 | 8 | 47 | 16 | 62 | 19 |
| 2:1 | 40 | 6 | 16 | 16 | 21 | 17 |

TABLE 9B

XPA.85.288, XPA.85.326 and XPA.85.327 and their expression-optimized versions, XPA.85.328, XPA.85.329 and XPA.85.330.

| | Titer relative to XB10 (average result from duplicate transfections) | | | | | | | |
|---|---|---|---|---|---|---|---|---|
| HC:LC Ratio | XB10 | XE17 | Original XPA.85.288 | Optimized XPA.85.328 | Original XPA.85.326 | Optimized XPA.85.329 | Original XPA.85.327 | Optimized XPA.85.330 |
| 1:1 | 100 | 26 | 7 | 78 | 25 | 87 | 19 | 125 |
| 1:2 | 55 | 30 | 14 | 59 | 86 | 91 | 75 | 101 |
| 1:4 | 39 | 21 | 7 | 26 | 37 | 37 | 49 | 58 |
| 2:1 | 84 | 9 | 1 | 23 | 7 | 24 | 4 | 16 |

TABLE 9C

XPA.85.331, XPA.85.332, XPA.85.333 and XPA.85.334

| HC:LC Ratio | Titer relative to XB10 (average result from duplicate transfections) | | | | | |
|---|---|---|---|---|---|---|
| | NXB10 | NXE17 | (XPA.85.331) | (XPA.85.332) | (XPA.85.333) | (XPA.85.334) |
| 1:1 | 100 | 29 | 33 | 28 | 37 | 19 |
| 1:2 | 71 | 20 | 75 | 68 | 98 | 28 |
| 1:4 | 13 | 8 | 26 | 37 | 42 | 9 |
| 2:1 | 40 | 8 | 6 | 5 | 6 | 2 |

Table 9. Results of CHO-K1 Manufacturability Assessment of Affinity-Matured Anti-PTH1R Antibodies.

Values reported are relative to expression of the "high-expressing" control antibody, XB10, set to 100 at a 1:1 the poor-expressing XE17 antibody (Table 9C). Expression was 2-2.5-fold higher at HC:LC ratios of 1:2. XPA.85.334 expression fell below the minimum acceptable level in this assay to qualify for initiating cell line development without further expression improvement.

Example 7: Measurement of the In Vivo Effects of Anti-PTH1R Receptor Antibodies

A. Thyroparathyroidextomized (TPTx) Model

Anti-human PT1-11R receptor antibodies found to be cross-reactive with rat PTH1R were tested in in vivo models of primary hyperparathyroidism (for PTH) and Humoral Hypercalcemia of Malignancy (HHM for PTHrP). In a thyroparathyroidectomized (TPTx) model, the effects of the endogenous calciotropic peptide hormones, PTH and calcitonin are eliminated by surgical removal of the thyroid and parathyroid glands in Sprague-Dawley (SD) male rats (Charles River Laboratories, Raleigh). Low postoperative serum calcium levels are then obtained in a tightly controlled setting. Thyroid pellets (L-thyroxine T4, 0.25 mg; 60 days slow release; Innovative. Research of America) are implanted subcutaneously under anesthesia. The jugular vein is then cannulated for continuous infusion of PTH(1-34) (1.25 µg/kg/hr at a rate of 1 mL/kg/hr for 6 hr. This model was used to evaluate the ability of PTH1R antibodies to affect the increase of serum calcium levels induced by PTH(1-34) intravenous infusion.

Figure 17:
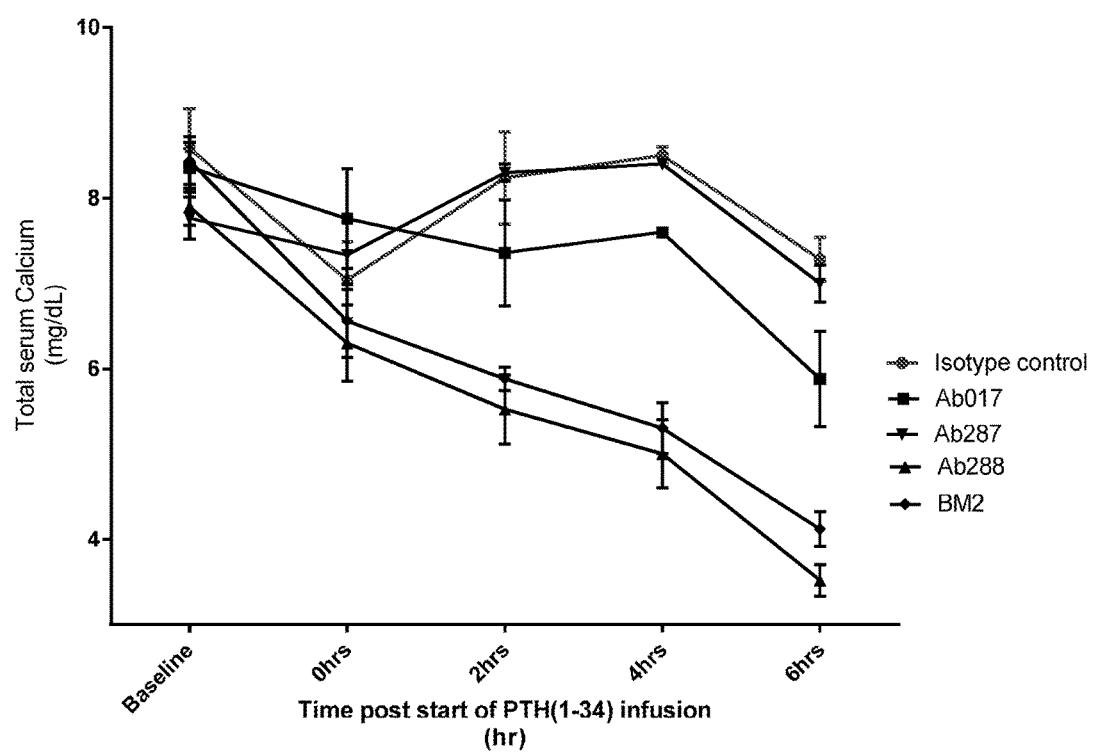
FIG. 17: PTH1R antibodies ability to reduce PTH(1-34)-induced elevation of serum calcium levels measured in vivo using a Thyroparathyroidectomized (TPTx) model. Sprague-Dawley (SD) male rats (n=5-6/group) were challenged intravenously with PTH1R antibodies XPA.85.017 (Ab017), XPA.85.287 (Ab287), XPA.85.288 (Ab288) and BM2, or an isotype control (15 mg/kg), 18 h before initiation of PTH(1-34) infusion. Serum calcium was measured before dosing (baseline), pre-infusion (T0), 2, 4 and 6 hr post start of infusion.

To determine whether anti-PTH1R receptor antibodies reduce PTH(1-34)-induced elevation of serum calcium levels, Sprague-Dawley (SD) male rats (n=5-6/group) were challenged intravenously with antibodies XPA.85.017 (Ab017), XPA.85.287 (Ab287), XPA.85.288 (Ab288) and BM2 (an anti-PTH antibody), or an isotype control (15 mg/kg), 18 hr before initiation of PTH(1-34) infusion (FIG. 17).

The anti-PTH antibody was based on Abgenix's antibody ID#183 (U.S. Pat. No. 7,318,925 B2. The heavy (HC) and light chain (LC) V region sequences were expression optimized for production in CHO cells and synthesized with appropriate restriction sites for cloning (GeneArt). DNAs were cloned into transient expression plasmids containing signal sequences and LC or HC constant regions. Each HC or LC is under control of the human CMV (hCMV) promoter and mouse light chain 3' untranslated region. The expression plasmids also contain the Epstein-Barr virus origin of replication to allow replication in cell lines containing the Epstein-Barr virus nuclear antigen. Transient expression using the Expi293 expression system (Life Technologies, Carlsbad, Calif.) was used to generate anti-PTH antibody for in vitro and in vivo studies. Antibody purification was carried out at Aragen Bioscience (Morgan Hill, Calif.).

Serum calcium was measured before dosing (baseline), pre-infusion (T0), 2, 4 and 6 hr post start of infusion. Over the first 4 hr infusion, the total calcium level in the isotype group increased. In rats receiving Ab287, the calcium level was comparable to the levels of the isotype control group. Calcium levels of rats receiving Ab017 slightly decreased. Compared to isotype controls, rats receiving BM2 and Ab288 had significantly lower levels of calcium throughout the infusion.

B. hPTH(1-34) Infusion Model

To further evaluate the effect of anti-PTH1R receptor antibodies on calcemic control, hPTH(1-34) was continuously infused subcutaneously (Alzet mini pump, 2ML1; 100/hr, 10 µg/kg/day) in normal Sprague Dawley rats (Harlan) for 7 days to mimic PTH hypersecretion in patients with hyperparathyroidism. Calcium was measured as biomarker to assess in vivo neutralization by a single intravenous administration of Ab288 (2 or 10 mg/kg; n=5/group), BM2 (10 mg/kg; n=5), or isotype control (10 mg/kg, n=2) 24 hr after pump implantation (FIG. 18).

Figure 18A:
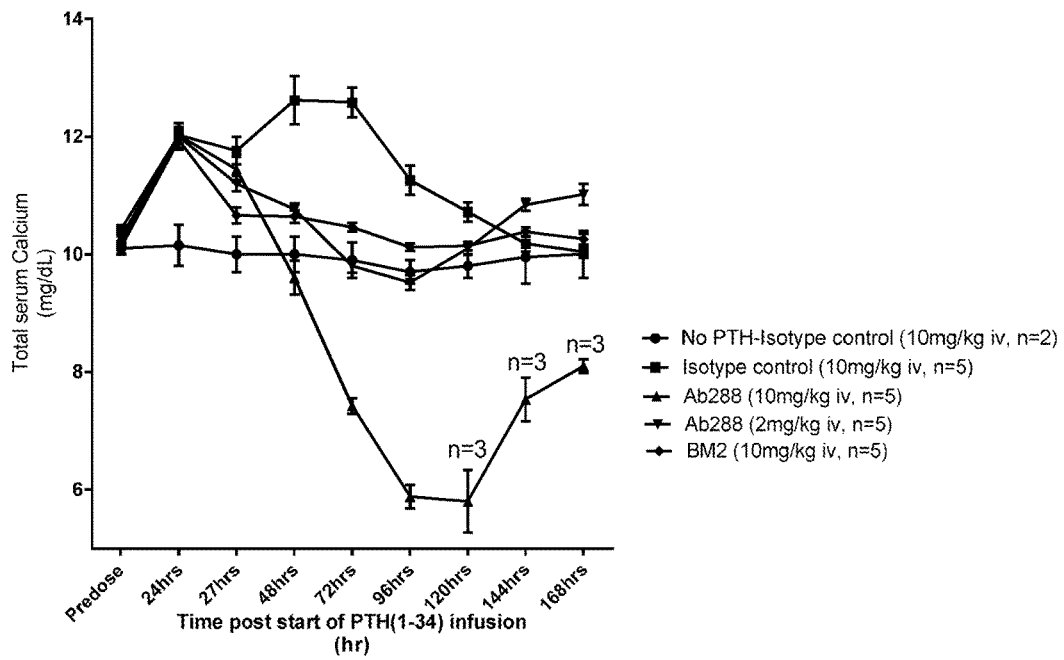
FIGS. 18A-18B: PTH1R antibodies ability to reduce PTH(1-34)-induced elevation of serum calcium levels measured in vivo using a continuous infusion model to mimic PTH hypersecretion in patients with hyperparathyroidism.

Serum calcium was measured before pump implantation (Predose), 24, 27 (3 hr post dose), 48, 72, 96, 120, 144 and 168 hours post pump implantation. Over the first 72 hour infusion, the total calcium level in the isotype group increased. Compared to isotype controls, rats receiving BM2 and Ab288 (2 and 10 mg/kg) had significantly lower levels of calcium 24 hr post dose and throughout the infusion: the effect on serum calcium levels of 2 mg/kg Ab288 was comparable to that of 10 mg/kg BM2. 10 mg/kg Ab288 produced a dramatic hypocalcemic effect (FIG. 18A).

Figure 18B:
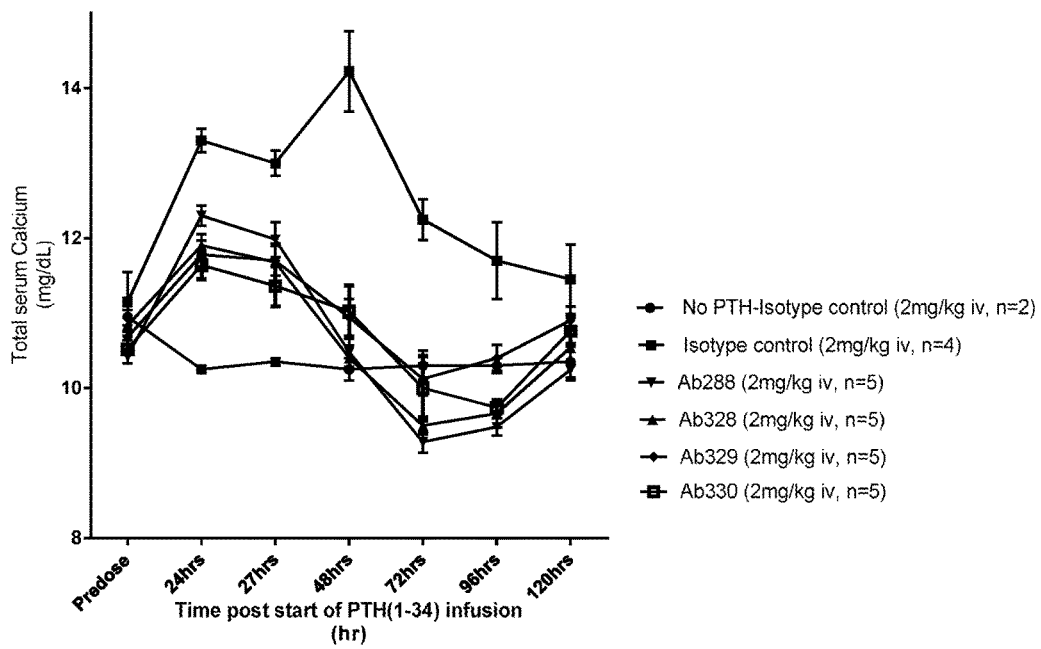

Antibodies, Ab328, Ab329 and Ab330 (2 mg/kg IV) were tested in a similar study where serum calcium was measured before pump implantation (Predose), 24, 27 (3 hr post dose), 48, 72, 96 and 120 hours post pump implantation. All antibodies significantly lowered levels of calcium 24 hr post dose and throughout the infusion, with Ab288 and Ab328 producing the most dramatic reduction in total serum calcium levels (FIG. 18B).

C. hPTHrP(1-36) Infusion Model

Similarly, the effects of anti-PTH1R receptor antibodies on inhibition of PTHrP activity were assessed by continuously infusing hPTHrP(1-36) subcutaneously (Alzet mini pump, 2ML1; 10 µl/hr, 100 mg/kg/day) in normal Sprague Dawley rats (Harlan) for 6 days to mimic hypercalcemia in patients with hyperparathyroidism. Calcium was measured as a biomarker to assess in vivo neutralization by a single intravenous administration of Ab288 (2 or 10 mg/kg; n=4/group), anti-PTHrP antibody MCB1.1 (10 mg/kg; n=5), or isotype control (10 mg/kg, n=3) 24 hr after pump implantation.

The anti-PTHrP antibody heavy chain and light chain V region sequences were based on Onuma et al., *Anticancer Research* 24:2665-2674, 2004. The heavy chain (HC) and light chain (LC) V region sequences were expression optimized for production in CHO cells and synthesized with the appropriate restriction sites (GeneArt) for cloning into transient expression plasmids containing signal sequences and LC or HC constant regions. Each HC or LC is under control of the human CMV (hCMV) promoter and mouse light chain 3' untranslated region. The expression plasmids also contain the Epstein-Barr virus origin of replication to allow replication in cell lines containing the Epstein-Barr virus nuclear antigen. Transient expression using the Expi293 expression system (Life Technologies, Carlsbad, Calif.) was used to generate anti-PTHrP antibody for in vitro and in vivo studies. Antibody purification was carried out at Aragen Bioscience (Morgan Hill, Calif.).

Figure 19A:
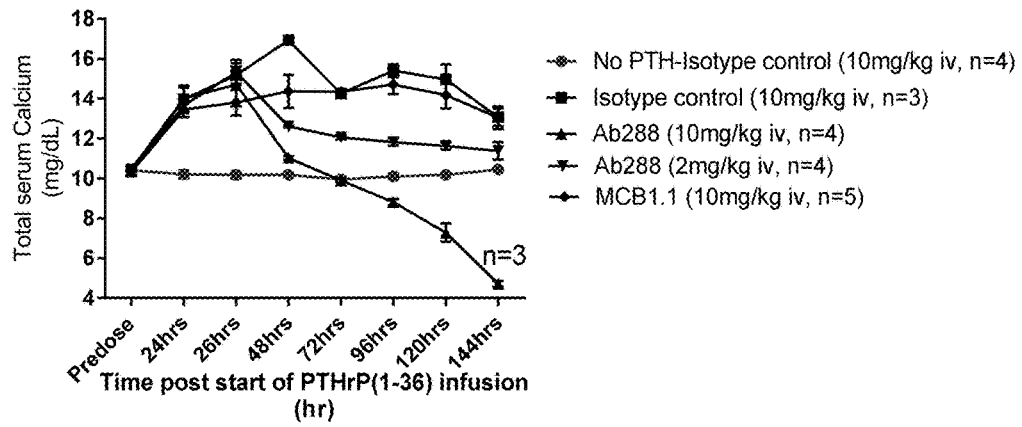
FIGS. 19A-19B: PTH1R antibodies' ability to reduce PTHrP(1-34)-induced elevation of serum calcium levels measured in vivo using a continuous infusion model to mimic hypercalcemia in patients with hyperparathyroidism. The effects of anti-PTH1R receptor antibodies on inhibition of PTHrP activity were assessed by continuously infusing hPTHrP(1-36) subcutaneously (Alzet mini pump, model 2ML1; 10 µl/hr, 100 mg/kg/day) in normal Sprague Dawley rats (Harlan) for 6 days to mimic hypercalcemia in patients with hyperparathyroidism.
Figure 19B:
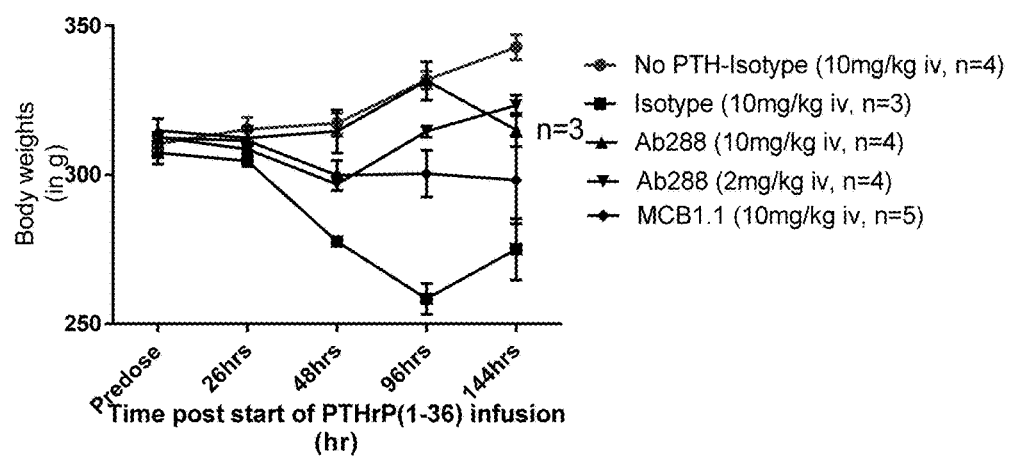

Serum calcium was measured before pump implantation (Predose), 24, 26 (2 hr post dose), 48, 72, 96, 120 and 144 hours post pump implantation (FIG. 19A). Body weights were measured before pump implantation (Predose), 26 (2 hr post dose), 48, 96 and 144 hours post pump implantation (FIG. 19B).

Over the first 48 hour infusion, the total calcium level in the isotype group increased. Compared to isotype controls, rats receiving MCB1.1 and Ab288 (2 and 10 mg/kg) had significantly lower levels of calcium 24 hr post dose. These lower calcium levels persisted throughout the infusion for Ab288 (2 and 10 mg/kg). The effect on serum calcium levels of 2 mg/kg Ab288 was more pronounced to that of 10 mg/kg MCB1.1. Ab288 (10 mg/kg) produced a dramatic hypocalcemic effect. PTHrP(1-36) infusion induced weight loss that was prevented by Ab288 (2 and 10 mg/kg).

This suggests anti-PTH1R antibodies could have health benefits and potentially prevent cachexia, a wasting disorder of adipose and skeletal muscle tissues that leads to profound weight loss.

Pilot studies had shown that infusion of doses of PTH and PTHrP can produce levels of serum calcium higher than 14 mg/dL linked to mortality. Treatment with anti-PTH1R antibody could prevent hypercalcemia (>14 mg/dL) and could therefore prevent mortality in HHM (survival benefit).

D. Tumor Model

To determine whether anti-PTH1R receptor antibodies reduce tumor-induced elevation of serum calcium levels, 6 week old CDF1 female mice, or Athymic Nude (NCr-nu/nu) mice were challenged intravenously with antibody XPA.85.328 (Ab328) (10 mg/kg), after serum calcium was found elevated in three different tumor models (mouse colon C26, human prostate PC-3 and human lung cancer HARA-B, respectively). The respective cells were cultured, and when the needed number of cells was obtained, each mouse were injected SC in the right flank with five million ($5 \times 10^6$) C26 cells, 10 million ($1 \times 10^7$) PC-3 cells or 10 million ($1 \times 10^7$) HARA-B cells in 0.1 mL of serum-free media. Serum calcium was measured regularly until hypercalcemia was observed (>12 mg/dL), usually when tumors were >1000 mg. Mice were then treated with Ab328 10 mg/kg iv, and in the HARA-B model, a separate group of mice with tumors >1 g was treated with the isotype (negative control; anti KLH G2) at 10 mg/kg iv, and the total calcium levels were determined 24 hours post dose.

In all three pilot studies, treatment with anti-PTH1R antibody Ab328 reduced tumor-induced hypercalcemia by >3 mg/dL, suggesting that the anti-PTH1R antibodies are also useful to treat cancers in which tumors result in elevated in vivo calcium levels in a subject.

Efficacy of Anti-PTH1R mAb, XPA.85.349, on Mouse Colon 26 Tumor-Related Hypercalcemia XPA.85.349 (Ab349), an expression-optimized variant of XPA.85.288, was evaluated in the mouse colon 26 model of Tumor-related Hypercalcemia. Six week old CDF1 female mice, or Athymic Nude (NCr-nu/nu) mice were used in the study. Colon 26 murine colon tumor cells were cultured and each mouse were injected subcutaneously in the right flank with seven million, five hundred thousand cells ($7.5 \times 10^6$) C26 cells in 0.1 mL of serum-free media. Serum calcium was measured regularly until hypercalcemia was observed (>12 mg/dL), usually when tumors were >1000 mg. Mice were then treated with Ab349 at 2 or 6 mg/kg intravenously, and a separate group of mice with tumors >1000 mg was treated with the isotype (negative control; anti KLH G2) at 6 mg/kg intravenously. Tumor weight and serum samples were collected at pretreatment, 24, 48 and 72 hours posttreatment. Total calcium levels were determined 24, 48, 72 and 120 hours post treatment. Tumor weights (mg) are calculated using the equation for an ellipsoid sphere $(l \times w^2)/2 = mm^3$, where l and w refer to the larger and smaller dimensions collected at each measurement and assuming unit density (1 $mm^3$=1 mg).

Figure 20A:
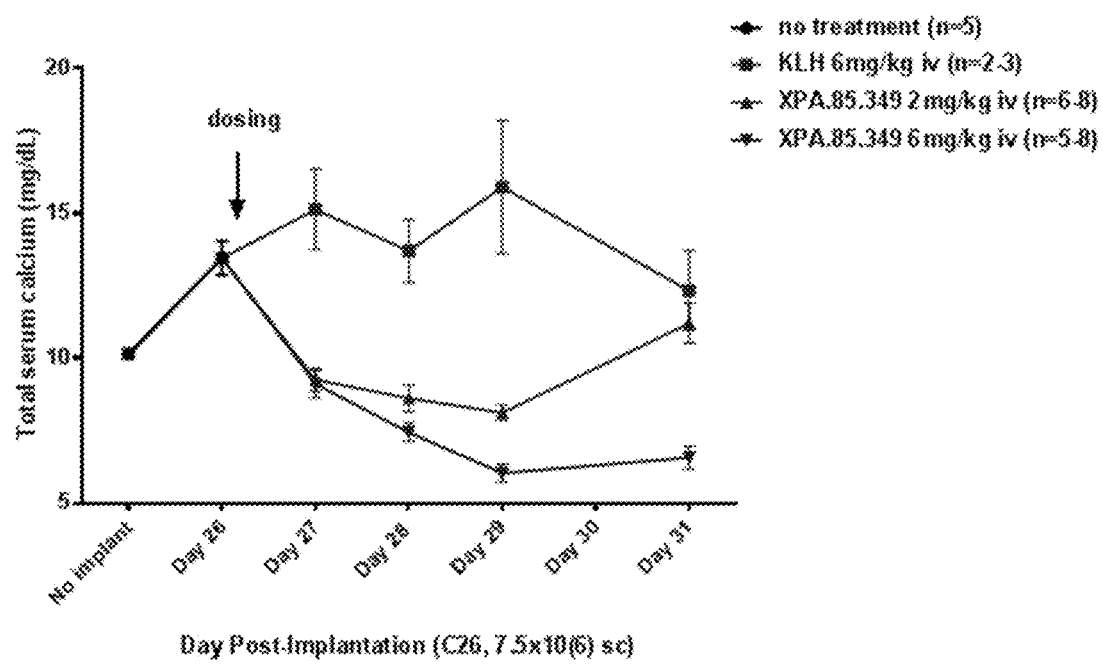
FIGS. 20A-20E: PTH1R antibody XPA.85.349 potently reduces mouse colon 26 tumor-related hypercalcemia for a sustained period. Total serum calcium was measured as a biomarker to assess in vivo neutralization by a single intravenous administration of PTH1R antibody XPA.85.349 (2 mg/kg; n=6-8/group or 6 mg/kg; n=5-8/group), anti-KLH.G2 negative control for binding (6 mg/kg; n=2-3), no treatment control (n=5), 24 hr after pump implantation (FIG. 20A shows mean serum total levels+/−S.E.M.). Mice body weight (FIG. 20B) and tumor weight (FIG. 20C) were measured over time (48 hours prior to dosing and 48, 72 and 120 hours post dose). Levels of PTHrP (FIG. 20D) and PTH1-84 (FIG. 20E) were also measured in the serum of mice 24, 48, 72 and 120 hours post dose with 2 or 6 mg/kg PTH1R antibody XPA.85.349, anti-KLH.G2 control antibody or prior to treatment and in animals without tumors.
Figure 20B:
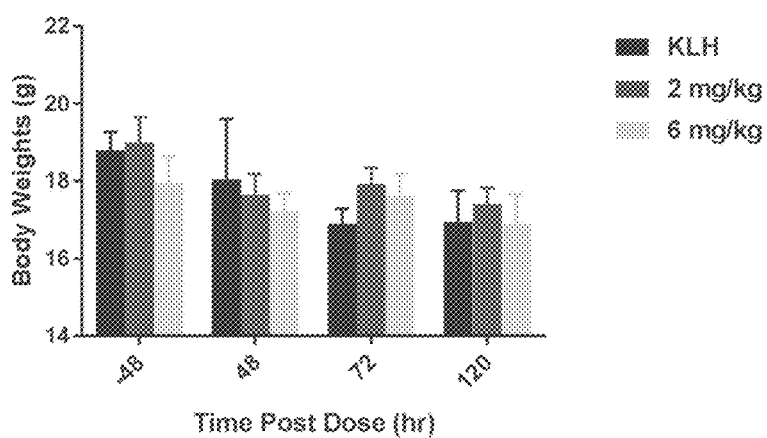
Figure 20C:
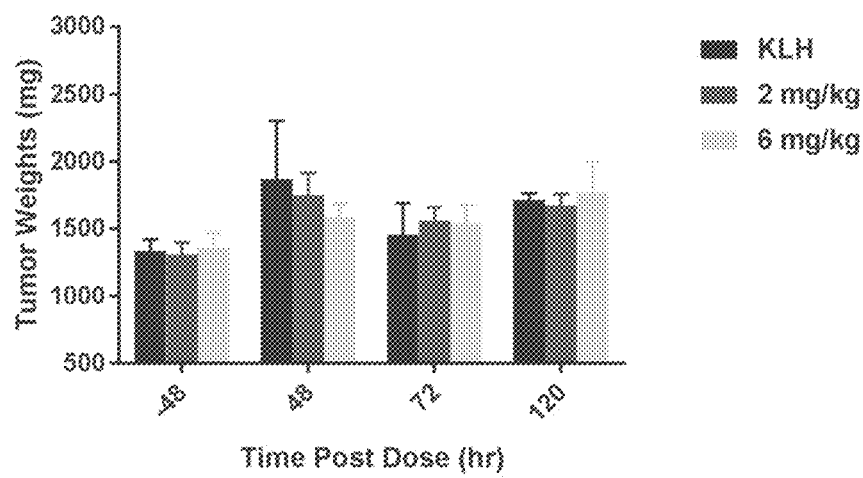

Anti-PTH1R Ab349 was found to potently reduce mouse colon 26 tumor-related hypercalcemia (i.e. significantly reduce total serum calcium) for a sustained period, up to 120 hours post dose (FIG. 20A). In this tumor model, Ab349 was capable of completely reversing hypercalcemia within 24 hours. The administration of Ab349 had no significant effect on body weight (FIG. 20B) or tumor weight (FIG. 20C) up to 120 hours post dose.

Figure 20D:
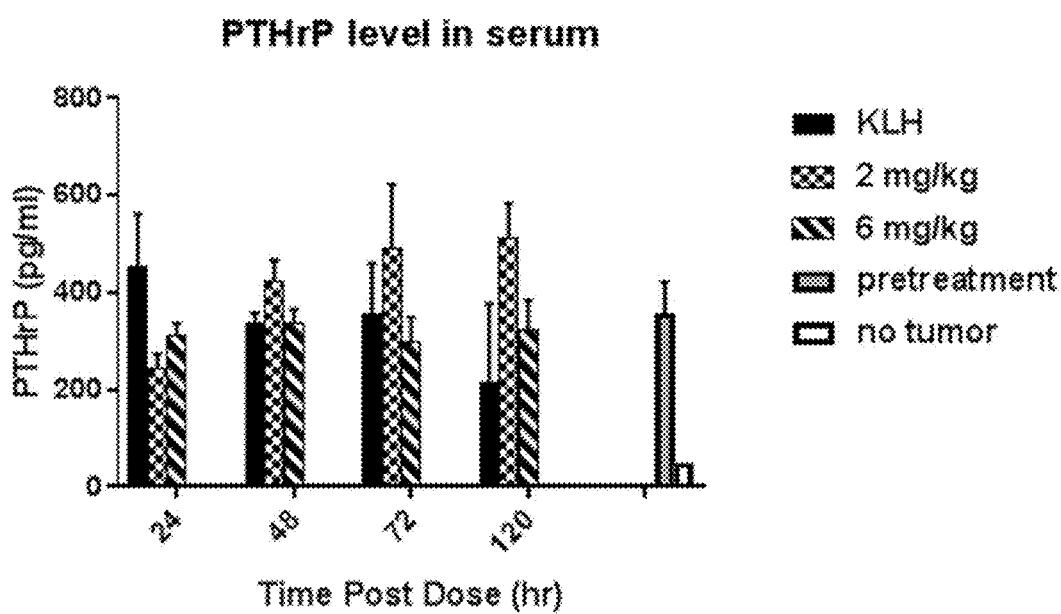
Figure 20E:
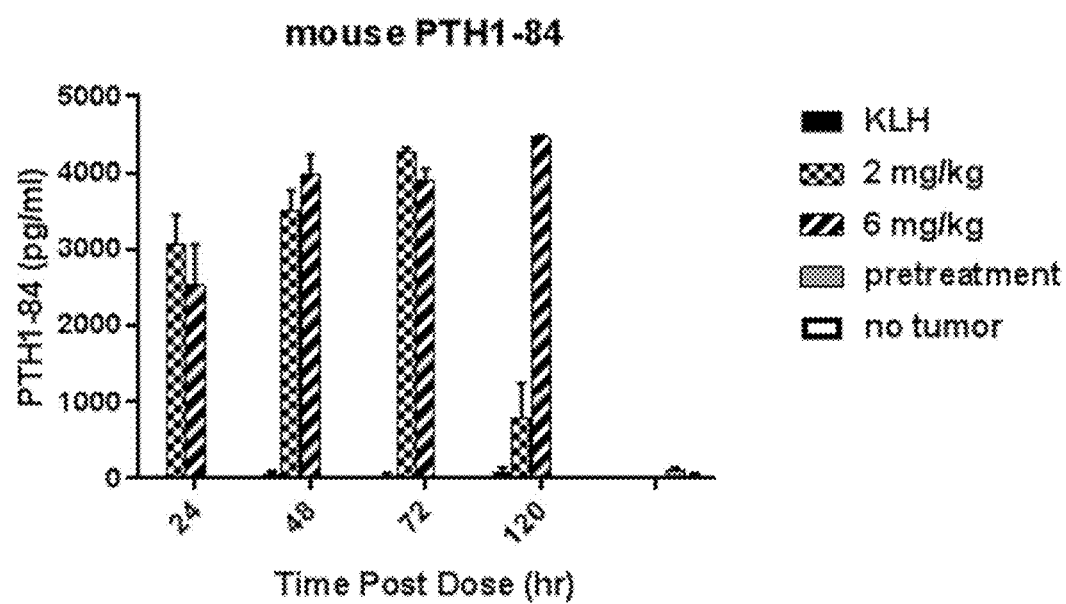

Levels of PTHrP and PTH in serum were measured at different time points post dosing with Ab349 antibodies. Antibodies were administered intravenously at 2 and 6 mg/kg at a period of hypercalcemia t0 (n=2-6 mice/group). Blood samples were collected from retro-orbital sinus at 24, 48, 72 and 120 hours post administration and the concentrations of PTHrP (Phoenix Pharmaceuticals, Inc—EIA Kit, catalog no.: EK-056-04) and mouse PTH 1-84 (QUIDEL Mouse PTH 1-84 ELISA kit, catalog no.: 60-2305) were measured. As shown in FIG. 20D, serum PTHrP is elevated in tumor-bearing mice, and although treatment with Ab349 did not appear to significantly change PTHrP levels, Ab349 did inhibit PTHrP activity. In contrast however, treatment with 2 or 6 mg/kg Ab349 significantly increased PTH levels up to 120 hours post dose (FIG. 20E).

Serum drug concentration (SDC) measurements were performed by enzyme-linked immunosorbent assay (ELISA). ELISA assays were performed as follows, ELISA plates were coated with 1 µg/mL goat anti-human Fc in PBS, plates were blocked with PBS/0.05% tween/1% BSA for 1-4 hours at room temperature. Serum samples at various dilutions in PBS/tween/BSA added and incubated 37° C. for 1 hr (in the final 5 minutes, 0.2 µg/ml biotin SP-conjugated Goat anti-human IgG(Fab') was added). Plates were subsequently rinsed with PBS/tween, incubated with Pierce p-Nitrophenyl Phosphate, Disodium Salt (pNPP) in 1×DEA buffer for 1 hr at room temperature. The colorimetric reaction was stopped by the addition of 1N NaOH. Plates were read at 405 nM on a spectrophotometer. SDC measurements showed normal excretion of Ab349 over a 120 hour period.

Several pharmacokinetic measurements were performed to create a pharmacokinetic profile of Ab349 following intravenous injection. CDF1 female mice were administered a single dose bolus of Ab349 at 2 mg/kg or 6 mg/kg. Blood samples were collected from retro-orbital sinus at 24, 48, 72 and 120 hours after the administration of Ab349 and its concentration measured by ELISA. Data were analyzed using WinNonlin. The pharmacokinetic parameters following 2 or 6 mg/kg Ab349 are shown in (Table 10). Ab349 was shown to have a half-life of up to 48 hrs in mice when given at 6 mg/kg.

TABLE 10

| pK Parameters For Ab349 | | | |
|---|---|---|---|
| Time (hr) | 2 mg/kg | 6 mg/kg | |
| Co | 7.2 | 47.8 | ug/ml |
| AUClast | 414 | 1832 | ug*hr/ml |
| AUCinf | 438 | 2116 | " |
| t½ | 26 | 48 | hr |
| Vz | 172 | 195 | ml/kg |
| Cl | 4.6 | 2.8 | ml/hr/kg |

In summary this highly potent PTH1R receptor antagonist antibody has the potential to become a valuable therapeutic agent in a variety of indications including hyperparathyroidism, humoral hypercalcemia of malignancy, and, potentially, the PTHrP-mediated cachexia seen in some cancers. Furthermore, the Ab349 antibody was effective at treating models of hypercalcemia at <2 mg/kg, with a <6 mg/kg maximum dose and an extended duration of action (i.e. lasting longer than the half-life).

Numerous modifications and variations in the disclosure as set forth in the above illustrative examples are expected to occur to those skilled in the art. Consequently only such limitations as appear in the appended claims should be placed on the disclosure.

The invention claimed is:
1. An antibody that binds parathyroid hormone receptor 1 (PTH1 R) with an affinity $K_d$ of $2\times10^{-6}$ M or less, wherein the antibody comprises
   (a) a heavy chain CDR1 amino acid sequence set forth in SEQ ID NOs: 30 or 45;
   (b) a heavy chain CDR2 amino acid sequence set forth in SEQ ID NOs: 31 or 46;
   (c) a heavy chain CDR3 amino acid sequence set forth SEQ ID NOs: 32 or 47;
   (d) a light chain CDR1 amino acid sequence set forth in SEQ ID NOs: 134 or 149;
   (e) a light chain CDR2 amino acid sequence set forth SEQ ID NOs: 135 or 150; and
   (f) a light chain CDR3 amino acid sequence set forth in SEQ ID NOs: 136 or 151.
2. The antibody of claim 1 wherein the antibody binds the N-terminal portion of PTH1R.
3. The antibody of claim 1 wherein the antibody does not bind parathyroid hormone receptor 2 (PTH2R).
4. The antibody of claim 1, wherein the antibody binds PTH1R on the surface of a cell.
5. The antibody of claim 1, wherein the antibody binds allosterically to PTH1R.
6. The antibody of any claim 1, wherein the antibody is a negative modulator antibody, optionally wherein the antibody is capable of weakening the binding affinity between PTH or PTHrP and with PTH1R by at least about 2-fold, optionally up to 1000-fold.
7. The antibody of claim 1, wherein the antibody inhibits calcium flux in a cell in response to stimulation of the receptor with parathyroid hormone (PTH) or parathyroid hormone related protein (PTHrP).
8. The antibody of claim 1, wherein the antibody inhibits PTH- or PTHrP-mediated cyclic adenosine mono-phosphate (cAMP) accumulation.
9. The antibody of claim 1 that is a monoclonal antibody.
10. The antibody of claim 1, that comprises
   i) an amino acid sequence at least 90% identical to a heavy chain variable region amino acid sequence set forth in SEQ ID NOs: 2 or 7; and
   ii) an amino acid sequence at least 90% identical to a light chain variable region amino acid sequence set forth in SEQ ID NOs: 106 or 111.
11. The antibody of claim 1, in which one or more light chain framework amino acids have been replaced with corresponding amino acid(s) from another human antibody amino acid sequence, optionally wherein the framework comprises one or more of the changes set out in FIG. 21.
12. An isolated nucleic acid molecule comprising a nucleotide sequence that encodes the heavy chain or light chain of claim 1.
13. An expression vector comprising the nucleic acid molecule of claim 12 operably linked to an expression control sequence.
14. A host cell comprising the vector of claim 13.
15. The host cell of claim 14, comprising a nucleic acid molecule encoding a heavy chain and a light chain variable region, wherein the heavy chain and light chain nucleic acids are expressed by different nucleic acids or on the same nucleic acid.
16. A method of using the host cell of claim 14 to produce an antibody, comprising culturing the host cell of claim 14 under suitable conditions and recovering said antibody.
17. A sterile pharmaceutical composition comprising the antibody of claim 1 and a pharmaceutically acceptable carrier.

18. A method for treating hypercalcemia associated with increased parathyroid hormone or parathyroid hormone related protein expression comprising the step of administering to a subject in need thereof a therapeutically effective amount of an antibody of claim 1 or a pharmaceutical composition of claim 17.
19. A method for treating a disease, condition or disorder associated with increased parathyroid hormone expression, increased parathyroid hormone related protein expression or parathyroid hormone receptor 1 (PTH1R) expression comprising the step of administering to a subject in need thereof a therapeutically effective amount of an antibody of claim 1 or a pharmaceutical composition of claim 17.
20. The method of claim 19, wherein the disease, condition or disorder is selected from the group consisting of cancer, PTH- or PTHrP-induced hypercalcemia, Humoral Hypercalcemia of Malignancy (HHM), familial hypocalciuric hypercalcemia, tuberculosis, sarcoidosis, Primary Hyperparathyroidism (PHPT), Secondary Hyperparathyroidism (SHPT) and cachexia.
21. The method of claim 20 wherein the disease is PHPT and the subject is a non-surgical patient or a patient who has failed surgery.
22. The method of claim 20 wherein the disease is SHPT and the subject has chronic kidney disease.
23. The method of claim 18 wherein the administration reduces the incidence of cancer metastasis in the subject compared to a subject not receiving the antibody.
24. The method of claim 23 wherein the metastasis includes metastasis to the bone or skeletal tissues, liver, lung, kidney or pancreas.
25. The method of claim 18 wherein the administration ameliorates one or more symptoms of hypercalcemia.
26. The method of claim 18, wherein the administration extends HHM survival due to reduced hypercalcemia and/or wasting syndrome.
27. The method of claim 18 wherein the antibody is administered intravenously, intraarterially, intraperitoneally, intramuscularly, intradermally or subcutaneously.
28. The method of claim 18 wherein the antibody is administered in combination with a second agent.
29. The method of claim 18 wherein the antibody is administered once per week, once every 2 weeks, twice per month, once monthly, once every two months, or once every three months.
30. A composition comprising an antibody of claim 1 or a pharmaceutical composition of claim 17 for use in treating a condition or disorder associated with increased parathyroid hormone expression or increased parathyroid hormone related protein expression.
31. A composition comprising an antibody of claim 1 or a pharmaceutical composition of claim 17 for use in treating a condition or disorder associated with hypercalcemia.
32. The antibody of claim 1, further comprising a heavy chain constant region, wherein the heavy chain constant region is a modified or unmodified IgG, IgM, IgA, IgD, IgE, a fragment thereof, or combinations thereof.
33. The antibody of claim 32, further comprising a human light chain constant region.
34. The antibody of claim 33, wherein the light chain constant region is a modified or unmodified lambda light chain constant region, a kappa light chain constant region, a fragment thereof, or combinations thereof.

* * * * *

UNITED STATES PATENT AND TRADEMARK OFFICE
CERTIFICATE OF CORRECTION

PATENT NO. : 10,519,250 B2  
APPLICATION NO. : 15/665788  
DATED : December 31, 2019  
INVENTOR(S) : Raphael D. Levy et al.

Page 1 of 1

It is certified that error appears in the above-identified patent and that said Letters Patent is hereby corrected as shown below:

In the Claims

At Column 187, Line 3, "(PTH1 R)" should be -- (PTH1R) --.

At Column 187, Line 3, "$K_d$ of $2 \times 10^{-6}$" should be -- $K_d$ of $2 \times 10^{-8}$ --.

At Column 187, Lines 9-10, "set forth SEQ ID Nos:" should be -- set forth in SEQ ID No: --.

At Column 187, Lines 13-14, "set forth SEQ ID Nos:" should be -- set forth in SEQ ID No: --.

At Column 187, Line 25, "The antibody of any claim 1," should be -- The antibody of claim 1, --.

Signed and Sealed this  
Eighteenth Day of January, 2022

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 260

<210> SEQ ID NO 1
<211> LENGTH: 123
<212> TYPE: PRT
<213> ORGANISM: Homo sapiens

<400> SEQUENCE: 1

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
        115                 120

<210> SEQ ID NO 2
<211> LENGTH: 123
<212> TYPE: PRT
<213> ORGANISM: Homo sapiens

<400> SEQUENCE: 2

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
        115                 120

<210> SEQ ID NO 3
<211> LENGTH: 123
<212> TYPE: PRT
<213> ORGANISM: Homo sapiens

<400> SEQUENCE: 3

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
                100                 105                 110

Thr Val Ser Ser Ala Ser Thr Lys Gly Pro Ser
            115                 120

<210> SEQ ID NO 4
<211> LENGTH: 123
<212> TYPE: PRT
<213> ORGANISM: Homo sapiens

<400> SEQUENCE: 4

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
                100                 105                 110

Thr Val Ser Ser Ala Ser Thr Lys Gly Pro Ser
            115                 120

<210> SEQ ID NO 5
<211> LENGTH: 123
<212> TYPE: PRT
<213> ORGANISM: Homo sapiens

<400> SEQUENCE: 5

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
                100                 105                 110
```

```
Thr Val Ser Ser Ala Ser Thr Lys Gly Pro Ser
        115                 120

<210> SEQ ID NO 6
<211> LENGTH: 123
<212> TYPE: PRT
<213> ORGANISM: Homo sapiens

<400> SEQUENCE: 6

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
        115                 120

<210> SEQ ID NO 7
<211> LENGTH: 123
<212> TYPE: PRT
<213> ORGANISM: Homo sapiens

<400> SEQUENCE: 7

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
        115                 120

<210> SEQ ID NO 8
<211> LENGTH: 123
<212> TYPE: PRT
<213> ORGANISM: Homo sapiens

<400> SEQUENCE: 8

Gln Met Gln Leu Val Gln Ser Gly Ala Glu Val Lys Lys Pro Gly Ser
1               5                   10                  15
```

-continued

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
        115                 120

<210> SEQ ID NO 9
<211> LENGTH: 123
<212> TYPE: PRT
<213> ORGANISM: Homo sapiens

<400> SEQUENCE: 9

Gln Met Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
        115                 120

<210> SEQ ID NO 10
<211> LENGTH: 123
<212> TYPE: PRT
<213> ORGANISM: Homo sapiens

<400> SEQUENCE: 10

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
            115                 120

<210> SEQ ID NO 11
<211> LENGTH: 123
<212> TYPE: PRT
<213> ORGANISM: Homo sapiens

<400> SEQUENCE: 11

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
            115                 120

<210> SEQ ID NO 12
<211> LENGTH: 123
<212> TYPE: PRT
<213> ORGANISM: Homo sapiens

<400> SEQUENCE: 12

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Val Ala Arg Leu Trp Gly Gln Gly Thr Leu Val
            100                 105                 110

Thr Val Ser Ser Ala Ser Thr Lys Gly Pro Ser
            115                 120

<210> SEQ ID NO 13
<211> LENGTH: 123
<212> TYPE: PRT
<213> ORGANISM: Homo sapiens

<400> SEQUENCE: 13

Gln Met Gln Leu Val Gln Ser Gly Ala Glu Val Lys Lys Pro Gly Ser

```
                1               5                  10                 15
Ser Val Lys Val Ser Cys Lys Ala Ser Gly Gly Thr Phe Ser Ser Tyr
                20                 25                 30

Ala Ile Ser Trp Val Arg Gln Ala Pro Gly Gln Gly Leu Glu Trp Met
            35                 40                 45

Gly Gly Ile Ile Pro Ile Phe Gly Thr Ala Asn Tyr Ala Gln Lys Phe
        50                 55                 60

Gln Gly Arg Val Thr Ile Thr Ala Asp Glu Ser Thr Ser Thr Ala Tyr
65                 70                 75                 80

Met Glu Leu Ser Ser Leu Arg Ser Glu Asp Thr Ala Val Tyr Tyr Cys
                85                 90                 95

Ala Arg Gly Tyr Val Val Ala Arg Leu Trp Gly Gln Gly Thr Leu Val
                100                105                110

Thr Val Ser Ser Ala Ser Thr Lys Gly Pro Ser
            115                120
```

<210> SEQ ID NO 14
<211> LENGTH: 123
<212> TYPE: PRT
<213> ORGANISM: Homo sapiens

<400> SEQUENCE: 14

```
Gln Met Gln Leu Val Gln Ser Gly Ala Glu Val Lys Lys Pro Gly Ser
1               5                  10                 15

Ser Val Lys Val Ser Cys Lys Ala Ser Gly Gly Thr Phe Ser Ser Tyr
                20                 25                 30

Ala Ile Ser Trp Val Arg Gln Ala Pro Gly Gln Gly Leu Glu Trp Met
            35                 40                 45

Gly Gly Ile Ile Pro Ile Phe Gly Thr Ala Asn Tyr Ala Gln Lys Phe
        50                 55                 60

Gln Gly Arg Val Thr Ile Thr Ala Asp Glu Ser Thr Ser Thr Ala Tyr
65                 70                 75                 80

Met Glu Leu Ser Ser Leu Arg Ser Glu Asp Thr Ala Val Tyr Tyr Cys
                85                 90                 95

Ala Arg Gly Tyr Val Val Ala Arg Leu Trp Gly Gln Gly Thr Leu Val
                100                105                110

Thr Val Ser Ser Ala Ser Thr Lys Gly Pro Ser
            115                120
```

<210> SEQ ID NO 15
<211> LENGTH: 123
<212> TYPE: PRT
<213> ORGANISM: Homo sapiens

<400> SEQUENCE: 15

```
Gln Met Gln Leu Val Gln Ser Gly Ala Glu Val Lys Lys Pro Gly Ser
1               5                  10                 15

Ser Val Lys Val Ser Cys Lys Ala Ser Gly Gly Thr Phe Ser Ser Tyr
                20                 25                 30

Ala Ile Ser Trp Val Arg Gln Ala Pro Gly Gln Gly Leu Glu Trp Met
            35                 40                 45

Gly Gly Ile Ile Pro Ile Phe Gly Thr Ala Asn Tyr Ala Gln Lys Phe
        50                 55                 60

Gln Gly Arg Val Thr Ile Thr Ala Asp Glu Ser Thr Ser Thr Ala Tyr
65                 70                 75                 80

Met Glu Leu Ser Ser Leu Arg Ser Glu Asp Thr Ala Val Tyr Tyr Cys
```

85                  90                  95
Ala Arg Gly Tyr Val Val Ala Arg Leu Trp Gly Gln Gly Thr Leu Val
                100                 105                 110
Thr Val Ser Ser Ala Ser Thr Lys Gly Pro Ser
            115                 120

<210> SEQ ID NO 16
<211> LENGTH: 123
<212> TYPE: PRT
<213> ORGANISM: Homo sapiens

<400> SEQUENCE: 16

Gln Met Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Tyr Val Val Ala Arg Leu Trp Gly Gln Gly Thr Leu Val
                100                 105                 110
Thr Val Ser Ser Ala Ser Thr Lys Gly Pro Ser
            115                 120

<210> SEQ ID NO 17
<211> LENGTH: 123
<212> TYPE: PRT
<213> ORGANISM: Homo sapiens

<400> SEQUENCE: 17

Gln Met Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Tyr Val Val Ala Arg Leu Trp Gly Gln Gly Thr Leu Val
                100                 105                 110
Thr Val Ser Ser Ala Ser Thr Lys Gly Pro Ser
            115                 120

<210> SEQ ID NO 18
<211> LENGTH: 128
<212> TYPE: PRT
<213> ORGANISM: Homo sapiens

<400> SEQUENCE: 18

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Thr Pro Gly Lys Glu Leu Gln Trp Val
        35                  40                  45

Ser Ala Ile Thr Pro Gly Gly Glu Gly Thr Tyr Tyr Ala Asp Val Val
    50                  55                  60

Lys Gly Arg Phe Thr Ile Ser Arg Asp Asn Ser Lys Asp Thr Leu Tyr
65                  70                  75                  80

Leu Gln Met Asp Ser Leu Arg Ala Glu Asp Thr Ala Val Tyr Tyr Cys
            85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ser Ala Ser Thr Lys Gly Pro Ser
        115                 120                 125

<210> SEQ ID NO 19
<211> LENGTH: 128
<212> TYPE: PRT
<213> ORGANISM: Homo sapiens

<400> SEQUENCE: 19

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Thr Pro Gly Lys Glu Leu Gln Trp Val
        35                  40                  45

Ser Ala Ile Thr Pro Gly Gly Glu Gly Thr Tyr Tyr Ala Asp Val Val
    50                  55                  60

Lys Gly Arg Phe Thr Ile Ser Arg Asp Asn Ser Lys Asp Thr Leu Tyr
65                  70                  75                  80

Leu Gln Met Asp Ser Leu Arg Ala Glu Asp Thr Ala Val Tyr Tyr Cys
            85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ser Ala Ser Thr Lys Gly Pro Ser
        115                 120                 125

<210> SEQ ID NO 20
<211> LENGTH: 128
<212> TYPE: PRT
<213> ORGANISM: Homo sapiens

<400> SEQUENCE: 20

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Thr Pro Gly Lys Glu Leu Gln Trp Val
        35                  40                  45

Ser Ala Ile Thr Pro Gly Gly Glu Gly Thr Tyr Tyr Ala Asp Val Val
    50                  55                  60

Lys Gly Arg Phe Thr Ile Ser Arg Asp Asn Ser Lys Asp Thr Leu Tyr
65                  70                  75                  80

Leu Gln Met Asp Ser Leu Arg Ala Glu Asp Thr Ala Val Tyr Tyr Cys
                85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ala Ser Thr Lys Gly Pro Ser
        115                 120                 125

<210> SEQ ID NO 21
<211> LENGTH: 128
<212> TYPE: PRT
<213> ORGANISM: Homo sapiens

<400> SEQUENCE: 21

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Thr Pro Gly Lys Glu Leu Gln Trp Val
        35                  40                  45

Ser Ala Ile Thr Pro Gly Gly Glu Gly Thr Tyr Tyr Ala Asp Val Val
    50                  55                  60

Lys Gly Arg Phe Thr Ile Ser Arg Asp Asn Ser Lys Asp Thr Leu Tyr
65                  70                  75                  80

Leu Gln Met Asp Ser Leu Arg Ala Glu Asp Thr Ala Val Tyr Tyr Cys
                85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ser Ala Ser Thr Lys Gly Pro Ser
        115                 120                 125

<210> SEQ ID NO 22
<211> LENGTH: 128
<212> TYPE: PRT
<213> ORGANISM: Homo sapiens

<400> SEQUENCE: 22

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Thr Pro Gly Lys Glu Leu Gln Trp Val
        35                  40                  45

Ser Ala Ile Thr Pro Gly Gly Glu Gly Thr Tyr Tyr Ala Asp Val Val
    50                  55                  60

Lys Gly Arg Phe Thr Ile Ser Arg Asp Asn Ser Lys Asp Thr Leu Tyr
65                  70                  75                  80

Leu Gln Met Asp Ser Leu Arg Ala Glu Asp Thr Ala Val Tyr Tyr Cys
                85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ser Ala Ser Thr Lys Gly Pro Ser
        115                 120                 125

<210> SEQ ID NO 23
<211> LENGTH: 128
<212> TYPE: PRT
<213> ORGANISM: Homo sapiens

<400> SEQUENCE: 23

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Thr Pro Gly Lys Glu Leu Gln Trp Val
        35                  40                  45

Ser Ala Ile Thr Pro Gly Gly Glu Gly Thr Tyr Tyr Ala Asp Val Val
    50                  55                  60

Lys Gly Arg Phe Thr Ile Ser Arg Asp Asn Ser Lys Asp Thr Leu Tyr
65                  70                  75                  80

Leu Gln Met Asp Ser Leu Arg Ala Glu Asp Thr Ala Val Tyr Tyr Cys
                85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ser Ala Ser Thr Lys Gly Pro Ser
        115                 120                 125

<210> SEQ ID NO 24
<211> LENGTH: 128
<212> TYPE: PRT
<213> ORGANISM: Homo sapiens

<400> SEQUENCE: 24

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Thr Pro Gly Lys Glu Leu Gln Trp Val
        35                  40                  45

Ser Ala Ile Thr Pro Gly Gly Glu Gly Thr Tyr Tyr Ala Asp Val Val
    50                  55                  60

Lys Gly Arg Phe Thr Ile Ser Arg Asp Asn Ser Lys Asp Thr Leu Tyr
65                  70                  75                  80

Leu Gln Met Asp Ser Leu Arg Ala Glu Asp Thr Ala Val Tyr Tyr Cys
                85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ser Ala Ser Thr Lys Gly Pro Ser
        115                 120                 125

<210> SEQ ID NO 25
<211> LENGTH: 128
<212> TYPE: PRT
<213> ORGANISM: Homo sapiens

<400> SEQUENCE: 25

Glu Val Gln Leu Val Glu Thr Gly Gly Gly Val Val Arg Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Thr Pro Gly Lys Glu Leu Gln Trp Val
        35                  40                  45

Ser Ala Ile Thr Pro Gly Gly Glu Gly Thr Tyr Tyr Ala Asp Val Val
    50                  55                  60

```
Lys Gly Arg Phe Thr Ile Ser Arg Asp Asn Ser Lys Asp Thr Leu Tyr
 65                  70                  75                  80

Leu Gln Met Asp Ser Leu Arg Ala Glu Asp Thr Ala Val Tyr Tyr Cys
                 85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ser Ala Ser Thr Lys Gly Pro Ser
        115                 120                 125
```

<210> SEQ ID NO 26
<211> LENGTH: 128
<212> TYPE: PRT
<213> ORGANISM: Homo sapiens

<400> SEQUENCE: 26

```
Glu Val Gln Leu Val Glu Thr Gly Gly Gly Val Val Arg Pro Gly Gly
 1               5                  10                  15

Ser Leu Arg Leu Ser Cys Ala Ala Ser Gly Phe Thr Phe Ser Ser Ser
             20                  25                  30

Ala Met Ser Trp Val Arg Gln Thr Pro Gly Lys Glu Leu Gln Trp Val
         35                  40                  45

Ser Ala Ile Thr Pro Gly Gly Glu Gly Thr Tyr Tyr Ala Asp Val Val
 50                  55                  60

Lys Gly Arg Phe Thr Ile Ser Arg Asp Asn Ser Lys Asp Thr Leu Tyr
 65                  70                  75                  80

Leu Gln Met Asp Ser Leu Arg Ala Glu Asp Thr Ala Val Tyr Tyr Cys
                 85                  90                  95

Ala Arg Asp Leu Tyr Gly Ser Tyr Gly Asp Ala Phe Asp Ile Trp Gly
            100                 105                 110

Gln Gly Thr Leu Val Thr Val Ser Ser Ala Ser Thr Lys Gly Pro Ser
        115                 120                 125
```

<210> SEQ ID NO 27
<211> LENGTH: 8
<212> TYPE: PRT
<213> ORGANISM: Homo sapiens

<400> SEQUENCE: 27

```
Gly Gly Thr Phe Ser Ser Tyr Ala
 1               5
```

<210> SEQ ID NO 28
<211> LENGTH: 8
<212> TYPE: PRT
<213> ORGANISM: Homo sapiens

<400> SEQUENCE: 28

```
Ile Ile Pro Ile Phe Gly Thr Ala
 1               5
```

<210> SEQ ID NO 29
<211> LENGTH: 9
<212> TYPE: PRT
<213> ORGANISM: Homo sapiens

<400> SEQUENCE: 29

```
Ala Arg Gly Tyr Val Val Ala Arg Leu
 1               5
```

<210> SEQ ID NO 30

```
<211> LENGTH: 8
<212> TYPE: PRT
<213> ORGANISM: Homo sapiens

<400> SEQUENCE: 30

Gly Gly Thr Phe Ser Ser Tyr Ala
1               5

<210> SEQ ID NO 31
<211> LENGTH: 8
<212> TYPE: PRT
<213> ORGANISM: Homo sapiens

<400> SEQUENCE: 31

Ile Ile Pro Ile Phe Gly Thr Ala
1               5

<210> SEQ ID NO 32
<211> LENGTH: 9
<212> TYPE: PRT
<213> ORGANISM: Homo sapiens

<400> SEQUENCE: 32

Ala Arg Gly Tyr Val Val Ala Arg Leu
1               5

<210> SEQ ID NO 33
<211> LENGTH: 8
<212> TYPE: PRT
<213> ORGANISM: Homo sapiens

<400> SEQUENCE: 33

Gly Gly Thr Phe Ser Ser Tyr Ala
1               5

<210> SEQ ID NO 34
<211> LENGTH: 8
<212> TYPE: PRT
<213> ORGANISM: Homo sapiens

<400> SEQUENCE: 34

Ile Ile Pro Ile Phe Gly Thr Ala
1               5

<210> SEQ ID NO 35
<211> LENGTH: 9
<212> TYPE: PRT
<213> ORGANISM: Homo sapiens

<400> SEQUENCE: 35

Ala Arg Gly Tyr Val Val Ala Arg Leu
1               5

<210> SEQ ID NO 36
<211> LENGTH: 8
<212> TYPE: PRT
<213> ORGANISM: Homo sapiens

<400> SEQUENCE: 36

Gly Gly Thr Phe Ser Ser Tyr Ala
1               5

<210> SEQ ID NO 37
<211> LENGTH: 8
<212> TYPE: PRT
```

```
<213> ORGANISM: Homo sapiens

<400> SEQUENCE: 37

Ile Ile Pro Ile Phe Gly Thr Ala
1               5

<210> SEQ ID NO 38
<211> LENGTH: 9
<212> TYPE: PRT
<213> ORGANISM: Homo sapiens

<400> SEQUENCE: 38

Ala Arg Gly Tyr Val Val Ala Arg Leu
1               5

<210> SEQ ID NO 39
<211> LENGTH: 8
<212> TYPE: PRT
<213> ORGANISM: Homo sapiens

<400> SEQUENCE: 39

Gly Gly Thr Phe Ser Ser Tyr Ala
1               5

<210> SEQ ID NO 40
<211> LENGTH: 8
<212> TYPE: PRT
<213> ORGANISM: Homo sapiens

<400> SEQUENCE: 40

Ile Ile Pro Ile Phe Gly Thr Ala
1               5

<210> SEQ ID NO 41
<211> LENGTH: 9
<212> TYPE: PRT
<213> ORGANISM: Homo sapiens

<400> SEQUENCE: 41

Ala Arg Gly Tyr Val Val Ala Arg Leu
1               5

<210> SEQ ID NO 42
<211> LENGTH: 8
<212> TYPE: PRT
<213> ORGANISM: Homo sapiens

<400> SEQUENCE: 42

Gly Gly Thr Phe Ser Ser Tyr Ala
1               5

<210> SEQ ID NO 43
<211> LENGTH: 8
<212> TYPE: PRT
<213> ORGANISM: Homo sapiens

<400> SEQUENCE: 43

Ile Ile Pro Ile Phe Gly Thr Ala
1               5

<210> SEQ ID NO 44
<211> LENGTH: 9
<212> TYPE: PRT
<213> ORGANISM: Homo sapiens
```

```
<400> SEQUENCE: 44

Ala Arg Gly Tyr Val Val Ala Arg Leu
1               5

<210> SEQ ID NO 45
<211> LENGTH: 8
<212> TYPE: PRT
<213> ORGANISM: Homo sapiens

<400> SEQUENCE: 45

Gly Gly Thr Phe Ser Ser Tyr Ala
1               5

<210> SEQ ID NO 46
<211> LENGTH: 8
<212> TYPE: PRT
<213> ORGANISM: Homo sapiens

<400> SEQUENCE: 46

Ile Ile Pro Ile Phe Gly Thr Ala
1               5

<210> SEQ ID NO 47
<211> LENGTH: 9
<212> TYPE: PRT
<213> ORGANISM: Homo sapiens

<400> SEQUENCE: 47

Ala Arg Gly Tyr Val Val Ala Arg Leu
1               5

<210> SEQ ID NO 48
<211> LENGTH: 8
<212> TYPE: PRT
<213> ORGANISM: Homo sapiens

<400> SEQUENCE: 48

Gly Gly Thr Phe Ser Ser Tyr Ala
1               5

<210> SEQ ID NO 49
<211> LENGTH: 8
<212> TYPE: PRT
<213> ORGANISM: Homo sapiens

<400> SEQUENCE: 49

Ile Ile Pro Ile Phe Gly Thr Ala
1               5

<210> SEQ ID NO 50
<211> LENGTH: 9
<212> TYPE: PRT
<213> ORGANISM: Homo sapiens

<400> SEQUENCE: 50

Ala Arg Gly Tyr Val Val Ala Arg Leu
1               5

<210> SEQ ID NO 51
<211> LENGTH: 8
<212> TYPE: PRT
<213> ORGANISM: Homo sapiens

<400> SEQUENCE: 51
```

Gly Gly Thr Phe Ser Ser Tyr Ala
1               5

<210> SEQ ID NO 52
<211> LENGTH: 8
<212> TYPE: PRT
<213> ORGANISM: Homo sapiens

<400> SEQUENCE: 52

Ile Ile Pro Ile Phe Gly Thr Ala
1               5

<210> SEQ ID NO 53
<211> LENGTH: 9
<212> TYPE: PRT
<213> ORGANISM: Homo sapiens

<400> SEQUENCE: 53

Ala Arg Gly Tyr Val Val Ala Arg Leu
1               5

<210> SEQ ID NO 54
<211> LENGTH: 8
<212> TYPE: PRT
<213> ORGANISM: Homo sapiens

<400> SEQUENCE: 54

Gly Gly Thr Phe Ser Ser Tyr Ala
1               5

<210> SEQ ID NO 55
<211> LENGTH: 8
<212> TYPE: PRT
<213> ORGANISM: Homo sapiens

<400> SEQUENCE: 55

Ile Ile Pro Ile Phe Gly Thr Ala
1               5

<210> SEQ ID NO 56
<211> LENGTH: 9
<212> TYPE: PRT
<213> ORGANISM: Homo sapiens

<400> SEQUENCE: 56

Ala Arg Gly Tyr Val Val Ala Arg Leu
1               5

<210> SEQ ID NO 57
<211> LENGTH: 8
<212> TYPE: PRT
<213> ORGANISM: Homo sapiens

<400> SEQUENCE: 57

Gly Gly Thr Phe Ser Ser Tyr Ala
1               5

<210> SEQ ID NO 58
<211> LENGTH: 8
<212> TYPE: PRT
<213> ORGANISM: Homo sapiens

<400> SEQUENCE: 58

Ile Ile Pro Ile Phe Gly Thr Ala
1               5

<210> SEQ ID NO 59
<211> LENGTH: 9
<212> TYPE: PRT
<213> ORGANISM: Homo sapiens

<400> SEQUENCE: 59

Ala Arg Gly Tyr Val Val Ala Arg Leu
1               5

<210> SEQ ID NO 60
<211> LENGTH: 8
<212> TYPE: PRT
<213> ORGANISM: Homo sapiens

<400> SEQUENCE: 60

Gly Gly Thr Phe Ser Ser Tyr Ala
1               5

<210> SEQ ID NO 61
<211> LENGTH: 8
<212> TYPE: PRT
<213> ORGANISM: Homo sapiens

<400> SEQUENCE: 61

Ile Ile Pro Ile Phe Gly Thr Ala
1               5

<210> SEQ ID NO 62
<211> LENGTH: 9
<212> TYPE: PRT
<213> ORGANISM: Homo sapiens

<400> SEQUENCE: 62

Ala Arg Gly Tyr Val Val Ala Arg Leu
1               5

<210> SEQ ID NO 63
<211> LENGTH: 8
<212> TYPE: PRT
<213> ORGANISM: Homo sapiens

<400> SEQUENCE: 63

Gly Gly Thr Phe Ser Ser Tyr Ala
1               5

<210> SEQ ID NO 64
<211> LENGTH: 8
<212> TYPE: PRT
<213> ORGANISM: Homo sapiens

<400> SEQUENCE: 64

Ile Ile Pro Ile Phe Gly Thr Ala
1               5

<210> SEQ ID NO 65
<211> LENGTH: 9
<212> TYPE: PRT
<213> ORGANISM: Homo sapiens

<400> SEQUENCE: 65

Ala Arg Gly Tyr Val Val Ala Arg Leu
1               5

```
<210> SEQ ID NO 66
<211> LENGTH: 8
<212> TYPE: PRT
<213> ORGANISM: Homo sapiens

<400> SEQUENCE: 66

Gly Gly Thr Phe Ser Ser Tyr Ala
1               5

<210> SEQ ID NO 67
<211> LENGTH: 8
<212> TYPE: PRT
<213> ORGANISM: Homo sapiens

<400> SEQUENCE: 67

Ile Ile Pro Ile Phe Gly Thr Ala
1               5

<210> SEQ ID NO 68
<211> LENGTH: 9
<212> TYPE: PRT
<213> ORGANISM: Homo sapiens

<400> SEQUENCE: 68

Ala Arg Gly Tyr Val Val Ala Arg Leu
1               5

<210> SEQ ID NO 69
<211> LENGTH: 8
<212> TYPE: PRT
<213> ORGANISM: Homo sapiens

<400> SEQUENCE: 69

Gly Gly Thr Phe Ser Ser Tyr Ala
1               5

<210> SEQ ID NO 70
<211> LENGTH: 8
<212> TYPE: PRT
<213> ORGANISM: Homo sapiens

<400> SEQUENCE: 70

Ile Ile Pro Ile Phe Gly Thr Ala
1               5

<210> SEQ ID NO 71
<211> LENGTH: 9
<212> TYPE: PRT
<213> ORGANISM: Homo sapiens

<400> SEQUENCE: 71

Ala Arg Gly Tyr Val Val Ala Arg Leu
1               5

<210> SEQ ID NO 72
<211> LENGTH: 8
<212> TYPE: PRT
<213> ORGANISM: Homo sapiens

<400> SEQUENCE: 72

Gly Gly Thr Phe Ser Ser Tyr Ala
1               5

<210> SEQ ID NO 73
<211> LENGTH: 8
```

<212> TYPE: PRT
<213> ORGANISM: Homo sapiens

<400> SEQUENCE: 73

Ile Ile Pro Ile Phe Gly Thr Ala
1               5

<210> SEQ ID NO 74
<211> LENGTH: 9
<212> TYPE: PRT
<213> ORGANISM: Homo sapiens

<400> SEQUENCE: 74

Ala Arg Gly Tyr Val Val Ala Arg Leu
1               5

<210> SEQ ID NO 75
<211> LENGTH: 8
<212> TYPE: PRT
<213> ORGANISM: Homo sapiens

<400> SEQUENCE: 75

Gly Gly Thr Phe Ser Ser Tyr Ala
1               5

<210> SEQ ID NO 76
<211> LENGTH: 8
<212> TYPE: PRT
<213> ORGANISM: Homo sapiens

<400> SEQUENCE: 76

Ile Ile Pro Ile Phe Gly Thr Ala
1               5

<210> SEQ ID NO 77
<211> LENGTH: 9
<212> TYPE: PRT
<213> ORGANISM: Homo sapiens

<400> SEQUENCE: 77

Ala Arg Gly Tyr Val Val Ala Arg Leu
1               5

<210> SEQ ID NO 78
<211> LENGTH: 8
<212> TYPE: PRT
<213> ORGANISM: Homo sapiens

<400> SEQUENCE: 78

Gly Phe Thr Phe Ser Ser Ser Ala
1               5

<210> SEQ ID NO 79
<211> LENGTH: 8
<212> TYPE: PRT
<213> ORGANISM: Homo sapiens

<400> SEQUENCE: 79

Ile Thr Pro Gly Gly Glu Gly Thr
1               5

<210> SEQ ID NO 80
<211> LENGTH: 14
<212> TYPE: PRT
<213> ORGANISM: Homo sapiens

```
<400> SEQUENCE: 80

Ala Arg Asp Leu Tyr Gly Ser Tyr Gly Asp Ala Phe Asp Ile
1               5                   10

<210> SEQ ID NO 81
<211> LENGTH: 8
<212> TYPE: PRT
<213> ORGANISM: Homo sapiens

<400> SEQUENCE: 81

Gly Phe Thr Phe Ser Ser Ser Ala
1               5

<210> SEQ ID NO 82
<211> LENGTH: 8
<212> TYPE: PRT
<213> ORGANISM: Homo sapiens

<400> SEQUENCE: 82

Ile Thr Pro Gly Gly Glu Gly Thr
1               5

<210> SEQ ID NO 83
<211> LENGTH: 14
<212> TYPE: PRT
<213> ORGANISM: Homo sapiens

<400> SEQUENCE: 83

Ala Arg Asp Leu Tyr Gly Ser Tyr Gly Asp Ala Phe Asp Ile
1               5                   10

<210> SEQ ID NO 84
<211> LENGTH: 8
<212> TYPE: PRT
<213> ORGANISM: Homo sapiens

<400> SEQUENCE: 84

Gly Phe Thr Phe Ser Ser Ser Ala
1               5

<210> SEQ ID NO 85
<211> LENGTH: 8
<212> TYPE: PRT
<213> ORGANISM: Homo sapiens

<400> SEQUENCE: 85

Ile Thr Pro Gly Gly Glu Gly Thr
1               5

<210> SEQ ID NO 86
<211> LENGTH: 14
<212> TYPE: PRT
<213> ORGANISM: Homo sapiens

<400> SEQUENCE: 86

Ala Arg Asp Leu Tyr Gly Ser Tyr Gly Asp Ala Phe Asp Ile
1               5                   10

<210> SEQ ID NO 87
<211> LENGTH: 8
<212> TYPE: PRT
<213> ORGANISM: Homo sapiens

<400> SEQUENCE: 87
```

Gly Phe Thr Phe Ser Ser Ser Ala
1               5

<210> SEQ ID NO 88
<211> LENGTH: 8
<212> TYPE: PRT
<213> ORGANISM: Homo sapiens

<400> SEQUENCE: 88

Ile Thr Pro Gly Gly Glu Gly Thr
1               5

<210> SEQ ID NO 89
<211> LENGTH: 14
<212> TYPE: PRT
<213> ORGANISM: Homo sapiens

<400> SEQUENCE: 89

Ala Arg Asp Leu Tyr Gly Ser Tyr Gly Asp Ala Phe Asp Ile
1               5                   10

<210> SEQ ID NO 90
<211> LENGTH: 8
<212> TYPE: PRT
<213> ORGANISM: Homo sapiens

<400> SEQUENCE: 90

Gly Phe Thr Phe Ser Ser Ser Ala
1               5

<210> SEQ ID NO 91
<211> LENGTH: 8
<212> TYPE: PRT
<213> ORGANISM: Homo sapiens

<400> SEQUENCE: 91

Ile Thr Pro Gly Gly Glu Gly Thr
1               5

<210> SEQ ID NO 92
<211> LENGTH: 14
<212> TYPE: PRT
<213> ORGANISM: Homo sapiens

<400> SEQUENCE: 92

Ala Arg Asp Leu Tyr Gly Ser Tyr Gly Asp Ala Phe Asp Ile
1               5                   10

<210> SEQ ID NO 93
<211> LENGTH: 8
<212> TYPE: PRT
<213> ORGANISM: Homo sapiens

<400> SEQUENCE: 93

Gly Phe Thr Phe Ser Ser Ser Ala
1               5

<210> SEQ ID NO 94
<211> LENGTH: 8
<212> TYPE: PRT
<213> ORGANISM: Homo sapiens

<400> SEQUENCE: 94

Ile Thr Pro Gly Gly Glu Gly Thr

-continued

<210> SEQ ID NO 95
<211> LENGTH: 14
<212> TYPE: PRT
<213> ORGANISM: Homo sapiens

<400> SEQUENCE: 95

Ala Arg Asp Leu Tyr Gly Ser Tyr Gly Asp Ala Phe Asp Ile
1               5                   10

<210> SEQ ID NO 96
<211> LENGTH: 8
<212> TYPE: PRT
<213> ORGANISM: Homo sapiens

<400> SEQUENCE: 96

Gly Phe Thr Phe Ser Ser Ser Ala
1               5

<210> SEQ ID NO 97
<211> LENGTH: 8
<212> TYPE: PRT
<213> ORGANISM: Homo sapiens

<400> SEQUENCE: 97

Ile Thr Pro Gly Gly Glu Gly Thr
1               5

<210> SEQ ID NO 98
<211> LENGTH: 14
<212> TYPE: PRT
<213> ORGANISM: Homo sapiens

<400> SEQUENCE: 98

Ala Arg Asp Leu Tyr Gly Ser Tyr Gly Asp Ala Phe Asp Ile
1               5                   10

<210> SEQ ID NO 99
<211> LENGTH: 8
<212> TYPE: PRT
<213> ORGANISM: Homo sapiens

<400> SEQUENCE: 99

Gly Phe Thr Phe Ser Ser Ser Ala
1               5

<210> SEQ ID NO 100
<211> LENGTH: 8
<212> TYPE: PRT
<213> ORGANISM: Homo sapiens

<400> SEQUENCE: 100

Ile Thr Pro Gly Gly Glu Gly Thr
1               5

<210> SEQ ID NO 101
<211> LENGTH: 14
<212> TYPE: PRT
<213> ORGANISM: Homo sapiens

<400> SEQUENCE: 101

Ala Arg Asp Leu Tyr Gly Ser Tyr Gly Asp Ala Phe Asp Ile
1               5                   10

<210> SEQ ID NO 102
<211> LENGTH: 8
<212> TYPE: PRT
<213> ORGANISM: Homo sapiens

<400> SEQUENCE: 102

Gly Phe Thr Phe Ser Ser Ser Ala
1               5

<210> SEQ ID NO 103
<211> LENGTH: 8
<212> TYPE: PRT
<213> ORGANISM: Homo sapiens

<400> SEQUENCE: 103

Ile Thr Pro Gly Gly Glu Gly Thr
1               5

<210> SEQ ID NO 104
<211> LENGTH: 14
<212> TYPE: PRT
<213> ORGANISM: Homo sapiens

<400> SEQUENCE: 104

Ala Arg Asp Leu Tyr Gly Ser Tyr Gly Asp Ala Phe Asp Ile
1               5                   10

<210> SEQ ID NO 105
<211> LENGTH: 114
<212> TYPE: PRT
<213> ORGANISM: Homo sapiens

<400> SEQUENCE: 105

Glu Thr Thr Leu Thr Gln Ser Pro Ala Phe Met Ser Ala Ser Val Gly
1               5                   10                  15

Asp Arg Val Thr Ile Thr Cys Gln Ala Ser Gln Asp Ile Asn Asn Phe
            20                  25                  30

Leu Asn Trp Tyr Gln Gln Lys Pro Gly Lys Ala Pro Lys Phe Leu Ile
        35                  40                  45

Tyr Asp Ala Ser Asn Leu Glu Lys Gly Val Pro Ser Lys Phe Ser Gly
    50                  55                  60

Arg Gly Ser Gly Thr Glu Phe Thr Leu Thr Ile Ser Ser Leu Gln Pro
65                  70                  75                  80

Glu Asp Ile Ala Thr Tyr Tyr Cys Gln Gln Tyr Arg Asp Phe Pro Leu
                85                  90                  95

Thr Phe Gly Gln Gly Thr Arg Leu Glu Ile Lys Arg Thr Val Ala Ala
            100                 105                 110

Pro Ser

<210> SEQ ID NO 106
<211> LENGTH: 119
<212> TYPE: PRT
<213> ORGANISM: Homo sapiens

<400> SEQUENCE: 106

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Gly
            20                  25                  30

Asp Gly His Asn Tyr Leu Ala Trp Tyr Leu Gln Lys Pro Gly Gln Ser 35                  40                  45
Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Leu Gln Thr Pro Leu Thr Phe Gly Gly Gly Thr Lys Leu Glu Ile Lys
                100                 105                 110

Arg Thr Val Ala Ala Pro Ser
                115

<210> SEQ ID NO 107
<211> LENGTH: 114
<212> TYPE: PRT
<213> ORGANISM: Homo sapiens

<400> SEQUENCE: 107

Glu Thr Thr Leu Thr Gln Ser Pro Ala Phe Met Ser Ala Ser Val Gly
 1               5                  10                  15

Asp Arg Val Thr Ile Thr Cys Gln Ala Ser Gln Asp Ile Asn Asn Phe
                20                  25                  30

Leu Asn Trp Tyr Gln Gln Lys Pro Gly Lys Ala Pro Lys Phe Leu Ile
                35                  40                  45

Tyr Asp Ala Ser Asn Leu Glu Lys Gly Val Pro Ser Arg Phe Ser Gly
        50                  55                  60

Arg Gly Ser Gly Thr Glu Phe Thr Leu Thr Ile Ser Ser Leu Gln Pro
 65                  70                  75                  80

Glu Asp Ile Ala Thr Tyr Tyr Cys Gln Gln Tyr Arg Asp Phe Pro Leu
                85                  90                  95

Thr Phe Gly Gln Gly Thr Arg Leu Glu Ile Lys Arg Thr Val Ala Ala
                100                 105                 110

Pro Ser

<210> SEQ ID NO 108
<211> LENGTH: 119
<212> TYPE: PRT
<213> ORGANISM: Homo sapiens

<400> SEQUENCE: 108

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ile
                20                  25                  30

Asp Gly Leu Thr Tyr Leu Tyr Trp Tyr Leu Gln Lys Pro Gly Gln Pro
                35                  40                  45

Pro Gln Leu Leu Ile Tyr Glu Val Ser His Arg Phe Ser Gly Val Ser
        50                  55                  60

Asp Lys Phe Ser Gly Ser Gly Ser Gly Thr Asp Phe Thr Leu Thr Ile
 65                  70                  75                  80

Ser Arg Val Glu Ala Glu Asp Val Gly Val Tyr Tyr Cys Met Gln Ser
                85                  90                  95

Leu His Leu Pro Ile Thr Phe Gly Gln Gly Thr Arg Leu Glu Ile Lys
                100                 105                 110

Arg Thr Val Ala Ala Pro Ser
                115

<210> SEQ ID NO 109
<211> LENGTH: 119
<212> TYPE: PRT
<213> ORGANISM: Homo sapiens

<400> SEQUENCE: 109

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ile
            20                  25                  30

Asp Gly Leu Thr Tyr Leu Tyr Trp Tyr Leu Gln Lys Pro Gly Gln Pro
        35                  40                  45

Pro Gln Leu Leu Ile Tyr Glu Val Ser His Arg Phe Ser Gly Val Ser
    50                  55                  60

Asp Lys Phe Ser Gly Ser Gly Ser Gly Thr Asp Phe Thr Leu Thr Ile
65                  70                  75                  80

Ser Arg Val Glu Ala Glu Asp Val Gly Val Tyr Tyr Cys Met Gln Ser
                85                  90                  95

Leu His Leu Pro Ile Thr Phe Gly Gln Gly Thr Arg Leu Glu Ile Lys
            100                 105                 110

Arg Thr Val Ala Ala Pro Ser
        115

<210> SEQ ID NO 110
<211> LENGTH: 119
<212> TYPE: PRT
<213> ORGANISM: Homo sapiens

<400> SEQUENCE: 110

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ile
            20                  25                  30

Asp Gly Lys Thr Tyr Leu Tyr Trp Tyr Leu Gln Lys Ser Gly Gln Ser
        35                  40                  45

Pro Gln Leu Leu Ile Tyr Glu Val Ser Asn Arg Phe Ser Gly Val Pro
    50                  55                  60

Asp Thr Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu His Phe Pro Ile Thr Phe Gly Gln Gly Thr Arg Leu Glu Ile Lys
            100                 105                 110

Arg Thr Val Ala Ala Pro Ser
        115

<210> SEQ ID NO 111
<211> LENGTH: 119
<212> TYPE: PRT
<213> ORGANISM: Homo sapiens

<400> SEQUENCE: 111

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ile
            20                  25                  30

-continued

Asp Gly Lys Thr Tyr Leu Tyr Trp Tyr Leu Gln Lys Ser Gly Gln Ser
            35                  40                  45

Pro Gln Leu Leu Ile Tyr Glu Val Ser Asn Arg Phe Ser Gly Val Pro
    50                  55                  60

Asp Thr Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu His Phe Pro Ile Thr Phe Gly Gln Gly Thr Arg Leu Glu Ile Lys
            100                 105                 110

Arg Thr Val Ala Ala Pro Ser
        115

<210> SEQ ID NO 112
<211> LENGTH: 114
<212> TYPE: PRT
<213> ORGANISM: Homo sapiens

<400> SEQUENCE: 112

Glu Thr Thr Leu Thr Gln Ser Pro Thr Phe Met Ser Ala Ser Val Gly
1               5                   10                  15

Asp Arg Val Thr Ile Thr Cys Gln Ala Ser Gln Asp Ile Asn Asn Phe
            20                  25                  30

Leu Asn Trp Tyr Gln Lys Pro Gly Lys Ala Pro Lys Phe Leu Ile
            35                  40                  45

Tyr Asp Ala Ser Asn Leu Glu Lys Gly Val Pro Ser Arg Phe Ser Gly
    50                  55                  60

Arg Gly Ser Gly Thr Glu Phe Thr Leu Thr Ile Ser Ser Leu Gln Pro
65                  70                  75                  80

Glu Asp Ile Ala Thr Tyr Tyr Cys Gln Gln Tyr Arg Asp Phe Pro Leu
                85                  90                  95

Thr Phe Gly Gln Gly Thr Arg Leu Glu Ile Lys Arg Thr Val Ala Ala
            100                 105                 110

Pro Ser

<210> SEQ ID NO 113
<211> LENGTH: 119
<212> TYPE: PRT
<213> ORGANISM: Homo sapiens

<400> SEQUENCE: 113

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ile
            20                  25                  30

Asp Gly Lys Ala Tyr Leu Tyr Trp Tyr Leu Gln Lys Pro Gly Gln Ser
            35                  40                  45

Pro His Leu Leu Ile Arg Glu Val Ser Thr Arg Phe Ser Gly Val Ser
    50                  55                  60

Asp Arg Phe Thr Gly Ser Gly Ser Gly Thr Asp Phe Thr Leu Glu Ile
65                  70                  75                  80

Ser Arg Val Glu Ala Glu Asp Val Gly Val Tyr Tyr Cys Met Gln Gly
                85                  90                  95

Leu His Leu Pro Pro Thr Phe Gly Gln Gly Thr Lys Val Glu Ile Lys
            100                 105                 110

Arg Thr Val Ala Ala Pro Ser

```
<210> SEQ ID NO 114
<211> LENGTH: 119
<212> TYPE: PRT
<213> ORGANISM: Homo sapiens

<400> SEQUENCE: 114

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ile
            20                  25                  30

Asp Gly Arg Thr Tyr Leu Tyr Trp Tyr Leu Gln Lys Ala Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile His Phe Pro Leu Thr Phe Gly Gly Gly Thr Lys Leu Glu Ile Lys
                100                 105                 110

Arg Thr Val Ala Ala Pro Ser
            115

<210> SEQ ID NO 115
<211> LENGTH: 119
<212> TYPE: PRT
<213> ORGANISM: Homo sapiens

<400> SEQUENCE: 115

Asp Ile Val Met Thr Gln Thr Pro Leu Ser Leu Ser Val Thr Pro Gly
1               5                   10                  15

Gln Pro Ala Ser Ile Thr Cys Lys Ser Ser Gln Ser Leu Leu His Ile
            20                  25                  30

Asp Gly Asn Thr Tyr Leu Tyr Trp Tyr Leu Gln Arg Pro Gly Gln Pro
        35                  40                  45

Pro Gln Leu Leu Ile Tyr Glu Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu His Phe Pro Ile Thr Phe Gly Gln Gly Thr Arg Leu Glu Ile Lys
                100                 105                 110

Arg Thr Val Ala Ala Pro Ser
            115

<210> SEQ ID NO 116
<211> LENGTH: 119
<212> TYPE: PRT
<213> ORGANISM: Homo sapiens

<400> SEQUENCE: 116

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ile
            20                  25                  30
```

Asp Gly Asn Thr Tyr Leu Tyr Trp Tyr Leu Gln Arg Pro Gly Gln Pro
            35                  40                  45

Pro Gln Leu Leu Ile Tyr Glu Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu His Phe Pro Ile Thr Phe Gly Gln Gly Thr Arg Leu Glu Ile Lys
                100                 105                 110

Arg Thr Val Ala Ala Pro Ser
            115

<210> SEQ ID NO 117
<211> LENGTH: 119
<212> TYPE: PRT
<213> ORGANISM: Homo sapiens

<400> SEQUENCE: 117

Asp Ile Val Met Thr Gln Thr Pro Leu Ser Leu Ser Val Thr Pro Gly
1               5                   10                  15

Gln Pro Ala Ser Ile Thr Cys Lys Ser Ser Gln Ser Leu Leu His Ile
            20                  25                  30

Asp Gly Lys Thr Tyr Leu Tyr Trp Phe Leu Gln Lys Pro Gly Gln Pro
            35                  40                  45

Pro Gln Leu Leu Ile Tyr Glu Val Ser Asn Arg Phe Ser Gly Val Pro
    50                  55                  60

Asp Arg Phe Ser Gly Thr Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu His Phe Pro Ile Thr Phe Gly Pro Gly Thr Arg Leu Glu Ile Lys
                100                 105                 110

Arg Thr Val Ala Ala Pro Ser
            115

<210> SEQ ID NO 118
<211> LENGTH: 119
<212> TYPE: PRT
<213> ORGANISM: Homo sapiens

<400> SEQUENCE: 118

Asp Val Val Met Thr Gln Thr Pro Leu Ser Leu Ser Val Thr Pro Gly
1               5                   10                  15

Gln Pro Ala Ser Phe Ser Cys Lys Ser Thr Gln Ser Leu Leu Trp Arg
            20                  25                  30

Asp Gly Asn Thr Tyr Leu Tyr Trp Tyr Leu Gln Lys Pro Gly Gln Ser
            35                  40                  45

Pro Gln Leu Leu Ile Tyr Glu Val Ser Gly Arg Phe Ser Gly Val Pro
    50                  55                  60

Glu Arg Phe Ser Gly Ser Gly Ser Gly Thr Asp Phe Thr Leu Glu Ile
65                  70                  75                  80

Ser Arg Val Glu Ala Glu Asp Val Gly Val Tyr Tyr Cys Met Gln Ser
                85                  90                  95

Ile His Phe Pro Leu Thr Phe Gly Gly Gly Thr Lys Leu Glu Ile Lys
                100                 105                 110

Arg Thr Val Ala Ala Pro Ser
        115

<210> SEQ ID NO 119
<211> LENGTH: 119
<212> TYPE: PRT
<213> ORGANISM: Homo sapiens

<400> SEQUENCE: 119

Asp Ile Val Met Thr Gln Thr Pro Leu Ser Leu Ser Val Thr Pro Gly
1               5                   10                  15

Gln Pro Ala Ser Ile Thr Cys Lys Ser Ser Gln Ser Leu Leu His Ile
            20                  25                  30

Asp Gly Lys Thr Tyr Leu Tyr Trp Phe Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ser
                85                  90                  95

Leu His Leu Pro Ile Thr Phe Gly Gln Gly Thr Arg Leu Glu Ile Lys
            100                 105                 110

Arg Thr Val Ala Ala Pro Ser
        115

<210> SEQ ID NO 120
<211> LENGTH: 119
<212> TYPE: PRT
<213> ORGANISM: Homo sapiens

<400> SEQUENCE: 120

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asp Gly Phe Asn Tyr Leu Gln Trp Tyr Leu Gln Lys Pro Gly Gln Ser
        35                  40                  45

Pro Gln Leu Leu Val His Leu Gly Ser Phe Arg Ala Ser Gly Val Pro
    50                  55                  60

Asp Arg Phe Ser Gly Ser Gly Ser Gly Thr Asp Phe Thr Leu Glu Ile
65                  70                  75                  80

Ser Arg Val Glu Ala Glu Asp Val Gly Leu Tyr Tyr Cys Met Gln Gly
                85                  90                  95

Leu Gln Thr Pro Pro Thr Phe Gly Pro Gly Thr Lys Val Glu Ile Lys
            100                 105                 110

Arg Thr Val Ala Ala Pro Ser
        115

<210> SEQ ID NO 121
<211> LENGTH: 119
<212> TYPE: PRT
<213> ORGANISM: Homo sapiens

<400> SEQUENCE: 121

Asp Ile Val Met Thr Gln Thr Pro Leu Ser Leu Ser Val Thr Pro Gly
1               5                   10                  15

-continued

```
Gln Pro Ala Ser Ile Ser Cys Lys Ser Ser Gln Ser Leu Phe His Asp
                20                  25                  30

His Gly Arg Thr His Leu Ser Trp Tyr Leu Lys Pro Gly Gln Pro
        35                  40                  45

Pro Gln Leu Leu Ile Phe Glu Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Pro Ala Phe Gly Gly Gly Thr Lys Leu Glu Ile Lys
            100                 105                 110

Arg Thr Val Ala Ala Pro Ser
        115
```

<210> SEQ ID NO 122
<211> LENGTH: 116
<212> TYPE: PRT
<213> ORGANISM: Homo sapiens

<400> SEQUENCE: 122

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Tyr Asn
                20                  25                  30

Tyr Val Ser Trp Tyr Gln Gln Phe Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Ser Arg
                85                  90                  95

Ser Pro Pro Trp Val Phe Gly Gly Gly Thr Lys Val Thr Val Leu Gly
            100                 105                 110

Gln Pro Lys Ala
        115
```

<210> SEQ ID NO 123
<211> LENGTH: 110
<212> TYPE: PRT
<213> ORGANISM: Homo sapiens

<400> SEQUENCE: 123

```
Ser Tyr Glu Leu Thr Gln Pro Ser Ser Val Ser Val Ser Pro Gly Gln
1               5                   10                  15

Thr Ala Ser Ile Thr Cys Ser Gly Asp Lys Leu Gly Glu Lys Tyr Ala
                20                  25                  30

Ser Trp Tyr Gln Gln Lys Pro Gly Gln Ser Pro Val Leu Val Met Phe
            35                  40                  45

Glu Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Trp Asp Ser Ser Trp Val Phe
                85                  90                  95
```

```
Gly Gly Gly Thr Gln Leu Thr Val Leu Gly Gln Pro Lys Ala
            100                 105                 110

<210> SEQ ID NO 124
<211> LENGTH: 116
<212> TYPE: PRT
<213> ORGANISM: Homo sapiens

<400> SEQUENCE: 124

Gln Ser Val Leu Thr Gln Pro Pro Ser Val Ser Ala Ala Pro Gly Gln
1               5                   10                  15

Arg Val Thr Ile Ser Cys Ser Gly Asn Thr Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Asp Asp Asn Lys Arg Pro Ser Gly Ile Pro Asp Arg Phe Ser
50                  55                  60

Gly Ser Lys Ser Gly Thr Ser Ala Thr Leu Gly Ile Ser Gly Leu Gln
65                  70                  75                  80

Thr Gly Asp Glu Ala Asp Tyr Tyr Cys Gly Thr Trp Asp Asn Ser Leu
                85                  90                  95

Asn Pro Pro Trp Val Phe Gly Gly Gly Thr Gln Leu Thr Val Leu Gly
            100                 105                 110

Gln Pro Lys Ala
        115

<210> SEQ ID NO 125
<211> LENGTH: 110
<212> TYPE: PRT
<213> ORGANISM: Homo sapiens

<400> SEQUENCE: 125

Ser Tyr Val Leu Thr Gln Pro Pro Ser Val Ser Val Ala Pro Gly Gln
1               5                   10                  15

Thr Ala Ser Ile Thr Cys Ser Gly Asp Asn Leu Gly Glu Lys Phe Val
            20                  25                  30

Ser Trp Tyr Gln Gln Lys Ala Gly Gln Ser Pro Val Leu Val Ile Phe
        35                  40                  45

Glu Asp Asn Lys Arg Pro Ser Gly Ile Pro Glu Arg Phe Ala Gly Ser
50                  55                  60

Asn Ser Gly Asn Arg Ala Thr Leu Thr Ile Arg Gly Thr Gln Ala Glu
65                  70                  75                  80

Asp Glu Ala Asp Tyr Tyr Cys Gln Ala Trp Asp Ser Ser Trp Val Phe
                85                  90                  95

Gly Gly Gly Thr Gln Leu Thr Val Leu Gly Gln Pro Lys Ala
            100                 105                 110

<210> SEQ ID NO 126
<211> LENGTH: 110
<212> TYPE: PRT
<213> ORGANISM: Homo sapiens

<400> SEQUENCE: 126

Ser Tyr Glu Leu Thr Gln Pro Pro Ser Val Ser Val Ala Pro Gly Gln
1               5                   10                  15

Thr Ala Thr Ile Thr Cys Ser Gly Asp Arg Leu Gly Asp Lys Phe Ile
            20                  25                  30

Ser Trp Tyr Gln Gln Lys Pro Gly Gln Ser Pro Leu Leu Val Ile Phe
```

```
                35                  40                  45
Glu Asp Asn Glu Arg Pro Ser Arg Ile Pro Glu Arg Phe Ser Gly Ser
 50                  55                  60
Asn Ser Gly Asn Ser Ala Thr Leu Thr Ile Ser Gly Thr Gln Ala Val
 65                  70                  75                  80
Asp Glu Ala Asp Tyr Tyr Cys Gln Ala Trp Asp Ser Ser Trp Val Phe
                 85                  90                  95
Gly Gly Gly Thr Gln Leu Thr Val Leu Gly Gln Pro Lys Ala
                100                 105                 110

<210> SEQ ID NO 127
<211> LENGTH: 110
<212> TYPE: PRT
<213> ORGANISM: Homo sapiens

<400> SEQUENCE: 127

Ser Tyr Val Leu Thr Gln Pro Pro Ser Val Ser Val Ala Pro Gly Gln
  1               5                  10                  15
Thr Ala Arg Ile Thr Cys Ser Gly Asp Lys Leu Gly Asp Arg Tyr Val
                 20                  25                  30
Ser Trp Tyr Gln Gln Lys Pro Gly Gln Ser Pro Val Leu Val Met Phe
                 35                  40                  45
Glu Asp Thr Gly Arg Pro Ala Gly Ile Pro Glu Arg Phe Ser Gly Ser
 50                  55                  60
Asn Ser Gly Asn Thr Ala Thr Leu Thr Ile Ser Gly Thr Gln Ala Glu
 65                  70                  75                  80
Asp Glu Ala Asp Tyr Tyr Cys Gln Ala Trp Gly Thr Ser Trp Val Phe
                 85                  90                  95
Gly Gly Gly Thr Gln Leu Thr Val Leu Gly Gln Pro Lys Ala
                100                 105                 110

<210> SEQ ID NO 128
<211> LENGTH: 116
<212> TYPE: PRT
<213> ORGANISM: Homo sapiens

<400> SEQUENCE: 128

Gln Ser Val Leu Thr Gln Pro Pro Ser Val Ser Ala Ala Pro Gly Gln
  1               5                  10                  15
Lys Val Thr Ile Ser Cys Ser Gly Thr Gly Ser Asn Ile Gly Ser Asn
                 20                  25                  30
Tyr Val Ala Trp Tyr Gln Gln Leu Pro Gly Thr Ala Pro Lys Leu Leu
                 35                  40                  45
Ile Tyr Asp Asp Asn Lys Arg Pro Ser Gly Thr Pro Asp Arg Phe Ser
 50                  55                  60
Gly Ser Lys Ser Gly Thr Ser Ala Thr Leu Val Ile Ala Gly Leu Gln
 65                  70                  75                  80
Thr Gly Asp Glu Ala Asp Tyr Tyr Cys Gly Thr Trp Asp Asn Thr Leu
                 85                  90                  95
Asn Val Gly Gly Val Phe Gly Gly Gly Thr Gln Leu Thr Val Leu Gly
                100                 105                 110
Gln Pro Lys Ala
                115

<210> SEQ ID NO 129
<211> LENGTH: 110
<212> TYPE: PRT
```

<213> ORGANISM: Homo sapiens

<400> SEQUENCE: 129

Ser Tyr Val Leu Thr Gln Pro Pro Ser Val Ser Ala Pro Gly Gln
1               5                   10                  15

Thr Ala Thr Ile Thr Cys Ser Gly Asp Asp Phe Gly Asp Lys Tyr Val
            20                  25                  30

Ser Trp Tyr Gln Gln Lys Pro Gly Gln Ser Pro Leu Leu Val Ile Phe
        35                  40                  45

Gln Asp Asn Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Trp Val Phe
                85                  90                  95

Gly Gly Gly Thr Lys Val Thr Val Leu Gly Gln Pro Lys Ala
            100                 105                 110

<210> SEQ ID NO 130
<211> LENGTH: 112
<212> TYPE: PRT
<213> ORGANISM: Homo sapiens

<400> SEQUENCE: 130

Ser Tyr Glu Leu Thr Gln Pro Pro Ser Val Ser Ala Pro Gly Gln
1               5                   10                  15

Thr Ala Thr Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Met Phe
        35                  40                  45

Glu Asn Arg Asp Arg Pro Ser Gly Ile Pro Asp Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Trp
                85                  90                  95

Val Phe Gly Gly Gly Thr Gln Leu Thr Val Leu Gly Gln Pro Lys Ala
            100                 105                 110

<210> SEQ ID NO 131
<211> LENGTH: 6
<212> TYPE: PRT
<213> ORGANISM: Homo sapiens

<400> SEQUENCE: 131

Gln Asp Ile Asn Asn Phe
1               5

<210> SEQ ID NO 132
<211> LENGTH: 3
<212> TYPE: PRT
<213> ORGANISM: Homo sapiens

<400> SEQUENCE: 132

Asp Ala Ser
1

<210> SEQ ID NO 133
<211> LENGTH: 9

```
<212> TYPE: PRT
<213> ORGANISM: Homo sapiens

<400> SEQUENCE: 133

Gln Gln Tyr Arg Asp Phe Pro Leu Thr
1               5

<210> SEQ ID NO 134
<211> LENGTH: 11
<212> TYPE: PRT
<213> ORGANISM: Homo sapiens

<400> SEQUENCE: 134

Gln Ser Leu Val Tyr Gly Asp Gly His Asn Tyr
1               5                   10

<210> SEQ ID NO 135
<211> LENGTH: 3
<212> TYPE: PRT
<213> ORGANISM: Homo sapiens

<400> SEQUENCE: 135

Leu Gly Ser
1

<210> SEQ ID NO 136
<211> LENGTH: 9
<212> TYPE: PRT
<213> ORGANISM: Homo sapiens

<400> SEQUENCE: 136

Met Gln Gly Leu Gln Thr Pro Leu Thr
1               5

<210> SEQ ID NO 137
<211> LENGTH: 6
<212> TYPE: PRT
<213> ORGANISM: Homo sapiens

<400> SEQUENCE: 137

Gln Asp Ile Asn Asn Phe
1               5

<210> SEQ ID NO 138
<211> LENGTH: 3
<212> TYPE: PRT
<213> ORGANISM: Homo sapiens

<400> SEQUENCE: 138

Asp Ala Ser
1

<210> SEQ ID NO 139
<211> LENGTH: 9
<212> TYPE: PRT
<213> ORGANISM: Homo sapiens

<400> SEQUENCE: 139

Gln Gln Tyr Arg Asp Phe Pro Leu Thr
1               5

<210> SEQ ID NO 140
<211> LENGTH: 11
<212> TYPE: PRT
<213> ORGANISM: Homo sapiens
```

<400> SEQUENCE: 140

Gln Ser Leu Leu His Ile Asp Gly Leu Thr Tyr
1               5                   10

<210> SEQ ID NO 141
<211> LENGTH: 3
<212> TYPE: PRT
<213> ORGANISM: Homo sapiens

<400> SEQUENCE: 141

Glu Val Ser
1

<210> SEQ ID NO 142
<211> LENGTH: 9
<212> TYPE: PRT
<213> ORGANISM: Homo sapiens

<400> SEQUENCE: 142

Met Gln Ser Leu His Leu Pro Ile Thr
1               5

<210> SEQ ID NO 143
<211> LENGTH: 11
<212> TYPE: PRT
<213> ORGANISM: Homo sapiens

<400> SEQUENCE: 143

Gln Ser Leu Leu His Ile Asp Gly Leu Thr Tyr
1               5                   10

<210> SEQ ID NO 144
<211> LENGTH: 3
<212> TYPE: PRT
<213> ORGANISM: Homo sapiens

<400> SEQUENCE: 144

Glu Val Ser
1

<210> SEQ ID NO 145
<211> LENGTH: 9
<212> TYPE: PRT
<213> ORGANISM: Homo sapiens

<400> SEQUENCE: 145

Met Gln Ser Leu His Leu Pro Ile Thr
1               5

<210> SEQ ID NO 146
<211> LENGTH: 11
<212> TYPE: PRT
<213> ORGANISM: Homo sapiens

<400> SEQUENCE: 146

Gln Ser Leu Leu His Ile Asp Gly Lys Thr Tyr
1               5                   10

<210> SEQ ID NO 147
<211> LENGTH: 3
<212> TYPE: PRT
<213> ORGANISM: Homo sapiens

<400> SEQUENCE: 147

Glu Val Ser
1

<210> SEQ ID NO 148
<211> LENGTH: 9
<212> TYPE: PRT
<213> ORGANISM: Homo sapiens

<400> SEQUENCE: 148

Met Gln Ser Leu His Phe Pro Ile Thr
1               5

<210> SEQ ID NO 149
<211> LENGTH: 11
<212> TYPE: PRT
<213> ORGANISM: Homo sapiens

<400> SEQUENCE: 149

Gln Ser Leu Leu His Ile Asp Gly Lys Thr Tyr
1               5                   10

<210> SEQ ID NO 150
<211> LENGTH: 3
<212> TYPE: PRT
<213> ORGANISM: Homo sapiens

<400> SEQUENCE: 150

Glu Val Ser
1

<210> SEQ ID NO 151
<211> LENGTH: 9
<212> TYPE: PRT
<213> ORGANISM: Homo sapiens

<400> SEQUENCE: 151

Met Gln Ser Leu His Phe Pro Ile Thr
1               5

<210> SEQ ID NO 152
<211> LENGTH: 6
<212> TYPE: PRT
<213> ORGANISM: Homo sapiens

<400> SEQUENCE: 152

Gln Asp Ile Asn Asn Phe
1               5

<210> SEQ ID NO 153
<211> LENGTH: 3
<212> TYPE: PRT
<213> ORGANISM: Homo sapiens

<400> SEQUENCE: 153

Asp Ala Ser
1

<210> SEQ ID NO 154
<211> LENGTH: 9
<212> TYPE: PRT
<213> ORGANISM: Homo sapiens

<400> SEQUENCE: 154

Gln Gln Tyr Arg Asp Phe Pro Leu Thr

<210> SEQ ID NO 155
<211> LENGTH: 11
<212> TYPE: PRT
<213> ORGANISM: Homo sapiens

<400> SEQUENCE: 155

Gln Ser Leu Leu His Ile Asp Gly Lys Ala Tyr
1               5                   10

<210> SEQ ID NO 156
<211> LENGTH: 3
<212> TYPE: PRT
<213> ORGANISM: Homo sapiens

<400> SEQUENCE: 156

Glu Val Ser
1

<210> SEQ ID NO 157
<211> LENGTH: 9
<212> TYPE: PRT
<213> ORGANISM: Homo sapiens

<400> SEQUENCE: 157

Met Gln Gly Leu His Leu Pro Pro Thr
1               5

<210> SEQ ID NO 158
<211> LENGTH: 11
<212> TYPE: PRT
<213> ORGANISM: Homo sapiens

<400> SEQUENCE: 158

Gln Ser Leu Leu His Ile Asp Gly Arg Thr Tyr
1               5                   10

<210> SEQ ID NO 159
<211> LENGTH: 3
<212> TYPE: PRT
<213> ORGANISM: Homo sapiens

<400> SEQUENCE: 159

Glu Val Ser
1

<210> SEQ ID NO 160
<211> LENGTH: 9
<212> TYPE: PRT
<213> ORGANISM: Homo sapiens

<400> SEQUENCE: 160

Met Gln Ser Ile His Phe Pro Leu Thr
1               5

<210> SEQ ID NO 161
<211> LENGTH: 11
<212> TYPE: PRT
<213> ORGANISM: Homo sapiens

<400> SEQUENCE: 161

Gln Ser Leu Leu His Ile Asp Gly Asn Thr Tyr
1               5                   10

```
<210> SEQ ID NO 162
<211> LENGTH: 3
<212> TYPE: PRT
<213> ORGANISM: Homo sapiens

<400> SEQUENCE: 162

Glu Ile Ser
1

<210> SEQ ID NO 163
<211> LENGTH: 9
<212> TYPE: PRT
<213> ORGANISM: Homo sapiens

<400> SEQUENCE: 163

Met Gln Ser Leu His Phe Pro Ile Thr
1               5

<210> SEQ ID NO 164
<211> LENGTH: 11
<212> TYPE: PRT
<213> ORGANISM: Homo sapiens

<400> SEQUENCE: 164

Gln Ser Leu Leu His Ile Asp Gly Asn Thr Tyr
1               5                   10

<210> SEQ ID NO 165
<211> LENGTH: 3
<212> TYPE: PRT
<213> ORGANISM: Homo sapiens

<400> SEQUENCE: 165

Glu Ile Ser
1

<210> SEQ ID NO 166
<211> LENGTH: 9
<212> TYPE: PRT
<213> ORGANISM: Homo sapiens

<400> SEQUENCE: 166

Met Gln Ser Leu His Phe Pro Ile Thr
1               5

<210> SEQ ID NO 167
<211> LENGTH: 11
<212> TYPE: PRT
<213> ORGANISM: Homo sapiens

<400> SEQUENCE: 167

Gln Ser Leu Leu His Ile Asp Gly Lys Thr Tyr
1               5                   10

<210> SEQ ID NO 168
<211> LENGTH: 3
<212> TYPE: PRT
<213> ORGANISM: Homo sapiens

<400> SEQUENCE: 168

Glu Val Ser
1

<210> SEQ ID NO 169
```

```
<211> LENGTH: 9
<212> TYPE: PRT
<213> ORGANISM: Homo sapiens

<400> SEQUENCE: 169

Met Gln Ser Leu His Phe Pro Ile Thr
1               5

<210> SEQ ID NO 170
<211> LENGTH: 11
<212> TYPE: PRT
<213> ORGANISM: Homo sapiens

<400> SEQUENCE: 170

Gln Ser Leu Leu Trp Arg Asp Gly Asn Thr Tyr
1               5                   10

<210> SEQ ID NO 171
<211> LENGTH: 3
<212> TYPE: PRT
<213> ORGANISM: Homo sapiens

<400> SEQUENCE: 171

Glu Val Ser
1

<210> SEQ ID NO 172
<211> LENGTH: 9
<212> TYPE: PRT
<213> ORGANISM: Homo sapiens

<400> SEQUENCE: 172

Met Gln Ser Ile His Phe Pro Leu Thr
1               5

<210> SEQ ID NO 173
<211> LENGTH: 11
<212> TYPE: PRT
<213> ORGANISM: Homo sapiens

<400> SEQUENCE: 173

Gln Ser Leu Leu His Ile Asp Gly Lys Thr Tyr
1               5                   10

<210> SEQ ID NO 174
<211> LENGTH: 3
<212> TYPE: PRT
<213> ORGANISM: Homo sapiens

<400> SEQUENCE: 174

Glu Val Ser
1

<210> SEQ ID NO 175
<211> LENGTH: 9
<212> TYPE: PRT
<213> ORGANISM: Homo sapiens

<400> SEQUENCE: 175

Met Gln Ser Leu His Leu Pro Ile Thr
1               5

<210> SEQ ID NO 176
<211> LENGTH: 11
<212> TYPE: PRT
```

```
<213> ORGANISM: Homo sapiens

<400> SEQUENCE: 176

Gln Ser Leu Leu His Ile Asp Gly Phe Asn Tyr
1               5                   10

<210> SEQ ID NO 177
<211> LENGTH: 3
<212> TYPE: PRT
<213> ORGANISM: Homo sapiens

<400> SEQUENCE: 177

Leu Gly Ser
1

<210> SEQ ID NO 178
<211> LENGTH: 9
<212> TYPE: PRT
<213> ORGANISM: Homo sapiens

<400> SEQUENCE: 178

Met Gln Gly Leu Gln Thr Pro Pro Thr
1               5

<210> SEQ ID NO 179
<211> LENGTH: 11
<212> TYPE: PRT
<213> ORGANISM: Homo sapiens

<400> SEQUENCE: 179

Gln Ser Leu Phe His Asp His Gly Arg Thr His
1               5                   10

<210> SEQ ID NO 180
<211> LENGTH: 3
<212> TYPE: PRT
<213> ORGANISM: Homo sapiens

<400> SEQUENCE: 180

Glu Ala Ser
1

<210> SEQ ID NO 181
<211> LENGTH: 9
<212> TYPE: PRT
<213> ORGANISM: Homo sapiens

<400> SEQUENCE: 181

Met Gln Gly Ile His Leu Pro Pro Ala
1               5

<210> SEQ ID NO 182
<211> LENGTH: 8
<212> TYPE: PRT
<213> ORGANISM: Homo sapiens

<400> SEQUENCE: 182

Ser Ser Asn Ile Gly Tyr Asn Tyr
1               5

<210> SEQ ID NO 183
<211> LENGTH: 3
<212> TYPE: PRT
<213> ORGANISM: Homo sapiens
```

<400> SEQUENCE: 183

Asp Asn Asn
1

<210> SEQ ID NO 184
<211> LENGTH: 12
<212> TYPE: PRT
<213> ORGANISM: Homo sapiens

<400> SEQUENCE: 184

Gly Thr Trp Asp Asn Ser Arg Ser Pro Pro Trp Val
1               5                   10

<210> SEQ ID NO 185
<211> LENGTH: 17
<212> TYPE: PRT
<213> ORGANISM: Homo sapiens

<400> SEQUENCE: 185

Lys Leu Gly Glu Lys Tyr Glu Asp Thr Gln Ala Trp Asp Ser Ser Trp
1               5                   10                  15

Val

<210> SEQ ID NO 186
<211> LENGTH: 3
<212> TYPE: PRT
<213> ORGANISM: Homo sapiens

<400> SEQUENCE: 186

Glu Asp Thr
1

<210> SEQ ID NO 187
<211> LENGTH: 8
<212> TYPE: PRT
<213> ORGANISM: Homo sapiens

<400> SEQUENCE: 187

Gln Ala Trp Asp Ser Ser Trp Val
1               5

<210> SEQ ID NO 188
<211> LENGTH: 8
<212> TYPE: PRT
<213> ORGANISM: Homo sapiens

<400> SEQUENCE: 188

Thr Ser Asn Ile Gly Asn Asn Phe
1               5

<210> SEQ ID NO 189
<211> LENGTH: 3
<212> TYPE: PRT
<213> ORGANISM: Homo sapiens

<400> SEQUENCE: 189

Asp Asp Asn
1

<210> SEQ ID NO 190
<211> LENGTH: 12
<212> TYPE: PRT
<213> ORGANISM: Homo sapiens

<400> SEQUENCE: 190

Gly Thr Trp Asp Asn Ser Leu Asn Pro Pro Trp Val
1               5                   10

<210> SEQ ID NO 191
<211> LENGTH: 6
<212> TYPE: PRT
<213> ORGANISM: Homo sapiens

<400> SEQUENCE: 191

Asn Leu Gly Glu Lys Phe
1               5

<210> SEQ ID NO 192
<211> LENGTH: 3
<212> TYPE: PRT
<213> ORGANISM: Homo sapiens

<400> SEQUENCE: 192

Glu Asp Asn
1

<210> SEQ ID NO 193
<211> LENGTH: 8
<212> TYPE: PRT
<213> ORGANISM: Homo sapiens

<400> SEQUENCE: 193

Gln Ala Trp Asp Ser Ser Trp Val
1               5

<210> SEQ ID NO 194
<211> LENGTH: 6
<212> TYPE: PRT
<213> ORGANISM: Homo sapiens

<400> SEQUENCE: 194

Arg Leu Gly Asp Lys Phe
1               5

<210> SEQ ID NO 195
<211> LENGTH: 3
<212> TYPE: PRT
<213> ORGANISM: Homo sapiens

<400> SEQUENCE: 195

Glu Asp Asn
1

<210> SEQ ID NO 196
<211> LENGTH: 8
<212> TYPE: PRT
<213> ORGANISM: Homo sapiens

<400> SEQUENCE: 196

Gln Ala Trp Asp Ser Ser Trp Val
1               5

<210> SEQ ID NO 197
<211> LENGTH: 6
<212> TYPE: PRT
<213> ORGANISM: Homo sapiens

<400> SEQUENCE: 197

```
Lys Leu Gly Asp Arg Tyr
1               5

<210> SEQ ID NO 198
<211> LENGTH: 3
<212> TYPE: PRT
<213> ORGANISM: Homo sapiens

<400> SEQUENCE: 198

Glu Asp Thr
1

<210> SEQ ID NO 199
<211> LENGTH: 8
<212> TYPE: PRT
<213> ORGANISM: Homo sapiens

<400> SEQUENCE: 199

Gln Ala Trp Gly Thr Ser Trp Val
1               5

<210> SEQ ID NO 200
<211> LENGTH: 8
<212> TYPE: PRT
<213> ORGANISM: Homo sapiens

<400> SEQUENCE: 200

Gly Ser Asn Ile Gly Ser Asn Tyr
1               5

<210> SEQ ID NO 201
<211> LENGTH: 3
<212> TYPE: PRT
<213> ORGANISM: Homo sapiens

<400> SEQUENCE: 201

Asp Asp Asn
1

<210> SEQ ID NO 202
<211> LENGTH: 12
<212> TYPE: PRT
<213> ORGANISM: Homo sapiens

<400> SEQUENCE: 202

Gly Thr Trp Asp Asn Thr Leu Asn Val Gly Gly Val
1               5                   10

<210> SEQ ID NO 203
<211> LENGTH: 6
<212> TYPE: PRT
<213> ORGANISM: Homo sapiens

<400> SEQUENCE: 203

Asp Phe Gly Asp Lys Tyr
1               5

<210> SEQ ID NO 204
<211> LENGTH: 3
<212> TYPE: PRT
<213> ORGANISM: Homo sapiens

<400> SEQUENCE: 204

Gln Asp Asn
1
```

<210> SEQ ID NO 205
<211> LENGTH: 8
<212> TYPE: PRT
<213> ORGANISM: Homo sapiens

<400> SEQUENCE: 205

Gln Ala Trp Asp Ser Asn Trp Val
1               5

<210> SEQ ID NO 206
<211> LENGTH: 6
<212> TYPE: PRT
<213> ORGANISM: Homo sapiens

<400> SEQUENCE: 206

Lys Leu Gly Asp Lys Tyr
1               5

<210> SEQ ID NO 207
<211> LENGTH: 3
<212> TYPE: PRT
<213> ORGANISM: Homo sapiens

<400> SEQUENCE: 207

Glu Asn Arg
1

<210> SEQ ID NO 208
<211> LENGTH: 10
<212> TYPE: PRT
<213> ORGANISM: Homo sapiens

<400> SEQUENCE: 208

Gln Ala Trp Asp Ser Ser Thr Ala Trp Val
1               5                   10

<210> SEQ ID NO 209
<211> LENGTH: 348
<212> TYPE: DNA
<213> ORGANISM: Homo sapiens

<400> SEQUENCE: 209
cagatgcagc tggtgcagtc tggggctgag gtgaagaagc ctggatcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagagggtat     300
gtagtagcca gactctgggg ccagggaacc ctggtcaccg tcagctca                  348

<210> SEQ ID NO 210
<211> LENGTH: 348
<212> TYPE: DNA
<213> ORGANISM: Homo sapiens

<400> SEQUENCE: 210
cagatgcagc tggtgcagtc tggggctgag gtgaagaagc ctggatcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180

```
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tctcctca                 348
```

<210> SEQ ID NO 211
<211> LENGTH: 348
<212> TYPE: DNA
<213> ORGANISM: Homo sapiens

<400> SEQUENCE: 211

```
cagatgcagc tggtgcagtc tggggctgag gtgaagaagc ctggatcctc ggtgaaggtc    60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tcagctca                 348
```

<210> SEQ ID NO 212
<211> LENGTH: 348
<212> TYPE: DNA
<213> ORGANISM: Homo sapiens

<400> SEQUENCE: 212

```
cagatgcagc tggtgcagtc tggcgccgaa gtgaagaaac ccggctcctc cgtgaaggtg    60
tcctgcaagg cctccggcgg caccttctcc agctacgcca tctcctgggt gcgacaggcc    120
ccaggccagg gcctggaatg gatgggcggc atcatcccca tcttcggcac cgccaactac    180
gcccagaaat tccagggcag agtgaccatc accgccgacg agtccacctc caccgcctac    240
atggaactgt cctccctgcg gagcgaggac accgccgtgt actactgcgc cagaggctac    300
gtggtggcca gactgtgggg ccagggcacc ctggtgaccg tgagctca                 348
```

<210> SEQ ID NO 213
<211> LENGTH: 348
<212> TYPE: DNA
<213> ORGANISM: Homo sapiens

<400> SEQUENCE: 213

```
cagatgcagc tggtgcagtc tggggctgag gtgaagaagc ctggatcctc ggtgaaggtc    60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tcagctca                 348
```

<210> SEQ ID NO 214
<211> LENGTH: 348
<212> TYPE: DNA
<213> ORGANISM: Homo sapiens

<400> SEQUENCE: 214

```
cagatgcagc tggtgcagtc tggcgccgaa gtgaagaaac ccggctcctc cgtgaaggtg    60
tcctgcaagg cctccggcgg caccttctcc agctacgcca tctcctgggt gcgacaggcc    120
ccaggccagg gcctggaatg gatgggcggc atcatcccca tcttcggcac cgccaactac    180
```

```
gcccagaaat tccagggcag agtgaccatc accgccgacg agtccacctc caccgcctac    240
atggaactgt cctccctgcg gagcgaggac accgccgtgt actactgcgc cagaggctac    300
gtggtggcca gactgtgggg ccagggcacc ctggtgaccg tgagctca                 348
```

<210> SEQ ID NO 215
<211> LENGTH: 348
<212> TYPE: DNA
<213> ORGANISM: Homo sapiens

<400> SEQUENCE: 215

```
cagatgcagc tggtgcagtc tggggctgag gtgaagaagc ctggatcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tcagctca                 348
```

<210> SEQ ID NO 216
<211> LENGTH: 348
<212> TYPE: DNA
<213> ORGANISM: Homo sapiens

<400> SEQUENCE: 216

```
cagatgcagc tggtgcagtc tggggctgag gtgaagaagc ctggatcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tcagctca                 348
```

<210> SEQ ID NO 217
<211> LENGTH: 348
<212> TYPE: DNA
<213> ORGANISM: Homo sapiens

<400> SEQUENCE: 217

```
cagatgcagc tggtgcagtc tggggctgag gtgaagaagc ctggatcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tcagctca                 348
```

<210> SEQ ID NO 218
<211> LENGTH: 348
<212> TYPE: DNA
<213> ORGANISM: Homo sapiens

<400> SEQUENCE: 218

```
cagatgcagc tggtgcagtc tggggctgag gtgaagaagc ctggatcctc ggtgaaggtc     60
tcctgcaagg cttctggagg caccttcagc agctatgcta tcagctgggt gcgacaggcc    120
```
cctggacaag ggcttgagtg gatgggaggg atcatccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tcagctca                 348

<210> SEQ ID NO 219
<211> LENGTH: 348
<212> TYPE: DNA
<213> ORGANISM: Homo sapiens

<400> SEQUENCE: 219
cagatgcagc tggtgcagtc tggggctgag gtgaagaagc ctggatcctc ggtgaaggtc    60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tcagctca                 348

<210> SEQ ID NO 220
<211> LENGTH: 348
<212> TYPE: DNA
<213> ORGANISM: Homo sapiens

<400> SEQUENCE: 220
cagatgcagc tggtgcagtc tggcgccgaa gtgaagaaac ccggctcctc cgtgaaggtg    60
tcctgcaagg cctccggcgg caccttctcc agctacgcca tctcctgggt gcgacaggcc    120
ccaggccagg gcctggaatg gatgggcggc atcatcccca tcttcggcac cgccaactac    180
gcccagaaat tccagggcag agtgaccatc accgccgacg agtccacctc caccgcctac    240
atggaactgt cctccctgcg gagcgaggac accgccgtgt actactgcgc cagaggctac    300
gtggtggcca gactgtgggg ccagggcacc ctggtgaccg tgagctca                 348

<210> SEQ ID NO 221
<211> LENGTH: 348
<212> TYPE: DNA
<213> ORGANISM: Homo sapiens

<400> SEQUENCE: 221
cagatgcagc tggtgcagtc tggggctgag gtgaagaagc ctggatcctc ggtgaaggtc    60
tcctgcaagg cttctggagg caccttcagc agctatgcta tcagctgggt gcgacaggcc    120
cctggacaag ggcttgagtg gatgggaggg atcatccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggtat    300
gtagtagcca gactctgggg ccagggaacc ctggtcaccg tcagctca                 348

<210> SEQ ID NO 222
<211> LENGTH: 339
<212> TYPE: DNA
<213> ORGANISM: Homo sapiens

<400> SEQUENCE: 222
gatgttgtga tgactcagac tccactctct ctgtccgtca cccctggaca gccggcctcc    60
ttctcctgca gtccactca gagcctcctg tggcgtgatg gaaacaccta tttgtattgg    120

```
tatctgcaga agccaggcca gtctccccag ctcctcatct atgaagtttc cggccgattc      180
tctggagtgc cagagagatt cagtggcagc gggtcaggga cagatttcac actggaaatc      240
agccgggtgg aggctgagga tgttggggtt tattactgca tgcaaagtat acactttcct      300
ctcactttcg gcggagggac caagctggag atcaaacgt                             339
```

<210> SEQ ID NO 223
<211> LENGTH: 348
<212> TYPE: DNA
<213> ORGANISM: Homo sapiens

<400> SEQUENCE: 223

```
cagatgcagc tggtgcagtc tggggctgag gtgaagaagc ctggatcctc ggtgaaggtc       60
tcctgcaagg cttctggagg caccttcagc agctatgcta tcagctgggt gcgacaggcc      120
cctggacaag ggcttgagtg gatgggaggg atcatcccta tctttggtac agcaaactac      180
gcacagaagt tccagggcag agtcacgatt accgcggacg aatccacgag cacagcctac      240
atggagctga gcagcctgag atctgaggac acggccgtgt attactgtgc gagagggtat      300
gtagtagcca gactctgggg ccagggaacc ctggtcaccg tcagctca                   348
```

<210> SEQ ID NO 224
<211> LENGTH: 348
<212> TYPE: DNA
<213> ORGANISM: Homo sapiens

<400> SEQUENCE: 224

```
cagatgcagc tggtgcagtc tggggctgag gtgaagaagc ctggatcctc ggtgaaggtc       60
tcctgcaagg cttctggagg caccttcagc agctatgcta tcagctgggt gcgacaggcc      120
cctggacaag ggcttgagtg gatgggaggg atcatcccta tctttggtac agcaaactac      180
gcacagaagt tccagggcag agtcacgatt accgcggacg aatccacgag cacagcctac      240
atggagctga gcagcctgag atctgaggac acggccgtgt attactgtgc gagagggtat      300
gtagtagcca gactctgggg ccagggaacc ctggtcaccg tcagctca                   348
```

<210> SEQ ID NO 225
<211> LENGTH: 348
<212> TYPE: DNA
<213> ORGANISM: Homo sapiens

<400> SEQUENCE: 225

```
cagatgcagc tggtgcagtc tggggctgag gtgaagaagc ctggatcctc ggtgaaggtc       60
tcctgcaagg cttctggagg caccttcagc agctatgcta tcagctgggt gcgacaggcc      120
cctggacaag ggcttgagtg gatgggaggg atcatcccta tctttggtac agcaaactac      180
gcacagaagt tccagggcag agtcacgatt accgcggacg aatccacgag cacagcctac      240
atggagctga gcagcctgag atctgaggac acggccgtgt attactgtgc gagagggtat      300
gtagtagcca gactctgggg ccagggaacc ctggtcaccg tcagctca                   348
```

<210> SEQ ID NO 226
<211> LENGTH: 363
<212> TYPE: DNA
<213> ORGANISM: Homo sapiens

<400> SEQUENCE: 226

```
gaggtgcagc tggtggagac tgggggaggt gtggtacggc ctgggggtc cctgagactc        60
```

```
tcctgtgcag cctctggatt cacctttagc agctctgcca tgagctgggt ccgccagact    120
ccagggaagg aactgcagtg ggtctcagct attactcctg gtggtgaggg gacatactac    180
gcagacgtcg tgaagggccg gttcaccatc tccagagaca attccaagga cacgctgtat    240
ctgcaaatgg acagcctgag agccgaggac acggctgttt attactgtgc gagagatttg    300
tacgggagct acggtgatgc ttttgatatc tggggccaag ggacactggt caccgtcagc    360
tca                                                                  363

<210> SEQ ID NO 227
<211> LENGTH: 363
<212> TYPE: DNA
<213> ORGANISM: Homo sapiens

<400> SEQUENCE: 227
gaggtgcagc tggtggagac tgggggaggt gtggtacggc ctgggggtc cctgagactc     60 tcctgtgcag cctctggatt cacctttagc agctctgcca tgagctgggt ccgccagact    120
ccagggaagg aactgcagtg ggtctcagct attactcctg gtggtgaggg gacatactac    180
gcagacgtcg tgaagggccg gttcaccatc tccagagaca attccaagga cacgctgtat    240
ctgcaaatgg acagcctgag agccgaggac acggctgttt attactgtgc gagagatttg    300
tacgggagct acggtgatgc ttttgatatc tggggccaag ggacactggt caccgtcagc    360
tca                                                                  363

<210> SEQ ID NO 228
<211> LENGTH: 363
<212> TYPE: DNA
<213> ORGANISM: Homo sapiens

<400> SEQUENCE: 228
gaggtgcagc tggtggagac tgggggaggt gtggtacggc ctgggggtc cctgagactc     60 tcctgtgcag cctctggatt cacctttagc agctctgcca tgagctgggt ccgccagact    120
ccagggaagg aactgcagtg ggtctcagct attactcctg gtggtgaggg gacatactac    180
gcagacgtcg tgaagggccg gttcaccatc tccagagaca attccaagga cacgctgtat    240
ctgcaaatgg acagcctgag agccgaggac acggctgttt attactgtgc gagagatttg    300
tacgggagct acggtgatgc ttttgatatc tggggccaag ggacactggt caccgtcagc    360
tca                                                                  363

<210> SEQ ID NO 229
<211> LENGTH: 363
<212> TYPE: DNA
<213> ORGANISM: Homo sapiens

<400> SEQUENCE: 229
gaggtgcagc tggtggagac tgggggaggt gtggtacggc ctgggggtc cctgagactc     60 tcctgtgcag cctctggatt cacctttagc agctctgcca tgagctgggt ccgccagact    120
ccagggaagg aactgcagtg ggtctcagct attactcctg gtggtgaggg gacatactac    180
gcagacgtcg tgaagggccg gttcaccatc tccagagaca attccaagga cacgctgtat    240
ctgcaaatgg acagcctgag agccgaggac acggctgttt attactgtgc gagagatttg    300
tacgggagct acggtgatgc ttttgatatc tggggccaag ggacactggt caccgtcagc    360
tca                                                                  363
```

```
<210> SEQ ID NO 230
<211> LENGTH: 363
<212> TYPE: DNA
<213> ORGANISM: Homo sapiens

<400> SEQUENCE: 230
gaggtgcagc tggtggagac tgggggaggt gtggtacggc ctgggggtc cctgagactc      60 tcctgtgcag cctctggatt cacctttagc agctctgcca tgagctgggt ccgccagact    120
ccagggaagg aactgcagtg ggtctcagct attactcctg gtggtgaggg gacatactac    180
gcagacgtcg tgaagggccg gttcaccatc tccagagaca attccaagga cacgctgtat    240
ctgcaaatgg acagcctgag agccgaggac acggctgttt attactgtgc gagagatttg    300 tacggcgagct acggtgatgc ttttgatatc tggggccaag ggacactggt caccgtcagc    360
tca                                                                 363

<210> SEQ ID NO 231
<211> LENGTH: 363
<212> TYPE: DNA
<213> ORGANISM: Homo sapiens

<400> SEQUENCE: 231
gaggtgcagc tggtggagac tgggggaggt gtggtacggc ctgggggtc cctgagactc      60 tcctgtgcag cctctggatt cacctttagc agctctgcca tgagctgggt ccgccagact    120
ccagggaagg aactgcagtg ggtctcagct attactcctg gtggtgaggg gacatactac    180
gcagacgtcg tgaagggccg gttcaccatc tccagagaca attccaagga cacgctgtat    240
ctgcaaatgg acagcctgag agccgaggac acggctgttt attactgtgc gagagatttg    300 tacggcgagct acggtgatgc ttttgatatc tggggccaag ggacactggt caccgtcagc    360
tca                                                                 363

<210> SEQ ID NO 232
<211> LENGTH: 363
<212> TYPE: DNA
<213> ORGANISM: Homo sapiens

<400> SEQUENCE: 232
gaggtgcagc tggtggagac tgggggaggt gtggtacggc ctgggggtc cctgagactc      60 tcctgtgcag cctctggatt cacctttagc agctctgcca tgagctgggt ccgccagact    120
ccagggaagg aactgcagtg ggtctcagct attactcctg gtggtgaggg gacatactac    180
gcagacgtcg tgaagggccg gttcaccatc tccagagaca attccaagga cacgctgtat    240
ctgcaaatgg acagcctgag agccgaggac acggctgttt attactgtgc gagagatttg    300 tacggcgagct acggtgatgc ttttgatatc tggggccaag ggacactggt caccgtcagc    360
tca                                                                 363

<210> SEQ ID NO 233
<211> LENGTH: 363
<212> TYPE: DNA
<213> ORGANISM: Homo sapiens

<400> SEQUENCE: 233
gaggtgcagc tggtggagac tgggggaggt gtggtacggc ctgggggtc cctgagactc      60 tcctgtgcag cctctggatt cacctttagc agctctgcca tgagctgggt ccgccagact    120
ccagggaagg aactgcagtg ggtctcagct attactcctg gtggtgaggg gacatactac    180
```

```
gcagacgtcg tgaagggccg gttcaccatc tccagagaca attccaagga cacgctgtat    240
ctgcaaatgg acagcctgag agccgaggac acggctgttt attactgtgc gagagatttg    300
tacgggagct acggtgatgc ttttgatatc tggggccaag ggacactggt caccgtcagc    360
tca                                                                  363
```

<210> SEQ ID NO 234
<211> LENGTH: 363
<212> TYPE: DNA
<213> ORGANISM: Homo sapiens

<400> SEQUENCE: 234

```
gaggtgcagc tggtggagac tgggggaggt gtggtacggc ctggggggtc cctgagactc    60
tcctgtgcag cctctggatt cacctttagc agctctgcca tgagctgggt ccgccagact    120
ccagggaagg aactgcagtg ggtctcagct attactcctg gtggtgaggg gacatactac    180
gcagacgtcg tgaagggccg gttcaccatc tccagagaca attccaagga cacgctgtat    240
ctgcaaatgg acagcctgag agccgaggac acggctgttt attactgtgc gagagatttg    300
tacgggagct acggtgatgc ttttgatatc tggggccaag ggacactggt caccgtcagc    360
tca                                                                  363
```

<210> SEQ ID NO 235
<211> LENGTH: 324
<212> TYPE: DNA
<213> ORGANISM: Homo sapiens

<400> SEQUENCE: 235

```
gaaacgacac tcacgcagtc tccagcattc atgtcagcat ctgtgggaga cagagtcacc    60
atcacttgcc aggcgagtca ggacattaac aacttttaa attggtatca gcagaaacca    120
gggaaagccc ctaagttcct gatctacgat gcttccaatt tggaaaaagg ggtcccatca    180
aagttcagtg gcgtggatc tgggacagaa tttactctca ccatcagcag cctgcagcct    240
gaagatattg caacatatta ctgtcaacaa tatcgtgatt tcccgctcac cttcggccaa    300
gggacacgac tggagattaa acgt                                           324
```

<210> SEQ ID NO 236
<211> LENGTH: 339
<212> TYPE: DNA
<213> ORGANISM: Homo sapiens

<400> SEQUENCE: 236

```
gatgttgtga tgactcagtc tccactctcc ctgcccgtca cccctggaga gccggcctcc    60
atctcctgca ggtctagtca gagcctcgtc tatggtgatg acacaactta tttggcttgg    120
tacctgcaga agccagggca gtctccacag ctcctgatct atttgggttc taatcgggcc    180
tccggggtcc ctgacaggtt cagtggcagt ggatcaggca cagatttac actgaaaatc    240 agcagagtgg aggctgagga tgttggggtt tattactgca tgcaaggtct acaaactccg    300
ctcactttcg gcggagggac caagctggag atcaaacgt                           339
```

<210> SEQ ID NO 237
<211> LENGTH: 324
<212> TYPE: DNA
<213> ORGANISM: Homo sapiens

<400> SEQUENCE: 237

```
gaaacgacac tcacgcagtc tccagcattc atgtcagcat ctgtgggaga cagagtcacc    60
```

| | | |
|---|---|---|
| atcacttgcc aggcgagtca ggacattaac aactttttaa attggtatca gcagaaacca | 120 | |
| gggaaagccc ctaagttcct gatctacgat gcttccaatt tggaaaaagg tgtcccatca | 180 | |
| aggttcagtg gcgtggatc tgggacggaa tttactctca ccatcagcag cctacagcct | 240 | |
| gaagatattg ctacatatta ctgtcaacaa tatcgtgatt cccgctcac cttcggccaa | 300 | |
| gggacacgac tggagattaa acgt | 324 | |

<210> SEQ ID NO 238
<211> LENGTH: 339
<212> TYPE: DNA
<213> ORGANISM: Homo sapiens

<400> SEQUENCE: 238

| | | |
|---|---|---|
| gacatcgtga tgacccagac cccactgtcc ctgtccgtga cccctggcca gcctgcctcc | 60 | |
| atctcctgca agtcctccca gtccctgctg cacatcgacg gcctgaccta cctgtactgg | 120 | |
| tatctgcaga agcccggcca gccccccag ctgctgatct acgaggtgtc ccaccggttc | 180 | |
| tccggcgtgt ccgacaagtt ctccggctcc ggcagcggca ccgacttcac cctgaccatc | 240 | |
| tcccggtgg aagccgagga cgtgggcgtg tactactgca tgcagagcct gcatctgccc | 300 | |
| atcaccttcg gccagggcac ccggctggaa atcaagcgt | 339 | |

<210> SEQ ID NO 239
<211> LENGTH: 339
<212> TYPE: DNA
<213> ORGANISM: Homo sapiens

<400> SEQUENCE: 239

| | | |
|---|---|---|
| gatattgtga tgacccagac tccactctct ctgtccgtca cccctggaca gccggcctcc | 60 | |
| atctcctgca agtctagtca gagcctcctg catattgatg gactgaccta tttgtattgg | 120 | |
| tacctgcaga agccaggcca gcctccacag ctcctgatct atgaagtttc ccaccggttc | 180 | |
| tctggagtgt cagataagtt cagtggcagc gggtcaggga cagatttcac actgacaatc | 240 | |
| agccgggtgg aggctgagga tgttggagtt tattactgca tgcagagttt acaccttccg | 300 | |
| atcaccttcg gccaagggac acgactggag attaaacgt | 339 | |

<210> SEQ ID NO 240
<211> LENGTH: 339
<212> TYPE: DNA
<213> ORGANISM: Homo sapiens

<400> SEQUENCE: 240

| | | |
|---|---|---|
| gatgtggtga tgacccagac ccctctgtcc ctgtccgtga cccctggcca gcctgcctcc | 60 | |
| atctcctgca agtcctccca gtccctgctg cacatcgacg gcaagaccta cctgtactgg | 120 | |
| tatctgcaga agtccggcca gtcccctcag ctgctgatct acgaggtgtc caaccggttc | 180 | |
| tccggcgtgc ccgacacctt ctccggctct ggctctggca ccgacttcac cctgaagatc | 240 | |
| tcccggtgg aagccgagga cgtgggcgtg tactactgca tgcagagcct gcacttcccc | 300 | |
| atcaccttcg gccagggcac ccggctggaa atcaagcgt | 339 | |

<210> SEQ ID NO 241
<211> LENGTH: 339
<212> TYPE: DNA
<213> ORGANISM: Homo sapiens

<400> SEQUENCE: 241

```
gatgttgtga tgacccagac tccactctct ctgtccgtca ccccggaca gccggcctcc    60 atctcctgta agtctagtca gagcctcctg catattgatg aaagaccta tttgtattgg   120 tacctgcaga agtcaggcca gtctccacag ctcctgatct atgaggtttc aaccggttc   180 tctggagtgc cagatacgtt cagtggcagc gggtcgggga cagatttcac actgaaaatc   240
agccgggtgg aggctgagga tgttggggtt tactactgca tgcagagtct acactttccg   300
atcaccttcg gccaggggac acgactggag attaaacgt                          339
```

```
<210> SEQ ID NO 242
<211> LENGTH: 324
<212> TYPE: DNA
<213> ORGANISM: Homo sapiens

<400> SEQUENCE: 242
gaaacgacac tcacgcagtc tccaacattc atgtcagcat ctgtgggaga cagagtcacc    60
atcacttgcc aggcgagtca ggacattaac aactttttaa attggtatca gcagaaacca   120
gggaaagccc ctaagttcct gatctacgat gcttccaatt tggaaaaagg tgtcccatca   180
aggttcagtg gcgtggatc tgggacggaa tttactctca ccatcagcag cctacagcct   240
gaagatattg ctacatatta ctgtcaacaa tatcgtgatt cccgctcac cttcggccaa   300 gggacacgac tcgagattaa acgt                                          324
```

```
<210> SEQ ID NO 243
<211> LENGTH: 339
<212> TYPE: DNA
<213> ORGANISM: Homo sapiens

<400> SEQUENCE: 243
gatgttgtga tgactcagac tccactctct ctgtccgtca ccctggaca gccggcctcc    60 atctcctgca agtccagtca gagcctccta catattgatg aaaggccta cttgtattgg   120 tacctgcaga agccaggcca gtctccacac ctcctaatcc gtgaagtctc cacccggttc   180
tctggagtgt cagataggtt cactggcagc gggtcaggga cagatttcac attggaaatc   240
agccgagtgg aggctgagga tgttggggtt tattactgca tgcaaggttt acaccttcct   300
ccgacgttcg gccaagggac caaggtggaa atcaaacgt                          339
```

```
<210> SEQ ID NO 244
<211> LENGTH: 339
<212> TYPE: DNA
<213> ORGANISM: Homo sapiens

<400> SEQUENCE: 244
gatgttgtga tgactcagac tccactctct ctgtccgtca ccctggaca gccggcctcc    60 atctcctgca agtctagtca gagcctcctc catattgatg aaggaccta tttgtattgg   120 tacctgcaaa aggcaggcca gcctccgcag ctcctgatct atgaagtttc caaccggttc   180
tctggagtgc cagataggtt cagtggcagc gggtcaggga cagatttcac actgaaaatc   240
agccgggtgg aggctgagga tgttggggtt tattactgca tgcaaagtat acatttttcct   300 ctcactttcg gcggagggac caagctggag atcaaacgt                          339
```

```
<210> SEQ ID NO 245
<211> LENGTH: 339
<212> TYPE: DNA
<213> ORGANISM: Homo sapiens

<400> SEQUENCE: 245
```

```
gatattgtga tgacccagac tccactctct ctgtccgtca cccctggaca gccggcctcc      60
attacctgca agtctagtca gagcctcctc catattgatg gaaacaccta tctgtattgg     120
tacctgcaga ggccaggcca gcctccacag ctcctgatct atgaaatttc aaccggttc      180 tctggagtgc cagataggtt cagtggcagc gggtcaggga cagatttcac actgaaaatc     240
agccgggtgg aggctgagga tgttggggtt tattactgca tgcaaagttt acactttccg     300
atcaccttcg gccaagggac acgactggag attaaacgt                            339

<210> SEQ ID NO 246
<211> LENGTH: 339
<212> TYPE: DNA
<213> ORGANISM: Homo sapiens

<400> SEQUENCE: 246
gacatcgtga tgacccagac ccctctgtcc ctgtccgtga cccctggcca gcctgccagc      60
atctcctgca agtcctccca gtccctgctg cacatcgacg gcaacaccta cctgtactgg     120
tatctgcagc ggccaggcca gcctccccag ctgctgatct acgagatctc caaccggttc     180
tccggcgtgc ccgaccggtt ctctggttcc ggctctggca ccgacttcac cctgaagatc     240
tccagagtgg aagccgagga cgtgggcgtg tactactgca tgcagagcct gcacttcccc     300
atcaccttcg gccagggcac ccggctggaa atcaagcgt                            339

<210> SEQ ID NO 247
<211> LENGTH: 339
<212> TYPE: DNA
<213> ORGANISM: Homo sapiens

<400> SEQUENCE: 247
gatattgtga tgacccagac tccactctct ctgtccgtca cccctggaca gccggcctcc      60
attacctgca agtctagtca gagcctcctc catattgatg gaaagaccta tttgtattgg     120
ttcttgcaga agccaggcca gcctccacaa cttttgatct atgaagtttc aaccggttc      180 tctggagtgc cagataggtt cagtggcacc gggtcaggga cagatttcac actgaaaatc     240
agccgggtgg aggctgagga tgttggcgtt tattactgca tgcaaagttt acactttccg     300
atcaccttcg gcccagggac acgactggag attaaacgt                            339

<210> SEQ ID NO 248
<211> LENGTH: 348
<212> TYPE: DNA
<213> ORGANISM: Homo sapiens

<400> SEQUENCE: 248
cagatgcagc tggtgcagtc tggggctgag gtgaagaagc ctggatcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagagggtat     300
gtagtagcca gactctgggg ccagggaacc ctggtcaccg tcagctca                  348

<210> SEQ ID NO 249
<211> LENGTH: 339
<212> TYPE: DNA
<213> ORGANISM: Homo sapiens
```

<400> SEQUENCE: 249

```
gatattgtga tgacccagac tccactctct ctgtccgtca cccctggaca gccggcctcc      60
attacctgca agtctagtca gagcctcctc catattgatg gaaagaccta tttgtattgg     120
ttcttgcaga agccaggcca gcctccacag ctcctgatct atgaagtttc aaaccgcttc     180
tctggagtgc cggataggtt cagtggcagc gggtcaggga cagatttcac actgaaaatc     240
agccgggtgg aggctgagga tgttggggctt tattactgca tgcagagttt acaccttccg    300
atcaccttcg gccaagggac acgactggag attaaacgt                            339
```

<210> SEQ ID NO 250
<211> LENGTH: 339
<212> TYPE: DNA
<213> ORGANISM: Homo sapiens

<400> SEQUENCE: 250

```
gatgttgtga tgactcagtc tccactctcc ctgcccgtca cccctggaga gccggcctcc      60
atctcctgca ggtctagtca gagcctccta catattgatg gatttaatta tttgcaatgg     120
tacctgcaga agccagggca gtctccacag ctcctggtcc atttgggttc ttttcgggcc     180
tccggggtcc ctgacaggtt cagtggcagt ggatcaggca cagatttac actggaaatc      240
agcagagttg aggctgagga tgttggactt tattactgca tgcaaggtct acaaactcct     300
cccactttcg gccctgggac caaagtggag atcaaacgt                            339
```

<210> SEQ ID NO 251
<211> LENGTH: 339
<212> TYPE: DNA
<213> ORGANISM: Homo sapiens

<400> SEQUENCE: 251

```
gatattgtga tgacccagac tccactctct ctgtccgtca cccctggaca gccggcctcc      60
atctcctgca agtctagtca gagcctgttt catgatcatg gaaggacgca cttgtcttgg     120
tacctgcaga agccaggcca gcctccacag ctcctgatct ttgaagcttc aaccggttc      180
tctggagtgc cagataggtt cagtggcagc gggtcaggga cagatttcac actgaagatc     240
agccgggtgg aggctgagga tgttgggggtt tattactgca tgcaaggtat acaccttcct    300
ccggctttcg gcggagggac caagctggag atcaaacgt                            339
```

<210> SEQ ID NO 252
<211> LENGTH: 336
<212> TYPE: DNA
<213> ORGANISM: Homo sapiens

<400> SEQUENCE: 252

```
cagtctgtgt tgacgcagcc gccctcagtg tctgcggccc caggacagaa ggtcaccatc      60
tcctgctctg gaagcagctc caacattggc tataattacg tatcctggta ccagcagttc     120
ccaggaacag ccccccaaact cctcatttat gacaataata gcgaccctc agggattcct     180
gaccgattct ctggctccaa gtctggcacg tcagccaccc tgggcatcac cggactccag     240
actggggacg aggccgatta ttactgcgga acatgggata cagccggag tcctccttgg      300
gtgttcggcg gagggaccaa ggtgaccgtc ctaggt                               336
```

<210> SEQ ID NO 253
<211> LENGTH: 318
<212> TYPE: DNA
<213> ORGANISM: Homo sapiens

<400> SEQUENCE: 253

| tcctatgagc tgacacagcc atcctcagtg tcagtgtccc caggacagac agccagcatc | 60 |
| acctgctctg gagataaatt gggggaaaaa tatgcttcct ggtatcaaca gaagccaggc | 120 |
| cagtcccctg tcctggtcat gtttgaagat acgaagcggc cctcagggat ccctgagcga | 180 |
| ttctctggct ccaactctgg gaacacagcc actctgacca tcagcgggac ccaggctgaa | 240 |
| gatgaggctg actattactg tcaggcgtgg gacagcagtt gggtgttcgg cggaggcacc | 300 |
| cagctgaccg tcctaggt | 318 |

<210> SEQ ID NO 254
<211> LENGTH: 336
<212> TYPE: DNA
<213> ORGANISM: Homo sapiens

<400> SEQUENCE: 254

| cagtctgtgc tgacgcagcc gccctcagtg tctgcggccc caggacagag ggtcaccatc | 60 |
| tcctgctctg gaaacaccct caacattgga ataattttg tatcctggta ccagcagctc | 120 |
| ccaggaacag ccccccaaact cctcatttat gacgataata agcgaccctc agggattcct | 180 |
| gaccgattct ctggctccaa gtctggcacg tcagctaccc tgggcatctc cggactccag | 240 |
| actggggacg aggccgatta ttactgcggc acatgggata cagcctgaa tcctccttgg | 300 |
| gtgttcggcg gaggcaccca gctgaccgtc ctaggt | 336 |

<210> SEQ ID NO 255
<211> LENGTH: 318
<212> TYPE: DNA
<213> ORGANISM: Homo sapiens

<400> SEQUENCE: 255

| tcctatgtgc tgactcagcc accctcagtg tccgtggccc caggacagac agccagcatc | 60 |
| acctgctctg gagataattt gggggaaaaa tttgtttcct ggtatcaaca gaaggcaggc | 120 |
| cagtcccctg tcttggtcat ctttgaagat aataagcggc cctcagggat ccctgagcga | 180 |
| ttcgctggct ccaactctgg gaacagagcc actctgacca tcaggggac ccaggctgaa | 240 |
| gatgaggctg actattactg tcaggcgtgg gacagcagct gggtgttcgg cggaggcacc | 300 |
| cagctgaccg tcctaggt | 318 |

<210> SEQ ID NO 256
<211> LENGTH: 318
<212> TYPE: DNA
<213> ORGANISM: Homo sapiens

<400> SEQUENCE: 256

| tcctatgagc tgacacagcc accctcagtg tccgtggccc caggacagac agccaccatc | 60 |
| acctgctctg gagatagatt gggcgataaa tttatctctt ggtatcagca gaagccaggc | 120 |
| cagtcccctc tactggtcat ctttgaagat aacgaacggc cctcacggat ccctgagcga | 180 |
| ttctctggct ccaactctgg caactctgcc actctgacca tcagcgggac ccaggctgta | 240 |
| gatgaggctg actattactg tcaggcgtgg gacagcagtt gggtgttcgg cggaggcacc | 300 |
| cagctgaccg tcctaggt | 318 |

<210> SEQ ID NO 257
<211> LENGTH: 318
<212> TYPE: DNA

<213> ORGANISM: Homo sapiens

<400> SEQUENCE: 257

```
tcctatgtgc tgactcagcc accctcagtg tccgtggccc caggacagac agcccgtatc    60
acctgctctg gagataaaatt ggggataga tatgtttcct ggtatcagca gaagccaggc   120
cagtcccctg tgttggtcat gtttgaagat accggcggc ccgcagggat ccctgagcga    180
ttctctggct ccaactctgg gaacacagcc actctgacca tcagcgggac ccaggcagaa   240
gatgaggctg actattactg tcaggcgtgg ggcacctcct gggttttcgg cggaggcacc   300
cagctgaccg tcctaggt                                                  318
```

<210> SEQ ID NO 258
<211> LENGTH: 336
<212> TYPE: DNA
<213> ORGANISM: Homo sapiens

<400> SEQUENCE: 258

```
cagtctgtgc tgacgcagcc gccctcagtg tctgcggccc caggacagaa ggtcaccatc    60
tcctgctctg gaaccggctc caacattggc agtaattatg tcgcctggta tcagcaactc   120
ccaggaacag ccccccaaact cctcatttat gacgataata agcgaccctc agggactcct   180
gaccgattct ctggctccaa gtctggcacg tcagccaccc tggtcatcgc cggactccag   240
actggggacg aggccgatta ttattgtgga acatgggata caccctgaa tgttgggggg    300
gtcttcggcg gaggcaccca gctgaccgtc ctaggt                              336
```

<210> SEQ ID NO 259
<211> LENGTH: 318
<212> TYPE: DNA
<213> ORGANISM: Homo sapiens

<400> SEQUENCE: 259

```
tcctatgtgc tgactcagcc accctcagtg tccgtggccc ccggacagac agccaccatc    60
acctgctcag gagatgattt cggcgataag tatgtgtctt ggtatcaaca gaagccaggc   120
cagtcccctc tactggtcat ctttcaggat aacgagcggc cctcaggat ccctgagcga    180
ttctctggct ccaactctgg gaacactgcc actttgacca tcagcgggac ccaggctatg   240
gatgaggctg actattactg tcaggcgtgg gacagcaatt gggtgttcgg cggagggacc   300
aaggtcaccg tcctaggt                                                  318
```

<210> SEQ ID NO 260
<211> LENGTH: 324
<212> TYPE: DNA
<213> ORGANISM: Homo sapiens

<400> SEQUENCE: 260

```
tcctatgagc tgacacagcc accctcagtg tccgtggccc caggacagac agccaccatc    60
acctgctctg gagataaatt ggggataaa tatgcttcct ggtatcagca gaagccaggc    120
cagtcccctg tcttggtcat gtttgagaat cgtgaccggc cctcagggat ccctgaccga   180
ttctctggct ccaattctgg gaacacagcc actctgacca tcagcgggac ccaggctatg   240
gatgaggctg actattactg tcaggcgtgg gacagcagca ctgcatgggt attcggcgga   300
ggcacccagc tgaccgtcct aggt                                           324
```